(12) United States Patent
Dylla et al.

(10) Patent No.: US 9,458,231 B2
(45) Date of Patent: Oct. 4, 2016

(54) MODULATORS AND METHODS OF USE

(75) Inventors: Scott J. Dylla, Mountain View, CA (US); Orit Foord, Foster City, CA (US); Robert A. Stull, Alameda, CA (US); Wade C. Anderson, Fairfield, CA (US); Saiyou Ohshima, Cupertino, CA (US)

(73) Assignee: Stemcentrx, Inc., South San Francisco, CA (US)

( * ) Notice: Subject to any disclaimer, the term of this patent is extended or adjusted under 35 U.S.C. 154(b) by 403 days.

(21) Appl. No.: 13/819,935

(22) PCT Filed: Sep. 2, 2011

(86) PCT No.: PCT/US2011/050439
§ 371 (c)(1),
(2), (4) Date: Jun. 17, 2013

(87) PCT Pub. No.: WO2012/031273
PCT Pub. Date: Mar. 8, 2012

(65) Prior Publication Data
US 2013/0302355 A1 Nov. 14, 2013

Related U.S. Application Data

(60) Provisional application No. 61/380,181, filed on Sep. 3, 2010.

(51) Int. Cl.
| | | |
|---|---|---|
| *A61K 39/00* | (2006.01) | |
| *C07K 16/18* | (2006.01) | |
| *A61K 39/395* | (2006.01) | |
| *A61K 47/48* | (2006.01) | |
| *C07K 16/28* | (2006.01) | |
| *C07K 16/30* | (2006.01) | |

(52) U.S. Cl.
CPC ........... *C07K 16/18* (2013.01); *A61K 39/3955* (2013.01); *A61K 39/39558* (2013.01); *A61K 47/48469* (2013.01); *A61K 47/48561* (2013.01); *A61K 47/48569* (2013.01); *C07K 16/2896* (2013.01); *C07K 16/30* (2013.01); *C07K 2317/24* (2013.01); *C07K 2317/34* (2013.01); *C07K 2317/76* (2013.01); *C07K 2317/77* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 5,514,787 A | 5/1996 | Atkinson | |
| 5,545,619 A | 8/1996 | Atkinson et al. | |
| 5,552,381 A | 9/1996 | Atkinson et al. | |
| 5,703,046 A | 12/1997 | Atkinson et al. | |
| 5,719,127 A | 2/1998 | Atkinson et al. | |
| 5,846,715 A | 12/1998 | Purcell et al. | |
| 5,851,528 A | 12/1998 | Ko et al. | |
| 6,010,873 A | 1/2000 | Atkinson et al. | |
| 6,086,876 A | 7/2000 | Karp et al. | |
| 6,130,062 A | 10/2000 | Milland et al. | |
| 6,218,520 B1 | 4/2001 | Atkinson | |
| 6,482,404 B1 | 11/2002 | White et al. | |
| 6,495,735 B1 | 12/2002 | White et al. | |
| 6,521,450 B1 | 2/2003 | Atkinson et al. | |
| 7,148,038 B2 | 12/2006 | Mather | |
| 7,425,421 B2 | 9/2008 | Dertinger | |
| 7,462,352 B2 | 12/2008 | Hansen et al. | |
| 7,534,431 B2 | 5/2009 | McBride et al. | |
| 7,575,893 B2 | 8/2009 | Simmons | |
| 7,744,878 B2 | 6/2010 | Mather | |
| 8,309,354 B2 | 11/2012 | Mather et al. | |
| 2002/0115065 A1 | 8/2002 | Logtenberg et al. | |
| 2003/0108966 A1* | 6/2003 | Mather ............. C07K 16/2896 435/7.23 |
| 2003/0129677 A1 | 7/2003 | Martens et al. | |
| 2004/0038281 A1 | 2/2004 | Hung | |
| 2004/0126762 A1 | 7/2004 | Morris et al. | |
| 2004/0241158 A1 | 12/2004 | McBride et al. | |
| 2005/0026197 A1 | 2/2005 | Dertinger | |
| 2006/0257398 A1 | 11/2006 | Hansen et al. | |
| 2007/0128202 A1 | 6/2007 | Mather | |
| 2007/0190529 A1 | 8/2007 | Ridder et al. | |
| 2008/0166342 A1 | 7/2008 | Hansen et al. | |
| 2008/0175870 A1 | 7/2008 | Mather et al. | |
| 2008/0187966 A1 | 8/2008 | Simmons | |
| 2009/0202487 A1 | 8/2009 | Chang et al. | |
| 2009/0203538 A1 | 8/2009 | Sugioka et al. | |
| 2010/0004431 A1* | 1/2010 | Bernett et al. ............. 530/387.9 |
| 2010/0034817 A1 | 2/2010 | Abbas et al. | |
| 2010/0255011 A1 | 10/2010 | Lieber et al. | |
| 2013/0061340 A1 | 3/2013 | Dylla et al. | |
| 2013/0061342 A1 | 3/2013 | Dylla et al. | |

(Continued)

FOREIGN PATENT DOCUMENTS

| | | |
|---|---|---|
| CN | 1756561 A | 4/2006 |
| EP | 2078732 | 7/2004 |

(Continued)

OTHER PUBLICATIONS

Harris et al "Efficient generation of monoclonal antibodies for specific protein domains using recombinant immunoglobulin fusion proteins: pitfalls and solutions" *J Immunol Methods.* Oct. 15, 2002;268(2):245-58.
Liszewski et al., "Membrane cofactor protein (MCP or CD46): newest member of the regulators of complement activation gene cluster." *Annu Rev Immunol.* 1991;9:431-55.
Manchester et al., "Measles virus and C3 binding sites are distinct on membrane cofactor protein (CD46)." *Proc Nati Acad Sci USA.* Mar. 14, 1995;92(6):2303-7.
Offficial action dated Mar. 27, 2015 issued in Australian application (No. 2011295715).
Offficial action dated Apr. 30, 2014 issued in Chinese application (No. 201180053061.9).

(Continued)

*Primary Examiner* — Julie Wu
(74) *Attorney, Agent, or Firm* — Womble Carlyle Sandridge & Rice, LLP

(57) ABSTRACT

Novel modulators, including antibodies and derivatives thereof, and methods of using such modulators to treat hyperproliferative disorders are provided.

9 Claims, 31 Drawing Sheets

(56) References Cited

U.S. PATENT DOCUMENTS

| | | |
|---|---|---|
| 2013/0260385 A1 | 10/2013 | Dylla et al. |
| 2015/0030636 A1 | 1/2015 | Dylla et al. |

FOREIGN PATENT DOCUMENTS

| | | |
|---|---|---|
| EP | 1975239 | 10/2008 |
| EP | 1 523 496 | 6/2011 |
| EP | 2 339 010 | 6/2011 |
| EP | 1 441 766 | 9/2011 |
| JP | 2005-511525 | 4/2005 |
| WO | WO 91/18097 | 11/1991 |
| WO | WO 97/38109 | 10/1997 |
| WO | WO 01/88537 | 11/2001 |
| WO | WO 02/18948 | 3/2002 |
| WO | WO 03/032814 | 4/2003 |
| WO | WO 2004/058298 | 7/2004 |
| WO | WO 2008/008917 | 1/2008 |
| WO | WO 2008/034076 | 3/2008 |
| WO | WO 2008/091908 | 7/2008 |
| WO | WO 2009/090656 | 7/2009 |
| WO | WO 2009/126558 | 10/2009 |
| WO | WO 2011/143637 | 11/2011 |
| WO | WO 2012/031280 | 3/2012 |
| WO | WO 2013/119964 | 8/2013 |
| WO | WO 2015/031698 | 3/2015 |

OTHER PUBLICATIONS

Offficial action dated Feb. 15, 2015 issued in Chinese application (No. 201180053061.9).

Offficial action dated Sep. 18, 2015 issued in Chinese application (No. 201180053061.9).

Offficial action dated Jun. 10, 2014 issued in European application (No. 11820900.6).

Offficial action dated Jul. 13, 2015 issued in European application (No. 11820900.6).

Offficial action dated Aug. 21, 2015 issued in Japanese application (No. 2013-527360).

Offficial action dated Oct. 25, 2013 issued in New Zealand application (No. 608814).

Offficial action dated Jun. 9, 2015 issued in New Zealand application (No. 708510).

Astier et al., "Alterations in CD46-mediated Tr1 regulatory T cells in patients with multiple sclerosis," *J Clin Invest*, 116(12): 3252-7 (2006).

Buettner et al., "Activated signal transducers and activators of transcription 3 signaling induces CD46 expression and protects human cancer cells from complement-dependent cytotoxicity," *Mol Cancer Res*, 5(8): 823-32 (2007).

Cardone et al., "Complement regulator CD46 temporally regulates cytokine production by conventional and unconventional T cells," *Nature Immunology*, 11(9): 862-71 (2010).

Cattaneo, "Four viruses, two bacteria, and one receptor: membrane cofactor protein (CD46) as pathogens' magnet," *J Virol*, 78(9): 4385-8 (2004).

Christiansen et al., "Chimeric CD46/DAF molecules reveal a cryptic functional role for SCR1 of DAF in regulating complement activation," *Mol Immunol*, 37: 687-96 (2000).

Christiansen et al., "Engineering of recombinant soluble CD46: an inhibitor of complement activation," *Immunology*, 87(3):348-54 (1996).

Crucell, press release, "Centocor returns rights to anti-CD46 to Crucell," Dec. 24, 2002.

Dispensieri et al., "Phase I trial of administration of Edmonston strain of measles," http://webconferences.com/nihoba/691_Russell.pdf.

Fishelson et al., "Obstacles to cancer immunotherapy: expression of membrane complement regulatory proteins (mCRPs) in tumors," *Mol Immunol*, 40: 109-23 (2003).

Gancz et al., "Cancer resistance to complement dependent cytotoxicity (CDC): problem-oriented research and development," *Mol Immunol*, 46: 2794-2800 (2009).

Goslings et al., "Membrane-bound regulators of complement activation in uveal melanomas. CD46, CD55, and CD59 in uveal melanomas," *Invest Ophthalmol Vis Sci*, 37(9): 1884-91 (1996).

Hara et al., "High expression of membrane cofactor protein of complement (CD46) in human leukaemia cell lines: implication of an alternatively spliced form containing the $ST^A$ domain in CD46 up-regulation," *Scand J Immunol*, 42: 581-90 (1995).

Hara et al., "Soluble forms of membrane cofactor protein (CD46, MCP) are present in plasma, tears, and seminal fluid in normal subjects," *Clin Exp Immunol*, 89: 490-4 (1992).

Hsu et al., "Artificial mutations and natural variations in the CD46 molecules from human and monkey cells define regions important for measles virus binding," *J Virol*, 71(8): 6144-54 (1997).

Johnstone et al., "Identification and quantification of complement regulator CD46 on normal human tissues," *Immunology*, 79: 341-7 (1993).

Jurianz et al., "Neutralization of complement regulatory proteins augments lysis of breast carcinoma cells targeted with rhumAb anti-HER2," *Immunopharmacology*, 42: 209-18 (1999).

Karosi et al., "Disease-associated novel CD46 splicing variants and pathologic bone remodeling in otosclerosis," *Laryngoscope*, 118: 1669-76 (2008).

Kawano et al., "Elevated serum levels of soluble membrane cofactor protein (CD46, MCP) in patients with systemic lupus erythematosus (SLE)," *Clin Exp Immunol*, 116(3): 542-6 (1999).

Kemper et al., "Membrane cofactor protein (MCP; CD46) expression in transgenic mice," *Clin Exp Immunol*, 124: 180-9 (2001).

Liszewski et al., "Dissecting sites important for complement regulatory activity in membrane cofactor protein (MCP; CD46)," *J Biol Chem*, 272: 37692-37701 (2000).

Liszewski et al., "Emerging roles and new functions of CD46," *Springer Semin Immunopathol*, 27(3): 345-58 (2005).

Liszewski et al., "Membrane cofactor protein (CD46) of complement. Processing differences related to alternatively spliced cytoplasmic domains," *J Biol Chem*, 269(14): 10776-9 (1994).

Madjd et al., "Do poor-prognosis breast tumours express membrane cofactor proteins (CD46)?" *Cancer Immunol Immunother*, 54: 149-56 (2005).

Maisner et al., "Membrane cofactor protein (CD46) is a basolateral protein that is not endocytosed. Importance of the tetrapeptide FTSL at the carboxyl terminus," *J Biol Chem*, 272(33): 20793-9 (1997).

Murphy, "The ADAMs: signalling scissors in the tumour microenvironment," *Nature Reviews*, 8: 929-941 (2008).

Myers et al., "Preclinical pharmacology and toxicology of intravenous MV-NIS, an oncolytic measles virus administered with or without cyclophosphamide," *Clin Pharmacol Ther*, 82(6): 700-10 (2007).

Persson et al., "Structure of extracellular portion of CD46 provides insights into its interactions with complement proteins and pathogens," *PLoS Pathog*, 6(9): e1001122 (2010).

Pintér et al., "Presence of autoantibodies against complement regulatory proteins in relapsing-remitting multiple sclerosis," *J Neurovirol*, 6 Suppl 2: S42-6 (2000).

Purcell et al., "Alternatively spliced RNAs encode several isoforms of CD46 (MCP), a regulator of complement activation," *Immunogenetics*, 33(5-6):335-44 (1991).

Ravindranath et al., "Cell-surface density of complement restriction factors (CD46, CD55, and CD59): oral squamous cell carcinoma versus other solid tumors," *Oral Surg Oral Med Oral Pathol Oral Radiol Endod*, 103 (2): 231-9 (2007).

Riley-Vargas et al., "CD46: expanding beyond complement regulation," *Trends Immunol*, 25(9): 496-503 (2004).

Riley-Vargas et al., "Expression of Membrane Cofactor Protein (MCR; CD46) on spermatozoa: Just a complement inhibitor?" *Mod Asp Immunobiol*, 3(2): 75-78 (2003).

Russell, "How polarity shapes the destiny of T cells," *J Cell Sci*, 121(2): 131-6 (2007).

(56) References Cited

OTHER PUBLICATIONS

Schmitt et al., "Expression and regulation by interferon-γ of the membrane-bound complement regulators CD46 (MCP), CD55 (DAF) and CD59 in gastrointestinal tumours," *Eur J Cancer*, 35(1): 117-24 (1999).

Seya et al., "Complement-mediated tumor cell damage induced by antibodies against membrane cofactor protein (MCP, CD46)," *J Exp Med*, 172: 1673-80 (1990).

Seya et al., "Human membrane cofactor protein (MCP, CD46): multiple isoforms and functions," *Int J Biochem Cell Biol*, 31: 1255-60 (1999).

Silver et al., "Transduction and oncolytic profile of a potent replication-competent adenovirus 11p vector (RCAd11pGFP) in colon carcinoma cells," *PLoS One*, 6(3): e17532 (2011).

Surowiak et al., "CD46 expression is indicative of shorter revival-free survival for ovarian cancer patients," *Anticancer Res*, 26: 4943-8 (2006).

Teuchert et al., "Importance of the carboxyl-terminal FTSL motif of membrane cofactor protein for basolateral sorting and endocytosis. Positive and negative modulation by signals inside and outside the cytoplasmic tail," *J Biol Chem*, 274(28): 19979-84 (1999).

Trouw et al., "Autoantibodies to complement components," *Mol Immunol*, 38(2-3): 199-206 (2001).

Vleminckx et al., "Genetic manipulation of E-cadherin expression by epithelial tumor cells reveals an invasion suppressor role," *Cell*, 66: 107-119 (1991).

Weyand et al., "Monoclonal antibody detection of CD46 clustering beneath *Neisseria gonorrhoeae* microcolonies, *Infect Immun*," 74(4): 2428-35 (2006).

Wu et al., "Persistence of CD133+ cells in human and mouse glioma cell lines: detailed characterization of GL261 glioma cells with cancer stem cell-like properties," *Stem Cells Dev*, 17: 173-184 (2008).

Xi Ng et al., "Discrimination between alternatively spliced STP-A and -B isoforms of CD46," *Immunology*, 83(1): 122-7 (1994).

Zell et al., "Down-regulation of CD55 and CD46 expression by anti-sense phosphorothioate oligonucleotides (S-ODNs) sensitizes tumor cells to complement attack," *Clin Exp Immunol*, 150(3): 576-584 (2007).

PCT International Search Report and Written Opinion for International Application No. PCT/US2011/050439, mailed May 31, 2012 (11 pages).

Official action dated Nov. 1, 2015 issued in Israeli application (No. 224969).

Offficial action dated Jan. 12, 2016 issued in Australian application (No. 2011295715).

Offficial action dated May 19, 2016 issued in New Zealand application (No. 608814).

* cited by examiner

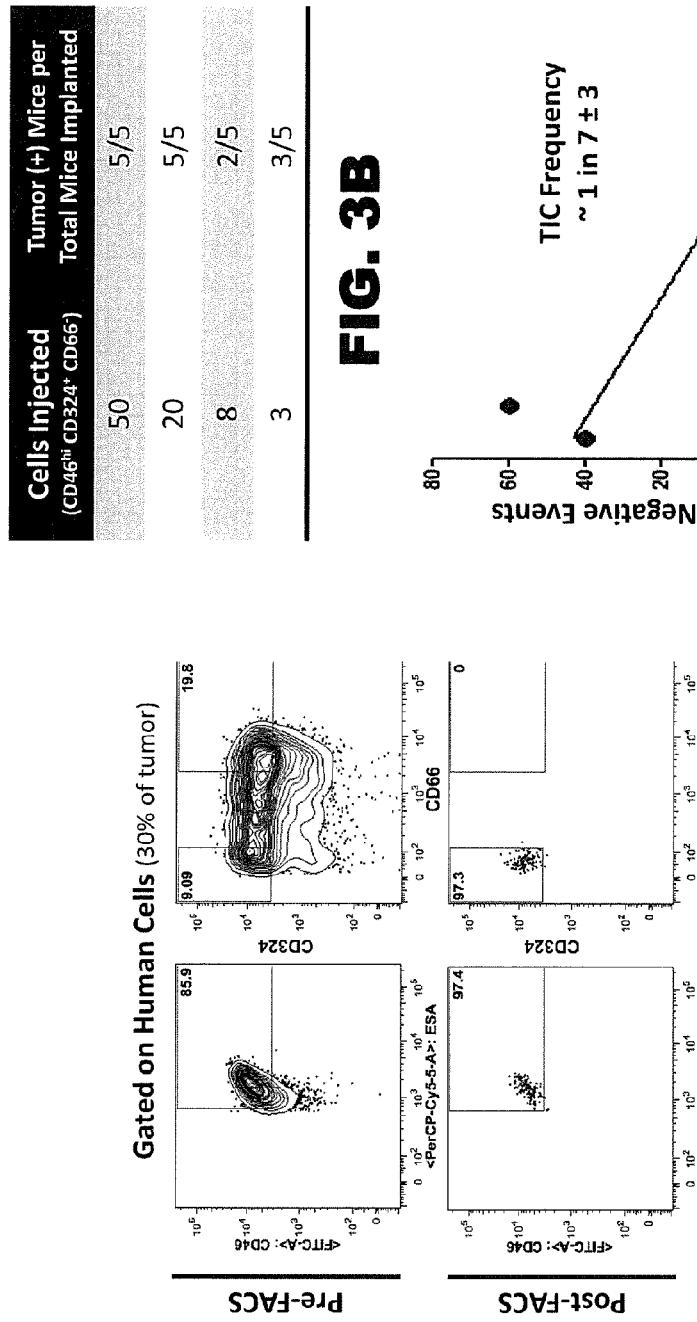
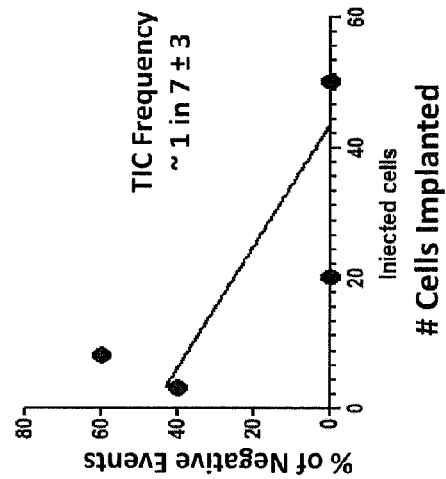
FIG. 3A
FIG. 3B
FIG. 3C

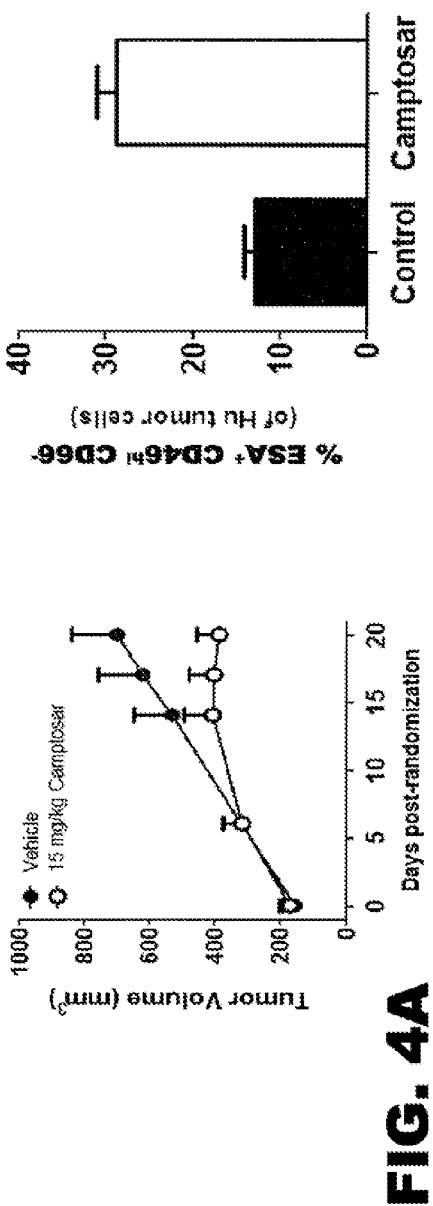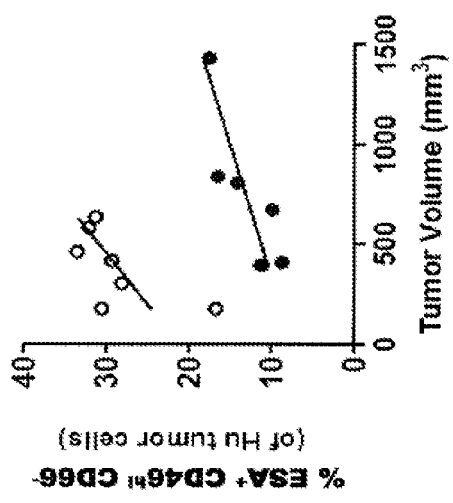
FIG. 4A
FIG. 4B
FIG. 4C
Effects of Irinotecan (i.e. Camptosar) on the Frequency of Tumor Perpetuating Cells in Colorectal Cancer

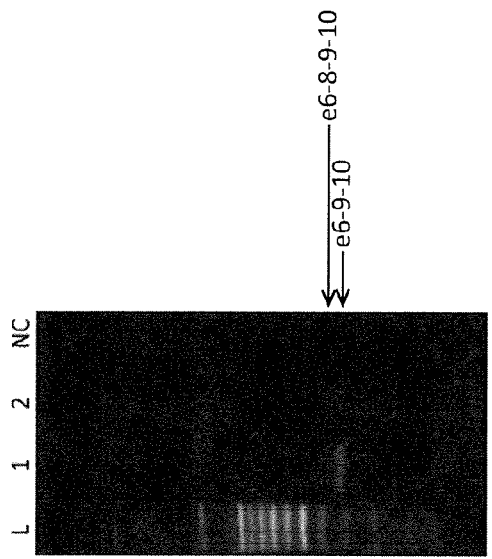

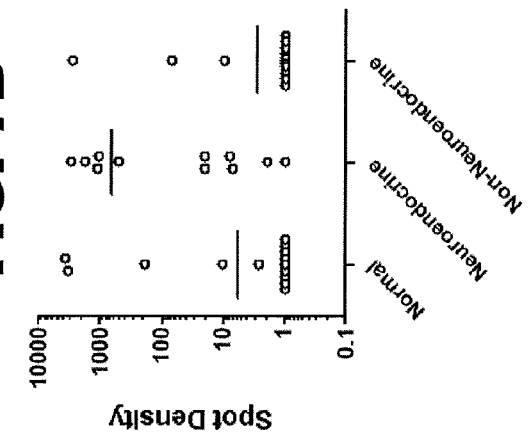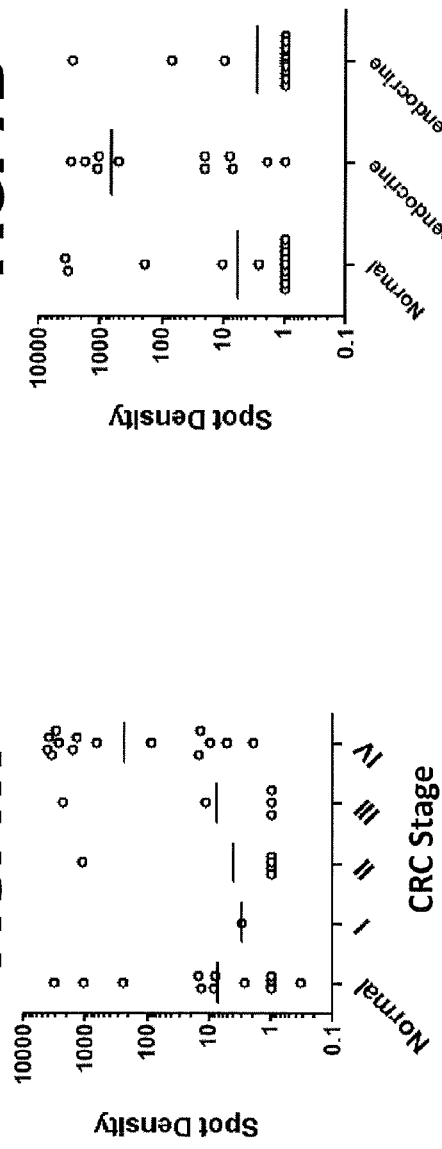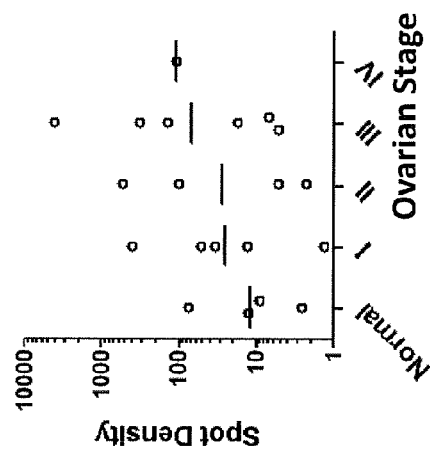
Protein Expression of CD46 in Exemplary Tumor Samples
FIG. 7A
FIG. 7B
FIG. 7C

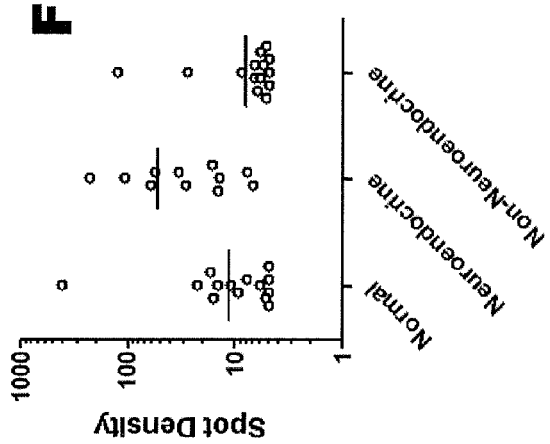
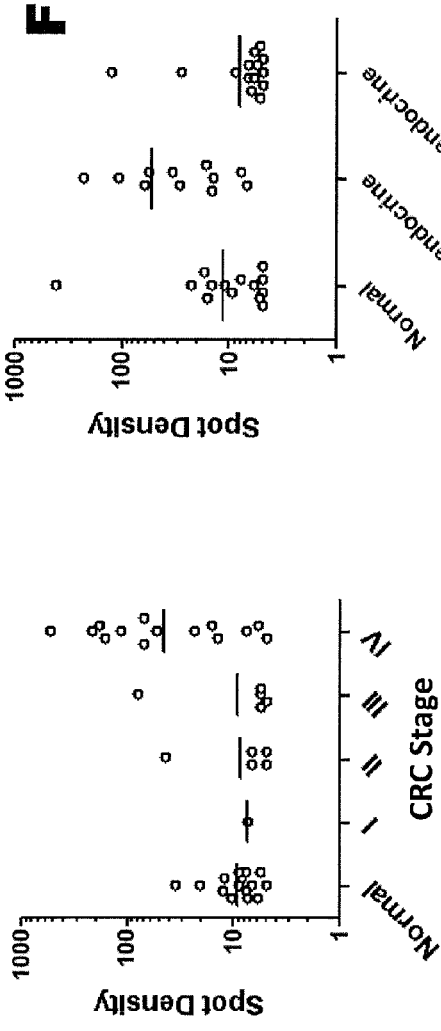
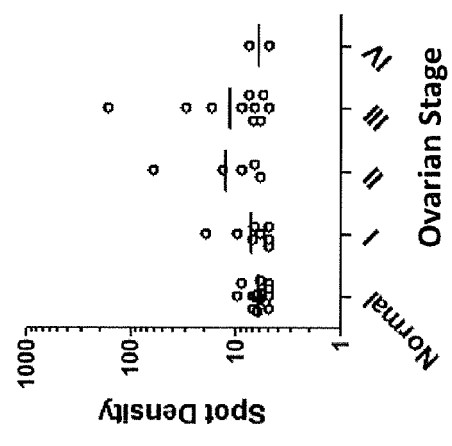
FIG. 8A
FIG. 8B
FIG. 8C

Internalization of Anti-CD46 Antibodies

Anti-CD46 Antibody-Mediated Delivery of Saporin to Cells

SC1.N29    Heavy chain - nucleotide sequence (SEQ ID NO: 14)
1      GAGGTTCAGCTGCAGCAGTCTGGGGCAGAGCTTGTGAAGCCAGGGGCCTCAGTCAAGTTG
61     TCCTGCACAGCTTCTGGCTTCAACATTAAAGACACCTATATGCACTGGGTGAAGCAGAGG
121    CCTGAACAGGGCCTGGAGTGGATTGGAAGGATTGATCCTGCGAATGGTAATATTAAATAT
181    GACCCGAAGTTCCAGGGCAAGGCCACTATAACATCAGACACATCCTCCAACACAGCCTAC
241    CTGCAGCTCAGCAGCCTGACATCTGAGGACACTGCCGTCTATTACTGTGCTCACCCCTCC
301    TATGATTACGACAGGAACTATGCTATGGACTACTGGGGTCAAGGAACCTCAGTCACCGTC
361    TCCTCA SC1.N29    Heavy chain - protein sequence (SEQ ID NO: 15)
1      EVQLQQSGAELVKPGASVKLSCTASGFNIKDTYMHWVKQRPEQGLEWIGR
51     IDPANGNIKYDPKFQGKATITSDTSSNTAYLQLSSLTSEDTAVYYCAHPS
101    YDYDRNYAMDYWGQGTSVTVSS

FIG. 10A

SC1.N29    Light chain - nucleotide sequence (SEQ ID NO: 16)
1      GACATCGTGCTGACTCAGTTTCCAGCCATCCTGTCTGTGAGTCCAGGAGAAAGAGTCAGT
61     TTCTCCTGCAGGGCCAGTCAGAGCATTGGCACAAGCTTACACTGGTATCAGCAAAGAACA
121    AATGGTTCTCCAAGGCTTCTCATGAAGTATGCCTTCTGAGTCTATCTCTGGGATCCCTTCC
181    AGGTTTAGTGGCAGTGGATCAGGGACAGATTTTACTCTTAGCATCAACAGTGTGGAGTCT
241    GAAGATATTGCAGATTATTACTGTCAACAAAGTTATAGCTGGCCGCTCACGTTCGGTGCT
301    GGGACCAAGCTGGAGCTGAAACGGGCT SC1.N29    Light chain - protein sequence (SEQ ID NO: 17)
1      DIVLTQFPAILSVSPGERVSFSCRASQSIGTSLHWYQQRTNGSPRLLMKY
51     ASESISGIPSRFSGSGSGTDFTLSINSVESEDIADYYCQQSYSWPLTFGA
101    GTKLELKR

---

SC1.N35    Heavy chain - nucleotide sequence (SEQ ID NO: 18)
1      GAAGTGCAGCTGGTGGAGTCTGGGGGAGGCTTAGTGAAGCCTGGAGGGTCCCTGAAACTC
61     TCCTGTGCAGCCTCTGGATTCACTTTCAGTGACTATTACATGTATTGGGTTCGCCAGACT
121    CCGGAAAAGAGGCTGGAGTGGGTCGCAACCATTAGTGATGGTGGTACTTACATTTACTAT
181    CCAGACAGTGTGAAGGGGCGATTCACCATCTCCAGAGACAATGCCAAGAACAACCTGTAC
241    CTGCAAATGAGCAGTCTGAAGTCTGAGGACACAGCCATGTATTACTGTGTTAGAGATATA
301    GACTACGATACTAGCTATCCCTGGTTTGCTTACTGGGGCCAAGGGACTCTGGTCACTGTC
361    TCTGCAGCCAAAACAACAGCCCCATCG SC1.N35    Heavy chain - protein sequence (SEQ ID NO: 19)
1      EVQLVESGGGLVKPGGSLKLSCAASGFTFSDYYMYWVRQTPEKRLEWVAT
51     ISDGGTYIYYPDSVKGRFTISRDNAKNNLYLQMSSLKSEDTAMYYCVRDI
101    DYDTSYPWFAYWGQGTLVTVSAAKTTAPSV

FIG. 10B

SC1.N35    Light chain - nucleotide sequence (SEQ ID NO: 20)
1      GATATCCAGATGACACAGACTACATCCTCCCTGTCTGCCTCTCTGGGAGACAGAGTCACC
61     ATCAGTTGCAGTGCAAGTCAGGGCATTAGCAATTATTTAAACTGGTATCAGCAGAAACCA
121    GATGGAACTGTTAAACTCCTGATCTATTACACATCAAGTTTACACTCAGGAGTCCCATCA
181    AGGTTCAGTGGCAGTGGGTCTGGGACAGATTATTCTCTCACCATCAACAACCTGGAACCT
241    GAAGATATTGCCACTTACTATTGTCAGCAGTATAGTAAGCTTCCGTGGACGTTCGGTGGA
301    GGCACCAAGCTGGAAATCAAACGGGCTGATGCTGCACCAACTGT SC1.N35    Light chain - protein sequence (SEQ ID NO: 21)
1      RCDIQMTQTTSSLSASLGDRVTISCSASQGISNYLNWYQQKPDGTVKLLI
51     YYTSSLHSGVPSRFSGSGSGTDYSLTINNLEPEDIATYYCQQYSKLPWTF
101    GGGTKLEIKRADAAPT SC1.N50      Heavy chain - nucleotide sequence (SEQ ID NO: 22)
1     GAGGTCCTGCTGCATCAGTCTGGACCTGAGCTGGTGAAGCCTGGGGCTTCAGTGAAGATT
61    CCCTGCAAGGCTTCTGGATACACATTCACTGACTACAACATGGACTGGGTGAAGCAGAGC
121   CATGGAAAGAGCCTTGAGTGGATTGGAGATATTAATCCTAACAATGGTGGTACTTTCTAC
181   AACCAGAAGTTCAAGGGCAAGGCCACATTGACTGTACACAAGTCCTCCAGCACAGCCTTC
241   ATGGAGCTCCGCAGCCTGACATCTGAGGACACTGCAGTCTATTATTGTACAAGATCAAAG
301   TATGATAACTATCCCTGGTTTGCTTACTGGGGCCAAGGGACTCTGGTCACTGTCTCTGCA SC1.N50      Heavy chain - protein sequence (SEQ ID NO: 23)
1     EVLLHQSGPELVKPGASVKIPCKASGYTFTDYNMDWVKQSHGKSLEWIGD
51    INPNNGGTFYNQKFKGKATLTVHKSSSTAFMELRSLTSEDTAVYYCTRSK
101   YDNYPWFAYWGQGTLVTVSA

FIG. 10C

SC1.N50      Light chain - nucleotide sequence (SEQ ID NO: 24)
1     GATATCCAGATGACACAGATTACATCCTCCCTGTCTGCCTCTCTGGGAGACAGAGTCACC
61    ATCAGTTGCAGTGCAAGTCAGGGCATTAGCAACTATTTAAACTGGTATCAGCAGAAACCA
121   GATGGAACTGTTAAACTCCTGATCTATTACACATCAAGTTTACACTCAGGAGTCCCATCA
181   AGGTTCCGTGGCAGTGGGTCTGGGACAAATTATTCTCTCACCATCAGCAACCTGGAACCT
241   GAAGATATTGCCACTTACTATTGTCAGCAGTATATTAAGCTTCCGTGGACGTTCGGTGGA
301   GGCACCAAGCTGGAAATCAAACGG SC1.N50      Light chain - protein sequence (SEQ ID NO: 25)
1     DIQMTQITSSLSASLGDRVTISCSASQGISNYLNWYQQKPDGTVKLLIYY
51    TSSLHSGVPSRFRGSGSGTNYSLTISNLEPEDIATYYCQQYIKLPWTFGG
101   GTKLEIKR SC1.N53      Heavy chain - nucleotide sequence (SEQ ID NO: 26)
1     CAGGTTCAGCTGCAGCAGTCTGGACCTGAGCTGGTGAAGCCTGGGGCTTCAGTGAAGTTG
61    TCCTGCAAGGCTTCTGGCTACACCTTCACAAACTACGATATAAACTGGGTGAAGCAGAGG
121   CCTGGACAGGGACTTGAGTGGATTGGATGGATTTATCCTAGAGATGGTAGTTTTAAGTAC
181   AATGAGAAGTTCAAGGGCAAGGCCACATTGACTGTAGACACATCCTCCAGCACAGCGTAC
241   ATGGACCTCCACAGCCTGACATCTGAGGACTCTGCGGTCTTTTTCTGTGCAGTTTCGGAG
301   GATGGTTACCCCTGGTTTCCTTACTGGGGCCAAGGGACTCTGGTCACTGTCTCTGCA SC1.N53      Heavy chain - protein sequence (SEQ ID NO: 27)
1     QVQLQQSGPELVKPGASVKLSCKASGYTFTNYDINWVKQRPGQGLEWIGW
51    IYPRDGSFKYNEKFKGKATLTVDTSSSTAYMDLHSLTSEDSAVFFCAVSE
101   DGYPWFPYWGQGTLVTVSA

FIG. 10D

SC1.N53      Light chain - nucleotide sequence (SEQ ID NO: 28)
1     GGTATCCAGATGACACAGACAACATCCTCCCTGTCTGCCTCTCTGGGAGACAGAGTCACC
61    ATCAGTTGCAGTGCAAGTCAGGGCATTAGCAACTATTTAAACTGGTATCAGCAGAAACCA
121   GATGGAACTGTTAAACTCCTGATCTATTACACATCAAGTTTACACTCAGGAGTCCCATCA
181   AGGTTCAGTGGCAGTGGGTCTGGGACAGATTATTCTCTCACCATCAGCAACCTGGAACCT
241   GAAGATATTGCCACTTACTATTGTCAGCAGTATATTAAGCTTCCATTCACGTTCGGCTCG
301   GGGACAAAATTGGAAATAAAACGG SC1.N53      Light chain - protein sequence (SEQ ID NO: 29)
1     GIQMTQTTSSLSASLGDRVTISCSASQGISNYLNWYQQKPDGTVKLLIYY
51    TSSLHSGVPSRFSGSGSGTDYSLTISNLEPEDIATYYCQQYIKLPFTFGS
101   GTKLEIKR SC1.N71        Heavy chain - nucleotide sequence (SEQ ID NO: 30)
1       CAGGTGCAACTGAAGGAGTCAGGACCTGGCCTGGTGGCGCCCTCACAGAACCTGTCCATT
61      ACCTGCACTGTCTCTGGGTTCTCATTAACCAGCTATGATATAAGCTGGATTCGCCAGCCA
121     CCAGGAAAGGGTCTGGAGTGGCTTGGAGTAATATGGACTGATGGAGGCACAAATTATAAT
181     TCAGCTTTCATGTCCAGACTGAGCATCAGCAAGGACAACTCCAAGAGCCAAGTTTTCTTA
241     AAAATGAACAGTCTGCAAACTGATGACACAGCCATATATTACTGTGTAAGGGTCTATGAT
301     GGTTATCCCTGGTTTGCTTACTGGGGCCAAGGGACTCTGGTCACTGTCTCTGCA SC1.N71        Heavy chain - protein sequence (SEQ ID NO: 31)
1       SQVQLKESGPGLVAPSQNLSITCTVSGFSLTSYDISWIRQPPGKGLEWLG
51      VIWTDGGTNYNSAFMSRLSISKDNSKSQVFLKMNSLQTDDTAIYYCVRVY
101     DGYPWFAYWGQGTLVTVSA

FIG. 10E

SC1.N71        Light chain - nucleotide sequence (SEQ ID NO: 32)
1       GATATCCAGATGACACAGACTCCATCCTCCCTGTCTGCCTCTCTGGGAGACAGAGTCACC
61      ATCAGTTGCAGTGCAAGTCAGGGCATTAGCAATTATTTAAACTGGTATCAGCAGAAACCA
121     GATGGAACTGTTAAACTCCTGATCTATTACACATCAAGTTTACACTCAGGAGTCCCATCA
181     AGGTTCAGTGGCAGTGGGTCTGGGACAGATTATTCTCTCACCATCAGCAACCTGGAACCT
241     GAAGATATTGCCACTTACTATTGTCAGCAGTATATTAAGCTTCCGTGGACGTTCGGTGGA
301     GGCACCAAGCTGGCAATCAAACGG SC1.N71        Light chain - protein sequence (SEQ ID NO: 33)
1       DIQMTQTPSSLSASLGDRVTISCSASQGISNYLNWYQQKPDGTVKLLIYY
51      TSSLHSGVPSRFSGSGSGTDYSLTISNLEPEDIATYYCQQYIKLPWTFGG
101     GTKLAIKRADAAPTVSIFPP SC1.N91        Heavy chain - nucleotide sequence  (SEQ ID NO 34)
1       CAGATCCAGTTGGTGCAGTCTGGACCAGAACTGAAGAAGCCTGGAGAGACAGTCAAGATC
61      TCCTGCAAGGCTTCTGGTTATACCTTCACAGACTATTCAATGCACTGGGTGAAGCAGGCT
121     CCAGGAAAGGGTTTAAAGTGGATGGGCTTGATAAACACTGAGACTGGTGAGCCAGCATAT
181     GCAGATGACTTCAGGGGACGGTTAGACTTCTCTTTGGAAACCTCTGCCAGCACTGCCTAC
241     TTGCAGATCAACAACCTCAAGAATGAGGACACGGCTACATATTTCTGTGTTAGGTTTGCC
301     TACTGGGGCCACGGGACTCTGGTCACTGTCTCTGCA SC1.N91        Heavy chain - protein sequence  (SEQ ID NO: 35)
1       QIQLVQSGPELKKPGETVKISCKASGYTFTDYSMHWVKQAPGKGLKWMGL
51      INTETGEPAYADDFRGRLDFSLETSASTAYLQINNLKNEDTATYFCVRFA
101     YWGHGTLVTVSA

FIG. 10F

SC1.N91        Light chain - nucleotide sequence (SEQ ID NO: 36)
1       GACATTGTGATGTCACAGTCTCCATCCTCCCTGGCTGTGTCAGCAGGAGAGAAGGTCACT
61      ATGAGCTGCAAATCCAGTCAGAGTCTGCTCAACAGTAGAACCCGAAAGAACTACTTGGCT
121     TGGTACCAACAGAAACCAGGGCAGTCTCCTAAACTGCTGATCTACTGGGCATCTACTAGG
181     GAATCTGGGGTCCCTGATCGCTTCACAGGCAGTGGATCTGGGACAGATTTCACTCTCACC
241     ATCAGCAGTGTGCAGGCTGAAGACCTGGCAGTTTATTACTGCAAGCAATCTTATAATCTG
301     TGGACGTTCGGTGGAGGCACCAAGCTGGAAATCAAACGG SC1.N91        Light chain - protein sequence (SEQ ID NO: 37)
1       DIVMSQSPSSLAVSAGEKVTMSCKSSQSLLNSRTRKNYLAWYQQKPGQSP
51      KLLIYWASTRESGVPDRFTGSGSGTDFTLTISSVQAEDLAVYYCKQSYNL
101     WTFGGGTKLEIKR SC1.N106     Heavy chain - nucleotide sequence (SEQ ID NO: 38)
1     CAGATCCAGTTGGTGCAGTCTGGACCTGAGCTGAAGAAGCCTGGAGAGACAGTCAAGATC
61    TCCTGCAAGGCTTCTGGTTATGCCTTCACAGACTTTTCAATGCACTGGGTGAAACAGGCT
121   CCAGGAAAGGGTTTAAGGTGGATGGGCTGGATAAACACTGAGACTGGTGAGCCAACATAT
181   GCAGATGACTTCAAGGGACGGTTTGCCTTCTCTTTGGAAACCTCTGCCAGCACTGCCTAT
241   TTGCAGATCAAGAACCTCAAAAATGAGGACACGGCAACATATTTCTGTGTTAGGTTTGCT
301   TACTGGGGCCAAGGGACTCTGGTCACGGTCTCTGCA SC1.N106     Heavy chain - protein sequence (SEQ ID NO: 39)
1     QIQLVQSGPELKKPGETVKISCKASGYAFTDFSMHWVKQAPGKGLRWMGW
51    INTETGEPTYADDFKGRFAFSLETSASTAYLQIKNLKNEDTATYFCVRFA
101   YWGQGTLVTVSA

FIG. 10G

SC1.N106     Light chain - nucleotide sequence (SEQ ID NO: 40)
1     GACATTGTGATGTCACAGTCTCCATCCTCCCTGGCTGTGTCAGCAGGAGAGAAGGTCACT
61    ATGAGCTGCAAATCCAGTCAGAGTCTGCTCAACAGTAGAACCCGAAAGAACTACTTGGCT
121   TGGTACCAGCAGAAACCAGGGCAGTCTCCTAAACTGCTGATCTACTGGGCATCCACTAGG
181   GAATCGGGGTCCCTGATCGCTTCACAGGCAGTGGATCTGGGACAGATTTCACTCTCACC
241   ATCAGCAGTGTGCAGGCTGAAGACCTGGCAGTTTATTACTGCAAGCAATCTTATAATCTT
301   TGGACGTTCGGTGGAGGCACCAAGCTGGAAATCAGA SC1.N106     Light chain - protein sequence (SEQ ID NO: 41)
1     DIVMSQSPSSLAVSAGEKVTMSCKSSQSLLNSRTRKNYLAWYQQKPGQSP
51    KLLIYWASTRESGVPDRFTGSGSGTDFTLTISSVQAEDLAVYYCKQSYNL
101   WTFGGGTKLEIR SC1.N122.1   Heavy chain - nucleotide sequence (SEQ ID NO: 42)
1     CAGGTCCAACTGCAGCAGCCTGGGGCTGAGCTGGTGAGGCCTGGGGCTTCAGTGAAGCTG
61    TCCTGCAAGGCTTCTGGCTACACCTTCACCGCCTTCTGGATAAACTGGGTGAAACAGAGG
121   CCTGGACAAGGCCTTGAGTGGATCGGAAATATTTATCCTTCTGATAGTTATACTAACTAC
181   AATCAAAACTTCAAGGACAAGGCCACATTGACTGTAGACAAATCCTCCAGCACAGCCTAC
241   ATGCAGCTCAGCAGCCCGACATCTGAGGACTCTGCGGTCTATTACTGTGCAAGATCCGAT
301   TACTACGGTAGTAGCTACTATGCTCTGGACTACTGGGGTCAAGGAACCTCAGTCACCGTC
361   TCCTCAGCC SC1.N122.1   Heavy chain - protein sequence (SEQ ID NO: 43)
1     QVQLQQPGAELVRPGASVKLSCKASGYTFTAFWINWVKQRPGQGLEWIGN
51    IYPSDSYTNYNQNFKDKATLTVDKSSSTAYMQLSSPTSEDSAVYYCARSD
101   YYGSSYYALDYWGQGTSVTVSS

FIG. 10H

SC1.N122.1   Light chain - nucleotide sequence (SEQ ID NO: 44)
1     GACATTGTGGTGACCCAATCTCCAGCCTCTTTGGCTGTGTCTCTAGGGCAGAGGGCCACC
61    ATCTCCTGCAGAGCCAGCGAAAGTGTTGATAATTATGGCATTAGTTTTATGAACTGGTTC
121   CAACAGAAACCAGGACAGCCACCCAAACTCCTCATCTATGCTGCATCCAACCAAGGATCC
181   GGGGTCCCTGCCAGGTTTAGTGGCAGTGGGTCTGGGTCAGACTTCAGCCTCAACATCCAT
241   CCTATGGAGGAGGATGATCCTGCAATGTATTTCTGTCAGCAAAGTAAGGAGGTTCCATTC
301   ACGTTCGGCTCGGGGACAAAGTTGGAAATAAAACGG SC1.N122.1   Light chain - protein sequence (SEQ ID NO: 45)
1     DIVVTQSPASLAVSLGQRATISCRASESVDNYGISFMNWFQQKPGQPPKL
51    LIYAASNQGSGVPARFSGSGSGSDFSLNIHPMEEDDPAMYFCQQSKEVPF
101   TFGSGTKLEIKRADAAPTVSIFPT SC1.N149      Heavy chain - nucleotide sequence (SEQ ID NO: 46)
1       GAGGTCCTGCTGCAACAGTCTGGACCTGAACTGGTGAAGCCTGGGGCTTCAGTGAAGATT
61      CCCTGCAAGGCTTCTGGATACACATTCACTGACTACAACATGGACTGGGTGAAGCAGAGC
121     CATGGAAAGAGCCTTGAGTGGATTGGAGATATTAATCCTAACAATGGTGATACTTTCTAC
181     AACCAGAAGTTCAAGGGCAAGGCCACATTGACTGTACACAAGTCCTCCAGCACAGCCTTC
241     ATGGAGCTCCGCAGCCTGACATCTGAGGACACTGCAGTCTATTACTGTACAAGATCAAAG
301     TATGATAACTATCCCTGGTTTGCTTACTGGGGCCAAGGGACTCTGGTCACTGTCTCTGCA SC1.N149      Heavy chain - protein sequence (SEQ ID NO: 47)
1       EVLLQQSGPELVKPGASVKIPCKASGYTFTDYNMDWVKQSHGKSLEWIGD
51      INPNNGDTFYNQKFKGKATLTVHKSSSTAFMELRSLTSEDTAVYYCTRSK
101     YDNYPWFAYWGQGTLVTVSAAKTTPPSVYPLAPGCGDTTGSSVT

FIG. 10I

SC1.N149      Light chain - nucleotide sequence (SEQ ID NO: 48)
1       GATATCCAGATGACACAGACTACATCCTCCCTGTCTGCCTCTCTGGGAGACAGAGTCACC
61      ATCAGTTGCAGTGCAAGTCAGGACATTAACAATTATTTAAACTGGTATCAGCAGAAACCA
121     GATGGAACTGTTAAACTCCTGATCTATTACACATCAAGTTTACACTCAGGAGTCCCATCA
181     AGGTTCAGTGGCAGTGGGTCTGGGACAGATTATTCTCTCACCATCAGCAACCTGGAACCT
241     GAAGATATTGCCACTTACTATTGTCAGCAGTATATTAAGCTTCCGTGGACGTTCGGTGGA
301     GGCACCAAGCTGGAAATCAAACGG SC1.N149      Light chain - protein sequence (SEQ ID NO: 49)
1       DIQMTQTTSSLSASLGDRVTISCSASQDINNYLNWYQQKPDGTVKLLIYY
51      TSSLHSGVPSRFSGSGSGTDYSLTISNLEPEDIATYYCQQYIKLPWTFGG
101     GTKLEIKR

---

SC1.N7        Heavy chain - nucleotide sequence (SEQ ID NO: 50)
1       GAGGTCCAGCTGCAACAGTTTGGAGCTGAGCTGGTGAAGCCTGGGGCTTCAGTGAAGATA
61      TCTTGCAAGGCTTCTGGCTACACATTCACTGACTACAACATGGACTGGGTGAAACAGAGC
121     CCTGGAAAGAGCCTTGAGTGGATTGGAGATATTCATCCTAATTATGATACTTCTACCTAC
181     AACCAGAAGTTCAAGGGAAAGGCCACATTGACTGTAGACAAGTCCTCCAGCACAGCCTAC
241     ATGGAACTCCGCAGCCTGACATCTGAGGACACTGCAGTCTATTACTGTGCAAGAGAGGTG
301     CGACGGGGTTACTTCTTTGACTTCTGGGGCCAAGGCACCACTCTCACAGTCTCCTCA SC1.N7        Heavy chain - protein sequence (SEQ ID NO: 51)
1       EVQLQQFGAELVKPGASVKISCKASGYTFTDYNMDWVKQSPGKSLEWIGD
51      IHPNYDTSTYNQKFKGKATLTVDKSSSTAYMELRSLTSEDTAVYYCAREV
101     RRGYFFDFWGQGTTLTVSS

FIG. 10J

SC1.N7        Light chain - nucleotide sequence (SEQ ID NO: 52)
1       GATGTGTTGATGACCCAGTCTCCACTCTCCCTGCCTGTCAGTCTTGGAGATCAAGCCTCC
61      ATCTCTTGCAGATCTAGTCAGAGCATTGTACATAGTAATGGAAACACCTATTTAGAATGG
121     TACCTGCAGAAACCAGGCCAGTCTCCAAAGCTCCTGATCTACAAAGTTTCCAACCGATTT
181     TCTGGGGTCCCAGACAGGTTCAGTGGCAGTGGATCAGGGACAGATTTCACACTCAAGATC
241     AGCAGAGTGGAGGCTGAGGATCTGGGAGTTTATTTCTGCTTTCAAGGTTCACATGTTCCG
301     CTCACGTTCGGTGCTGGGACCAAGCTTGAGCTGAAACGG SC1.N7        Light chain - protein sequence (SEQ ID NO: 53)
1       DVLMTQSPLSLPVSLGDQASISCRSSQSIVHSNGNTYLEWYLQKPGQSPK
51      LLIYKVSNRFSGVPDRFSGSGSGTDFTLKISRVEAEDLGVYFCFQGSHVP
101     LTFGAGTKLELKR SC1.N54      Heavy chain - nucleotide sequence (SEQ ID NO: 54)
1      CAGGTCCAACTGCAGCAGCCTGGGGCTGAACTGGTGAAGCCTGGGGCTTCAGTGAAACTG
61     TCCTGCCAGACTTCTGGCTACACCTTCACCAGCTACTGGATGCACTGGGTAAAGCAGAGG
121    CCTGGACAAGGCCTTGAGTGGATTGGAGAGATTAATCCCAGCAACGGTCGTACTAACTAC
181    AATGAGAAGTTCAAGACCAAGGCCACACTGACTGTAGACAAATCCTCCACCACAGCCTAC
241    ATTCAACTCAACAGCCTGACATCTGAAGACTCTGCGGTCTATTACTGTGCAAGATTGCGG
301    GATTACGGAGGGTGGGGCCAAGGGACTCTGGTCACTGTCTCTGCA SC1.N54      Heavy chain - protein sequence (SEQ ID NO: 55)
1      QVQLQQPGAELVKPGASVKLSCQTSGYTFTSYWMHWVKQRPGQGLEWIGE
51     INPSNGRTNYNEKFKTKATLTVDKSSTTAYIQLNSLTSEDSAVYYCARLR
101    DYGGWGQGTLVTVSA

FIG. 10K

SC1.N54      Light chain - nucleotide sequence (SEQ ID NO: 56)
1      AACATTGTTATGACCCAATCTCCCAAATCCGTGTCCATGTCAGTAGGAGAGAGGGTCACC
61     TTGAGCTGCAAGGCCAGTGAGAATGTGAATACTTTTGTATCCTGGTTTCAACAGAAACCA
121    GATCAGTCTCCTAAACTGCTGATTTACGGGGCATCCAACCGGTACCCTGGGGTCCCCGAT
181    CGCTTCACAGGCAGTGGATCTGCAACAGAATTCACTCTGACCATCAGCAGTGTTCAGGCT
241    GAAGACCTTGCAGATTATCACTGTGGACAGAGTTACAGTTATCCGTACACGTTCGGAGGG
301    GGGACCAAGCTGGAAATAAAACGG SC1.N54      Light chain - protein sequence (SEQ ID NO: 57)
1      NIVMTQSPKSVSMSVGERVTLSCKASENVNTFVSWFQQKPDQSPKLLIYG
51     ASNRYPGVPDRFTGSGSATEFTLTISSVQAEDLADYHCGQSYSYPYTFGG
101    GTKLEIKR SC1.N56      Heavy chain - nucleotide sequence (SEQ ID NO: 58)
1      CAGATCCAGCTGCAGCAGTCTGGACCTGAGCTGGTGAAGCCTGGGGCTTCAGTGAAGATA
61     TCCTGCAAGGCTTCTGGCTACACCTTCACTGACTACTATATAAACTGGGTGAAGCAGAGG
121    CCTGGACAGGGACTTGAGTGGATTGGATGGATTTATCCTGGAAGCGGTAATACTAGGTAC
181    AATGAGAAGTTCAAGGGCAAGGCCACATTGACTGTAGACACATCCTCCAGCACAGCCTAC
241    ATGCAGCTCAGCAGCCTGACCTCTGAGGACTCTGCGGTCTATTTCTGTACAAGATATTAC
301    TACGCTGGTCGGTACGACTGGTACTTCGATGTCTGGGGCGCTAGGACCACGGTCACCGTC
361    TCCTCA SC1.N56      Heavy chain - protein sequence (SEQ ID NO: 59)
1      QIQLQQSGPELVKPGASVKISCKASGYTFTDYYINWVKQRPGQGLEWIGW
51     IYPGSGNTRYNEKFKGKATLTVDTSSSTAYMQLSSLTSEDSAVYFCTRYY
101    YAGRYDWYFDVWGARTTVTVSS

FIG. 10L

SC1.N56      Light chain - nucleotide sequence (SEQ ID NO: 60)
1      GGCATCAAGATGACCCAGTCTCCATCTTCCATGTATGCATCTCTCGGAGAGAGAGTCACT
61     ATCACTTGCAAGGCGAGTCAGGACGTTAATAGCTATTTAAGCTGGTTCCAGCAGAAACCA
121    GGGAAATCTCCTAAGACCCTGATCTATCGTGCAAACAGATTGGTAGATGGGGTCCCATCA
181    AGGTTCAGTGGCAGTGGATCTGGGCAAGATTATTCTCTCACCATCAGCAGCCTGGAGTAT
241    GAAGATATGGGAATTTATTATTGTCTACAGTATGATGAGTTTCCGTACACGTTCGGAGGG
301    GGGACCAAGCTGGAAATAAAACGG SC1.N56      Light chain - protein sequence (SEQ ID NO: 61)
1      GIKMTQSPSSMYASLGERVTITCKASQDVNSYLSWFQQKPGKSPKTLIYR
51     ANRLVDGVPSRFSGSGSGQDYSLTISSLEYEDMGIYYCLQYDEFPYTFGG
101    GTKLEIKRA SC1.N60      Heavy chain - nucleotide sequence (SEQ ID NO: 62)
1      GAGATCCAGCTGCAGCAGACTGGACCTGAGCTGGTGAAGCCTGGGGCTTCAGTGAAGATA
61     TCCTGCAAGGCTTCTGGTTATTCATTCACTGACTCCATCATGCTCTGGGTGAAGCAGAGC
121    CATGGAAAGAGCCTTGAATGGATTGGAAATATTAATCCTTACTATGGTAGTACTACCTAC
181    AATCTGAAGTTCAAGGGCAAGGCCACATTGACTGTAGACAAATCTTCCAGCACAGCCTAC
241    ATGCAGCTCAACAGTCTGACATCTGAGGACTCTGCAGTCTATTACTGTGCAAGAGGACTA
301    CGGGGTTACGGAGGATACTTTGACTACTGGGGCCAAGGCACCACTCTCACAGTCTCCTCA SC1.N60      Heavy chain - protein sequence (SEQ ID NO: 63)
1      EIQLQQTGPELVKPGASVKISCKASGYSFTDSIMLWVKQSHGKSLEWIGN
51     INPYYGSTTYNLKFKGKATLTVDKSSSTAYMQLNSLTSEDSAVYYCARGL
101    RGYGGYFDYWGQGTTLTVSS

FIG. 10M

SC1.N60      Light chain - nucleotide sequence (SEQ ID NO: 64)
1      GTGATGACCCAGTCTCCACTCTCTCTGCCTGTCAATATTGGAGATCAAGCCTCTATCTCT
61     TGCAAGTCTACTAAGAGTCTTCTGAATAGTGATGGATTCACTTATTTGGACTGGTACCTG
121    CAGAAGCCAGGCCAGTCTCCACAGCTCCTAATATATTTGGTTTCTAATCGATTTTCTGGA
181    GTTCCAGACAGGTTCAGTGGCAGTGGGTCAGGAACAGATTTCACACTCAAGATCAGCAGA
241    GTGGAGGCTGAGGATTTGGGAGTTTATTATTGCTTCCAGAGTAACTCTCTTCCATTCACG
301    TTCGGCTCGGGGACAAAGTTGGAAATAAAACGG SC1.N60      Light chain - protein sequence (SEQ ID NO: 65)
1      VMTQSPLSLPVNIGDQASISCKSTKSLLNSDGFTYLDWYLQKPGQSPQLL
51     IYLVSNRFSGVPDRFSGSGSGTDFTLKISRVEAEDLGVYYCFQSNSLPFT
101    FGSGTKLEIKR SC1.N66      Heavy chain - nucleotide sequence (SEQ ID NO: 66)
1      GAGGTCCAGCTGCAACAGTCTGGACCTGTACTGGTGAAGCCTGGGGCTTCAGTGAGGATG
61     TCCTGTAAGGCTTCTGGATACACATTCACTGACTACTATATGAACTGGGTGAAGCAGAGC
121    CATGGAAAGAGCCTTGAGTGGATTGGAGTTTTTAATCCTTACAACGGTGGCACTAACTAC
181    AACCAGAAGTTCAAGGGCAAGGCCACATTGACTGTTGACAAGTCCTCCAGTACAGCCTAC
241    ATGGAGCTCAACGGCCTGACATCTGAGGACTCTGCAGTCTATTACTGTGCCGATGGTTAC
301    TACAGTTACTATGCTATGGACTACTGGGGTCAAGGAACCTCACTCACCGTCTCCTCA SC1.N66      Heavy chain - protein sequence (SEQ ID NO: 67)
1      EVQLQQSGPVLVKPGASVRMSCKASGYTFTDYYMNWVKQSHGKSLEWIGV
51     FNPYNGGTNYNQKFKGKATLTVDKSSSTAYMELNGLTSEDSAVYYCADGY
101    YSYYAMDYWGQGTSLTVSS

FIG. 10N

SC1.N66      Light chain - nucleotide sequence (SEQ ID NO: 68)
1      GACATCAAGATGACCCAGTCTCCATCTTCCATGTATGCATCTCTAGGAGAGAGAGTCACT
61     ATCACTTGCAAGGCGAGTCAGGACATTAATAGCTATTTAAGCTGGTTCCACCAGAAACCA
121    GGGAAATCTCCTAAGACCCTGATCTATCGTGCAAACAGATTGGTAGATGGGGTCCCATCA
181    AGGTTCAGTGGCAGTGGATCTGGGCAAGATTATTCTCTCACCATCAGCAGCCTGGAGTTT
241    GAAGATATGGGAATTTATTATTGTCTACAGTATGATGACTTTCCGTACACGTTCGGAGGG
301    GGGACCAAGCTGGAAATAAAACGG SC1.N66      Light chain - protein sequence (SEQ ID NO: 69)
1      DIKMTQSPSSMYASLGERVTITCKASQDINSYLSWFHQKPGKSPKTLIYR
51     ANRLVDGVPSRFSGSGSGQDYSLTISSLEFEDMGIYYCLQYDDFPYTFGG
101    GTKLEIKR SC1.N77        Heavy chain - nucleotide sequence (SEQ ID NO: 70)
1       CAGATCCAGCTGCAGCAGTCTGGACCTGAACTGGTGAAGCCTGGGGCTTCAGTGAAGATA
61      TCCTGCAAGGCTTCTGGCTACACCTTCACTGACTACTATATAAACTGGGTGAAGCAGAAG
121     CCTGGACAGGGACTTGAGTGGATTGGATGGATTTATCCTGGAAGCGGTAATACTAAGTAC
181     AATGAGAAGTTCAAGGGCAAGGCCACATTGACTGTAGACACATCCTCCAGCACAGCCTAC
241     ATGCAGCTCAGCAGCCTGACATCTGAAGACACTGCTGTCTATTTCTGTGCAAGACTGGGA
301     TATTTCTACGGTAGTAGTTCCTGGTACTTCGATGTCTGGGGCGCAGGGACCACGGTCACC
361     GTCTCCTCA SC1.N77        Heavy chain - protein sequence (SEQ ID NO: 71)
1       QIQLQQSGPELVKPGASVKISCKASGYTFTDYYINWVKQKPGQGLEWIGW
51      IYPGSGNTKYNEKFKGKATLTVDTSSSTAYMQLSSLTSEDTAVYFCARLG
101     YFYGSSSWYFDVWGAGTTVTVSS SC1.N77        Light chain - nucleotide sequence (SEQ ID NO: 72)
1       GACATCAAGATGACCCAGTCTCCATCTTCCATGTATGCATCTCTAGGAGAGAGAGTCACT
61      ATCACCTGCAAGGCGAGTCAGGACATTAATAGCTATTCAGGCTGGTTCCAGCAGAAACCA
121     GGAAAATCTCCTAAGACCCTGATCTATCGTACAAACAGATTGGTAGATGGGGTCCCATCA
181     AGGTTCAGTGGCAGTGGATCTGGGCAAGATTATTCTCTCAGCATCAGCAGCCTGGAGTAT
241     GAAGATATGGGAATTTATTATTGTCTACAGTATGATGAGTTTCCGTACACGTTCGGAGGG
301     GGGACCAAGCTGGAAATAAAACGGG SC1.N77        Light chain - protein sequence (SEQ ID NO: 73)
1       DIKMTQSPSSMYASLGERVTITCKASQDINSYSGWFQQKPGKSPKTLIYR
51      TNRLVDGVPSRFSGSGSGQDYSLSISSLEYEDMGIYYCLQYDEFPYTFGG
101     GTKLEIKRADAAPTVSIFPT

SC1.N95        Heavy chain - nucleotide sequence (SEQ ID NO: 74)
1       CAGGTTCAGCTGCAGCAGTCTGGAGCTGAGCTGGCGAGGCCTGGGGCTTCAGTGAAGCTG
61      TCCTGCAAGGCTTCTGACTACACCTTCACAAGCTATGGTATAAGCTGGGTGAAGCAGAGA
121     ACTGGACAGGGCCTTGAGTGGATTGGAGAGATTTTTCCTAGAAGTGGCAATACTTACTAC
181     AATGAGAAGTTCAAGGGCAAGGCCACACTGACTGCAGACAAATCCTCCAGCACAGCCTAC
241     ATGGAGCTCCGCAGCCTGACATCTGAGGACTCTGCGGTCTATTTCTGTGCAAGGGGACTG
301     GGAGGTGCTATGGACTACTGGGGTCAAGGAACCTCAGTCATCGTCTCCTCA SC1.N95        Heavy chain - protein sequence (SEQ ID NO: 75)
1       QVQLQQSGAELARPGASVKLSCKASDYTFTSYGISWVKQRTGQLEWIGE
51      IFPRSGNTYYNEKFKGKATLTADKSSSTAYMELRSLTSEDSAVYFCARGL
101     GGAMDYWGQGTSVIVSS SC1.N95        Light chain - nucleotide sequence (SEQ ID NO: 76)
1       GATATTGTGATGACTCAGGCTGCACCCTCTGTACCTGTCACTCCTGGAGAGTCAGTATCC
61      ATCTCCTGCAGGTCTAGTAAGAGTCTCCTGCATAGTAATGGCAACACTTACTTGTATTGG
121     TTCCTGCAGAGGCCAGGCCAGTCTCCTCAGCTCCTGATATATCGGATGTCCAACCTTGCC
181     TCAGGAGTCCCAGACAGGTTCAGTGGCAGTGGGTCAGGAACAACTTTCACACTGAGAATC
241     AGTGGAGTGGAGGCTGAGGATGTGGGTGTTTATTATTGTATGCAACATCTAGAATATCCG
301     TGCACGTTCGGAGGGGGGACCAAGCTGGAAATAAAACGG SC1.N95        Light chain - protein sequence (SEQ ID NO: 77)
1       DIVMTQAAPSVPVTPGESVSISCRSSKSLLHSNGNTYLYWFLQRPGQSPQ
51      LLIYRMSNLASGVPDRFSGSGSGTTFTLRISGVEAEDVGVYYCMQHLEYP
101     CTFGGGTKLEIKR

FIG. 10P

SC1.N135    Heavy chain - nucleotide sequence (SEQ ID NO: 78)
1     GATGTGCAGCTGGTGGAGTCTGGGGGAGGCTTAGTGCAGCCTGGAGGGTCCCGGAAACTC
61    TCCTGTGCAGCCTCTGGATTCACTTTCAGTAGCTTTGGAATGCACTGGGTTCGTCAGGCT
121   CCAGAGAAGGGGCTGGAGTGGGTCGCATACATTAGTAGTGCCACTAGTGCCATCTACTAT
181   GCAGACACAGTGAAGGGCCGATTCACCATCTCCAGAGACAATCCCACGAACACCCTGTTC
241   CTGCAAATGACCAGTCTAAGGTCTGAGGACACGGCCATGTATTACTGTGCAAGAAAGGGG
301   AACAACTACTTTGACTACTGGGGCCAAGGCACCACTCTCACAGTCTCCTCAC SC1.N135    Heavy chain - protein sequence (SEQ ID NO: 79)
1     DVQLVESGGGLVQPGGSRKLSCAASGFTFSSFGMHWVRQAPEKGLEWVAY
51    ISSATSAIYYADTVKGRFTISRDNPTNTLFLQMTSLRSEDTAMYYCARKG
101   NNYFDYWGQGTTLTVSS

FIG. 10Q

SC1.N135    Light chain - nucleotide sequence (SEQ ID NO: 80)
1     CAAATTGTTCTCACCCAGTCTCCAGCAATCATGTCTGCATCTCCAGGGGAGAAGGTCACC
61    TTATCCTGCAGTGCCACCTCAAGTGTAACTTACATGCACTGGCTCCAGCAGAAGCCAGGA
121   TCCTCCCCCAAACCCTGGATTTATCGCACATCCAACCTGGCTTCTGGAGTCCCTGCTCGC
181   TTCCGTGGCAGTGGGTCTGGGACCTCTTACTCTCTCACAATCAGCAGCATGGAGGCTGAA
241   GATGCTGCCACTTATTACTGCCAGCAGTATCATAGTTACCCACCGACGTTCGGTGGAGGC
301   ACCAAGCTGGAAATCAAA SC1.N135    Light chain - protein sequence (SEQ ID NO: 81)
1     QIVLTQSPAIMSASPGEKVTLSCSATSSVTYMHWLQQKPGSSPKPWIYRT
51    SNLASGVPARFRGSGSGTSYSLTISSMEAEDAATYYCQQYHSYPPTFGGG
101   TKLEIKR SC1.N146    Heavy chain - nucleotide sequence (SEQ ID NO: 82)
1     GAGGTGCAGCTGGTGGAGTCTGGGGGAGGCTTAGTGAAGCCTGGAGGGTCCCTGAAACTC
61    TCCTGTGCAGCCTCTGGATTCACTTTCAGTAGCTTTGGCATGTCTTGGGTTCGCCAGACT
121   CCGGAGAAGAGGCTGGAGTGGGTCGCAGCCATTAATAGTAATGGTGGTAACACATACTAT
181   TCAGACACTGTGAAGGGCCGATTCACCATCTCCAGAGACAATGCCAAGAACACCCTGTAC
241   CTGCAAATGAGCAGTCTGAGGTCTGCGGACACTGCCTTGTATTACTGTGCAAGAGTGGTG
301   CACTTCGATGTCTGGGGCGCAGGGACCACGGTCACCGTCTCCTCA SC1.N146    Heavy chain - protein sequence (SEQ ID NO: 83)
1     EVQLVESGGGLVKPGGSLKLSCAASGFTFSSFGMSWVRQTPEKRLEWVAA
51    INSNGGNTYYSDTVKGRFTISRDNAKNTLYLQMSSLRSADTALYYCARVV
101   HFDVWGAGTTVTVSS

FIG. 10R

SC1.N146    Light chain - nucleotide sequence (SEQ ID NO: 84)
1     GCTATCCAGATGACACAGACTACATCCTCCCTGTCTGCCTCTCTGGGAGACAGAGTCACC
61    ATCAGTTGCAGTGCAAGTCAGGACATTAGCAATTATTTAAACTGGTATCAGCAGAAACCA
121   GATGGAACTGTTAAACTCCTGATCTATTACACATCAAGTTTACACTCAGGAGTCCCATCA
181   CGGTTCAGTGGCAGTGGGTCTGGGACAGATTATTCTCTCACCATCAGCAACGTGGAACCT
241   GAAGATGTTGCCACTTACTATTGTCAGCAATATAGTGAGCTTCCGTACACGTTCGGAGGG
301   GGGACCAAGCTGGAAATAAACCGG SC1.N146    Light chain - protein sequence (SEQ ID NO: 85)
1     AIQMTQTTSSLSASLGDRVTISCSASQDISNYLNWYQQKPDGTVKLLIYY
51    TSSLHSGVPSRFSGSGSGTDYSLTISNVEPEDVATYYCQQYSELPYTFGG
101   GTKLEINR

Genetic Arrangements of Distinct Anti-CD46 Antibodies

| | Clone | Isotype | VH | DH | JH | VK | JK | FIG |
|---|---|---|---|---|---|---|---|---|
| 1 | SC1.N7 | IgG2a/K | IGHV1-18 | IGHD2-14 | JH2 | IGKV1-117 | JK5 | 10J |
| 2 | SC1.N29 | IgG2a/K | IGHV14-3 | DSP2.2 | JH4 | IGKV5-48 | JK5 | 10A |
| 3 | SC1.N35 | IgG2a/K | IGHV5-4 | DSP2.x | JH3 | IGKV10-94 | JK1 | 10B |
| 4 | SC1.N50 | IgG2b/K | IGHV1-18 | DSP2.8 | JH3 | IGKV10-94 | JK1 | 10C |
| 5 | SC1.N53 | IgG1/K | J558.88.194 | DSP2.13inv | JH3 | IGKV10-94 | JK4 | 10D |
| 6 | SC1.N54 | IgG2a/K | J558.33 | DSP2.2 | JH3 | IGKV6-20 | JK2 | 10K |
| 7 | SC1.N56 | IgG2a/K | J558.87.193 | DFL16.1 | JH1 | IGKV14-111 | JK2 | 10L |
| 8 | SC1.N60 | IgG1/K | VHJ558 | DFL16.1 | JH2 | IGKV1-99 | JK4 | 10M |
| 9 | SC1.N66 | IgG2c/K | IGHV1-19 | DSP2.9 | JH4 | IGKV14-111 | JK2 | 10N |
| 10 | SC1.N71 | IgG2a/K | VHQ52.a13.37 | DSP2.9 | JH3 | IGKV10-94 | JK1 | 10E |
| 11 | SC1.N77 | IgG2a/K | IGHV1-11 | DFL16.1 | JH1 | IGKV14-111 | JK2 | 10O |
| 12 | SC1.N91 | IgG2b/K | IGHV9-2-1 | none | JH3 | IGKV8-21 | JK1 | 10F |
| 13 | SC1.N95 | IgG2a/K | VHJ558 | DQ52a.1 | JH4 | IGKV2-137 | JK2 | 10P |
| 14 | SC1.N106 | IgG2b/K | IGHV9-2-1 | none | JH3 | IGKV8-21 | JK1 | 10G |
| 15 | SC1.N122 | IgG2a/K | J558.40 | DFL16.1 | JH4 | IGKV3-2 | JK4 | 10H |
| 16 | SC1.N135 | IgG2b/K | IGHV5-17 | DQ52 | JH2 | IGKV4-61 | JK1 | 10Q |
| 17 | SC1.N146 | IgG1/K | IGHV5-6-2 | DFL16.3 | JH1 | IGKV10-94 | JK2 | 10R |
| 18 | SC1.N149 | IgG2b/K | IGHV1-18 | DSP2.8 | JH3 | IGKV10-94 | JK1 | 10I |

FIG. 11A

Complementarity Determining Regions of Distinct Anti-CD46 Antibodies

| | Clone | CDRH1 (SEQ ID NOS 86-103) | CDRH2 (SEQ ID NOS 104-121) | CDRH3 (SEQ ID NOS 122-139) | CDRL1 (SEQ ID NOS 140-157) | CDRL2 (SEQ ID NOS 158-175) | CDRL3 (SEQ ID NOS 176-193) |
|---|---|---|---|---|---|---|---|
| 1 | SC1.N7 | GYTFTDYN | IHPNYDTS | AREVRRGYFFDF | QSIVHSNGNTY | KVSNRFS | FQGSHVPLT |
| 2 | SC1.N29 | GFNIKDTY | IDPANGNI | AHPSYDYDRNYAMDY | QSIGTS | YASESIS | QQSYSWPLT |
| 3 | SC1.N35 | GFTFSDYY | ISDGGTYI | VRDIDYDTSYPWFAY | QGINNY | YTSSLHS | QQYSKLPWT |
| 4 | SC1.N50 | GYTFTDYN | INPNNGGT | TRSKYDNYPWFAY | QGISNY | YTSSLHS | QQYIKLPWT |
| 5 | SC1.N53 | GYTFTNYD | IYPRDGSF | AVSEVGHPWFPY | QGISNY | YTSSLHS | QQYIKLPFT |
| 6 | SC1.N54 | GYTFTSYW | INPSNGRT | ARLRDYGG | ENVNTF | GASNRYP | GQSYSYPYT |
| 7 | SC1.N56 | GYTFTDYY | IYPGSGNT | TRYYAGRYDWYFDV | QDVNSY | RANRLVD | LQYDEFPYT |
| 8 | SC1.N60 | GYSFTDSI | INPYYGST | ARGLRGYGGYFDY | KSLLNSDGFTY | LVSNRFS | FQSNSLPFT |
| 9 | SC1.N66 | GYTFTDYY | FNPYNGGT | ADGYYSYYAMDY | QDINSY | RANRLVD | LQYDFFPYT |
| 10 | SC1.N71 | GFSLTSYD | IWTDGGT | VRVYDGYPWFAY | QGISNY | YTSSLHS | QQYIKLPWT |
| 11 | SC1.N77 | GYTFTDYY | IYPGSGNT | ARLGYFYGSSSWYFDV | QDINSY | RTNRLVD | LQYDEFPYT |
| 12 | SC1.N91 | GYTFTDYS | INTETGEP | VRFAY | QSLLNSRTRKNY | WASTRES | KQSYNLWT |
| 13 | SC1.N95 | DYTFTSYG | IFPRSGNT | ARGLGGAMDY | KSLLHSNGNTY | RMSNLAS | MQHLEYPCT |
| 14 | SC1.N106 | GYAFTDFS | INTETGEP | VRFAY | QSLLNSRTRKNY | WASTRES | KQSYNLWT |
| 15 | SC1.N122 | GYTFTAFW | IYPSDSYT | ARSDYYGSSYYALDY | ESVDNYGISF | AASNQGS | QQSKEVPFT |
| 16 | SC1.N135 | GFTFSSFG | ISSATSAI | ARKGNNYFDY | SSVTY | RTSNLAS | QQYHSYPPT |
| 17 | SC1.N146 | TFTFSSFG | INSNGGNT | ARVVHFDV | QDISNY | YTSSLHS | QQYSELPYT |
| 18 | SC1.N149 | GYTFTDYN | INPNNGDT | TRSKYDNYPWFAY | QDINNY | YTSSLHS | QQYIKLPWT |

FIG. 11B

Humanized SC1.N71 heavy chain

```
1                                                  50
CAGGTGCAGCTGCAGGAGTCGGGCCCAGGACTGGTGAAGCCTTCGGAGAC
-Q--V--Q--L--Q--E--S--G--P--G--L--V--K--P--S--E--T
51                                                100
CCTGTCCCTCACCTGCACTGTCTCTGGTGGCTCCGTCAGTAGTTACGACA
--L--S--L--T--C--T--V--S--G--G--S--V--S--S--Y--D--
101                                               150
TTAGCTGGATCCGGCAGCCCCCAGGGAAGGGACTGGAGTGGATTGGGGTT
I--S--W--I--R--Q--P--P--G--K--G--L--E--W--I--G--V-
151                                               200
ATCTGGACCGATGGGGGCACCAACTACAACTCCGCCTTCATGAGTCGAGT
-I--W--T--D--G--G--T--N--Y--N--S--A--F--M--S--R--V
201                                               250
CACCATATCAGTAGACACGTCCAAGAACCAGTTCTCCCTGAAGCTGAGCT
--T--I--S--V--D--T--S--K--N--Q--F--S--L--K--L--S--
251                                               300
CTGTGACCGCTGCGGACACGGCCGTGTATTACTGTGCGAGAGTCTATGAT
S--V--T--A--A--D--T--A--V--Y--Y--C--A--R--V--Y--D-
301                                               350
GGTTATCCCTGGTTTGCTTACTGGGGCCAGGGCACCCTGGTCACCGTCTC
-G--Y--P--W--F--A--Y--W--G--Q--G--T--L--V--T--V--S
351
CTCA      (SEQ ID NO: 198)
--S-      (SEQ ID NO: 199)
```

FIG. 13A

Humanized SC1.N71 light chain

```
1                                                  50
GACATCCAGATGACCCAGTCTCCATCCTCCCTGTCTGCATCTGTAGGAGA
-D--I--Q--M--T--Q--S--P--S--S--L--S--A--S--V--G--D
51                                                100
CAGAGTCACCATCACTTGCCGGGCAAGTCAGGGCATTAGCAATTATTTAA
--R--V--T--I--T--C--R--A--S--Q--G--I--S--N--Y--L--
101                                               150
ATTGGTATCAGCAGAAACCAGGGAAAGCCCCTAAGCTCCTGATCTATTAC
N--W--Y--Q--Q--K--P--G--K--A--P--K--L--L--I--Y--Y-
151                                               200
ACATCCAGTTTGCACAGTGGGGTCCCATCAAGGTTCAGTGGCAGTGGATC
-T--S--S--L--H--S--G--V--P--S--R--F--S--G--S--G--S
201                                               250
TGGGACAGATTTCACTCTCACCATCAGCAGTCTGCAACCTGAAGATTTTG
--G--T--D--F--T--L--T--I--S--S--L--Q--P--E--D--F--
251                                               300
CAACTTACTACTGTCAACAGTATATTAAGCTTCCGTGGACGTTCGGTGGA
A--T--Y--Y--C--Q--Q--Y--I--K--L--P--W--T--F--G--G-
301
GGCACCAAGCTGGAAATCAAACGG     (SEQ ID NO: 200)
-G--T--K--L--E--I--K--R-     (SEQ ID NO: 201)
```

```
Humanized SC1.N149 heavy chain 1                                                  50
CAGGTTCAGCTGGTGCAGTCTGGAGCTGAGGTGAAGAAGCCTGGGGCCTC
-Q--V--Q--L--V--Q--S--G--A--E--V--K--K--P--G--A--S
51                                                100
AGTGAAGGTCTCCTGCAAGGCTTCTGGTTACACCTTTACCGACTACAACA
--V--K--V--S--C--K--A--S--G--Y--T--F--T--D--Y--N--
101                                               150
TGGACTGGGTGCGACAGGCCCCTGGACAAGGGCTTGAGTGGATGGGAGAT
M--D--W--V--R--Q--A--P--G--Q--G--L--E--W--M--G--D-
151                                               200
ATTAATCCTAACAATGGTGATACTTTCTACAACCAGAAGTTCAAGGGCAG
-I--N--P--N--N--G--D--T--F--Y--N--Q--K--F--K--G--R
201                                               250
AGTCACCATGACCACAGACACATCCACGAGCACAGCCTACATGGAGCTGA
--V--T--M--T--T--D--T--S--T--S--T--A--Y--M--E--L--
251                                               300
GGAGCCTGAGATCTGACGACACGGCCGTGTATTACTGTGCGAGATCAAAG
R--S--L--R--S--D--D--T--A--V--Y--Y--C--A--R--S--K-
301                                               350
TATGATAACTATCCCTGGTTTGCTTACTGGGGCCAAGGGACTCTGGTCAC
-Y--D--N--Y--P--W--F--A--Y--W--G--Q--G--T--L--V--T
351                                               400
TGTCTCTTCC           (SEQ ID NO: 202)
--V--S--S-           (SEQ ID NO: 203)
```

FIG. 13B

```
Humanized SC1.N149 kappa light chain 1                                                  50
GGACATCCAGATGACCCAGTCTCCATCCTCCCTGTCTGCATCTGTAGGAG
-D--I--Q--M--T--Q--S--P--S--S--L--S--A--S--V--G--
51                                                100
ACAGAGTCACCATCACTTGCCGGGCAAGTCAGGACATTAACAATTATTTA
D--R--V--T--I--T--C--R--A--S--Q--D--I--N--N--Y--L-
101                                               150
AATTGGTATCAGCAGAAACCAGGGAAAGCCCCTAAGCTCCTGATCTATTA
-N--W--Y--Q--Q--K--P--G--K--A--P--K--L--L--I--Y--Y
151                                               200
CACATCCAGTTTGCACAGTGGGGTCCCATCAAGGTTCAGTGGCAGTGGAT
--T--S--S--L--H--S--G--V--P--S--R--F--S--G--S--G--
201                                               250
CTGGGACAGATTTCACTCTCACCATCAGCAGTCTGCAACCTGAAGATTTT
S--G--T--D--F--T--L--T--I--S--S--L--Q--P--E--D--F-
251                                               300
GCAACTTACTACTGTCAACAGTATATTAAGCTTCCGTGGACGTTCGGTGG
-A--T--Y--Y--C--Q--Q--Y--I--K--L--P--W--T--F--G--G
301                                               350
 AGGCACCAAGCTGGAAATCAAACGG    (SEQ ID NO: 204)
--G--T--K--L--E--I--K--R-     (SEQ ID NO: 205)
```

Selected CD46 Modulator Characteristics

| SC1 Clone | Domain | Affinity (nM) | Western Reactivity | Cynomolgus XR | Marmoset XR | Squirrel Monkey XR |
|---|---|---|---|---|---|---|
| N29.8 | exon 9 | 1.0$^F$ | NR/R | ND | ND | ND |
| N35.6 | 4 | 5.0$^F$ | NR | Yes | Yes | No |
| N50.3 | 4 | 1.0$^F$ | NR | Yes | Yes | No |
| N53.5 | 4 | 4.0$^F$ | NR | Yes | Yes | Weak |
| N54.4 | 3/4 | 1.0$^F$ | ND | Yes | Yes | Weak |
| N56.1 | 1/2 | 1.0$^F$ | ND | Yes | No | ND |
| N71.1 | 3/4 | 1.1$^B$ | NR | Yes | Yes | Weak |
| N95.1 | 1 | 8.0$^F$ | ND | Weak | No | No |
| N122.1 | 3/4 | 2.0$^F$ | NR | Yes | Yes | Yes |
| N135.1 | 1/2 | 1.0$^F$ | ND | Yes | No | ND |
| N146.2 | 1 | 1.5$^B$ | NR/R | No | No | No |
| N149.2 | 3/4 | 1.1$^B$ | NR | Yes | Yes | Weak |

FIG. 14

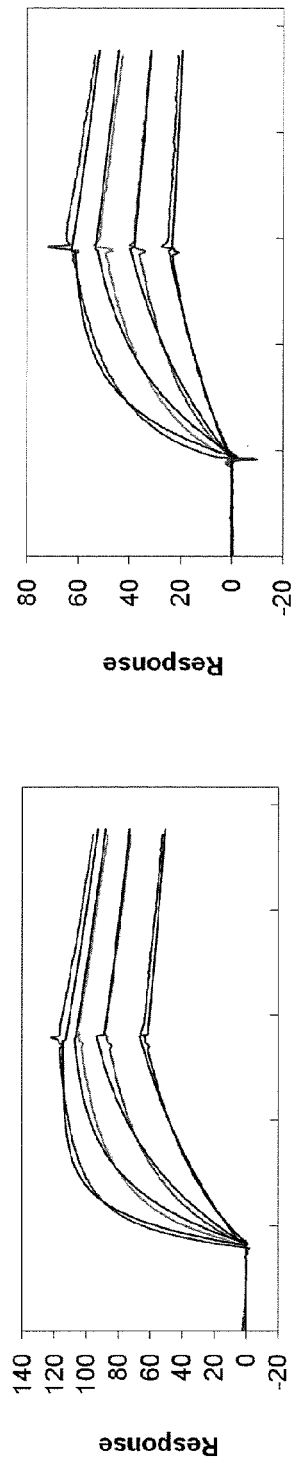
FIG. 15A
FIG. 15B
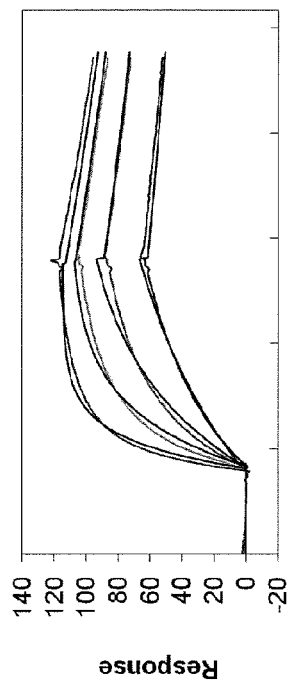
FIG. 15C

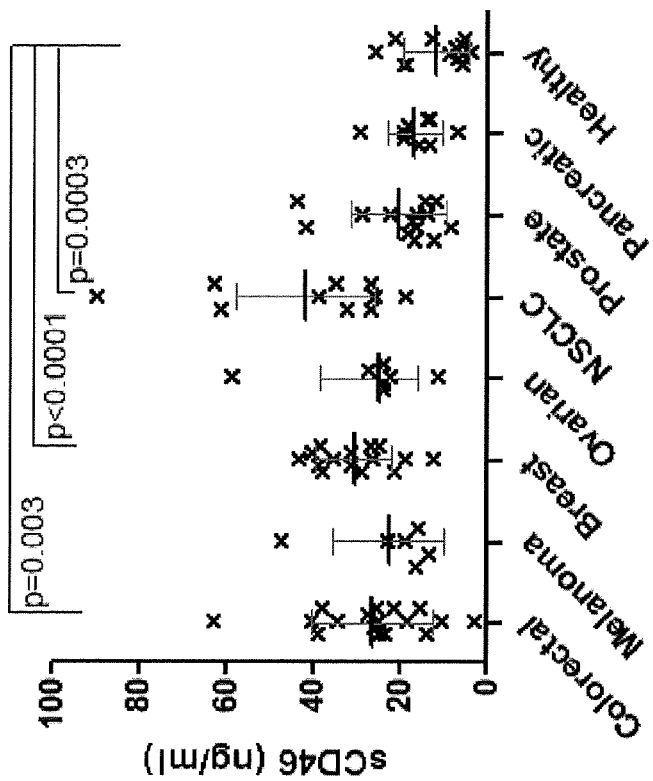
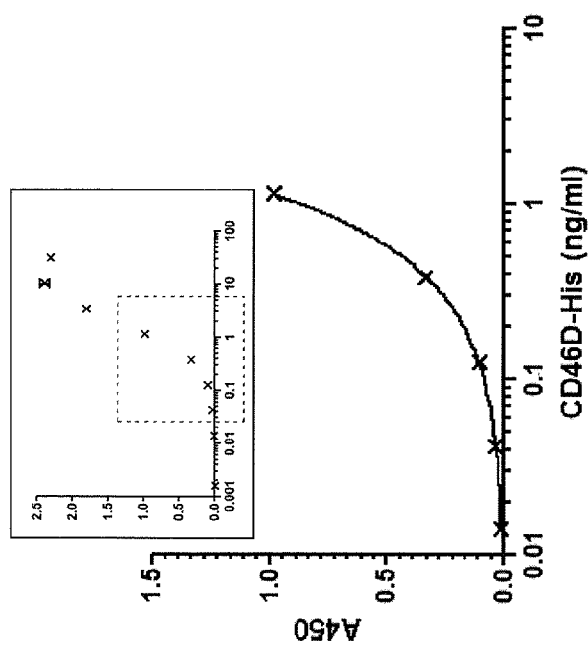
FIG. 16B
FIG. 16A

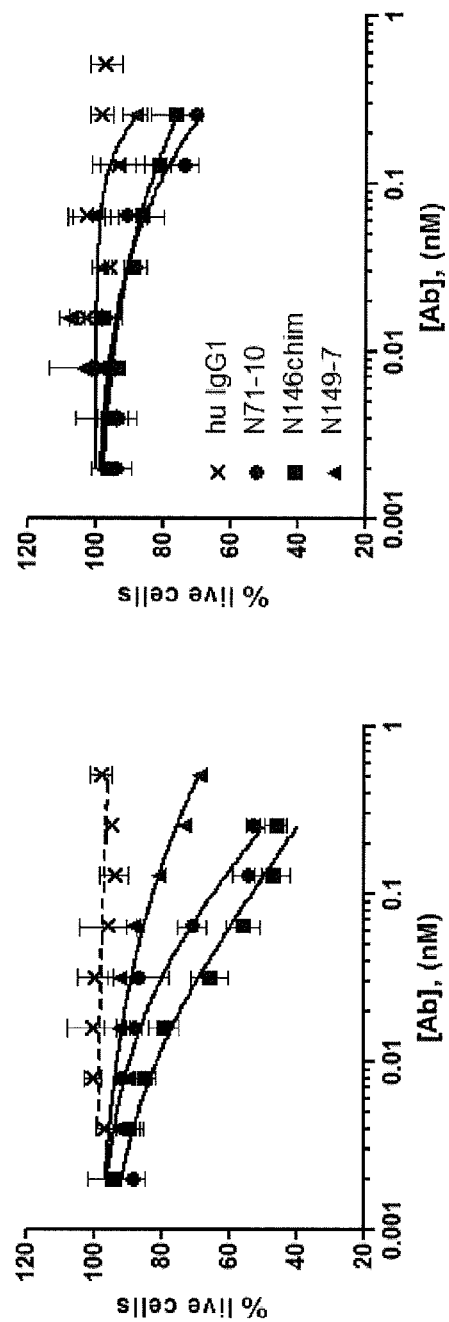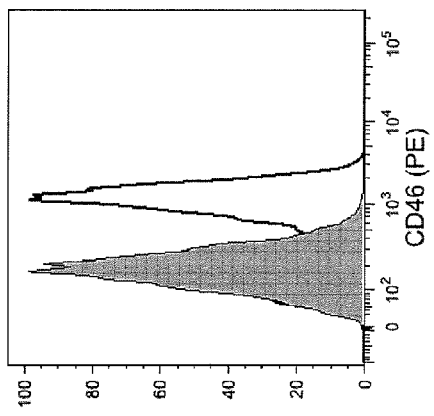
FIG. 18A
FIG. 18B

FIG. 19A

CD46 Modulators Mediate Receptor Dependent Toxin Uptake

- MOPC-bio + SA-SAP
- N149 alone
- N149-bio + SA-SAP

CD46 Modulators Sensitize Tumors to Chemotherapy

MODULATORS AND METHODS OF USE

CROSS REFERENCED APPLICATIONS

This application claims the benefit under 35 U.S.C. 119(e) of U.S. Provisional Application Ser. No. 61/380,181 filed Sep. 3, 2010, which is incorporated herein by reference in its entirety.

FIELD OF THE INVENTION

This application generally relates to compositions and methods of their use in treating or ameliorating hyperproliferative disorders, their expansion, recurrence, relapse or metastasis. In a broad aspect the present invention relates to the use of CD46 modulators, including CD46 antagonists and fusion constructs, for the treatment or prophylaxis of neoplastic disorders. In particularly preferred embodiments the present invention provides for the use of anti-CD46 antibodies for the immunotherapeutic treatment of malignancies comprising a reduction in tumor initiating cell frequency.

BACKGROUND OF THE INVENTION

Stem and progenitor cell differentiation and cell proliferation are normal ongoing processes that act in concert to support tissue growth during organogenesis, and cell replacement and repair of most tissues during the lifetime of all living organisms. Differentiation and proliferation decisions are often controlled by numerous factors and signals that are balanced to maintain cell fate decisions and tissue architecture. Normal tissue architecture is maintained as a result of cells responding to microenvironmental cues that regulate cell division and tissue maturation. Accordingly, cell proliferation and differentiation normally occurs only as necessary for the replacement of damaged or dying cells or for growth. Unfortunately, disruption of cell proliferation and/or differentiation can result from a myriad of factors including, for example, the under- or overabundance of various signaling chemicals, the presence of altered microenvironments, genetic mutations or some combination thereof. When normal cellular proliferation and/or differentiation is disturbed or somehow disrupted it can lead to various diseases or disorders including cancer.

Conventional treatments for cancer include chemotherapy, radiotherapy, surgery, immunotherapy (e.g., biological response modifiers, vaccines or targeted therapeutics) or combinations thereof. Sadly, far too many cancers are non-responsive or minimally responsive to such conventional treatments leaving few options for patients. For example, some patient subpopulations exhibit gene mutations (e.g., KRAS,) that render them non-responsive despite the general effectiveness of certain therapies. Moreover, depending on the type of cancer some available treatments, such as surgery, may not be viable alternatives. Limitations inherent in current standard of care therapeutics are particularly evident when attempting to care for patients who have undergone previous treatments and have subsequently relapsed. In such cases the failed therapeutic regimens and resulting patient deterioration may contribute to refractory tumors often manifest themselves as a more aggressive disease that ultimately proves to be incurable. Although there have been great improvements in the diagnosis and treatment of cancer over the years, overall survival rates for many solid tumors have remained largely unchanged due to the failure of existing therapies to prevent relapse, tumor recurrence and metastases. Thus, it remains a challenge to develop more targeted and potent therapies.

One promising area of research involves the use of targeted therapeutics to go after the tumorigenic "seed" cells that appear to underlie many cancers. To that end most solid tissues are now known to contain adult, tissue-resident stem cell populations that generate differentiated cell types that comprise the majority of that tissue. Tumors arising in these tissues similarly consist of heterogeneous populations of cells that also arise from stem cells, but differ markedly in their overall proliferation and organization. While it is increasingly recognized that the majority of tumor cells have a limited ability to proliferate, a minority population of cancer cells (commonly known as cancer stem cells or CSC) have the exclusive ability to extensively self-renew thereby enabling them with tumor reinitiating capacity. More specifically, the cancer stem cell hypothesis proposes that there is a distinct subset of cells (i.e. CSC) within each tumor (approximately 0.1-10%) that is capable of indefinite self-renewal and of generating tumor cells progressively limited in their replication capacity as a result of their differentiation to tumor progenitor cells, and subsequently to terminally differentiated tumor cells.

In recent years it has become more evident these CSC (also known as tumor perpetuating cells or TPC) might be more resistant to traditional chemotherapeutic agents or radiation and thus persist after standard of care clinical therapies to later fuel the growth of relapsing tumors, secondary tumors and metastases. Moreover, there is growing evidence suggests that pathways that regulate organogenesis and/or the self-renewal of normal tissue-resident stem cells are deregulated or altered in CSC, resulting in the continuous expansion of self-renewing cancer cells and tumor formation. See generally Al-Hajj et al., 2004, PMID: 15378087; and Dalerba et al., 2007, PMID: 17548814; each of which is incorporated herein in its entirety by reference. Thus, the effectiveness of traditional, as well as more recent targeted treatment methods, has apparently been limited by the existence and/or emergence of resistant cancer cells that are capable of perpetuating the cancer even in face of these diverse treatment methods. Huff et al., European Journal of Cancer 42: 1293-1297 (2006) and Zhou et al., Nature Reviews Drug Discovery 8: 806-823 (2009) each of which is incorporated herein in its entirety by reference. Such observations are confirmed by the consistent inability of traditional debulking agents to substantially increase patient survival when suffering from solid tumors, and through the development of an increasingly sophisticated understanding as to how tumors grow, recur and metastasize. Accordingly, recent strategies for treating neoplastic disorders have recognized the importance of eliminating, depleting, silencing or promoting the differentiation of tumor perpetuating cells so as to diminish the possibility of tumor recurrence, metastasis or patient relapse.

Efforts to develop such strategies have incorporated recent work involving non-traditional xenograft (NTX) models, wherein primary human solid tumor specimens are implanted and passaged exclusively in immunocompromised mice. Such techniques confirm the existence of a subpopulation of cells with the unique ability to generate heterogeneous tumors and fuel their growth indefinitely. As previously hypothesized, work in NTX models has confirmed that identified CSC subpopulations of tumor cells appear more resistant to debulking regimens such as chemotherapy and radiation, potentially explaining the disparity between clinical response rates and overall survival. Further, employment of NTX models in CSC research has sparked a fundamental change in drug discovery and preclinical evaluation of drug candidates that may lead to CSC-targeted therapies having a major impact on tumor recurrence and metastasis thereby improving patient survival rates. While progress has been made, inherent technical difficulties associated with handling primary and/or xenograft tumor tissue, along with a lack of experimental platforms to characterize CSC identity and differentiation potential, pose major challenges. As such, there remains a substantial need to selectively target cancer stem cells and develop diagnostic, prophylactic or therapeutic compounds or methods that may be used in the treatment, prevention and/or management of hyperproliferative disorders.

SUMMARY OF THE INVENTION

These and other objectives are provided for by the present invention which, in a broad sense, is directed to methods, compounds, compositions and articles of manufacture that may be used in the treatment of CD46 associated disorders (e.g., hyperproliferative disorders or NEOPLASTIC disorders). To that end, the present invention provides novel CD46 modulators that effectively target cancer stem cells and may be used to treat patients suffering from a wide variety of malignancies. In certain embodiments the disclosed CD46 modulators may comprise any compound that recognizes, competes, agonizes, antagonizes, interacts, binds or associates with the CD46 polypeptide, its ligand or its gene and modulates, adjusts, alters, changes or modifies the impact of the CD46 protein on one or more physiological pathways. In selected embodiments of the invention, CD46 modulators may comprise CD46 itself or fragments thereof, either in an isolated form or fused or associated with other moieties (e.g., Fc-CD46, PEG-CD46 or CD46 associated with a targeting moiety). In other selected embodiments CD46 modulators may comprise CD46 antagonists which, for the purposes of the instant application, shall be held to mean any construct or compound that recognizes, competes, interacts, binds or associates with CD46 and neutralizes, eliminates, reduces, sensitizes, reprograms, inhibits or controls the growth of neoplastic cells including tumor initiating cells. In preferred embodiments the CD46 modulators of the instant invention comprise anti-CD46 antibodies, or fragments or derivatives thereof, that have unexpectedly been found to silence, neutralize, reduce, decrease, deplete, moderate, diminish, reprogram, eliminate, or otherwise inhibit the ability of tumor initiating cells to propagate, maintain, expand, proliferate or otherwise facilitate the survival, recurrence, regeneration and/or metastasis of neoplastic cells.

In one embodiment the CD46 modulator may comprise a humanized antibody wherein said antibody comprises a heavy chain variable region amino acid sequence as set forth in SEQ ID NO: 199 and a light chain variable region amino acid sequence as set forth in SEQ ID NO: 201. In other preferred embodiments the invention will be in the form of a composition comprising hSC1.N71 antibody and a pharmaceutically acceptable carrier. In another preferred embodiment the CD46 modulator may comprise a humanized antibody wherein said antibody comprises a heavy chain variable region amino acid sequence as set forth in SEQ ID NO: 203 and a light chain variable region amino acid sequence as set forth in SEQ ID NO: 205. In yet other preferred embodiments the invention will be in the form of a composition comprising hSC1.N149 antibody and a pharmaceutically acceptable carrier.

In certain other embodiments the invention will comprise a CD46 modulator that reduces the frequency of tumor initiating cells upon administration to a subject. Preferably the reduction in frequency will be determined using in vitro or in vivo limiting dilution analysis. In particularly preferred embodiments such analysis may be conducted using in vivo limiting dilution analysis comprising transplant of live human tumor cells into immunocompromised mice. Alternatively, the limiting dilution analysis may be conducted using in vitro limiting dilution analysis comprising limiting dilution deposition of live human tumor cells into in vitro colony supporting conditions. In either case, the analysis, calculation or quantification of the reduction in frequency will preferably comprise the use of Poisson distribution statistics to provide an accurate accounting. It will be appreciated that, while such quantification methods are preferred, other, less labor intensive methodology such as flow cytometry or immunohistochemistry may also be used to provide the desired values and, accordingly, are expressly contemplated as being within the scope of the instant invention. In such cases the reduction in frequency may be determined using flow cytometric analysis or immunohistochemical detection of tumor cell surface markers known to enrich for tumor initiating cells.

As such, in another preferred embodiment of the instant invention comprises a method of treating a CD46 associated disorder comprising administering a therapeutically effective amount of a CD46 modulator to a subject in need thereof whereby the frequency of tumor initiating cells is reduced. Again, the reduction in the tumor initiating cell frequency will preferably be determined using in vitro or in vivo limiting dilution analysis.

In this regard it will be appreciated that the present invention is based, at least in part, upon the discovery that the CD46 polypeptide is associated with tumor perpetuating cells (i.e., cancer stem cells) that are involved in the etiology of various neoplasia. More specifically, the instant application unexpectedly shows that the administration of various exemplary CD46 modulators can reduce, inhibit or eliminate tumorigenic signaling by tumor initiating cells (i.e., reduce the frequency of tumor initiating cells). This reduced signaling, whether by reduction or elimination or reprogramming or silencing of the tumor initiating cells or by modifying tumor cell morphology (e.g., induced differentiation, niche disruption), in turn allows for the more effective treatment of CD46 associated disorders by inhibiting tumorigenesis, tumor maintenance, expansion and/or metastasis and recurrence. In other embodiments the disclosed modulators may interfere, suppress or otherwise retard CD46 mediated signaling that may fuel tumor growth. Further, as will be discussed in more detail below, the CD46 polypeptide is intimately involved in the complement pathway. Intervention in this pathway, using the novel CD46 modulators described herein, may further ameliorate the disorder by more than one mechanism (i.e., tumor initiating cell reduction and disruption of complement) to provide an additive or synergistic effect.

Thus, another preferred embodiment of the invention comprises a method of treating a CD46 mediated disorder in a subject in need thereof comprising the step of administering a CD46 modulator to said subject. In particularly preferred embodiments the CD46 modulator will be associated (e.g., conjugated) with an anti-cancer agent. In addition such disruption and collateral benefits may be achieved whether the subject tumor tissue exhibits elevated levels of CD46 or reduced or depressed levels of CD46 as compared with normal adjacent tissue.

It will further be appreciated that the CD46 modulators of the instant invention may be fabricated and selected to react with a single isoform or a select few isoforms (i.e. splice variants) of the CD46 molecule or, conversely, may comprise a pan-CD46 modulator that reacts or associates with some or all of the CD46 isoforms. More specifically, as disclosed herein and set forth in the Examples below, preferred modulators such as antibodies may be generated and selected so that they react with domains that are exhibited by single splice variants (e.g., at specific exon junctions) or with domains that are conserved across multiple or all CD46 isoforms (e.g., exons 1-6). This is significant with respect to the instant invention in that, as shown in Example 5 below, certain splice variants have been found to be preferably expressed on TIC and may serve as therapeutic targets that provide for the selective reduction in tumorigenic cell frequency and/or depletion of cancer stem cell populations.

Accordingly, in a selected embodiment the invention comprises a pan-CD46 modulator. In other selected embodiments the invention comprises a CD46 modulator that immunospecifically associates with one or more splice variants. Preferably the splice variants may be selected from the group consisting of CD46D, CD46F and CD46J. In yet other embodiments the present invention comprises a method of treating a subject in need thereof comprising administering a therapeutically effective amount of a pan-CD46 modulator. Still other embodiments comprise a method of treating a subject in need thereof comprising administering a therapeutically effective amount of a CD46 modulator that immunospecifically associates with one or more splice variants.

Other facets of the instant invention exploit the ability of the disclosed modulators to potentially disrupt multiple oncogenic survival pathways while simultaneously silencing tumor initiating cells. Such multi-active CD46 modulators (e.g., CD46 antagonists) may prove to be particularly effective when used in combination with standard of care anti-cancer agents or debulking agents. In addition, two or more CD46 antagonists (e.g. antibodies that specifically bind to two discrete epitopes on CD46) may be used in combination in accordance with the present teachings. Moreover, as discussed in some detail below, the CD46 modulators of the present invention may be used in a conjugated or unconjugated state and, optionally, as a sensitizing agent in combination with a variety chemical or biological anti-cancer agents.

Thus, another preferred embodiment of the instant invention comprises a method of sensitizing a tumor in a subject for treatment with an anti-cancer agent comprising the step of administering a CD46 modulator to said subject. In a particularly preferred aspect of the invention the CD46 modulator will specifically result in a reduction of tumor initiating cell frequency is as determined using in vitro or in vivo limiting dilution analysis.

Similarly, as the compounds of the instant invention may exert therapeutic benefits through various physiological mechanisms, the present invention is also directed to selected effectors or modulators that are specifically fabricated to exploit certain cellular processes. For example, in certain embodiments the preferred modulator may be engineered to associate with CD46 on or near the surface of the tumor initiating cell and stimulate the subject's immune response. In other embodiments the modulator may comprise an antibody directed to an epitope that neutralizes CD46 activity and increases concentrations of CD46 substrate in the tumor microenvironment which may impact signaling. In yet other embodiments the disclosed modulators may act by depleting or eliminating the CD46 associated cells. As such, it is important to appreciate that the present invention is not limited to any particular mode of action but rather encompasses any method or CD46 modulator that achieves the desired outcome.

Within such a framework preferred embodiments of the disclosed embodiments are directed to a method of treating a subject suffering from neoplastic disorder comprising the step of administering a therapeutically effective amount of at least one neutralizing CD46 modulator.

Other embodiments are directed to a method of treating a subject suffering from a CD46 associated disorder comprising the step of administering a therapeutically effective amount of at least one depleting CD46 modulator.

In yet another embodiment the present invention provides methods of maintenance therapy wherein the disclosed effectors are administered over a period of time following an initial procedure (e.g., chemotherapeutic, radiation or surgery) designed to remove at least a portion of the tumor mass. Such therapeutic regimens may be administered over a period of weeks, a period of months or even a period of years wherein the CD46 modulators may act prophylactically to inhibit metastasis and/or tumor recurrence. In yet other embodiments the disclosed modulators may be administrated in concert with known debulking regimens to prevent or retard metastasis.

Beyond the therapeutic uses discussed above it will also be appreciated that the modulators of the instant invention may be used to diagnose CD46 related disorders and, in particular, hyperproliferative disorders. As such, a preferred embodiment comprises a method of diagnosing a hyperproliferative disorder in a subject in need thereof comprising the steps of:
 a. obtaining a tissue sample from said subject;
 b. contacting the tissue sample with at least one CD46 modulator; and
 c. detecting or quantifying the CD46 modulator associated with the sample.

Such methods may be easily discerned in conjunction with the instant application and may be readily performed using generally available commercial technology such as automatic plate readers, dedicated reporter systems, etc. In preferred embodiments the detecting or quantifying step will comprise a reduction of tumor initiating cell frequency and detection thereof. Moreover, limiting dilution analysis may be conducted as previously alluded to above and will preferably employ the use of Poisson distribution statistics to provide an accurate accounting as to the reduction of frequency.

In a similar vein the present invention also provides kits that are useful in the diagnosis and monitoring of CD46 associated disorders such as cancer. To this end the present invention preferably provides an article of manufacture useful for diagnosing or treating CD46 associated disorders comprising a receptacle comprising a CD46 modulator and instructional materials for using said CD46 modulator to treat or diagnose the CD46 associated disorder.

Other preferred embodiments of the invention also exploit the properties of the disclosed modulators as an instrument useful for identifying, isolating, sectioning or enriching populations or subpopulations of tumor initiating cells through methods such as fluorescence activated cell sorting (FACS) or laser mediated sectioning.

As such, another preferred embodiment of the instant invention is directed to a method of identifying, isolating, sectioning or enriching a population of tumor initiating cells comprising the step of contacting said tumor initiating cells with a CD46 modulator.

The foregoing is a summary and thus contains, by necessity, simplifications, generalizations, and omissions of detail; consequently, those skilled in the art will appreciate that the summary is illustrative only and is not intended to be in any way limiting. Other aspects, features, and advantages of the methods, compositions and/or devices and/or other subject matter described herein will become apparent in the teachings set forth herein. The summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

BRIEF DESCRIPTION OF THE FIGURES

FIGS. 3A-C shows flow cytometry and fluorescence activated cell sorting (FACS) data demonstrating tumor perpetuating capability of $CD46^{hi}$ cells by serial passage in non-traditional xenograft models;

FIGS. 4A-C graphically illustrate the effect of irinotecan on the frequency of $CD46^{hi}$ tumor perpetuating cells in colorectal cancer;

FIGS. 5A-C shows CD46 splice variant isoform expression in colorectal cancer tumor perpetuating cells, tumor progenitor cells, and non-tumorigenic cells;

FIGS. 7A-C are graphical representations showing, respectively, expression of CD46 protein in colorectal normal adjacent and tumor cells (FIG. 7A), pancreatic normal adjacent and tumor cells of neuroendocrine and non-neuroendocrine subtypes (FIG. 7B), and ovarian normal adjacent and tumor cells (FIG. 7C);

FIGS. 8A-C are graphical representations showing expression of CD46 splice variants that contain exon10 in, respectively, colorectal normal adjacent and tumor cells (FIG. 8A), pancreatic normal adjacent and tumor cells of neuroendocrine and non-neuroendocrine subtypes (FIG. 8B), and ovarian normal adjacent and tumor cells (FIG. 8C);

FIGS. 10A-R provide the nucleic acid and amino acid sequences of the heavy and light chain variable regions of eighteen discrete anti-CD46 antibodies isolated and cloned as described in the Examples herein;

FIGS. 11A and 11B are tabular representations showing, respectively, the genetic arrangement and the heavy and light chain CDR sequences derived from VBASE2 analysis of eighteen discrete CD46 modulators isolated and cloned as described in the Examples herein;

FIGS. 13A and 13B respectively illustrate the nucleic acid and amino acid sequences of the heavy (SEQ ID NO: 198 and SEQ ID NO: 199) and light chain (SEQ ID NO: 200 and SEQ ID NO: 201) variable regions of hSC1.N71 (FIG. 13A) and the nucleic acid and amino acid sequences of the heavy (SEQ ID NO: 202 and SEQ ID NO: 203) and light chain (SEQ ID NO: 204 and SEQ ID NO: 205) variable regions of hSC1.N149 wherein the CDR sequences as defined as by Kabat et al. are underlined;

FIG. 14 provides immunochemical characteristics of twelve discrete CD46 modulators in a tabular format;

FIGS. 15A-15C represent the measured affinity of murine antibody SC1.N71 (FIG. 15A) and the humanized antibody derivative h SC1.N71 (FIG. 15B) against four different concentrations of antigen, and provides a tabular summary including the measured values (FIG. 15C);

FIGS. 16A and 16B illustrate, respectively, a standard curve generated using the disclosed modulators and the plasma concentration of soluble CD46 as measured in samples obtained from healthy subjects and patients suffering from various neoplasia and extrapolated from the standard curve;

FIGS. 18A and 18B illustrate the ability of the disclosed CD46 modulators to associate with CD46 expressed on the cell surface (FIG. 18A) and mediate cell death of $CD46^{hi}$ cells while lentiviral induced $CD46^{-/lo}$ are relatively immune (FIG. 18B);

FIGS. 19A and 19B show that the CD46 modulators of the instant invention can mediate receptor dependent uptake and internalization of streptavidin-ZAP conjugates wherein relatively low killing is observed in the absence of modulator (FIG. 19A) and that the disclosed modulators effectively mediate killing across different tumor types (FIG. 19B); and FIGS. 20A and 20B depict the ability of the CD46 modulators to chemosensitize cancer stem cells wherein FIG. 20A shows the effect of the disclosed modulators as compared to a control and FIG. 20B demonstrates that CD46 modulators can delay tumor recurrence and increase progression free survival when compared to chemotherapy alone.

DETAILED DESCRIPTION OF THE INVENTION

I. Introduction

Figure 1A:
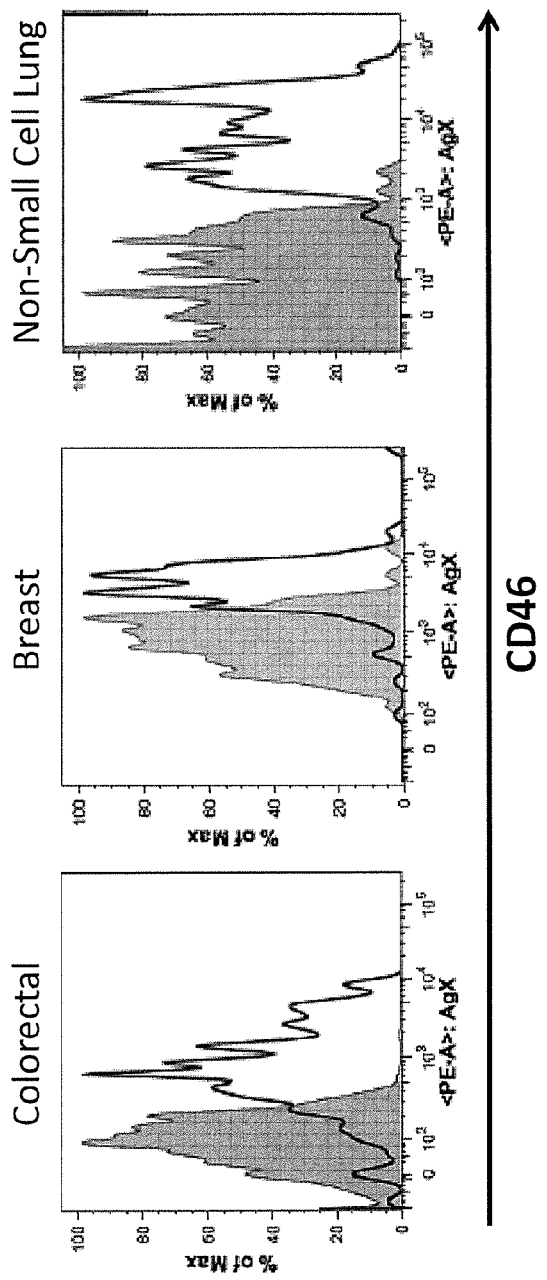
FIGS. 1A and 1B depict, respectively, flow cytometry data of CD46 expression on solid tumor specimens from patients with colorectal cancer, breast cancer, or non-small cell lung cancer (FIG. 1A) and patient-derived non-traditional xenograft tumor specimens from colorectal cancer cells, pancreatic cancer cells, breast cancer cells, non-small cell lung cancer cells, melanoma cells, ovarian cancer cells, and head & neck cancer cells (FIG. 1B)

In a broad sense, embodiments of the present invention are directed to novel CD46 modulators and their use in treating, managing, ameliorating or preventing the occurrence of hyperproliferative disorders including cancer. Without wishing to be bound by any particular theory, it has been discovered that the disclosed modulators are effective in reducing or retarding tumor growth and eliminating or neutralizing tumorigenic cells as well as altering the sensitivity of such cells to anti-cancer agents. Further, it has surprisingly been discovered that there is a heretofore unknown phenotypic association between selected tumor perpetuating cells (TPC) and the protein known as CD46. In this regard it has been found that selected TPC (i.e., cancer stem cells or CSC), express elevated levels of CD46, including specific splice variants, when compared to normal tissue as well as when compared to tumor progenitor cells (TProg), and non-tumorigenic (NTG) cells that together comprise much of a solid tumor. Thus, in selected embodiments CD46 comprises a tumor associated marker (or antigen) and has been found to provide an effective agent for the detection, sensitization and/or suppression of TPC and related neoplasia due to elevated levels of the protein associated with the surface of selected cells and in the tumor microenvironment. More specifically, and even more surprisingly given that CD46 is apparently secreted (at least to some extent), it has further been discovered that CD46 modulators, including Fc-CD46 constructs and immunoreactive antagonists (e.g., antibodies to the protein), may be useful in depleting, sensitizing, eliminating, reducing, reprogramming, promoting the differentiation of, or otherwise precluding or limiting the ability of these tumor perpetuating cells to spread and/or continue to fuel tumor growth or recurrence in a patient.

In preferred embodiments the CD46 modulators of the present invention will comprise nucleotides, oligonucleotides, polynucleotides, peptides or polypeptides. As previously alluded to and discussed in detail below, selected embodiments disclosed herein will comprise antibodies to CD46 in conjugated or unconjugated forms. Other embodiments of the CD46 modulators will preferably comprise CD46 or a form, variant, derivative or fragment thereof including, for example, CD46 fusion constructs (e.g., CD46-Fc, CD46-targeting moiety, etc.) or CD46-conjugates (e.g., CD46-PEG, CD46-cytotoxic agent, etc.). In yet other embodiments the modulators may operate on the genetic level and may comprise compounds as antisense constructs, siRNA, miRNA and the like. The foregoing CD46 modulators may attenuate the growth, propagation or survival of tumor perpetuating cells and/or associated neoplasia through competitive mechanisms, agonizing or antagonizing selected pathways or eliminating or depleting specific cells (including non-TPC support cells) depending, for example, on the form of CD46 modulator or dosing and method of delivery.

In view of these discoveries those skilled in the art will appreciate that particularly preferred embodiments of the invention are largely directed to CD46 modulators and their use in reducing the frequency of tumor initiating cells. As will be discussed extensively herein, CD46 modulators compatible with instant invention broadly comprise any compound that associates, binds, complexes or otherwise reacts or competes with CD46 and, optionally, provides for a reduction in tumor perpetuating cell frequency. Exemplary modulators disclosed herein comprise nucleotides, oligonucleotides, polynucleotides, peptides or polypeptides. In certain preferred embodiments the selected modulators will comprise antibodies to CD46 or immunoreactive fragments or derivatives thereof. Such antibodies may be antagonistic or agonistic in nature. In other preferred embodiments effectors compatible with the instant invention will comprise CD46 constructs comprising CD46 itself or a reactive fragment thereof. It will be appreciated that such CD46 constructs may comprise fusion proteins and can include reactive domains from other polypeptides such as immunoglobulins, stapled peptides or biological response modifiers. In still other preferred aspects the CD46 effector or modulator will comprise a nucleic acid assembly that exerts the desired effects at a genomic level. Still other modulators compatible with the instant teachings will be discussed in detail below.

In a related note, the following discussion pertains to CD46 modulators, CD46 antagonists and anti-CD46 antibodies. While a more detailed definition of each term is provided below, it will be appreciated that the terms are largely interchangeable for the purposes of this disclosure and should not be construed narrowly unless dictated by the context. For example, if a point is made relating to CD46 antagonists it is also applicable to those antibodies of the instant invention that happen to be antagonistic. Similarly, the term CD46 modulators expressly include disclosed CD46 antagonists and anti-CD46 antibodies and references to the latter are also applicable to modulators to the extent not precluded by context.

II. CD46

CD46 is also known as membrane cofactor protein or MCP. It is a type I transmembrane protein that is widely expressed but has a number of isoforms as a result of alternate exon splicing and glycosylation. Recently Karosi et al., *Laryngoscope* 118: 1669-1676 (September 2008), which is incorporated herein by reference in its entirety, reported detecting fourteen isoforms of the molecule. The mRNA is transcribed from a single gene located at chromosome 1q32 and undergoes extensive alternative splicing to produce multiple transcripts encoding the various protein isoforms. Of the 14 exons comprising the gene, it appears that exons 1-6 are conserved in all CD46 protein isoforms, whereas exons 7 to 9 encode variably utilized serine-threonin-proline ("STP") rich regions, leading to the major hypervariability in the protein isoforms. Exons 11 and 12 encode the transmembrane region of CD46, while exons 13 and 14 encode the cytoplasmic tail of the protein. The longest mRNA transcript, variant A (NM_002389), contains sequences from all fourteen exons of the gene. Variable splicing of exons 7, 8, 9, and 13 is believed to yield the majority of CD46's fourteen isoforms, with the predominant observed protein isoforms of 66 and 56 kDa arising from alternative inclusion or exclusion of exon 8. Alternate inclusion/exclusion of exon 13 leads to changes in the encoded sequence of the cytoplasmic tail of the molecule, with the suggestion that these changes affect subcellular trafficking, stability, and the signaling properties of the protein.

As set forth in Karosi et al., CD46 mRNA isoform D comprises exons 1-6, 8-12 and 14 of the CD46 gene (equivalent to the sequence NM_153826, encoding the protein NP_722548), isoform F comprises exons 1-6, 9-12, and 14 (equivalent to the sequence NM_172353, encoding NP_758863), and isoform J comprises exons 1-6, 8, 10-12, and 14 (equivalent to the sequence NM_172356, encoding NP_758866). More specifically the CD46 molecule comprises four N-terminal short consensus repeat (SCR) modules ("Sushi" domains: 4 Cysteines in a 1-3, 2-4 linkage topology), where these SCR domains are encoded by the first six exons of the gene. The SCR2, 3, and 4 modules have the C3b/C4b binding and regulatory activity (discussed below), while the SCR1 module and sequences distal of SCR4 are not essential for complement regulatory function, The membrane-proximal extracellular sequence, encoded by the alternatively utilized exons 7-9 as well as exon 10, is heavily glycosylated, mainly via O-linked carbohydrates.

For the purposes of the instant disclosure the term "CD46" shall be held to mean any protein as set forth immediately above including any splice variant or immunoreactive fragment thereof as well as any nucleic acid sequence encoding such proteins, splice variants or fragments unless otherwise contextually dictated. Thus, as discussed herein a "CD46 marker" would broadly include any detectable protein, peptide or nucleic acid sequence that constitutes or encodes for CD46. In preferred embodiments the CD46 marker will comprise the full-length glycoprotein (variant A) or splice variant or immunoreactive fragment thereof. Even more preferably the CD46 protein marker will be present on the cell surface of the selected tumorigenic cell population. In other preferred embodiments the CD46 marker will comprise a nucleic acid sequence (e.g., DNA or mRNA) encoding full length CD46, a splice variant or fragment thereof.

With respect to the aforementioned variants it will further be appreciated that the CD46 modulators of the instant invention may be fabricated and selected to react with a single isoform (i.e. splice variant) or a select few isoforms of the CD46 molecule or, conversely, may comprise a pan-CD46 modulator that reacts or associates with most or all of the CD46 isoforms. More specifically, as disclosed herein and set forth in the Examples below, disclosed modulators such as antibodies may be generated and selected so that they react with domains that are exhibited by single splice variants (e.g., at specific exon junctions) or with domains that are conserved across multiple or all CD46 isoforms (e.g., exons 1-6). This is significant with respect to the instant invention in that, as shown in Example 5 below, certain splice variants have been found to be preferably expressed on TIC and may serve as therapeutic targets that provide for the selective reduction in tumorigenic cell frequency and/or depletion of cancer stem cell populations.

In any event a number of biological functions have been attributed to CD46, many of which involve regulation of the immune system. One major immunomodulatory function of CD46 involves the regulation of complement to protect host cells from damage by the complement proteins that are a part of the innate immune response of higher eukaryotes. Specifically, CD46 is a cofactor for Factor I mediated proteolytic cleavage of complement proteins C3b and C4b. It has been shown to activate C3 convertases, molecules that cleave C3b into inactive fragments, and thereby protect against inappropriate complement activation. On top of its role in innate immunity, CD46 also regulates the acquired immune response. Signaling through CD46 leads to T cell proliferation, and differentiation toward a specific class of regulatory T cells, called Tr1, characterized by production of large amounts of IL-10, an anti-inflammatory cytokine. In addition, because spermatozoa express high levels of CD46, it has been suggested that CD46 is involved in reproduction, perhaps in the fusion of sperm to oocyte. CD46 also seems to be highly expressed in the placenta and may serve to protect the fetus from immune rejection by the mother.

CD46 has further been shown to be ubiquitously expressed on most normal human cells, with the exception of red blood cells. For example, there are reports of strong expression in epithelial cells, moderate expression in lymphocytes and endothelium, and weak expression in other cells such as osteoclasts, osteocytes, interstitial cells and muscle cells. Due to its widespread expression, a number of human pathogens have evolved strategies to utilize CD46 as a receptor or co-receptor for binding to cells as a precursor to infection. These pathogens include human herpes virus 6, measles virus, some serotypes of adenoviruses, and pathogenic species from the Neisseria family of commensal bacteria. Certain retroviruses are believed to evade complement-mediated immunity by bearing CD46 mimics on their surfaces (Stoiber et al, Molecular Immunology 2005; Saifuddin et al, J Gen Virol, 1997).

CD46 has also been implicated in a number of diseases, including autoimmune disorders such as multiple sclerosis (MS). MS is a chronic inflammatory disease in which an autoimmune response is mounted against the myelin protein that insulates neuronal axons, resulting in demyelination and subsequent damaged conduction by these cells, with consequent neurological disturbances and deficits. MS leads to scaring (scleroses) of the white matter of the brain and spinal cord. It is a complex disease with a complicated etiology comprised of immunologic, genetic and environmental components, and although several mechanisms have been explored, the understanding of MS pathogenesis is far from complete. Because of its role in regulating T-cell immunity and inflammation, CD46 is believed to be involved in MS pathogenesis. More specifically, recent data have shown that CD46 is defective or compromised in multiple sclerosis, with IL-10 production being severely impaired in these patients. This lack of IL-10 production probably participates in the inflammation observed in patients with multiple sclerosis (A. L. Astier, Immunology. 2008 June; 124(2): 149-154 which is incorporated herein by reference). In some cases it may be that autoreactive anti-CD46 antibodies are impairing the normal function of the molecule. To the extent that these antibodies act as modulators such as those described herein they are within the scope of the present invention and may be used accordingly.

In addition to its presence on normal cells, CD46 expression levels may be increased in certain cancers. For example, elevated CD46 expression has been reported in breast cancer (Thorsteinsson et al. *APMIS* 106:869-78 (1998); Hofman et al. *Breast Cancer Res. Treat.* 32:213-9 (1994)); colon/colorectal cancer (Andrew et al. *Cancer Res.* 50: 5225-30 (1990); Koretz et al. *Br. J. Cancer* 68:926-31 (1993); Juhl et al. *J. Surg. Oncol.* 64:222-30 (1997); Bjorge et al. *Cancer Immunol. Immunother.* 42:185-92 (1996)); lung cancer (Varsano et al. *Clin. Exp. Immunol.* 113:173-82 (1998); Varsano et al. *Am. J. Respir. Cell. Mol. Biol.* 19:522-9 (1998)); ovarian cancer (Bjorge et al. *Int. J. Cancer* 70: 14-25 (1997)); renal cancer (Blok et al. *Lab. Invest.* 80:335-44 (2000); Gorter et al. Lab. Invest. 74:1039-49 (1996)); pancreatic cancer (Juhl et al. *J. Surg. Oncol.* 64:222-30 (1997)); and prostate cancer (Jarvis et al. *J. Allergy Clin. Immunol* 99 (NO. I, PART 2): 5215 (1997); Liu, *Cancer Res.* 60:3429-3434 (2000)); see also, PCT WO 02/18948; PCT WO 01/88537.

In the time since the protein was first described, a number of antibodies to CD46 have been produced. These include: E4.3 (CD46-SCR1) Sparrow et al., Hum Immunol 1983 7:1; M177 (CD46-SCR2) Seya et al., J Immunol 1990 145:238; J4/48 (CD46-SCR1) Pesando et al., J Immunol 1986 137: 3689; GB24 (CD46-SCR3/4) Hsi et al., Am J Reprod Immunol Microbiol 1988 18:21; H316 (CD46-SCR1) Stern et al., J Immunol 1986 137:1604; MH61 (CD46-SCR3) Okabe et al. Fertil Steril 1990 54:1121; TRA-2-10 (CD46-SCR1) Cho et al., Clin Exp Immunol 1991 83:257; MCI 20.6 (CD46-SCR1) Naniche et al., J Virol 1993 67:6025; 158.2A5 Vilella et al.; 197.2B1 Vilella et al.; and MPA7 U.S. Pat. No. 7,744,878 each of which is incorporated herein by reference. See generally Loveland et al., Prot Rev on the Web: http://prow.nci.nih.gov/guide/2027814670g.htm. For many of the antibodies in the aforementioned list the reactive short consensus repeat domain (SCR) is provided.

III. Tumor Initiating Cells

In contrast to any teachings of the prior art, the present invention provides CD46 modulators that are particularly useful for targeting tumor initiating cells, and especially tumor perpetuating cells, thereby facilitating the treatment, management or prevention of neoplastic disorders. More specifically, as previously indicated it has surprisingly been found that specific tumor cell subpopulations express CD46 and likely modify localized coordination of morphogen signaling important to cancer stem cell self-renewal and cell survival. Thus, in preferred embodiments modulators of CD46 may be used to reduce tumor initiating cell frequency in accordance with the present teachings and thereby facilitate the treatment or management of hyperproliferative diseases.

As used herein, the term tumor initiating cell (TIC) encompasses both tumor perpetuating cells (TPC; i.e., cancer stem cells or CSC) and highly proliferative tumor progenitor cells (termed TProg), which together generally comprise a unique subpopulation (i.e. 0.1-40%) of a bulk tumor or mass. For the purposes of the instant disclosure the terms tumor perpetuating cells and cancer stem cells are equivalent and may be used interchangeably herein. Conversely, TPC differ from TProg in that they can completely recapitulate the composition of tumor cells existing within a tumor and have unlimited self-renewal capacity as demonstrated by serial transplantation (two or more passages through mice) of low numbers of isolated cells. As will be discussed in more detail below fluorescence-activated cell sorting (FACS) using appropriate cell surface markers is a reliable method to isolate highly enriched cell subpopulations (>99.5% purity) due, at least in part, to its ability to discriminate between single cells and clumps of cells (i.e. doublets, etc.). Using such techniques it has been shown that when low cell numbers of highly purified TProg cells are transplanted into immunocompromised mice they can fuel tumor growth in a primary transplant. However, unlike purified TPC subpopulations the TProg generated tumors do not completely reflect the parental tumor in phenotypic cell heterogeneity and are demonstrably inefficient at reinitiating serial tumorigenesis in subsequent transplants. In contrast, TPC subpopulations completely reconstitute the cellular heterogeneity of parental tumors and can efficiently initiate tumors when serially isolated and transplanted. Thus, those skilled in the art will recognize that a definitive difference between TPC and TProg, though both may be tumor generating in primary transplants, is the unique ability of TPC to perpetually fuel heterogeneous tumor growth upon serial transplantation at low cell numbers. Other common approaches to characterize TPC involve morphology and examination of cell surface markers, transcriptional profile, and drug response although marker expression may change with culture conditions and with cell line passage in vitro.

Accordingly, for the purposes of the instant invention tumor perpetuating cells, like normal stem cells that support cellular hierarchies in normal tissue, are preferably defined by their ability to self-renew indefinitely while maintaining the capacity for multilineage differentiation. Tumor perpetuating cells are thus capable of generating both tumorigenic progeny (i.e., tumor initiating cells: TPC and TProg) and non-tumorigenic (NTG) progeny. As used herein a non-tumorigenic cell (NTG) refers to a tumor cell that arises from tumor initiating cells, but does not itself have the capacity to self-renew or generate the heterogeneous lineages of tumor cells that comprise a tumor. Experimentally, NTG cells are incapable of reproducibly forming tumors in mice, even when transplanted in excess cell numbers.

As indicated, TProg are also categorized as tumor initiating cells (or TIC) due to their limited ability to generate tumors in mice. TProg are progeny of TPC and are typically capable of a finite number of non-self-renewing cell divisions. Moreover, TProg cells may further be divided into early tumor progenitor cells (ETP) and late tumor progenitor cells (LTP), each of which may be distinguished by phenotype (e.g., cell surface markers) and different capacities to recapitulate tumor cell architecture. In spite of such technical differences, both ETP and LTP differ functionally from TPC in that they are generally less capable of serially reconstituting tumors when transplanted at low cell numbers and typically do not reflect the heterogeneity of the parental tumor. Notwithstanding the foregoing distinctions, it has also been shown that various TProg populations can, on rare occasion, gain self-renewal capabilities normally attributed to stem cells and themselves become TPC (or CSC). In any event both types of tumor-initiating cells are likely represented in the typical tumor mass of a single patient and are subject to treatment with the modulators as disclosed herein. That is, the disclosed compositions are generally effective in reducing the frequency or altering the chemosensitivity of such CD46 positive tumor initiating cells regardless of the particular embodiment or mix represented in a tumor.

In the context of the instant invention, TPC are more tumorigenic, relatively more quiescent and often more chemoresistant than the TProg (both ETP and LTP), NTG cells and the tumor-infiltrating non-TPC derived cells (e.g., fibroblasts/stroma, endothelial & hematopoietic cells) that comprise the bulk of a tumor. Given that conventional therapies and regimens have, in large part, been designed to both debulk tumors and attack rapidly proliferating cells, TPC are likely to be more resistant to conventional therapies and regimens than the faster proliferating TProg and other bulk tumor cell populations. Further, TPC often express other characteristics that make them relatively chemoresistant to conventional therapies, such as increased expression of multi-drug resistance transporters, enhanced DNA repair mechanisms and anti-apoptotic proteins. These properties, each of which contribute to drug tolerance by TPC, constitute a key reason for the failure of standard oncology treatment regimens to ensure long-term benefit for most patients with advanced stage neoplasia; i.e. the failure to adequately target and eradicate those cells that fuel continued tumor growth and recurrence (i.e. TPC or CSC).

Unlike many of the aforementioned prior art treatments, the novel compositions of the present invention preferably reduce the frequency of tumor initiating cells upon administration to a subject regardless of the form or specific target (e.g., genetic material, CD46 or CD46 ligand) of the selected modulator. As noted above, the reduction in tumor initiating cell frequency may occur as a result of a) elimination, depletion, sensitization, silencing or inhibition of tumor initiating cells; b) controlling the growth, expansion or recurrence of tumor initiating cells; c) interrupting the initiation, propagation, maintenance, or proliferation of tumor initiating cells; or d) by otherwise hindering the survival, regeneration and/or metastasis of the tumorigenic cells. In some embodiments, the reduction in the frequency of tumor initiating cells occurs as a result of a change in one or more physiological pathways. The change in the pathway, whether by reduction or elimination of the tumor initiating cells or by modifying their potential (e.g., induced differentiation, niche disruption) or otherwise interfering with their ability to exert affects on the tumor environment or other cells, in turn allows for the more effective treatment of CD46-associated disorders by inhibiting tumorigenesis, tumor maintenance and/or metastasis and recurrence.

Among the methods that can be used to assess such a reduction in the frequency of tumor initiating cells is limiting dilution analysis either in vitro or in vivo, preferably followed by enumeration using Poisson distribution statistics or assessing the frequency of predefined definitive events such as the ability to generate tumors in vivo or not. While such limiting dilution analysis are the preferred methods of calculating reduction of tumor initiating cell frequency, other, less demanding methods, may also be used to effectively determine the desired values, albeit slightly less accurately, and are entirely compatible with the teachings herein. Thus, as will be appreciated by those skilled in the art, it is also possible to determine reduction of frequency values through well-known flow cytometric or immunohistochemical means. As to all the aforementioned methods see, for example, Dylla et al. 2008, PMCID: PMC2413402 & Hoey et al. 2009, PMID: 19664991; each of which is incorporated herein by reference in its entirety.

With respect to limiting dilution analysis, in vitro enumeration of tumor initiating cell frequency may be accomplished by depositing either fractionated or unfractionated human tumor cells (e.g. from treated and untreated tumors, respectively) into in vitro growth conditions that foster colony formation. In this manner, colony forming cells might be enumerated by simple counting and characterization of colonies, or by analysis consisting of, for example, the deposition of human tumor cells into plates in serial dilutions and scoring each well as either positive or negative for colony formation at least 10 days after plating. In vivo limiting dilution experiments or analyses, which are generally more accurate in their ability to determine tumor initiating cell frequency encompass the transplantation of human tumor cells, from either untreated control or treated conditions, for example, into immunocompromised mice in serial dilutions and subsequently scoring each mouse as either positive or negative for tumor formation at least 60 days after transplant. The derivation of cell frequency values by limiting dilution analysis in vitro or in vivo is preferably done by applying Poisson distribution statistics to the known frequency of positive and negative events, thereby providing a frequency for events fulfilling the definition of a positive event; in this case, colony or tumor formation, respectively.

As to other methods compatible with the instant invention that may be used to calculate tumor initiating cell frequency, the most common comprise quantifiable flow cytometric techniques and immunohistochemical staining procedures. Though not as precise as the limiting dilution analysis techniques described immediately above, these procedures are much less labor intensive and provide reasonable values in a relatively short time frame. Thus, it will be appreciated that a skilled artisan may use flow cytometric cell surface marker profile determination employing one or more antibodies or reagents that bind art recognized cell surface proteins known to enrich for tumor initiating cells (e.g., potentially compatible markers are set forth in Example 1 below) and thereby measure TIC levels from various samples. In still another compatible method one skilled in the art might enumerate TIC frequency in situ (i.e. tissue section) by immunohistochemistry using one or more antibodies or reagents that are able to bind cell surface proteins thought to demarcate these cells.

Using any of the above-referenced methods it is then possible to quantify the reduction in frequency of TIC (or the TPC therein) provided by the disclosed CD46 modulators in accordance with the teachings herein. In some instances, the compounds of the instant invention may reduce the frequency of TIC (by a variety of mechanisms noted above, including elimination, induced differentiation, niche disruption, silencing, etc.) by 10%, 15%, 20%, 25%, 30% or even by 35%. In other embodiments, the reduction in frequency of TIC may be on the order of 40%, 45%, 50%, 55%, 60% or 65%. In certain embodiments, the disclosed compounds my reduce the frequency of TIC by 70%, 75%, 80%, 85%, 90% or even 95%. Of course it will be appreciated that any reduction of the frequency of the TIC likely results in a corresponding reduction in the tumorigenicity, persistence, recurrence and aggressiveness of the neoplasia.

IV. CD46 Modulators

In any event, the present invention is directed to the use of CD46 modulators, including CD46 antagonists, for the diagnosis, treatment and/or prophylaxis of any one of a number of CD46 associated malignancies. The disclosed modulators may be used alone or in conjunction with a wide variety of anti-cancer compounds such as chemotherapeutic or immunotherapeutic agents or biological response modifiers. In other selected embodiments, two or more discrete CD46 modulators may be used in combination to provide enhanced anti-neoplastic effects or may be used to fabricate multispecific constructs.

In certain embodiments, the CD46 modulators of the present invention will comprise nucleotides, oligonucleotides, polynucleotides, peptides or polypeptides. Even more preferably the modulators will comprise soluble CD46 (sCD46) or a form, variant, derivative or fragment thereof including, for example, CD46 fusion constructs (e.g., CD46-Fc, CD46-targeting moiety, etc.) or CD46-conjugates (e.g., CD46-PEG, CD46-cytotoxic agent, CD46-brm, etc.). It will also be appreciated that, in other embodiments, the CD46 modulators comprise antibodies (e.g., anti-CD46 mAbs) or immunoreactive fragments or derivatives thereof. In particularly preferred embodiments the modulators of the instant invention will comprise neutralizing antibodies or derivatives or fragments thereof. In other embodiments the CD46 modulators may comprise internalizing antibodies. In still other embodiments the CD46 modulators may comprise depleting antibodies. Moreover, as with the aforementioned fusion constructs, these antibody modulators may be conjugated, linked or otherwise associated with selected cytotoxic agents, polymers, biological response modifiers (BRMs) or the like to provide directed immunotherapies with various (and optionally multiple) mechanisms of action. In yet other embodiments the modulators may operate on the genetic level and may comprise compounds as antisense constructs, siRNA, micro RNA and the like.

It will further be appreciated that the disclosed CD46 modulators may deplete or eliminate or inhibit growth, propagation or survival of tumor cells, particularly TPC, and/or associated neoplasia through a variety of mechanisms, including agonizing or antagonizing selected pathways or eliminating specific cells depending, for example, on the form of CD46 modulator, any associated payload or dosing and method of delivery. Accordingly, while preferred embodiments disclosed herein are directed to the depletion, inhibition or silencing of specific tumor cell subpopulations such as tumor perpetuating cells it must be emphasized that such embodiments are merely illustrative and not limiting in any sense. Rather, as set forth in the appended claims, the present invention is broadly directed to CD46 modulators and their use in the treatment, management or prophylaxis of various CD46 mediated hyperproliferative disorders irrespective of any particular mechanism or target tumor cell population.

In the same sense disclosed embodiments of the instant invention comprise one or more CD46 antagonists. To that end it will be appreciated that CD46 antagonists of the instant invention may comprise any ligand, polypeptide, peptide, fusion protein, antibody or immunologically active fragment or derivative thereof that recognizes, reacts, binds, combines, competes, associates or otherwise interacts with the CD46 protein or fragment thereof and eliminates, silences, reduces, inhibits, hinders, restrains or controls the growth of tumor initiating cells or other neoplastic cells including bulk tumor or NTG cells. In selected embodiments the CD46 modulator comprises a CD46 antagonist.

As used herein an antagonist refers to a molecule capable of neutralizing, blocking, inhibiting, abrogating, reducing or interfering with the activities of a particular or specified protein, including the binding of receptors to ligands or the interactions of enzymes with substrates. More generally antagonists of the invention may comprise antibodies and antigen-binding fragments or derivatives thereof, proteins, peptides, glycoproteins, glycopeptides, glycolipids, polysaccharides, oligosaccharides, nucleic acids, antisense constructs, siRNA, miRNA, bioorganic molecules, peptidomimetics, pharmacological agents and their metabolites, transcriptional and translation control sequences, and the like. Antagonists may also include small molecule inhibitors, fusion proteins, receptor molecules and derivatives which bind specifically to the protein thereby sequestering its binding to its substrate target, antagonist variants of the protein, antisense molecules directed to the protein, RNA aptamers, and ribozymes against the protein.

As used herein and applied to two or more molecules or compounds, the term recognizes or specifically recognizes shall be held to mean the reaction, binding, specific binding, combination, association, interaction, connection, linkage, uniting, coalescence, merger or joining, covalently or non-covalently, of the molecules whereby one molecule exerts an effect on the other molecule.

Moreover, as demonstrated in the examples herein, some modulators of human CD46 may, in certain cases, cross-react with CD46 from a species other than human (e.g., murine). In other cases exemplary modulators may be specific for one or more isoforms of human CD46 and will not exhibit cross reactivity with CD46 orthologs from other species.

In any event, those skilled in the art will appreciate that the disclosed modulators may be used in a conjugated or unconjugated form. That is, the modulator may be associated with or conjugated to (e.g. covalently or non-covalently) pharmaceutically active compounds, biological response modifiers, cytotoxic or cytostatic agents, diagnostic moieties or biocompatible modifiers. In this respect it will be understood that such conjugates may comprise peptides, polypeptides, proteins, fusion proteins, nucleic acid molecules, small molecules, mimetic agents, synthetic drugs, inorganic molecules, organic molecules and radioisotopes. Moreover, as indicated above the selected conjugate may be covalently or non-covalently linked to the CD46 modulator in various molar ratios depending, at least in part, on the method used to effect the conjugation.

V. Antibodies a. Overview

As previously alluded to particularly preferred embodiments of the instant invention comprise CD46 modulators in the form of antibodies. The term antibody herein is used in the broadest sense and specifically covers synthetic antibodies, monoclonal antibodies, oligoclonal or polyclonal antibodies, multiclonal antibodies, recombinantly produced antibodies, intrabodies, multispecific antibodies, bispecific antibodies, monovalent antibodies, multivalent antibodies, human antibodies, humanized antibodies, chimeric antibodies, primatized antibodies, Fab fragments, F(ab') fragments, single-chain FvFcs (scFvFc), single-chain Fvs (scFv), anti-idiotypic (anti-Id) antibodies and any other immunologically active antibody fragments so long as they exhibit the desired biological activity (i.e., CD46 association or binding). In a broader sense, the antibodies of the present invention include immunoglobulin molecules and immunologically active fragments of immunoglobulin molecules, i.e., molecules that contain an antigen binding site, where these fragments may or may not be fused to another immunoglobulin domain including, but not limited to, an Fc region or fragment thereof. Further, as outlined in more detail herein, the terms antibody and antibodies specifically include Fc variants as described below, including full length antibodies and variant Fc-Fusions comprising Fc regions, or fragments thereof, optionally comprising at least one amino acid residue modification and fused to an immunologically active fragment of an immunoglobulin.

As will be discussed in more detail below, the generic term antibodies or immunoglobulin comprises five distinct classes of antibody that can be distinguished biochemically and, depending on the amino acid sequence of the constant domain of their heavy chains, can readily be assigned to the appropriate class. For historical reasons, the major classes of intact antibodies are termed IgA, IgD, IgE, IgG, and IgM. In humans, the IgG and IgA classes may be further divided into recognized subclasses (isotypes), i.e., IgG1, IgG2, IgG3, IgG4, IgA1, and IgA2 depending on structure and certain biochemical properties. It will be appreciated that the IgG isotypes in humans are named in order of their abundance in serum with IgG1 being the most abundant.

While all five classes of antibodies (i.e. IgA, IgD, IgE, IgG, and IgM) and all isotypes (i.e., IgG1, IgG2, IgG3, IgG4, IgA1, and IgA2), as well as variations thereof, are within the scope of the present invention, preferred embodiments comprising the IgG class of immunoglobulin will be discussed in some detail solely for the purposes of illustration. It will be understood that such disclosure is, however, merely demonstrative of exemplary compositions and methods of practicing the present invention and not in any way limiting of the scope of the invention or the claims appended hereto.

In this respect, human IgG immunoglobulins comprise two identical light polypeptide chains of molecular weight approximately 23,000 Daltons, and two identical heavy chains of molecular weight 53,000-70,000 depending on the isotype. Heavy-chain constant domains that correspond to the different classes of antibodies are denoted by the corresponding lower case Greek letter $\alpha$, $\delta$, $\epsilon$, $\gamma$, and $\mu$, respectively. The light chains of the antibodies from any vertebrate species can be assigned to one of two clearly distinct types, called kappa ($\kappa$) and lambda ($\lambda$), based on the amino acid sequences of their constant domains. Those skilled in the art will appreciate that the subunit structures and three-dimensional configurations of different classes of immunoglobulins are well known.

The four chains are joined by disulfide bonds in a Y configuration wherein the light chains bracket the heavy chains starting at the mouth of the Y and continuing through the variable region to the dual ends of the Y. Each light chain is linked to a heavy chain by one covalent disulfide bond while two disulfide linkages in the hinge region join the heavy chains. The respective heavy and light chains also have regularly spaced intrachain disulfide bridges the number of which may vary based on the isotype of IgG.

Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. In this regard, it will be appreciated that the variable domains of both the light ($V_L$) and heavy ($V_H$) chain portions determine antigen recognition and specificity. Conversely, the constant domains of the light chain ($C_L$) and the heavy chain ($C_H 1$, $C_H 2$ or $C_H 3$) confer and regulate important biological properties such as secretion, transplacental mobility, circulation half-life, complement binding, and the like. By convention the numbering of the constant region domains increases as they become more distal from the antigen binding site or amino-terminus of the antibody. Thus, the amino or N-terminus of the antibody comprises the variable region and the carboxy or C-terminus comprises the constant region. Thus, the $C_H 3$ and $C_L$ domains actually comprise the carboxy-terminus of the heavy and light chain, respectively.

The term variable refers to the fact that certain portions of the variable domains differ extensively in sequence among immunoglobulins and these hot spots largely define the binding and specificity characteristics of a particular antibody. These hypervariable sites manifest themselves in three segments, known as complementarity determining regions (CDRs), in both the light-chain and the heavy-chain variable domains respectively. The more highly conserved portions of variable domains flanking the CDRs are termed framework regions (FRs). More specifically, in naturally occurring monomeric IgG antibodies, the six CDRs present on each arm of the antibody are short, non-contiguous sequences of amino acids that are specifically positioned to form the antigen binding site as the antibody assumes its three dimensional configuration in an aqueous environment.

The framework regions comprising the remainder of the heavy and light variable domains show less inter-molecular variability in amino acid sequence. Rather, the framework regions largely adopt a β-sheet conformation and the CDRs form loops which connect, and in some cases form part of, the β-sheet structure. Thus, these framework regions act to form a scaffold that provides for positioning the six CDRs in correct orientation by inter-chain, non-covalent interactions. The antigen-binding site formed by the positioned CDRs defines a surface complementary to the epitope on the immunoreactive antigen (i.e. CD46). This complementary surface promotes the non-covalent binding of the antibody to the immunoreactive antigen epitope. It will be appreciated that the position of CDRs can be readily identified by one of ordinary skill in the art.

As discussed in more detail below all or part of the heavy and light chain variable regions may be recombined or engineered using standard recombinant and expression techniques to provide effective antibodies. That is, the heavy or light chain variable region from a first antibody (or any portion thereof) may be mixed and matched with any selected portion of the heavy or light chain variable region from a second antibody. For example, in one embodiment, the entire light chain variable region comprising the three light chain CDRs of a first antibody may be paired with the entire heavy chain variable region comprising the three heavy chain CDRs of a second antibody to provide an operative antibody. Moreover, in other embodiments, individual heavy and light chain CDRs derived from various antibodies may be mixed and matched to provide the desired antibody having optimized characteristics. Thus, an exemplary antibody may comprise three light chain CDRs from a first antibody, two heavy chain CDRs derived from a second antibody and a third heavy chain CDR from a third antibody.

More specifically, in the context of the instant invention it will be appreciated that any of the disclosed heavy and light chain CDRs in FIG. 11B may be rearranged in this manner to provide optimized anti-CD46 (e.g. anti-CD46) antibodies in accordance with the instant teachings.

In any event, the complementarity determining regions residue numbers may be defined as those of Kabat et al. (1991, NIH Publication 91-3242, National Technical Information Service, Springfield, Va.), specifically, residues 24-34 (CDR1), 50-56 (CDR2) and 89-97 (CDR3) in the light chain variable domain and 31-35 (CDR1), 50-65 (CDR2) and 95-102 (CDR3) in the heavy chain variable domain. Note that CDRs vary considerably from antibody to antibody (and by definition will not exhibit homology with the Kabat consensus sequences). Maximal alignment of framework residues frequently requires the insertion of spacer residues in the numbering system, to be used for the Fv region. In addition, the identity of certain individual residues at any given Kabat site number may vary from antibody chain to antibody chain due to interspecies or allelic divergence. See also Chothia et al., J. Mol. Biol. 196:901-917 (1987) and by MacCallum et al., J. Mol. Biol. 262:732-745 (1996) where the definitions include overlapping or subsets of amino acid residues when compared against each other. Each of the aforementioned references is incorporated herein by reference in its entirety and the amino acid residues which encompass CDRs as defined by each of the above cited references are set forth for comparison.

| CDR Definitions | | | |
|---|---|---|---|
| | Kabat[1] | Chothia[2] | MacCallum[3] |
| $V_H$ CDR1 | 31-35 | 26-32 | 30-35 |
| $V_H$ CDR2 | 50-65 | 53-55 | 47-58 |
| $V_H$ CDR3 | 95-102 | 96-101 | 93-101 |
| $V_L$ CDR1 | 24-34 | 26-32 | 30-36 |
| $V_L$ CDR2 | 50-56 | 50-52 | 46-55 |
| $V_L$ CDR3 | 89-97 | 91-96 | 89-96 |

[1]Residue numbering follows the nomenclature of Kabat et al., supra
[2]Residue numbering follows the nomenclature of Chothia et al., supra
[3]Residue numbering follows the nomenclature of MacCallum et al., supra For purposes of convenience the CDRs set forth in FIG. 11B are defined derived from VBASE2 analysis though given the content of the instant application one skilled in the art could readily identify and enumerate the CDRs as defined by Kabat et al. or MacCallum et al. for each respective heavy and light chain sequence. In this regard CDRs as defined by Kabat et al. were used for the humanization analysis set forth in Example 16 and are underlined in FIGS. 13A and 13B which depict the humanized antibody sequences. Accordingly, antibodies comprising CDRs defined by all such nomenclature are expressly included within the scope of the instant invention. More broadly the term variable region CDR amino acid residue includes amino acids in a CDR as identified using any sequence or structure based method as set forth above.

As used herein the term variable region framework (FR) amino acid residues refers to those amino acids in the framework region of an Ig chain. The term framework region or FR region as used herein, includes the amino acid residues that are part of the variable region, but are not part of the CDRs (e.g., using the Kabat definition of CDRs). Therefore, a variable region framework is a non-contiguous sequence between about 100-120 amino acids in length but includes only those amino acids outside of the CDRs.

For the specific example of a heavy chain variable region and for the CDRs as defined by Kabat et al., framework region 1 corresponds to the domain of the variable region encompassing amino acids 1-30; framework region 2 corresponds to the domain of the variable region encompassing amino acids 36-49; framework region 3 corresponds to the domain of the variable region encompassing amino acids 66-94, and framework region 4 corresponds to the domain of the variable region from amino acids 103 to the end of the variable region. The framework regions for the light chain are similarly separated by each of the light claim variable region CDRs. Similarly, using the definition of CDRs by Chothia et al. or McCallum et al. the framework region boundaries are separated by the respective CDR termini as described above.

With the aforementioned structural considerations in mind, those skilled in the art will appreciate that the antibodies of the present invention may comprise any one of a number of functional embodiments. In this respect, compatible antibodies may comprise any immunoreactive antibody (as the term is defined herein) that provides the desired physiological response in a subject. While any of the disclosed antibodies may be used in conjunction with the present teachings, certain embodiments of the invention will comprise chimeric, humanized or human monoclonal antibodies or immunoreactive fragments thereof. Yet other embodiments may, for example, comprise homogeneous or heterogeneous multimeric constructs, Fc variants and conjugated or glycosylationally altered antibodies. Moreover, it will be understood that such configurations are not mutually exclusive and that compatible individual antibodies may comprise one or more of the functional aspects disclosed herein. For example, a compatible antibody may comprise a single chain diabody with humanized variable regions or a fully human full length IgG3 antibody with Fc modifications that alter the glycosylation pattern to modulate serum half-life. Other exemplary embodiments are readily apparent to those skilled in the art and may easily be discernable as being within the scope of the invention.

b. Antibody Generation

As is well known various host animals, including rabbits, mice, rats, etc. may be inoculated and used to provide antibodies in accordance with the teachings herein. Art known adjuvants that may be used to increase the immunological response, depending on the inoculated species include, but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*. Such adjuvants may protect the antigen from rapid dispersal by sequestering it in a local deposit, or they may contain substances that stimulate the host to secrete factors that are chemotactic for macrophages and other components of the immune system. Preferably, if a polypeptide is being administered, the immunization schedule will involve two or more administrations of the polypeptide, spread out over several weeks.

After immunization of an animal with a CD46 immunogen including selected splice variants and/or peptides, antibodies and/or antibody-producing cells can be obtained from the animal using art recognized techniques. In some embodiments, polyclonal anti-CD46 antibody-containing serum is obtained by bleeding or sacrificing the animal. The serum may be used for research purposes in the form obtained from the animal or, in the alternative, the anti-CD46 antibodies may be partially or fully purified to provide immunoglobulin fractions or homogeneous antibody preparations.

c. Monoclonal Antibodies

While polyclonal antibodies may be used in conjunction with certain aspects of the present invention, preferred embodiments comprise the use of CD46 reactive monoclonal antibodies. As used herein, the term monoclonal antibody or mAb refers to an antibody obtained from a population of substantially homogeneous antibodies, i.e., the individual antibodies comprising the population are identical except for possible mutations, e.g., naturally occurring mutations, that may be present in minor amounts. Thus, the modifier monoclonal indicates the character of the antibody as not being a mixture of discrete antibodies and may be used in conjunction with any type of antibody. In certain embodiments, such a monoclonal antibody includes an antibody comprising a polypeptide sequence that binds or associates with CD46, wherein the CD46-binding polypeptide sequence was obtained by a process that includes the selection of a single target binding polypeptide sequence from a plurality of polypeptide sequences.

In preferred embodiments, antibody-producing cell lines are prepared from cells isolated from the immunized animal. After immunization, the animal is sacrificed and lymph node and/or splenic B cells are immortalized by means well known in the art. Methods of immortalizing cells include, but are not limited to, transfecting them with oncogenes, infecting them with an oncogenic virus and cultivating them under conditions that select for immortalized cells, subjecting them to carcinogenic or mutating compounds, fusing them with an immortalized cell, e.g., a myeloma cell, and inactivating a tumor suppressor gene. If fusion with myeloma cells is used, the myeloma cells preferably do not secrete immunoglobulin polypeptides (a non-secretory cell line). Immortalized cells are screened using CD46, or an immunoreactive portion thereof. In a preferred embodiment, the initial screening is performed using an enzyme-linked immunoassay (ELISA) or a radioimmunoassay.

More generally, discrete monoclonal antibodies consistent with the present invention can be prepared using a wide variety of techniques known in the art including hybridoma, recombinant techniques, phage display technologies, yeast libraries, transgenic animals (e.g. a XenoMouse® or HuMAb Mouse®) or some combination thereof. For example, monoclonal antibodies can be produced using hybridoma techniques such as broadly described above and taught in more detail in Harlow et al., Antibodies: A Laboratory Manual, (Cold Spring Harbor Laboratory Press, 2nd ed. 1988); Hammerling, et al., in: Monoclonal Antibodies and T-Cell Hybridomas 563-681 (Elsevier, N.Y., 1981) each of which is incorporated herein. Using the disclosed protocols, antibodies are preferably raised in mammals by multiple subcutaneous or intraperitoneal injections of the relevant antigen and an adjuvant. As previously discussed, this immunization generally elicits an immune response that comprises production of antigen-reactive antibodies (that may be fully human if the immunized animal is transgenic) from activated splenocytes or lymphocytes. While the resulting antibodies may be harvested from the serum of the animal to provide polyclonal preparations, it is generally more desirable to isolate individual lymphocytes from the spleen, lymph nodes or peripheral blood to provide homogenous preparations of monoclonal antibodies. Most typically, the lymphocytes are obtained from the spleen and immortalized to provide hybridomas.

For example, as described above, the selection process can be the selection of a unique clone from a plurality of clones, such as a pool of hybridoma clones, phage clones, or recombinant DNA clones. It should be understood that a selected CD46 binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody of this invention. In contrast to polyclonal antibody preparations, which typically include discrete antibodies directed against different determinants (epitopes), each monoclonal antibody of a monoclonal antibody preparation is directed against a single determinant on an antigen. In addition to their specificity, monoclonal antibody preparations are advantageous in that they are typically uncontaminated by other immunoglobulins that may be cross-reactive.

d. Chimeric Antibodies

In another embodiment, the antibody of the invention may comprise chimeric antibodies derived from covalently joined protein segments from at least two different species or types of antibodies. It will be appreciated that, as used herein, the term chimeric antibodies is directed to constructs in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., Proc. Natl. Acad. Sci. USA, 81:6851-6855 (1984)). In one exemplary embodiment, a chimeric antibody in accordance with the teachings herein may comprise murine $V_H$ and $V_L$ amino acid sequences and constant regions derived from human sources. In other compatible embodiments a chimeric antibody of the present invention may comprise a CDR grafted or humanized antibody as described below.

Generally, a goal of making a chimeric antibody is to create a chimera in which the number of amino acids from the intended subject species is maximized. One example is the CDR-grafted antibody, in which the antibody comprises one or more complementarity determining regions (CDRs) from a particular species or belonging to a particular antibody class or subclass, while the remainder of the antibody chain(s) is/are identical with or homologous to a corresponding sequence in antibodies derived from another species or belonging to another antibody class or subclass. For use in humans, the variable region or selected CDRs from a rodent antibody often are grafted into a human antibody, replacing the naturally occurring variable regions or CDRs of the human antibody. These constructs generally have the advantages of providing full strength modulator functions (e.g., CDC, ADCC, etc.) while reducing unwanted immune responses to the antibody by the subject.

e. Humanized Antibodies

Similar to the CDR grafted antibody is a humanized antibody. Generally, a humanized antibody is produced from a monoclonal antibody raised initially in a non-human animal. As used herein humanized forms of non-human (e.g., murine) antibodies are chimeric antibodies that contain minimal sequence derived from non-human immunoglobulin. In one embodiment, a humanized antibody is a human immunoglobulin (recipient antibody) in which residues from a CDR of the recipient are replaced by residues from a CDR of a non-human species (donor antibody) such as mouse, rat, rabbit, or nonhuman primate having the desired specificity, affinity, and/or capacity.

In selected embodiments, the acceptor antibody may comprise consensus sequences. To create consensus human frameworks, frameworks from several human heavy chain or light chain amino acid sequences may be aligned to identify a consensus amino acid sequence. Moreover, in many instances, one or more framework residues in the variable domain of the human immunoglobulin are replaced by corresponding non-human residues from the donor antibody. These framework substitutions are identified by methods well known in the art, e.g., by modeling of the interactions of the CDR and framework residues to identify framework residues important for antigen binding and sequence comparison to identify unusual framework residues at particular positions. Such substitutions help maintain the appropriate three-dimensional configuration of the grafted CDR(s) and often improve infinity over similar constructs with no framework substitutions. Furthermore, humanized antibodies may comprise residues that are not found in the recipient antibody or in the donor antibody. These modifications may be made to further refine antibody performance using well-known techniques.

CDR grafting and humanized antibodies are described, for example, in U.S. Pat. Nos. 6,180,370, 5,693,762, 5,693, 761, 5,585,089, and 5,530,101. In general, a humanized antibody will comprise substantially all of at least one, and typically two, variable domains, in which all or substantially all of the CDRs correspond to those of a non-human immunoglobulin, and all or substantially all of the framework regions are those of a human immunoglobulin sequence. The humanized antibody optionally will also comprise at least a portion of an immunoglobulin constant region (Fc), typically that of a human immunoglobulin. For further details, see, e.g., Jones et al., Nature 321:522-525 (1986); Riechmann et al., Nature 332:323-329 (1988); and Presta, Curr. Op. Struct. Biol. 2:593-596 (1992). See also, e.g., Vaswani and Hamilton, Ann. Allergy, Asthma & Immunol. 1: 105-115 (1998); Harris, Biochem. Soc. Transactions 23:1035-1038 (1995); Hurle and Gross, Curr. Op. Biotech. 5:428-433 (1994); and U.S. Pat. Nos. 6,982,321 and 7,087, 409. Still another method is termed humaneering and is described, for example, in U.S. 2005/0008625. For the purposes of the present application the term humanized antibodies will be held to expressly include CDR grafted antibodies (i.e. human antibodies comprising one or more grafted non-human CDRs) with no or minimal framework substitutions.

Additionally, a non-human anti-CD46 antibody may also be modified by specific deletion of human T cell epitopes or deimmunization by the methods disclosed in WO 98/52976 and WO 00/34317. Briefly, the heavy and light chain variable regions of an antibody can be analyzed for peptides that bind to MHC Class II; these peptides represent potential T-cell epitopes (as defined in WO 98/52976 and WO 00/34317). For detection of potential T-cell epitopes, a computer modeling approach termed peptide threading can be applied, and in addition a database of human MHC class II binding peptides can be searched for motifs present in the $V_H$ and $V_L$ sequences, as described in WO 98/52976 and WO 00/34317. These motifs bind to any of the 18 major MHC class II DR allotypes, and thus constitute potential T cell epitopes. Potential T-cell epitopes detected can be eliminated by substituting small numbers of amino acid residues in the variable regions, or by single amino acid substitutions. As far as possible, conservative substitutions are made. Often, but not exclusively, an amino acid common to a position in human germline antibody sequences may be used. After the deimmunizing changes are identified, nucleic acids encoding $V_H$ and $V_L$ can be constructed by mutagenesis or other synthetic methods (e.g., de novo synthesis, cassette replacement, and so forth). A mutagenized variable sequence can, optionally, be fused to a human constant region.

In selected embodiments, at least 60%, 65%, 70%, 75%, or 80% of the humanized antibody variable region residues will correspond to those of the parental framework region (FR) and CDR sequences. In other embodiments at least 85% or 90% of the humanized antibody residues will correspond to those of the parental framework region (FR) and CDR sequences. In a further preferred embodiment, greater than 95% of the humanized antibody residues will correspond to those of the parental framework region (FR) and CDR sequences.

Humanized antibodies may be fabricated using common molecular biology and biomolecular engineering techniques as described herein. These methods include isolating, manipulating, and expressing nucleic acid sequences that encode all or part of immunoglobulin Fv variable regions from at least one of a heavy or light chain. Sources of such nucleic acid are well known to those skilled in the art and, for example, may be obtained from a hybridoma, eukaryotic cell or phage producing an antibody or immunoreactive fragment against a predetermined target, as described above, from germline immunoglobulin genes, or from synthetic constructs. The recombinant DNA encoding the humanized antibody can then be cloned into an appropriate expression vector.

Human germline sequences, for example, are disclosed in Tomlinson, I. A. et al. (1992) J. Mol. Biol. 227:776-798; Cook, G. P. et al. (1995) Immunol. Today 16: 237-242; Chothia, D. et al. (1992) J. Mol. Bio. 227:799-817; and Tomlinson et al. (1995) EMBO J. 14:4628-4638. The V BASE directory provides a comprehensive directory of human immunoglobulin variable region sequences (See Retter et al., (2005) Nuc Acid Res 33: 671-674). These sequences can be used as a source of human sequence, e.g., for framework regions and CDRs. As set forth herein consensus human framework regions can also be used, e.g., as described in U.S. Pat. No. 6,300,064.

f. Human Antibodies

In addition to the aforementioned antibodies, those skilled in the art will appreciate that the antibodies of the present invention may comprise fully human antibodies. For the purposes of the instant application the term human antibody comprises an antibody which possesses an amino acid sequence that corresponds to that of an antibody produced by a human and/or has been made using any of the techniques for making human antibodies as disclosed herein. This definition of a human antibody specifically excludes a humanized antibody comprising non-human antigen-binding residues.

Human antibodies can be produced using various techniques known in the art. As alluded to above, phage display techniques may be used to provide immunoactive binding regions in accordance with the present teachings. Thus, certain embodiments of the invention provide methods for producing anti-CD46 antibodies or antigen-binding portions thereof comprising the steps of synthesizing a library of (preferably human) antibodies on phage, screening the library with CD46 or an antibody-binding portion thereof, isolating phage that bind CD46, and obtaining the immunoreactive fragments from the phage. By way of example, one method for preparing the library of antibodies for use in phage display techniques comprises the steps of immunizing a non-human animal comprising human or non-human immunoglobulin loci with CD46 or an antigenic portion thereof to create an immune response, extracting antibody-producing cells from the immunized animal; isolating RNA encoding heavy and light chains of antibodies of the invention from the extracted cells, reverse transcribing the RNA to produce cDNA, amplifying the cDNA using primers, and inserting the cDNA into a phage display vector such that antibodies are expressed on the phage. More particularly, DNA encoding the $V_H$ and $V_L$ domains are recombined together with an scFv linker by PCR and cloned into a phagemid vector (e.g., p CANTAB 6 or pComb 3 HSS). The vector may then be electroporated in E. coli and then the E. coli is infected with helper phage. Phage used in these methods are typically filamentous phage including fd and M13 and the $V_H$ and $V_L$ domains are usually recombinantly fused to either the phage gene III or gene VIII.

Recombinant human anti-CD46 antibodies of the invention may be isolated by screening a recombinant combinatorial antibody library prepared as above. In a preferred embodiment, the library is a scFv phage display library, generated using human $V_L$ and $V_H$ cDNAs prepared from mRNA isolated from B cells. Methods for preparing and screening such libraries are well known in the art and kits for generating phage display libraries are commercially available (e.g., the Pharmacia Recombinant Phage Antibody System, catalog no. 27-9400-01; and the Stratagene SurfZAP™ phage display kit, catalog no. 240612). There also are other methods and reagents that can be used in generating and screening antibody display libraries (see, e.g., U.S. Pat. No. 5,223,409; PCT Publication Nos. WO 92/18619, WO 91/17271, WO 92/20791, WO 92/15679, WO 93/01288, WO 92/01047, WO 92/09690; Fuchs et al., Bio/Technology 9:1370-1372 (1991); Hay et al., Hum. Antibod. Hybridomas 3:81-85 (1992); Huse et al., Science 246:1275-1281 (1989); McCafferty et al., Nature 348:552-554 (1990); Griffiths et al., EMBO J. 12:725-734 (1993); Hawkins et al., J. Mol. Biol. 226:889-896 (1992); Clackson et al., Nature 352:624-628 (1991); Gram et al., Proc. Natl. Acad. Sci. USA 89:3576-3580 (1992); Garrad et al., Bio/Technology 9:1373-1377 (1991); Hoogenboom et al., Nuc. Acid Res. 19:4133-4137 (1991); and Barbas et al., Proc. Natl. Acad. Sci. USA 88:7978-7982 (1991).

The antibodies produced by naive libraries (either natural or synthetic) can be of moderate affinity ($K_a$ of about $10^6$ to $10^7$ $M^{-1}$), but affinity maturation can also be mimicked in vitro by constructing and reselecting from secondary libraries as described in the art. For example, mutation can be introduced at random in vitro by using error-prone polymerase (reported in Leung et al., Technique, 1: 11-15 (1989)) in the method of Hawkins et al., J. Mol. Biol., 226: 889-896 (1992) or in the method of Gram et al., Proc. Natl. Acad. Sci. USA, 89: 3576-3580 (1992). Additionally, affinity maturation can be performed by randomly mutating one or more CDRs, e.g. using PCR with primers carrying random sequence spanning the CDR of interest, in selected individual Fv clones and screening for higher affinity clones. WO 9607754 described a method for inducing mutagenesis in a complementarity determining region of an immunoglobulin light chain to create a library of light chain genes. Another effective approach is to recombine the $V_H$ or $V_L$ domains selected by phage display with repertoires of naturally occurring V domain variants obtained from unimmunized donors and screen for higher affinity in several rounds of chain reshuffling as described in Marks et al., Biotechnol., 10: 779-783 (1992). This technique allows the production of antibodies and antibody fragments with a dissociation constant $K_d$ ($k_{off}/k_{on}$) of about $10^{-9}$ M or less.

It will further be appreciated that similar procedures may be employed using libraries comprising eukaryotic cells (e.g., yeast) that express binding pairs on their surface. As with phage display technology, the eukaryotic libraries are screened against the antigen of interest (i.e., CD46) and cells expressing candidate-binding pairs are isolated and cloned. Steps may be taken to optimize library content and for affinity maturation of the reactive binding pairs. See, for example, U.S. Pat. No. 7,700,302 and U.S.P.N. 2010/0056386. In one embodiment, the human antibody is selected from a phage library, where that phage library expresses human antibodies (Vaughan et al. Nature Biotechnology 14:309-314 (1996): Sheets et al. Proc. Natl. Acad. Sci. 95:6157-6162 (1998)); Hoogenboom and Winter, J. Mol. Biol, 227:381 (1991); Marks et al., J. MoI. Biol, 222:581 (1991)). In other embodiments human binding pairs may be isolated from combinatorial antibody libraries generated in eukaryotic cells such as yeast. See e.g., U.S. Pat. No. 7,700,302. Such techniques advantageously allow for the screening of large numbers of candidate modulators and provide for relatively easy manipulation of candidate sequences (e.g., by affinity maturation or recombinant shuffling).

Human antibodies can also be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and U.S. Pat. No. 6,075,181 and U.S. Pat. No. 6,150,584 regarding Xenomouse® technology along with the following scientific publications: Marks et al., Bio/Technology 10: 779-783 (1992); Lonberg et al., Nature 368: 856-859 (1994); Morrison, Nature 368:812-13 (1994); Fishwild et al., Nature Biotechnology 14: 845-51 (1996); Neuberger, Nature Biotechnology 14: 826 (1996); Lonberg and Huszar, Intern. Rev. Immunol. 13:65-93 (1995). Alternatively, the human antibody may be prepared via immortalization of human B-lymphocytes producing an antibody directed against a target antigen (such B lymphocytes may be recovered from an individual suffering from a neoplastic disorder or may have been immunized in vitro). See, e.g., Cole et al., Monoclonal Antibodies and Cancer Therapy, Alan R. Liss, p. 77 (1985); Boerner et al., J. Immunol, 147 (1):86-95 (1991); and U.S. Pat. No. 5,750,373.

VI. Antibody Characteristics

No matter how obtained or which of the aforementioned forms the antibody modulator takes (e.g., humanized, human, etc.) the preferred embodiments of the disclosed modulators may exhibit various characteristics. In this regard anti-CD46 antibody-producing cells (e.g., hybridomas or yeast colonies) may be selected, cloned and further screened for desirable characteristics including, for example, robust growth, high antibody production and, as discussed in more detail below, desirable antibody characteristics. Hybridomas can be expanded in vivo in syngeneic animals, in animals that lack an immune system, e.g., nude mice, or in cell culture in vitro. Methods of selecting, cloning and expanding hybridomas and/or colonies, each of which produces a discrete antibody species, are well known to those of ordinary skill in the art.

a. Neutralizing Antibodies

In particularly preferred embodiments the modulators of the instant invention will comprise neutralizing antibodies or derivative or fragment thereof. The term neutralizing antibody or neutralizing antagonist refers to an antibody or antagonist that binds to or interacts with CD46 or any ligand or enzyme and prevents binding of the ligand or enzyme to its binding partner (e.g., CD46) or substrate thereby interrupting the biological response that otherwise would result from the interaction of the molecules. In assessing the binding and specificity of an antibody or immunologically functional fragment or derivative thereof, an antibody or fragment will substantially inhibit binding of a ligand or enzyme to its binding partner or substrate when an excess of antibody reduces the quantity of binding partner bound to the target molecule by at least about 20%, 30%, 40%, 50%, 60%, 70%, 80%, 85%, 90%, 95%, 97%, 99% or more (as measured in an in vitro competitive binding assay such as set forth in the Examples herein). In the case of antibodies to CD46, a neutralizing antibody or antagonist will preferably diminish the ability of CD46 with respect to inactivation of complement components C3b and C4b by serum factor I by at least about 20%, 30%, 40%, 50%, 60%, 70%, 80%, 85%, 90%, 95%, 97%, 99% or more and thereby reduce the concentration of free glypicans. It will be appreciated that this diminished activity may be measured directly using art recognized techniques or may be measured by the impact such reduction will have on complement activity.

b. Internalizing Antibodies

While evidence indicates that CD46 may be secreted by the cell, at least some CD46 remains likely remains associated with the cell surface thereby allowing for internalization of the disclosed modulators. Accordingly, anti-CD46 antibodies may be internalized, at least to some extent, by cells that express CD46. For example, an anti-CD46 antibody that binds to CD46 on the surface of a tumor-initiating cell may be internalized by the tumor-initiating cell. In particularly preferred embodiments such anti-CD46 antibodies may be associated with or conjugated to cytotoxic moieties that kill the cell upon internalization.

As used herein, an anti-CD46 antibody that internalizes is one that is taken up by the cell upon binding to CD46 associated with a mammalian cell. The internalizing antibody includes antibody fragments, human or humanized antibody and antibody conjugates. Internalization may occur in vitro or in vivo. For therapeutic applications, internalization may occur in vivo. The number of antibody molecules internalized may be sufficient or adequate to kill a CD46-expressing cell, especially a CD46-expressing tumor initiating cell. Depending on the potency of the antibody or antibody conjugate, in some instances, the uptake of a single antibody molecule into the cell is sufficient to kill the target cell to which the antibody binds. For example, certain toxins are highly potent in killing such that internalization of one molecule of the toxin conjugated to the antibody is sufficient to kill the tumor cell. Whether an anti-CD46 antibody internalizes upon binding CD46 on a mammalian cell can be determined by various assays including those described in the Examples below. Methods of detecting whether an antibody internalizes into a cell are described in U.S. Pat. No. 7,619,068 which is incorporated herein by reference in its entirety.

c. Depleting Antibodies

In other preferred embodiments the modulators of the instant invention will comprise depleting antibodies or derivative or fragment thereof. The term depleting antibody refers to an antibody or fragment that binds to or associates with CD46 on or near the cell surface and induces, promotes or causes the death or elimination of the cell (e.g., by complement-dependent cytotoxicity or antibody-dependent cellular cytotoxicity). In some embodiments discussed more fully below the selected depleting antibodies will be associated or conjugated to a cytotoxic agent. Preferably a depleting antibody will be able to remove, eliminate or kill at least 20%, 30%, 40%, 50%, 60%, 70%, 80%, 85%, 90%, 95%, 97%, or 99% of tumor perpetuating cells in a defined cell population. In some embodiments the cell population may comprise enriched, sectioned, purified or isolated tumor perpetuating cells. In other embodiments the cell population may comprise whole tumor samples or heterogeneous tumor extracts that comprise tumor perpetuating cells. Those skilled in the art will appreciate that standard biochemical techniques as described in the Examples below may be used to monitor and quantify the depletion of tumor perpetuating cells in accordance with the teachings herein.

d. Epitope Binding

It will further be appreciated the disclosed anti-CD46 antibodies will associate with, or bind to, discrete epitopes or determinants presented by the selected target(s). As used herein the term epitope refers to that portion of the target antigen capable of being recognized and specifically bound by a particular antibody. When the antigen is a polypeptide such as CD46, epitopes can be formed both from contiguous amino acids and noncontiguous amino acids juxtaposed by tertiary folding of a protein. Epitopes formed from contiguous amino acids are typically retained upon protein denaturing, whereas epitopes formed by tertiary folding are typically lost upon protein denaturing. An epitope typically includes at least 3, and more usually, at least 5 or 8-10 amino acids in a unique spatial conformation. More specifically, the skilled artisan will appreciate the term epitope includes any protein determinant capable of specific binding to an immunoglobulin or T-cell receptor or otherwise interacting with a molecule. Epitopic determinants generally consist of chemically active surface groupings of molecules such as amino acids or carbohydrate or sugar side chains and generally have specific three dimensional structural characteristics, as well as specific charge characteristics. Additionally an epitope may be linear or conformational. In a linear epitope, all of the points of interaction between the protein and the interacting molecule (such as an antibody) occur linearly along the primary amino acid sequence of the protein. In a conformational epitope, the points of interaction occur across amino acid residues on the protein that are linearly separated from one another.

Once a desired epitope on an antigen is determined, it is possible to generate antibodies to that epitope, e.g., using the techniques described in the present invention. Alternatively, during the discovery process, the generation and characterization of antibodies may elucidate information about desirable epitopes. From this information, it is then possible to competitively screen antibodies for binding to the same epitope. An approach to achieve this is to conduct competition studies to find antibodies that competitively bind with one another, i.e. the antibodies compete for binding to the antigen. A high throughput process for binning antibodies based upon their cross-competition is described in WO 03/48731.

As used herein, the term binning refers to a method to group antibodies based on their antigen binding characteristics. The assignment of bins is somewhat arbitrary, depending on how different the observed binding patterns of the antibodies tested. Thus, while the technique is a useful tool for categorizing antibodies of the instant invention, the bins do not always directly correlate with epitopes and such initial determinations should be further confirmed by other art recognized methodology.

With this caveat one can determine whether a selected primary antibody (or fragment thereof) binds to the same epitope or cross competes for binding with a second antibody by using methods known in the art and set forth in the Examples herein. In one embodiment, one allows the primary antibody of the invention to bind to CD46 under saturating conditions and then measures the ability of the secondary antibody to bind to CD46. If the test antibody is able to bind to CD46 at the same time as the primary anti-CD46 antibody, then the secondary antibody binds to a different epitope than the primary antibody. However, if the secondary antibody is not able to bind to CD46 at the same time, then the secondary antibody binds to the same epitope, an overlapping epitope, or an epitope that is in close proximity to the epitope bound by the primary antibody. As known in the art and detailed in the Examples below, the desired data can be obtained using solid phase direct or indirect radioimmunoassay (RIA), solid phase direct or indirect enzyme immunoassay (EIA), sandwich competition assay, a Biacore™ system (i.e., surface plasmon resonance—GE Healthcare), a ForteBio® Analyzer (i.e., biolayer interferometry—ForteBio, Inc.) or flow cytometric methodology. The term surface plasmon resonance, as used herein, refers to an optical phenomenon that allows for the analysis of real-time biospecific interactions by detection of alterations in protein concentrations within a biosensor matrix. In a particularly preferred embodiment, the analysis is performed using a Biacore or ForteBio instrument as demonstrated in the Examples below.

The term compete when used in the context of antibodies that compete for the same epitope means competition between antibodies is determined by an assay in which the antibody or immunologically functional fragment under test prevents or inhibits specific binding of a reference antibody to a common antigen. Typically, such an assay involves the use of purified antigen bound to a solid surface or cells bearing either of these, an unlabeled test immunoglobulin and a labeled reference immunoglobulin. Competitive inhibition is measured by determining the amount of label bound to the solid surface or cells in the presence of the test immunoglobulin. Usually the test immunoglobulin is present in excess. Antibodies identified by competition assay (competing antibodies) include antibodies binding to the same epitope as the reference antibody and antibodies binding to an adjacent epitope sufficiently proximal to the epitope bound by the reference antibody for steric hindrance to occur. Additional details regarding methods for determining competitive binding are provided in the Examples herein. Usually, when a competing antibody is present in excess, it will inhibit specific binding of a reference antibody to a common antigen by at least 40%, 45%, 50%, 55%, 60%, 65%, 70% or 75%. In some instance, binding is inhibited by at least 80%, 85%, 90%, 95%, or 97% or more.

Besides epitope specificity the disclosed antibodies may be characterized using a number of different physical characteristics including, for example, binding affinities, melting temperature (Tm), and isoelectric points.

e. Binding Affinity

In this respect, the present invention further encompasses the use of antibodies that have a high binding affinity for CD46. An antibody of the invention is said to specifically bind its target antigen when the dissociation constant $K_d$ ($k_{off}/k_{on}$) is $\leq 10^{-8}$M. The antibody specifically binds antigen with high affinity when the $K_d$ is $\leq 5 \times 10^{-9}$M, and with very high affinity when the $K_d$ is $\leq 5 \times 10^{-10}$M. In one embodiment of the invention, the antibody has a $K_d$ of $\leq 10^{-9}$M and an off-rate of about $1 \times 10^{-4}$/sec. In one embodiment of the invention, the off-rate is $<1 \times 10^{-5}$/sec. In other embodiments of the invention, the antibodies will bind to CD46 with a $K_d$ of between about $10^{-8}$M and $10^{-10}$M, and in yet another embodiment it will bind with a $K_d < 2 \times 10^{-10}$M. Still other selected embodiments of the present invention comprise antibodies that have a disassociation constant or $K_d$ ($k_{off}/k_{on}$) of less than $10^{-2}$M, less than $5 \times 10^{-2}$M, less than $10^{-3}$M, less than $5 \times 10^{-3}$M, less than $10^{-4}$M, less than $5 \times 10^{-4}$M, less than $10^{-5}$M, less than $5 \times 10^{-5}$M, less than $10^{-6}$M, less than $5 \times 10^{-6}$M, less than $10^{-7}$M, less than $5 \times 10^{-7}$M, less than $10^{-8}$M, less than $5 \times 10^{-8}$M, less than $10^{-9}$M, less than $5 \times 10^{-9}$M, less than $10^{-10}$M, less than $5 \times 10^{-10}$M, less than $10^{-11}$M, less than $5 \times 10^{-11}$M, less than $10^{-12}$M, less than $5 \times 10^{-12}$M, less than $10^{-13}$M, less than $5 \times 10^{-13}$M, less than $10^{-14}$M, less than $5 \times 10^{-14}$M, less than $10^{-15}$M or less than $5 \times 10^{-15}$M.

In specific embodiments, an antibody of the invention that immunospecifically binds to CD46 has an association rate constant or $k_{on}$ rate (CD46 (Ab)+antigen (Ag) $\xrightarrow{k_{on}}$ Ab-Ag) of at least $10^5 M^{-1}s^{-1}$, at least $2 \times 10^5 M^{-1}s^{-1}$, at least $5 \times 10^5 M^{-1}s^{-1}$, at least $10^6 M^{-1}s^{-1}$, at least $5 \times 10^6 M^{-1}s^{-1}$, at least $10^7 M^{-1}s^{-1}$, at least $5 \times 10^7 M^{-1}s^{-1}$, or at least $10^8 M^{-1}s^{-1}$.

In another embodiment, an antibody of the invention that immunospecifically binds to CD46 has a $k_{off}$ rate (CD46 (Ab)+antigen (Ag) $\xrightarrow{k_{off}}$ Ab-Ag) of less than $10^{-1}s^{-1}$, less than $5 \times 10^{-1}s^{-1}$, less than $10^{-2}s^{-1}$, less than $5 \times 10^{-2}s^{-1}$, less than $10^{-3}s^{-1}$, less than $5 \times 10^{-3}s^{-1}$, less than $10^{-4}s^{-1}$, less than $5 \times 10^{-4}s^{-1}$, less than $10^{-5}s^{-1}$, less than $5 \times 10^{-5}s^{-1}$, less than $10^{-6}s^{-1}$, less than $5 \times 10^{-6}s^{-1}$, less than $10^{-7}s^{-1}$, less than $5 \times 10^{-7}s^{-1}$, less than $10^{-8}s^{-1}$, less than $5 \times 10^{-8}s^{-1}$, less than $10^{-9}s^{-1}$, less than $5 \times 10^{-9}s^{-1}$ or less than $10^{-10}s^{-1}$.

In other selected embodiments of the present invention anti-CD46 antibodies will have an affinity constant or $K_a$ ($k_{on}/k_{off}$) of at least $10^2 M^{-1}$, at least $5 \times 10^2 M^{-1}$, at least $10^3 M^{-1}$, at least $5 \times 10^3 M^{-1}$, at least $10^4 M^{-1}$, at least $5 \times 10^4 M^{-1}$, at least $10^5 M^{-1}$, at least $5 \times 10^5 M^{-1}$, at least $10^6 M^{-1}$, at least $5 \times 10^6 M^{-1}$, at least $10^7 M^{-1}$, at least $5 \times 10^7 M^{-1}$, at least $10^8 M^{-1}$, at least $5 \times 10^8 M^{-1}$, at least $10^9 M^{-1}$, at least $5 \times 10^9 M^{-1}$, at least $10^{10} M^{-1}$, at least $5 \times 10^{10} M^{-1}$, at least $10^{11} M^{-1}$, at least $5 \times 10^{11} M^{-1}$, at least $10^{12} M^{-1}$, at least $5 \times 10^{12} M^{-1}$, at least $10^{13} M^{-1}$, at least $5 \times 10^{13} M^{-1}$, at least $10^{14} M^{-1}$, at least $5 \times 10^{14} M^{-1}$, at least $10^{15} M^{-1}$ or at least $5 \times 10^{15} M^{-1}$.

f. Isoelectric Points

In addition to the aforementioned binding properties, anti-CD46 antibodies and fragments thereof, like all polypeptides, have an Isoelectric Point (pI), which is generally defined as the pH at which a polypeptide carries no net charge. It is known in the art that protein solubility is typically lowest when the pH of the solution is equal to the isoelectric point (pI) of the protein. Therefore it is possible to optimize solubility by altering the number and location of ionizable residues in the antibody to adjust the pI. For example the pI of a polypeptide can be manipulated by making the appropriate amino acid substitutions (e.g., by substituting a charged amino acid such as a lysine, for an uncharged residue such as alanine). Without wishing to be bound by any particular theory, amino acid substitutions of an antibody that result in changes of the pI of said antibody may improve solubility and/or the stability of the antibody. One skilled in the art would understand which amino acid substitutions would be most appropriate for a particular antibody to achieve a desired pI.

The pI of a protein may be determined by a variety of methods including but not limited to, isoelectric focusing and various computer algorithms (see for example Bjellqvist et al., 1993, Electrophoresis 14:1023). In one embodiment, the pI of the anti-CD46 antibodies of the invention is between is higher than about 6.5, about 7.0, about 7.5, about 8.0, about 8.5, or about 9.0. In another embodiment, the pI of the anti-CD46 antibodies of the invention is between is higher than 6.5, 7.0, 7.5, 8.0, 8.5, or 9.0. In yet another embodiment, substitutions resulting in alterations in the pI of antibodies of the invention will not significantly diminish their binding affinity for CD46. As discussed in more detail below, it is specifically contemplated that the substitution(s) of the Fc region that result in altered binding to FcγR may also result in a change in the pI. In a preferred embodiment, substitution(s) of the Fc region are specifically chosen to effect both the desired alteration in FcγR binding and any desired change in pI. As used herein, the pI value is defined as the pI of the predominant charge form.

g. Thermal Stability

It will further be appreciated that the Tm of the Fab domain of an antibody can be a good indicator of the thermal stability of an antibody and may further provide an indication of the shelf-life. Tm is merely the temperature of 50% unfolding for a given domain or sequence. A lower Tm indicates more aggregation/less stability, whereas a higher Tm indicates less aggregation/more stability. Thus, antibodies or fragments or derivatives having higher Tm are preferable. Moreover, using art-recognized techniques it is possible to alter the composition of the anti-CD46 antibodies or domains thereof to increase or optimize molecular stability. See, for example, U.S. Pat. No. 7,960,142. Thus, in one embodiment, the Fab domain of a selected antibody has a Tm value higher than at least 50° C., 55° C., 60° C., 65° C., 70° C., 75° C., 80° C., 85° C., 90° C., 95° C., 100° C., 105° C., 110° C., 115° C. or 120° C. In another embodiment, the Fab domain of an antibody has a Tm value higher than at least about 50° C., about 55° C., about 60° C., about 65° C., about 70° C., about 75° C., about 80° C., about 85° C., about 90° C., about 95° C., about 100° C., about 105° C., about 110° C., about 115° C. or about 120° C. Thermal melting temperatures (Tm) of a protein domain (e.g., a Fab domain) can be measured using any standard method known in the art, for example, by differential scanning calorimetry (see, e.g., Vermeer et al., 2000, Biophys. J. 78:394-404; Vermeer et al., 2000, Biophys. J. 79: 2150-2154 both incorporated herein by reference).

VII. CD46 Modulator Fragments and Derivatives

Whether the agents of the present invention comprise intact fusion constructs, antibodies, fragments or derivatives, the selected modulators will react, bind, combine, complex, connect, attach, join, interact or otherwise associate with CD46 and thereby provide the desired anti-neoplastic effects. Those of skill in the art will appreciate that modulators comprising anti-CD46 antibodies interact or associate with CD46 through one or more binding sites expressed on the antibody. More specifically, as used herein the term binding site comprises a region of a polypeptide that is responsible for selectively binding to a target molecule of interest (e.g., enzyme, antigen, ligand, receptor, substrate or inhibitor). Binding domains comprise at least one binding site (e.g. an intact IgG antibody will have two binding domains and two binding sites). Exemplary binding domains include an antibody variable domain, a receptor-binding domain of a ligand, a ligand-binding domain of a receptor or an enzymatic domain. For the purpose of the instant invention the enzymatically active region of CD46 (e.g., as part of an Fc-CD46 fusion construct) may comprise a binding site for a substrate (e.g., a glypican).

a. Fragments

Regardless of which form of the modulator (e.g. chimeric, humanized, etc.) is selected to practice the invention, it will be appreciated that immunoreactive fragments of the same may be used in accordance with the teachings herein. In the broadest sense, the term antibody fragment comprises at least a portion of an intact antibody (e.g. a naturally occurring immunoglobulin). More particularly the term fragment refers to a part or portion of an antibody or antibody chain (or CD46 molecule in the case of Fc fusions) comprising fewer amino acid residues than an intact or complete antibody or antibody chain. The term antigen-binding fragment refers to a polypeptide fragment of an immunoglobulin or antibody that binds antigen or competes with intact antibody (i.e., with the intact antibody from which they were derived) for antigen binding (i.e., specific binding). As used herein, the term fragment of an antibody molecule includes antigen-binding fragments of antibodies, for example, an antibody light chain ($V_L$), an antibody heavy chain ($V_H$), a single chain antibody (scFv), a F(ab')2 fragment, a Fab fragment, an Fd fragment, an Fv fragment, single domain antibody fragments, diabodies, linear antibodies, single-chain antibody molecules and multispecific antibodies formed from antibody fragments. Similarly, an enzymatically active fragment of CD46 comprises a portion of the CD46 molecule that retains its ability to interact with CD46 substrates and modify them (e.g., clip them) in a manner similar to that of an intact CD46 (though maybe with somewhat less efficiency).

Those skilled in the art will appreciate fragments can be obtained via chemical or enzymatic treatment of an intact or complete modulator (e.g., antibody or antibody chain) or by recombinant means. In this regard, while various antibody fragments are defined in terms of the digestion of an intact antibody, one of skill will appreciate that such fragments may be synthesized de novo either chemically or by using recombinant DNA methodology. Thus, the term antibody, as used herein, explicitly includes antibodies or fragments or derivatives thereof either produced by the modification of whole antibodies or synthesized de novo using recombinant DNA methodologies.

More specifically, papain digestion of antibodies produces two identical antigen-binding fragments, called Fab fragments, each with a single antigen-binding site, and a residual Fc fragment, whose name reflects its ability to crystallize readily. Pepsin treatment yields an $F(ab')_2$ fragment that has two antigen-binding sites and is still capable of cross-linking antigen. The Fab fragment also contains the constant domain of the light chain and the first constant domain ($C_H1$) of the heavy chain. Fab' fragments differ from Fab fragments by the addition of a few residues at the carboxy terminus of the heavy-chain $C_H1$ domain including one or more cysteines from the antibody hinge region. Fab'-SH is the designation herein for Fab' in which the cysteine residue(s) of the constant domains bear at least one free thiol group. $F(ab')_2$ antibody fragments originally were produced as pairs of Fab' fragments that have hinge cysteines between them. Other chemical couplings of antibody fragments are also known. See, e.g., Fundamental Immunology, W. E. Paul, ed., Raven Press, N.Y. (1999), for a more detailed description of other antibody fragments.

It will further be appreciated that an Fv fragment is an antibody fragment that contains a complete antigen recognition and binding site. This region is made up of a dimer of one heavy and one light chain variable domain in tight association, which can be covalent in nature, for example in scFv. It is in this configuration that the three CDRs of each variable domain interact to define an antigen binding site on the surface of the $V_H$-$V_L$ dimer. Collectively, the six CDRs or a subset thereof confer antigen binding specificity to the antibody. However, even a single variable domain (or half of an Fv comprising only three CDRs specific for an antigen) has the ability to recognize and bind antigen, although usually at a lower affinity than the entire binding site.

In other embodiments an antibody fragment, for example, is one that comprises the Fc region, retains at least one of the biological functions normally associated with the Fc region when present in an intact antibody, such as FcRn binding, antibody half life modulation, ADCC function and complement binding. In one embodiment, an antibody fragment is a monovalent antibody that has an in vivo half life substantially similar to an intact antibody. For example, such an antibody fragment may comprise on antigen binding arm linked to an Fc sequence capable of conferring in vivo stability to the fragment.

b. Derivatives

In another embodiment, it will further be appreciated that the modulators of the invention may be monovalent or multivalent (e.g., bivalent, trivalent, etc.). As used herein the term valency refers to the number of potential target (i.e., CD46) binding sites associated with an antibody. Each target binding site specifically binds one target molecule or specific position or locus on a target molecule. When an antibody of the instant invention comprises more than one target binding site (multivalent), each target binding site may specifically bind the same or different molecules (e.g., may bind to different ligands or different antigens, or different epitopes or positions on the same antigen). For the purposes of the instant invention, the subject antibodies will preferably have at least one binding site specific for human CD46. In one embodiment the antibodies of the instant invention will be monovalent in that each binding site of the molecule will specifically bind to a single CD46 position or epitope. In other embodiments, the antibodies will be multivalent in that they comprise more than one binding site and the different binding sites specifically associate with more than a single position or epitope. In such cases the multiple epitopes may be present on the selected CD46 polypeptide or spice variant or a single epitope may be present on CD46 while a second, different epitope may be present on another molecule or surface. See, for example, U.S.P.N. 2009/0130105.

As alluded to above, multivalent antibodies may immunospecifically bind to different epitopes of the desired target molecule or may immunospecifically bind to both the target molecule as well as a heterologous epitope, such as a heterologous polypeptide or solid support material. While preferred embodiments of the anti-CD46 antibodies only bind two antigens (i.e. bispecific antibodies), antibodies with additional specificities such as trispecific antibodies are also encompassed by the instant invention. Examples of bispecific antibodies include, without limitation, those with one arm directed against CD46 and the other arm directed against any other antigen (e.g., an modulator cell marker). Methods for making bispecific antibodies are known in the art. Traditional production of full-length bispecific antibodies is based on the coexpression of two immunoglobulin heavy chain-light chain pairs, where the two chains have different specificities (Millstein et al., 1983, Nature, 305: 537-539). Other more sophisticated compatible multispecific constructs and methods of their fabrication are set forth in U.S.P.N. 2009/0155255.

In yet other embodiments, antibody variable domains with the desired binding specificities (antibody-antigen combining sites) are fused to immunoglobulin constant domain sequences. The fusion preferably is with an immunoglobulin heavy chain constant domain, comprising at least part of the hinge, $C_H2$, and/or $C_H3$ regions. In one example, the first heavy-chain constant region ($C_H1$) containing the site necessary for light chain binding is present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when, the expression of at least two polypeptide chains in equal ratios results in high yields or when the ratios are of no particular significance.

In one embodiment of this approach, the bispecific antibodies are composed of a hybrid immunoglobulin heavy chain with a first binding specificity in one arm (e.g., CD46), and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., 1986, Methods in Enzymology, 121:210. According to another approach described in WO96/27011, a pair of antibody molecules can be engineered to maximize the percentage of heterodimers that are recovered from recombinant cell culture. The preferred interface comprises at least a part of the $C_H3$ domain of an antibody constant domain. In this method, one or more small amino acid side chains from the interface of the first antibody molecule are replaced with larger side chains (e.g. tyrosine or tryptophan). Compensatory cavities of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies also include cross-linked or heteroconjugate antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

VIII. CD46 Modulators—Constant Region Modifications a. Fc Region and Fc Receptors In addition to the various modifications, substitutions, additions or deletions to the variable or binding region of the disclosed modulators (e.g., Fc-CD46 or anti-CD46 antibodies) set forth above, those skilled in the art will appreciate that selected embodiments of the present invention may also comprise substitutions or modifications of the constant region (i.e. the Fc region). More particularly, it is contemplated that the CD46 modulators of the invention may contain inter alia one or more additional amino acid residue substitutions, mutations and/or modifications which result in a compound with preferred characteristics including, but not limited to: altered pharmacokinetics, increased serum half life, increase binding affinity, reduced immunogenicity, increased production, altered Fc ligand binding, enhanced or reduced ADCC or CDC activity, altered glycosylation and/or disulfide bonds and modified binding specificity. In this regard it will be appreciated that these Fc variants may advantageously be used to enhance the effective anti-neoplastic properties of the disclosed modulators.

The term Fc region herein is used to define a C-terminal region of an immunoglobulin heavy chain, including native sequence Fc regions and variant Fc regions. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue. A functional Fc region possesses an effector function of a native sequence Fc region. Exemplary effector functions include C1q binding; CDC; Fc receptor binding; ADCC; phagocytosis; down regulation of cell surface receptors (e.g. B cell receptor; BCR), etc. Such effector functions generally require the Fc region to be combined with a binding domain (e.g., an antibody variable domain) and can be assessed using various assays as disclosed, for example, in definitions herein.

Fc receptor or FcR describes a receptor that binds to the Fc region of an antibody. In some embodiments, an FcR is a native human FcR. In some embodiments, an FcR is one that binds an IgG antibody (a gamma receptor) and includes receptors of the FcγRI, Fc.R11, and FcγRIII subclasses, including allelic variants and alternatively spliced forms of those receptors. FcγII receptors include FcγRIIA (an activating receptor) and FcγRIIB (an inhibiting receptor), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FγRIIB contains an immunoreceptor tyrosine-based inhibition motif (ITIM) in its cytoplasmic domain. (see, e.g., Daeron, Annu. Rev. Immunol. 15:203-234 (1997)). FcRs are reviewed, for example, in Ravetch and Kinet, Annu. Rev.

Immunol 9:457-92 (1991); Capel et al., Immunomethods 4:25-34 (1994); and de Haas et al., J. Lab. Clin. Med. 126:330-41 (1995). Other FcRs, including those to be identified in the future, are encompassed by the term FcR herein. The term Fc receptor or FcR also includes the neonatal receptor, FcRn, which, in certain instances, is responsible for the transfer of maternal IgGs to the fetus (Guyer et al., J. Immunol. 117:587 (1976) and Kim et al., J. Immunol. 24:249 (1994)) and regulation of homeostasis of immunoglobulins. Methods of measuring binding to FcRn are known (see, e.g., Ghetie and Ward., Immunol. Today 18(12): 592-598 (1997); Ghetie et al., Nature Biotechnology, 15(7): 637-640 (1997); Hinton et al., J. Biol. Chem. 279(8):6213-6216 (2004); WO 2004/92219 (Hinton et al.).

b. Fc Functions

As used herein complement dependent cytotoxicity and CDC refer to the lysing of a target cell in the presence of complement. The complement activation pathway is initiated by the binding of the first component of the complement system (C1q) to a molecule, an antibody for example, complexed with a cognate antigen. To assess complement activation, a CDC assay, e.g. as described in Gazzano-Santoro et al., 1996, J. Immunol. Methods, 202:163, may be performed.

Further, antibody-dependent cell-mediated cytotoxicity or ADCC refers to a form of cytotoxicity in which secreted Ig bound onto Fc receptors (FcRs) present on certain cytotoxic cells (e.g., Natural Killer (NK) cells, neutrophils, and macrophages) enables these cytotoxic effector cells to bind specifically to an antigen-bearing target cell and subsequently kill the target cell with cytotoxins. Specific high-affinity IgG antibodies directed to the target arm cytotoxic cells and are absolutely required for such killing. Lysis of the target cell is extracellular, requires direct cell-to-cell contact, and does not involve complement.

CD46 modulator variants with altered FcR binding affinity or ADCC activity is one which has either enhanced or diminished FcR binding activity and/or ADCC activity compared to a parent or unmodified antibody or to a modulator comprising a native sequence Fc region. The modulator variant which displays increased binding to an FcR binds at least one FcR with better affinity than the parent or unmodified antibody or to a modulator comprising a native sequence Fc region. A variant which displays decreased binding to an FcR, binds at least one FcR with worse affinity than the parent or unmodified antibody or to a modulator comprising a native sequence Fc region. Such variants which display decreased binding to an FcR may possess little or no appreciable binding to an FcR, e.g., 0-20% binding to the FcR compared to a native sequence IgG Fc region, e.g. as determined techniques well known in the art.

As to FcRn, the antibodies of the instant invention also comprise or encompass Fc variants with modifications to the constant region that provide half-lives (e.g., serum half-lives) in a mammal, preferably a human, of greater than 5 days, greater than 10 days, greater than 15 days, preferably greater than 20 days, greater than 25 days, greater than 30 days, greater than 35 days, greater than 40 days, greater than 45 days, greater than 2 months, greater than 3 months, greater than 4 months, or greater than 5 months. The increased half-lives of the antibodies (or Fc containing molecules) of the present invention in a mammal, preferably a human, results in a higher serum titer of said antibodies or antibody fragments in the mammal, and thus, reduces the frequency of the administration of said antibodies or antibody fragments and/or reduces the concentration of said antibodies or antibody fragments to be administered. Antibodies having increased in vivo half-lives can be generated by techniques known to those of skill in the art. For example, antibodies with increased in vivo half-lives can be generated by modifying (e.g., substituting, deleting or adding) amino acid residues identified as involved in the interaction between the Fc domain and the FcRn receptor (see, e.g., International Publication Nos. WO 97/34631; WO 04/029207; U.S. Pat. No. 6,737,056 and U.S.P.N. 2003/0190311. Binding to human FcRn in vivo and serum half life of human FcRn high affinity binding polypeptides can be assayed, e.g., in transgenic mice or transfected human cell lines expressing human FcRn, or in primates to which the polypeptides with a variant Fc region are administered. WO 2000/42072 describes antibody variants with improved or diminished binding to FcRns. See also, e.g., Shields et al. J. Biol. Chem. 9(2):6591-6604 (2001).

c. Glycosylation Modifications

In still other embodiments, glycosylation patterns or compositions of the antibodies of the invention are modified. More particularly, preferred embodiments of the present invention may comprise one or more engineered glycoforms, i.e., an altered glycosylation pattern or altered carbohydrate composition that is covalently attached to a molecule comprising an Fc region. Engineered glycoforms may be useful for a variety of purposes, including but not limited to enhancing or reducing effector function, increasing the affinity of the antibody for a target antigen or facilitating production of the antibody. In cases where reduced effector function is desired, it will be appreciated that the molecule may be engineered to express in an aglycosylated form. Such carbohydrate modifications can be accomplished by, for example, altering one or more sites of glycosylation within the antibody sequence. That is, one or more amino acid substitutions can be made that result in elimination of one or more variable region framework glycosylation sites to thereby eliminate glycosylation at that site (see e.g. U.S. Pat. Nos. 5,714,350 and 6,350,861. Conversely, enhanced effector functions or improved binding may be imparted to the Fc containing molecule by engineering in one or more additional glycosylation sites.

Additionally or alternatively, an Fc variant can be made that has an altered glycosylation composition, such as a hypofucosylated antibody having reduced amounts of fucosyl residues or an antibody having increased bisecting GlcNAc structures. These and similar altered glycosylation patterns have been demonstrated to increase the ADCC ability of antibodies. Engineered glycoforms may be generated by any method known to one skilled in the art, for example by using engineered or variant expression strains, by co-expression with one or more enzymes (for example N-acetylglucosaminyltransferase III (GnTI11)), by expressing a molecule comprising an Fc region in various organisms or cell lines from various organisms or by modifying carbohydrate(s) after the molecule comprising Fc region has been expressed. See, for example, Shields, R. L. et al. (2002) J. Biol. Chem. 277:26733-26740; Umana et al. (1999) Nat. Biotech. 17:176-1, as well as, European Patent No: EP 1,176,195; PCT Publications WO 03/035835; WO 99/54342, Umana et al, 1999, Nat. Biotechnol 17:176-180; Davies et al., 20017 Biotechnol Bioeng 74:288-294; Shields et al, 2002, J Biol Chem 277:26733-26740; Shinkawa et al., 2003, J Biol Chem 278:3466-3473) U.S. Pat. No. 6,602,684; U.S.P.N. 2003/0157108; U.S.P.N. 2003/0003097; PCT WO 00/61739A1; PCT WO 01/292246A1; PCT WO 02/311140A1; PCT WO 02/30954A1; Potillegent™ technology (Biowa, Inc.); GlycoMAb™ glycosylation engineering technology (GLYCART biotechnology AG); WO 00061739; EA01229125; U.S.P.N. 2003/0115614; Okazaki et al., 2004, JMB, 336: 1239-49.

IX. Modulator Expression a. Overview

DNA encoding the desired CD46 modulators may be readily isolated and sequenced using conventional procedures (e.g., by using oligonucleotide probes that are capable of binding specifically to genes encoding antibody heavy and light chains). Isolated and subcloned hybridoma cells (or phage or yeast derived colonies) may serve as a preferred source of such DNA if the modulator is an antibody. If desired, the nucleic acid can further be manipulated as described herein to create agents including fusion proteins, or chimeric, humanized or fully human antibodies. More particularly, the isolated DNA (which may be modified) can be used to clone constant and variable region sequences for the manufacture antibodies as described in U.S. Pat. No. 7,709,611.

This exemplary method entails extraction of RNA from the selected cells, conversion to cDNA, and amplification by PCR using antibody specific primers. Suitable primers are well known in the art and, as exemplified herein, are readily available from numerous commercial sources. It will be appreciated that, to express a recombinant human or non-human antibody isolated by screening of a combinatorial library, the DNA encoding the antibody is cloned into a recombinant expression vector and introduced into host cells including mammalian cells, insect cells, plant cells, yeast, and bacteria. In yet other embodiments, the modulators are introduced into and expressed by simian COS cells, NS0 cells, Chinese Hamster Ovary (CHO) cells or myeloma cells that do not otherwise produce the desired construct. As will be discussed in more detail below, transformed cells expressing the desired modulator may be grown up in relatively large quantities to provide clinical and commercial supplies of the fusion construct or immunoglobulin.

Whether the nucleic acid encoding the desired portion of the CD46 modulator is obtained or derived from phage display technology, yeast libraries, hybridoma based technology, synthetically or from commercial sources, it is to be understood that the present invention explicitly encompasses nucleic acid molecules and sequences encoding CD46 modulators including fusion proteins and anti-CD46 antibodies or antigen-binding fragments or derivatives thereof. The invention further encompasses nucleic acids or nucleic acid molecules (e.g., polynucleotides) that hybridize under high stringency, or alternatively, under intermediate or lower stringency hybridization conditions (e.g., as defined below), to polynucleotides complementary to nucleic acids having a polynucleotide sequence that encodes a modulator of the invention or a fragment or variant thereof. The term nucleic acid molecule or isolated nucleic acid molecule, as used herein, is intended to include at least DNA molecules and RNA molecules. A nucleic acid molecule may be single-stranded or double-stranded, but preferably is double-stranded DNA. Moreover, the present invention comprises any vehicle or construct, incorporating such modulator encoding polynucleotide including, without limitation, vectors, plasmids, host cells, cosmids or viral constructs.

The term isolated nucleic acid means a that the nucleic acid was (i) amplified in vitro, for example by polymerase chain reaction (PCR), (ii) recombinantly produced by cloning, (iii) purified, for example by cleavage and gel-electrophoretic fractionation, or (iv) synthesized, for example by chemical synthesis. An isolated nucleic acid is a nucleic acid that is available for manipulation by recombinant DNA techniques.

More specifically, nucleic acids that encode a modulator, including one or both chains of an antibody of the invention, or a fragment, derivative, mutein, or variant thereof, polynucleotides sufficient for use as hybridization probes, PCR primers or sequencing primers for identifying, analyzing, mutating or amplifying a polynucleotide encoding a polypeptide, antisense nucleic acids for inhibiting expression of a polynucleotide, and complementary sequences of the foregoing are also provided. The nucleic acids can be any length. They can be, for example, 5, 10, 15, 20, 25, 30, 35, 40, 45, 50, 75, 100, 125, 150, 175, 200, 250, 300, 350, 400, 450, 500, 750, 1,000, 1,500, 3,000, 5,000 or more nucleotides in length, and/or can comprise one or more additional sequences, for example, regulatory sequences, and/or be part of a larger nucleic acid, for example, a vector. These nucleic acids can be single-stranded or double-stranded and can comprise RNA and/or DNA nucleotides, and artificial variants thereof (e.g., peptide nucleic acids). Nucleic acids encoding modulators of the invention, including antibodies or immunoreactive fragments or derivatives thereof, have preferably been isolated as described above.

b. Hybridization and Identity

As indicated, the invention further provides nucleic acids that hybridize to other nucleic acids under particular hybridization conditions. Methods for hybridizing nucleic acids are well known in the art. See, e.g., Current Protocols in Molecular Biology, John Wiley & Sons, N.Y. (1989), 6.3.1-6.3.6. For the purposes of the instant application, a moderately stringent hybridization condition uses a prewashing solution containing 5× sodium chloride/sodium citrate (SSC), 0.5% SDS, 1.0 mM EDTA (pH 8.0), hybridization buffer of about 50% formamide, 6×SSC, and a hybridization temperature of 55° C. (or other similar hybridization solutions, such as one containing about 50% formamide, with a hybridization temperature of 42° C.), and washing conditions of 60° C., in 0.5×SSC, 0.1% SDS. A stringent hybridization condition hybridizes in 6×SSC at 45° C., followed by one or more washes in 0.1×SSC, 0.2% SDS at 68° C. Furthermore, one of skill in the art can manipulate the hybridization and/or washing conditions to increase or decrease the stringency of hybridization such that nucleic acids comprising nucleotide sequences that are at least 65, 70, 75, 80, 85, 90, 95, 98 or 99% identical to each other typically remain hybridized to each other. More generally, for the purposes of the instant disclosure the term substantially identical with regard to a nucleic acid sequence may be construed as a sequence of nucleotides exhibiting at least about 85%, or 90%, or 95%, or 97% sequence identity to the reference nucleic acid sequence.

The basic parameters affecting the choice of hybridization conditions and guidance for devising suitable conditions are set forth by, for example, Sambrook, Fritsch, and Maniatis (1989, Molecular Cloning: A Laboratory Manual, Cold Spring Harbor Laboratory Press, Cold Spring Harbor, N.Y., chapters 9 and 11; and Current Protocols in Molecular Biology, 1995, Ausubel et al., eds., John Wiley & Sons, Inc., sections 2.10 and 6.3-6.4), and can be readily determined by those having ordinary skill in the art based on, for example, the length and/or base composition of the nucleic acid.

It will further be appreciated that nucleic acids may, according to the invention, be present alone or in combination with other nucleic acids, which may be homologous or heterologous. In preferred embodiments, a nucleic acid is functionally linked to expression control sequences that may be homologous or heterologous with respect to said nucleic acid. In this context the term homologous means that a nucleic acid is also functionally linked to the expression control sequence naturally and the term heterologous means that a nucleic acid is not functionally linked to the expression control sequence naturally.

c. Expression

A nucleic acid, such as a nucleic acid expressing RNA and/or protein or peptide, and an expression control sequence are functionally linked to one another, if they are covalently linked to one another in such a way that expression or transcription of said nucleic acid is under the control or under the influence of said expression control sequence. If the nucleic acid is to be translated into a functional protein, then, with an expression control sequence functionally linked to a coding sequence, induction of said expression control sequence results in transcription of said nucleic acid, without causing a frame shift in the coding sequence or said coding sequence not being capable of being translated into the desired protein or peptide.

The term expression control sequence comprises according to the invention promoters, ribosome binding sites, enhancers and other control elements that regulate transcription of a gene or translation of mRNA. In particular embodiments of the invention, the expression control sequences can be regulated. The exact structure of expression control sequences may vary as a function of the species or cell type, but generally comprises 5'-untranscribed and 5'- and 3'-untranslated sequences which are involved in initiation of transcription and translation, respectively, such as TATA box, capping sequence, CAAT sequence, and the like. More specifically, 5'-untranscribed expression control sequences comprise a promoter region that includes a promoter sequence for transcriptional control of the functionally linked nucleic acid. Expression control sequences may also comprise enhancer sequences or upstream activator sequences.

According to the invention the term promoter or promoter region relates to a nucleic acid sequence which is located upstream (5') to the nucleic acid sequence being expressed and controls expression of the sequence by providing a recognition and binding site for RNA-polymerase. The promoter region may include further recognition and binding sites for further factors that are involved in the regulation of transcription of a gene. A promoter may control the transcription of a prokaryotic or eukaryotic gene. Furthermore, a promoter may be inducible and may initiate transcription in response to an inducing agent or may be constitutive if transcription is not controlled by an inducing agent. A gene that is under the control of an inducible promoter is not expressed or only expressed to a small extent if an inducing agent is absent. In the presence of the inducing agent the gene is switched on or the level of transcription is increased. This is mediated, in general, by binding of a specific transcription factor.

Promoters which are preferred according to the invention include promoters for SP6, T3 and T7 polymerase, human U6 RNA promoter, CMV promoter, and artificial hybrid promoters thereof (e.g. CMV) where a part or parts are fused to a part or parts of promoters of genes of other cellular proteins such as e.g. human GAPDH (glyceraldehyde-3-phosphate dehydrogenase), and including or not including (an) additional intron(s).

According to the invention, the term expression is used in its most general meaning and comprises the production of RNA or of RNA and protein/peptide. It also comprises partial expression of nucleic acids. Furthermore, expression may be carried out transiently or stably.

In a preferred embodiment, a nucleic acid molecule is according to the invention present in a vector, where appropriate with a promoter, which controls expression of the nucleic acid. The term vector is used here in its most general meaning and comprises any intermediary vehicle for a nucleic acid which enables said nucleic acid, for example, to be introduced into prokaryotic and/or eukaryotic cells and, where appropriate, to be integrated into a genome. Vectors of this kind are preferably replicated and/or expressed in the cells. Vectors may comprise plasmids, phagemids, bacteriophages or viral genomes. The term plasmid as used herein generally relates to a construct of extrachromosomal genetic material, usually a circular DNA duplex, which can replicate independently of chromosomal DNA.

In practicing the present invention it will be appreciated that many conventional techniques in molecular biology, microbiology, and recombinant DNA technology are optionally used. Such conventional techniques relate to vectors, host cells and recombinant methods as defined herein. These techniques are well known and are explained in, for example, Berger and Kimmel, Guide to Molecular Cloning Techniques, Methods in Enzymology volume 152 Academic Press, Inc., San Diego, Calif.; Sambrook et al., Molecular Cloning—A Laboratory Manual (3rd Ed.), Vol. 1-3, Cold Spring Harbor Laboratory, Cold Spring Harbor, N.Y., 2000 and Current Protocols in Molecular Biology, F. M. Ausubel et al., eds., supra Other useful references, e.g. for cell isolation and culture (e.g., for subsequent nucleic acid or protein isolation) include Freshney (1994) Culture of Animal Cells, a Manual of Basic Technique, third edition, Wiley-Liss, New York and the references cited therein; Payne et al. (1992) Plant Cell and Tissue Culture in Liquid Systems John Wiley & Sons, Inc. New York, N.Y.; Gamborg and Phillips (Eds.) (1995) Plant Cell, Tissue and Organ Culture; Fundamental Methods Springer Lab Manual, Springer-Verlag (Berlin Heidelberg New York) and Atlas and Parks (Eds.) The Handbook of Microbiological Media (1993) CRC Press, Boca Raton, Fla. Methods of making nucleic acids (e.g., by in vitro amplification, purification from cells, or chemical synthesis), methods for manipulating nucleic acids (e.g., site-directed mutagenesis, by restriction enzyme digestion, ligation, etc.), and various vectors, cell lines and the like useful in manipulating and making nucleic acids are described in the above references. In addition, essentially any polynucleotide (including, e.g., labeled or biotinylated polynucleotides) can be custom or standard ordered from any of a variety of commercial sources.

Thus, in one aspect, the present invention provides recombinant host cells allowing recombinant expression of antibodies of the invention or portions thereof. Antibodies produced by expression in such recombinant host cells are referred to herein as recombinant antibodies. The present invention also provides progeny cells of such host cells, and antibodies produced by the same.

The term recombinant host cell (or simply host cell), as used herein, means a cell into which a recombinant expression vector has been introduced. It should be understood that recombinant host cell and host cell mean not only the particular subject cell but also the progeny of such a cell. Because certain modifications may occur in succeeding generations due to either mutation or environmental influences, such progeny may not, in fact, be identical to the parent cell, but are still included within the scope of the term host cell as used herein. Such cells may comprise a vector according to the invention as described above.

In another aspect, the present invention provides a method for making an antibody or portion thereof as described herein. According to one embodiment, said method comprises culturing a cell transfected or transformed with a vector as described above, and retrieving the antibody or portion thereof.

As indicated above, expression of an antibody of the invention (or fragment or variants thereof) preferably comprises expression vector(s) containing a polynucleotide that encodes the desired anti-CD46 antibody. Methods that are well known to those skilled in the art can be used to construct expression vectors comprising antibody coding sequences and appropriate transcriptional and translational control signals. These methods include, for example, in vitro recombinant DNA techniques, synthetic techniques, and in vivo genetic recombination. Embodiments of the invention, thus, provide replicable vectors comprising a nucleotide sequence encoding an anti-CD46 antibody of the invention (e.g., a whole antibody, a heavy or light chain of an antibody, a heavy or light chain variable domain of an antibody, or a portion thereof, or a heavy or light chain CDR, a single chain Fv, or fragments or variants thereof), operably linked to a promoter. In preferred embodiments such vectors may include a nucleotide sequence encoding the heavy chain of an antibody molecule (or fragment thereof), a nucleotide sequence encoding the light chain of an antibody (or fragment thereof) or both the heavy and light chain.

Once the nucleotides of the present invention have been isolated and modified according to the teachings herein, they may be used to produce selected modulators including anti-CD46 antibodies or fragments thereof.

X. Modulator Production and Purification

Using art recognized molecular biology techniques and current protein expression methodology, substantial quantities of the desired modulators may be produced. More specifically, nucleic acid molecules encoding modulators, such as antibodies obtained and engineered as described above, may be integrated into well known and commercially available protein production systems comprising various types of host cells to provide preclinical, clinical or commercial quantities of the desired pharmaceutical product. It will be appreciated that in preferred embodiments the nucleic acid molecules encoding the modulators are engineered into vectors or expression vectors that provide for efficient integration into the selected host cell and subsequent high expression levels of the desired CD46 modulator.

Preferably nucleic acid molecules encoding CD46 modulators and vectors comprising these nucleic acid molecules can be used for transfection of a suitable mammalian, plant, bacterial or yeast host cell though it will be appreciated that prokaryotic systems may be used for modulator production. Transfection can be by any known method for introducing polynucleotides into a host cell. Methods for the introduction of heterologous polynucleotides into mammalian cells are well known in the art and include dextran-mediated transfection, calcium phosphate precipitation, polybrene-mediated transfection, protoplast fusion, electroporation, encapsulation of the polynucleotide(s) in liposomes, and direct microinjection of the DNA into nuclei. In addition, nucleic acid molecules may be introduced into mammalian cells by viral vectors. Methods of transforming mammalian cells are well known in the art. See, e.g., U.S. Pat. Nos. 4,399,216, 4,912,040, 4,740,461, and 4,959,455. Further, methods of transforming plant cells are well known in the art, including, e.g., *Agrobacterium*-mediated transformation, biolistic transformation, direct injection, electroporation and viral transformation. Methods of transforming bacterial and yeast cells are also well known in the art.

Moreover, the host cell may be co-transfected with two expression vectors of the invention, for example, the first vector encoding a heavy chain derived polypeptide and the second vector encoding a light chain derived polypeptide. The two vectors may contain identical selectable markers that enable substantially equal expression of heavy and light chain polypeptides. Alternatively, a single vector may be used which encodes, and is capable of expressing, both heavy and light chain polypeptides. In such situations, the light chain is preferably placed before the heavy chain to avoid an excess of toxic free heavy chain. The coding sequences for the heavy and light chains may comprise cDNA or genomic DNA.

a. Host-Expression Systems

A variety of host-expression vector systems, many commercially available, are compatible with the teachings herein and may be used to express the modulators of the invention. Such host-expression systems represent vehicles by which the coding sequences of interest may be expressed and subsequently purified, but also represent cells which may, when transformed or transfected with the appropriate nucleotide coding sequences, express a molecule of the invention in situ. Such systems include, but are not limited to, microorganisms such as bacteria (e.g., *E. coli, B. subtilis, streptomyces*) transformed with recombinant bacteriophage DNA, plasmid DNA or cosmid DNA expression vectors containing modulator coding sequences; yeast (e.g., *Saccharomyces, Pichia*) transfected with recombinant yeast expression vectors containing modulator coding sequences; insect cell systems infected with recombinant virus expression vectors (e.g., baculovirus) containing modulator coding sequences; plant cell systems (e.g., *Nicotiana, Arabidopsis*, duckweed, corn, wheat, potato, etc.) infected with recombinant virus expression vectors (e.g., cauliflower mosaic virus, CaMV; tobacco mosaic virus, TMV) or transfected with recombinant plasmid expression vectors (e.g., Ti plasmid) containing modulator coding sequences; or mammalian cell systems (e.g., COS, CHO, BHK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the molecule being expressed. For example, when a large quantity of such a protein is to be produced, for the generation of pharmaceutical compositions of a modulator, vectors which direct the expression of high levels of fusion protein products that are readily purified may be desirable. Such vectors include, but are not limited to, the *E. coli* expression vector pUR278 (Ruther et al., EMBO 1. 2:1791 (1983)), in which the coding sequence may be ligated individually into the vector in frame with the lac Z coding region so that a fusion protein is produced; pIN vectors (Inouye & Inouye, Nucleic Acids Res. 13:3101-3109 (1985); Van Heeke & Schuster, J. Biol. Chem. 24:5503-5509 (1989)); and the like. pGEX vectors may also be used to express foreign polypeptides as fusion proteins with glutathione 5-transferase (GST). In general, such fusion proteins are soluble and can easily be purified from lysed cells by adsorption and binding to matrix glutathione agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) may be used as a vector to express foreign genes. The virus grows in *Spodoptera frugiperda* cells. The coding sequences may be cloned individually into non-essential regions (for example, the polyhedrin gene) of the virus and placed under control of an AcNPV promoter (for example, the polyhedrin promoter).

In mammalian host cells, a number of viral-based expression systems may be used to introduce the desired nucleotide sequence. In cases where an adenovirus is used as an expression vector, the coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the molecule in infected hosts (e.g., see Logan & Shenk, Proc. Natl. Acad. Sci. USA 8 1:355-359 (1984)). Specific initiation signals may also be required for efficient translation of inserted coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see, e.g., Bittner et al., Methods in Enzymol. 153:51-544 (1987)). Thus, compatible mammalian cell lines available as hosts for expression are well known in the art and include many immortalized cell lines available from the American Type Culture Collection (ATCC). These include, inter alia, Chinese hamster ovary (CHO) cells, NS0 cells, SP2 cells, HEK-293T cells, 293 Freestyle cells (Life Technologies), NIH-3T3 cells, HeLa cells, baby hamster kidney (BHK) cells, African green monkey kidney cells (COS), human hepatocellular carcinoma cells (e.g., Hep G2), A549 cells, and a number of other cell lines.

For long-term, high-yield production of recombinant proteins stable expression is preferred. Accordingly, cell lines that stably express the selected modulator may be engineered using standard art recognized techniques. Rather than using expression vectors that contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the molecule. Such engineered cell lines may be particularly useful in screening and evaluation of compositions that interact directly or indirectly with the molecule.

A number of selection systems are well known in the art and may be used including, but not limited to, the herpes simplex virus thymidine kinase (Wigler et al., Cell 11:223 (1977)), hypoxanthineguanine phosphoribosyltransferase (Szybalska & Szybalski, Proc. Natl. Acad. Sci. USA 48:202 (1992)), and adenine phosphoribosyltransferase (Lowy et al., Cell 22:8 17 (1980)) genes can be employed in tk-, hgprt- or aprt-cells, respectively. Also, antimetabolite resistance can be used as the basis of selection for the following genes: dhfr, which confers resistance to methotrexate (Wigler et al., Natl. Acad. Sci. USA 77:357 (1980); O'Hare et al., Proc. Natl. Acad. Sci. USA 78:1527 (1981)); gpt, which confers resistance to mycophenolic acid (Mulligan & Berg, Proc. Natl. Acad. Sci. USA 78:2072 (1981)); neo, which confers resistance to the aminoglycoside G-418 (Clinical Pharmacy 12:488-505; Wu and Wu, Biotherapy 3:87-95 (1991); Tolstoshev, Ann. Rev. Pharmacol. Toxicol. 32:573-596 (1993); Mulligan, Science 260:926-932 (1993); and Morgan and Anderson, Ann. Rev. Biochem. 62: 191-217 (1993); TIB TECH 11(5):155-2 15 (May, 1993)); and hygro, which confers resistance to hygromycin (Santerre et al., Gene 30:147 (1984)). Methods commonly known in the art of recombinant DNA technology may be routinely applied to select the desired recombinant clone, and such methods are described, for example, in Ausubel et al. (eds.), Current Protocols in Molecular Biology, John Wiley & Sons, NY (1993); Kriegler, Gene Transfer and Expression, A Laboratory Manual, Stockton Press, NY (1990); and in Chapters 12 and 13, Dracopoli et al. (eds), Current Protocols in Human Genetics, John Wiley & Sons, NY (1994); Colberre-Garapin et al., J. Mol. Biol. 150:1 (1981). It will be appreciated that one particularly preferred method of establishing a stable, high yield cell line comprises the glutamine synthetase gene expression system (the GS system) which provides an efficient approach for enhancing expression under certain conditions. The GS system is discussed in whole or part in connection with EP patents 0 216 846, 0 256 055, 0 323 997 and 0 338 841 each of which is incorporated herein by reference.

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function and/or purification of the protein. Different host cells have characteristic and specific mechanisms for the post-translational processing and modification of proteins and gene products. As known in the art appropriate cell lines or host systems can be chosen to ensure the desired modification and processing of the expressed polypeptide. To this end, eukaryotic host cells that possess the cellular machinery for proper processing of the primary transcript, glycosylation, and phosphorylation of the gene product are particularly effective for use in the instant invention. Accordingly, particularly preferred mammalian host cells include, but are not limited to, CHO, VERY, BHK, HeLa, COS, NS0, MDCK, 293, 3T3, W138, as well as breast cancer cell lines such as, for example, BT483, Hs578T, HTB2, BT2O and T47D, and normal mammary gland cell line such as, for example, CRL7O3O and HsS78Bst. Depending on the modulator and the selected production system, those of skill in the art may easily select and optimize appropriate host cells for efficient expression of the modulator.

b. Chemical Synthesis

Besides the aforementioned host cell systems, it will be appreciated that the modulators of the invention may be chemically synthesized using techniques known in the art (e.g., see Creighton, 1983, Proteins: Structures and Molecular Principles, W.H. Freeman & Co., N.Y., and Hunkapiller, M., et al., 1984, Nature 310:105-111). For example, a peptide corresponding to a polypeptide fragment of the invention can be synthesized by use of a peptide synthesizer. Furthermore, if desired, nonclassical amino acids or chemical amino acid analogs can be introduced as a substitution or addition into a polypeptide sequence. Non-classical amino acids include, but are not limited to, to the D-isomers of the common amino acids, 2,4-diaminobutyric acid, a-amino isobutyric acid, 4-aminobutyric acid, Abu, 2-amino butyric acid, g-Abu, e-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, b-alanine, fluoro-amino acids, designer amino acids such as b-methyl amino acids, Ca-methyl amino acids, Na-methyl amino acids, and amino acid analogs in general. Furthermore, the amino acid can be D (dextrorotary) or L (levorotary).

c. Transgenic Systems

The CD46 modulators of the invention also can be produced transgenically through the generation of a mammal or plant that is transgenic for the immunoglobulin heavy and light chain sequences (or fragments or derivatives or variants thereof) of interest and production of the desired compounds in a recoverable form. In connection with the transgenic production in mammals, anti-CD46 antibodies, for example, can be produced in, and recovered from, the milk of goats, cows, or other mammals. See, e.g., U.S. Pat. Nos. 5,827,690, 5,756,687, 5,750,172, and 5,741,957. In some embodiments, non-human transgenic animals that comprise human immunoglobulin loci are immunized with CD46 or an immunogenic portion thereof, as described above. Methods for making antibodies in plants are described, e.g., in U.S. Pat. Nos. 6,046,037 and 5,959,177.

In accordance with the teachings herein non-human transgenic animals or plants may be produced by introducing one or more nucleic acid molecules encoding a CD46 modulator of the invention into the animal or plant by standard transgenic techniques. See Hogan and U.S. Pat. No. 6,417,429. The transgenic cells used for making the transgenic animal can be embryonic stem cells or somatic cells or a fertilized egg. The transgenic non-human organisms can be chimeric, nonchimeric heterozygotes, and nonchimeric homozygotes. See, e.g., Hogan et al., Manipulating the Mouse Embryo: A Laboratory Manual 2nd ed., Cold Spring Harbor Press (1999); Jackson et al., Mouse Genetics and Transgenics: A Practical Approach, Oxford University Press (2000); and Pinkert, Transgenic Animal Technology: A Laboratory Handbook, Academic Press (1999). In some embodiments, the transgenic non-human animals have a targeted disruption and replacement by a targeting construct that encodes, for example, a heavy chain and/or a light chain of interest. In one embodiment, the transgenic animals comprise and express nucleic acid molecules encoding heavy and light chains that specifically bind to CD46. While anti-CD46 antibodies may be made in any transgenic animal, in particularly preferred embodiments the non-human animals are mice, rats, sheep, pigs, goats, cattle or horses. In further embodiments the non-human transgenic animal expresses the desired pharmaceutical product in blood, milk, urine, saliva, tears, mucus and other bodily fluids from which it is readily obtainable using art recognized purification techniques.

It is likely that modulators, including antibodies, expressed by different cell lines or in transgenic animals will have different glycosylation patterns from each other. However, all modulators encoded by the nucleic acid molecules provided herein, or comprising the amino acid sequences provided herein are part of the instant invention, regardless of the glycosylation state of the molecule, and more generally, regardless of the presence or absence of post-translational modification(s). In addition the invention encompasses modulators that are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited, to specific chemical cleavage by cyanogen bromide, trypsin, chymotrypsin, papain, V8 protease, $NaBH_4$, acetylation, formylation, oxidation, reduction, metabolic synthesis in the presence of tunicamycin, etc. Various post-translational modifications are also encompassed by the invention include, for example, e.g., N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of procaryotic host cell expression. Moreover, as set forth in the text and Examples below the polypeptides may also be modified with a detectable label, such as an enzymatic, fluorescent, radioisotopic or affinity label to allow for detection and isolation of the modulator.

d. Purification

Once a modulator of the invention has been produced by recombinant expression or any one of the other techniques disclosed herein, it may be purified by any method known in the art for purification of immunoglobulins, or more generally by any other standard technique for the purification of proteins. In this respect the modulator may be isolated. As used herein, an isolated CD46 modulator is one that has been identified and separated and/or recovered from a component of its natural environment. Contaminant components of its natural environment are materials that would interfere with diagnostic or therapeutic uses for the polypeptide and may include enzymes, hormones, and other proteinaceous or nonproteinaceous solutes. Isolated modulators include a modulator in situ within recombinant cells because at least one component of the polypeptide's natural environment will not be present.

When using recombinant techniques, the CD46 modulator (e.g. an anti-CD46 antibody or derivative or fragment thereof) can be produced intracellularly, in the periplasmic space, or directly secreted into the medium. If the desired molecule is produced intracellularly, as a first step, the particulate debris, either host cells or lysed fragments, may be removed, for example, by centrifugation or ultrafiltration. For example, Carter, et al., Bio/Technology 10:163 (1992) describe a procedure for isolating antibodies that are secreted to the periplasmic space of E. coli. Briefly, cell paste is thawed in the presence of sodium acetate (pH 3.5), EDTA, and phenylmethylsulfonylfluoride (PMSF) over about 30 minutes. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The modulator (e.g., fc-CD46 or anti-CD46 antibody) composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the selected construct. Protein A can be used to purify antibodies that are based on human IgG1, IgG2 or IgG4 heavy chains (Lindmark, et al., J Immunol Meth 62:1 (1983)). Protein G is recommended for all mouse isotypes and for human IgG3 (Guss, et al., EMBO J. 5:1567 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_H3$ domain, the Bakerbond ABX™ resin (J. T. Baker; Phillipsburg, N.J.) is useful for purification. Other techniques for protein purification such as fractionation on an ion-exchange column, ethanol precipitation, reverse phase HPLC, chromatography on silica, chromatography on heparin, sepharose chromatography on an anion or cation exchange resin (such as a polyaspartic acid column), chromatofocusing, SDS-PAGE and ammonium sulfate precipitation are also available depending on the antibody to be recovered. In particularly preferred embodiments the modulators of the instant invention will be purified, at least in part, using Protein A or Protein G affinity chromatography.

XI. Conjugated CD46 Modulators

Once the modulators of the invention have been purified according to the teachings herein they may be linked with, fused to, conjugated to (e.g., covalently or non-covalently) or otherwise associated with pharmaceutically active or diagnostic moieties or biocompatible modifiers. As used herein the term conjugate will be used broadly and held to mean any molecule associated with the disclosed modulators regardless of the method of association. In this respect it will be understood that such conjugates may comprise peptides, polypeptides, proteins, polymers, nucleic acid molecules, small molecules, mimetic agents, synthetic drugs, inorganic molecules, organic molecules and radioisotopes. Moreover, as indicated above the selected conjugate may be covalently or non-covalently linked to the modulator and exhibit various molar ratios depending, at least in part, on the method used to effect the conjugation.

In preferred embodiments it will be apparent that the modulators of the invention may be conjugated or associated with proteins, polypeptides or peptides that impart selected characteristics (e.g., biotoxins, biomarkers, purification tags, etc.). More generally, in selected embodiments the present invention encompasses the use of modulators or fragments thereof recombinantly fused or chemically conjugated (including both covalent and non-covalent conjugations) to a heterologous protein or polypeptide wherein the polypeptide comprises at least 10, at least 20, at least 30, at least 40, at least 50, at least 60, at least 70, at least 80, at least 90 or at least 100 amino acids. The construct does not necessarily need to be directly linked, but may occur through linker sequences. For example, antibodies may be used to target heterologous polypeptides to particular cell types expressing CD46, either in vitro or in vivo, by fusing or conjugating the modulators of the present invention to antibodies specific for particular cell surface receptors. Moreover, modulators fused or conjugated to heterologous polypeptides may also be used in in vitro immunoassays and may be compatible with purification methodology known in the art. See e.g., International publication No. WO 93/21232; European Patent No. EP 439,095; Naramura et al., 1994, Immunol. Lett. 39:91-99; U.S. Pat. No. 5,474,981; Gillies et al., 1992, PNAS 89:1428-1432; and Fell et al., 1991, J. Immunol. 146:2446-2452.

a. Biocompatible Modifiers

In a preferred embodiment, the modulators of the invention may be conjugated or otherwise associated with biocompatible modifiers that may be used to adjust, alter, improve or moderate modulator characteristics as desired. For example, antibodies or fusion constructs with increased in vivo half-lives can be generated by attaching relatively high molecular weight polymer molecules such as commercially available polyethylene glycol (PEG) or similar biocompatible polymers. Those skilled in the art will appreciate that PEG may be obtained in many different molecular weight and molecular configurations that can be selected to impart specific properties to the antibody (e.g. the half-life may be tailored). PEG can be attached to modulators or antibody fragments or derivatives with or without a multifunctional linker either through site-specific conjugation of the PEG to the N- or C-terminus of said antibodies or antibody fragments or via epsilon-amino groups present on lysine residues. Linear or branched polymer derivatization that results in minimal loss of biological activity may be used. The degree of conjugation can be closely monitored by SDS-PAGE and mass spectrometry to ensure optimal conjugation of PEG molecules to antibody molecules. Unreacted PEG can be separated from antibody-PEG conjugates by, e.g., size exclusion or ion-exchange chromatography. In a similar manner, the disclosed modulators can be conjugated to albumin in order to make the antibody or antibody fragment more stable in vivo or have a longer half life in vivo. The techniques are well known in the art, see e.g., International Publication Nos. WO 93/15199, WO 93/15200, and WO 01/77137; and European Patent No. 0 413, 622. Other biocompatible conjugates are evident to those of ordinary skill and may readily be identified in accordance with the teachings herein.

b. Diagnostic or Detection Agents

In other preferred embodiments, modulators of the present invention, or fragments or derivatives thereof, are conjugated to a diagnostic or detectable agent which may be a biological molecule (e.g., a peptide or nucleotide) or a small molecule or radioisotope. Such modulators can be useful for monitoring the development or progression of a hyperproliferative disorder or as part of a clinical testing procedure to determine the efficacy of a particular therapy including the disclosed modulators. Such markers may also be useful in purifying the selected modulator, separating or isolating TIC or in preclinical procedures or toxicology studies.

Such diagnosis and detection can be accomplished by coupling the modulator to detectable substances including, but not limited to, various enzymes comprising for example horseradish peroxidase, alkaline phosphatase, beta-galactosidase, or acetylcholinesterase; prosthetic groups, such as but not limited to streptavidin/biotin and avidin/biotin; fluorescent materials, such as but not limited to, umbelliferone, fluorescein, fluorescein isothiocynate, rhodamine, dichlorotriazinylamine fluorescein, dansyl chloride or phycoerythrin; luminescent materials, such as but not limited to, luminol; bioluminescent materials, such as but not limited to, luciferase, luciferin, and aequorin; radioactive materials, such as but not limited to iodine ($^{131}I$, $^{125}I$, $^{123}I$, $^{121}I$,), carbon ($^{14}C$), sulfur ($^{35}S$), tritium ($^{3}H$), indium ($^{115}In$, $^{113}In$, $^{112}In$, $^{111}In$,), and technetium ($^{99}Tc$), thallium ($^{201}Ti$) gallium ($^{68}Ga$, $^{67}Ga$), palladium ($^{103}Pd$), molybdenum ($^{99}Mo$), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, $^{113}$Sn, and $^{117}$Tin; positron emitting metals using various positron emission tomographies, noradioactive paramagnetic metal ions, and molecules that are radiolabeled or conjugated to specific radioisotopes. In such embodiments appropriate detection methodology is well known in the art and readily available from numerous commercial sources.

As indicated above, in other embodiments the modulators or fragments thereof can be fused to marker sequences, such as a peptide or fluorophore to facilitate purification or diagnostic procedures such as immunohistochemistry or FACs. In preferred embodiments, the marker amino acid sequence is a hexa-histidine peptide, such as the tag provided in a pQE vector (Qiagen), among others, many of which are commercially available. As described in Gentz et al., 1989, Proc. Natl. Acad. Sci. USA 86:821-824, for instance, hexa-histidine provides for convenient purification of the fusion protein. Other peptide tags useful for purification include, but are not limited to, the hemagglutinin "HA" tag, which corresponds to an epitope derived from the influenza hemagglutinin protein (Wilson et al., 1984, Cell 37:767) and the "flag" tag (U.S. Pat. No. 4,703,004).

c. Therapeutic Moieties

As previously alluded to the modulators or fragments or derivatives thereof may also be conjugated, linked or fused to or otherwise associated with a therapeutic moiety such as a cytotoxin or cytotoxic agent, e.g., a cytostatic or cytocidal agent, a therapeutic agent or a radioactive metal ion, e.g., alpha or beta-emitters. As used herein a cytotoxin or cytotoxic agent includes any agent or therapeutic moiety that is detrimental to cells and may inhibit cell growth or survival. Examples include paclitaxel, cytochalasin B, gramicidin D, ethidium bromide, emetine, mitomycin, etoposide, tenoposide, vincristine, vinblastine, colchicin, doxorubicin, daunorubicin, dihydroxy anthracin, maytansinoids such as DM-1 and DM-4 (Immunogen, Inc.), dione, mitoxantrone, mithramycin, actinomycin D, 1-dehydrotestosterone, glucocorticoids, procaine, tetracaine, lidocaine, propranolol, puromycin, epirubicin, and cyclophosphamide and analogs or homologs thereof. Additional cytoxins comprise auristatins, including monomethyl auristatin E (MMAE) and monomethyl auristatin F (MMAF) (Seattle Genetics, Inc.), amanitins such as alpha-amanitin, beta-amanitin, gamma-amanitin or epsilon-amanitin (Heidelberg Pharma AG), DNA minor groove binding agents such as duocarmycin derivatives (Syntarga, B.V.) and modified pyrrolobenzodiazepine dimers (PBDs, Spirogen, Ltd). Furthermore, in one embodiment the CD46 modulators of the instant invention may be associated with anti-CD3 binding molecules to recruit cytotoxic T-cells and have them target the tumor initiating cells (BiTE technology; see e.g., Fuhrmann, S. et. al. *Annual Meeting of AACR Abstract No.* 5625 (2010) which is incorporated herein by reference).

Additional compatible therapeutic moieties comprise cytotoxic agents including, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BCNU) and lomustine (CCNU), cyclothosphamide, busulfan, dibromomannitol, streptozotocin, mitomycin C, and cisdichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). A more extensive list of therapeutic moieties can be found in PCT publication WO 03/075957 and U.S.P.N. 2009/0155255 each of which is incorporated herein by reference.

The selected modulators can also be conjugated to therapeutic moieties such as radioactive materials or macrocyclic chelators useful for conjugating radiometal ions (see above for examples of radioactive materials). In certain embodiments, the macrocyclic chelator is 1,4,7,10-tetraazacyclododecane-N,N',N'',N'''-tetraacetic acid (DOTA) which can be attached to the antibody via a linker molecule. Such linker molecules are commonly known in the art and described in Denardo et al., 1998, Clin Cancer Res. 4:2483; Peterson et al., 1999, Bioconjug. Chem. 10:553; and Zimmerman et al., 1999, Nucl. Med. Biol. 26:943.

Exemplary radioisotopes that may be compatible with this aspect of the invention include, but are not limited to, iodine ($^{131}$I, $^{125}$I, $^{123}$I, $^{121}$I) carbon ($^{14}$C), copper ($^{62}$Cu, $^{64}$Cu, $^{67}$Cu), sulfur ($^{35}$S), tritium ($^{3}$H), indium ($^{115}$In, $^{113}$In, $^{112}$In, $^{111}$In,), bismuth ($^{212}$Bi, $^{213}$Bi), technetium ($^{99}$Tc), thallium ($^{201}$Ti) gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, $^{113}$Sn, $^{117}$Tin, $^{225}$Ac, $^{76}$Br, and $^{211}$At. Other radionuclides are also available as diagnostic and therapeutic agents, especially those in the energy range of 60 to 4,000 keV. Depending on the condition to be treated and the desired therapeutic profile, those skilled in the art may readily select the appropriate radioisotope for use with the disclosed modulators.

CD46 modulators of the present invention may also be conjugated to a therapeutic moiety or drug that modifies a given biological response. That is, therapeutic agents or moieties compatible with the instant invention are not to be construed as limited to classical chemical therapeutic agents. For example, in particularly preferred embodiments the drug moiety may be a protein or polypeptide or fragment thereof possessing a desired biological activity. Such proteins may include, for example, a toxin such as abrin, ricin A, Onconase (or another cytotoxic RNase), pseudomonas exotoxin, cholera toxin, or diphtheria toxin; a protein such as tumor necrosis factor, α-interferon, β-interferon, nerve growth factor, platelet derived growth factor, tissue plasminogen activator, an apoptotic agent, e.g., TNF-α, TNF-β, AIM I (see, International Publication No. WO 97/33899), AIM II (see, International Publication No. WO 97/34911), Fas Ligand (Takahashi et al., 1994, J. Immunol., 6:1567), and VEGI (see, International Publication No. WO 99/23105), a thrombotic agent or an anti-angiogenic agent, e.g., angiostatin or endostatin; or, a biological response modifier such as, for example, a lymphokine (e.g., interleukin-1 ("IL-1"), interleukin-2 ("IL-2"), interleukin-6 ("IL-6"), granulocyte macrophage colony stimulating factor ("GM-CSF"), and granulocyte colony stimulating factor ("G-CSF")), or a growth factor (e.g., growth hormone ("GH")). As set forth above, methods for fusing or conjugating modulators to polypeptide moieties are known in the art. In addition to the previously disclosed subject references see, e.g., U.S. Pat. Nos. 5,336,603; 5,622,929; 5,359,046; 5,349,053; 5,447, 851, and 5,112,946; EP 307,434; EP 367,166; PCT Publications WO 96/04388 and WO 91/06570; Ashkenazi et al., 1991, PNAS USA 88:10535; Zheng et al., 1995, J Immunol 154:5590; and Vil et al., 1992, PNAS USA 89:11337 each of which is incorporated herein by reference. The association of a modulator with a moiety does not necessarily need to be direct, but may occur through linker sequences. Such linker molecules are commonly known in the art and described in Denardo et al., 1998, Clin Cancer Res 4:2483; Peterson et al., 1999, Bioconjug Chem 10:553; Zimmerman et al., 1999, Nucl Med Biol 26:943; Garnett, 2002, Adv Drug Deliv Rev 53:171 each of which is incorporated herein.

More generally, techniques for conjugating therapeutic moieties or cytotoxic agents to modulators are well known. Moieties can be conjugated to modulators by any art-recognized method, including, but not limited to aldehyde/Schiff linkage, sulphydryl linkage, acid-labile linkage, cis-aconityl linkage, hydrazone linkage, enzymatically degradable linkage (see generally Garnett, 2002, Adv Drug Deliv Rev 53:171). Also see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., 1982, Immunol. Rev. 62:119. In preferred embodiments a CD46 modulator that is conjugated to a therapeutic moiety or cytotoxic agent may be internalized by a cell upon binding to a CD46 molecule associated with the cell surface thereby delivering the therapeutic payload.

XII. Diagnostics and Screening

As indicated, the present invention provides methods for detecting or diagnosing hyperproliferative disorders and methods of screening cells from a patient to identify a tumor initiating cell. Such methods include identifying an individual having cancer for treatment or monitoring progression of a cancer comprising contacting a sample obtained from a patient with a CD46 modulator as described herein and detecting presence or absence, or level of association of the modulator to bound or free CD46 in the sample. When the modulator comprises an antibody or immunologically active fragment thereof the association with CD46 in the sample indicates that the sample may contain tumor perpetuating cells (e.g., a cancer stem cells) indicating that the individual having cancer may be effectively treated with a CD46 modulator as described herein. The methods may further comprise a step of comparing the level of binding to a control. Conversely, when the selected modulator is Fc-CD46 the enzymatic properties of the molecule as described herein may be monitored (directly or indirectly) when in contact with the sample to provide the desired information. Other diagnostic methods compatible with the teachings herein are well known in the art and can be practiced using commercial materials such as dedicated reporting systems.

Exemplary compatible assay methods include radioimmunoassays, enzyme immunoassays, competitive-binding assays, fluorescent immunoassay, immunoblot assays, Western Blot analysis, flow cytometry assays, and ELISA assays. More generally detection of CD46 in a biological sample or the measurement of CD46 enzymatic activity (or inhibition thereof) may be accomplished using any art-known assay.

In another aspect, and as discussed in more detail below, the present invention provides kits for detecting, monitoring or diagnosing a hyperproliferative disorder, identifying individual having such a disorder for possible treatment or monitoring progression (or regression) of the disorder in a patient, wherein the kit comprises a modulator as described herein, and reagents for detecting the impact of the modulator on a sample.

The CD46 modulators and cells, cultures, populations and compositions comprising the same, including progeny thereof, can also be used to screen for or identify compounds or agents (e.g., drugs) that affect a function or activity of tumor initiating cells or progeny thereof by interacting with CD46 (e.g., the polypeptide or genetic components thereof). The invention therefore further provides systems and methods for evaluation or identification of a compound or agent that can affect a function or activity tumor initiating cells or progeny thereof by associating with CD46 or its substrates. Such compounds and agents can be drug candidates that are screened for the treatment of a hyperproliferative disorder, for example. In one embodiment, a system or method includes tumor initiating cells exhibiting CD46 and a compound or agent (e.g., drug), wherein the cells and compound or agent (e.g., drug) are in contact with each other.

The invention further provides methods of screening and identifying CD46 modulators or agents and compounds for altering an activity or function of tumor initiating cells or progeny cells. In one embodiment, a method includes contacting tumor initiating cells or progeny thereof with a test agent or compound; and determining if the test agent or compound modulates an activity or function of the $CD46^{hi}$ tumor initiating cells.

A test agent or compound modulating a CD46 related activity or function of such tumor initiating cells or progeny thereof within the population identifies the test agent or compound as an active agent. Exemplary activity or function that can be modulated include changes in cell morphology, expression of a marker, differentiation or de-differentiation, maturation, proliferation, viability, apoptosis or cell death neuronal progenitor cells or progeny thereof.

Contacting, when used in reference to cells or a cell culture or method step or treatment, means a direct or indirect interaction between the composition (e.g., $CD46^{hi}$ cell or cell culture) and another referenced entity. A particular example of a direct interaction is physical interaction. A particular example of an indirect interaction is where a composition acts upon an intermediary molecule which in turn acts upon the referenced entity (e.g., cell or cell culture).

In this aspect of the invention modulates indicates influencing an activity or function of tumor initiating cells or progeny cells in a manner compatible with detecting the effects on cell activity or function that has been determined to be relevant to a particular aspect (e.g., metastasis or proliferation) of the tumor initiating cells or progeny cells of the invention. Exemplary activities and functions include, but are not limited to, measuring morphology, developmental markers, differentiation, proliferation, viability, cell respiration, mitochondrial activity, membrane integrity, or expression of markers associated with certain conditions. Accordingly, a compound or agent (e.g., a drug candidate) can be evaluated for its effect on tumor initiating cells or progeny cells, by contacting such cells or progeny cells with the compound or agent and measuring any modulation of an activity or function of tumor initiating cells or progeny cells as disclosed herein or would be known to the skilled artisan.

Methods of screening and identifying agents and compounds include those suitable for high throughput screening, which include arrays of cells (e.g., microarrays) positioned or placed, optionally at pre-determined locations or addresses. High-throughput robotic or manual handling methods can probe chemical interactions and determine levels of expression of many genes in a short period of time. Techniques have been developed that utilize molecular signals (e.g., fluorophores) and automated analyses that process information at a very rapid rate (see, e.g., Pinhasov et al., Comb. Chem. High Throughput Screen. 7:133 (2004)). For example, microarray technology has been extensively utilized to probe the interactions of thousands of genes at once, while providing information for specific genes (see, e.g., Mocellin and Rossi, Adv. Exp. Med. Biol. 593:19 (2007)).

Such screening methods (e.g., high-throughput) can identify active agents and compounds rapidly and efficiently. For example, cells can be positioned or placed (pre-seeded) on a culture dish, tube, flask, roller bottle or plate (e.g., a single multi-well plate or dish such as an 8, 16, 32, 64, 96, 384 and 1536 multi-well plate or dish), optionally at defined locations, for identification of potentially therapeutic molecules. Libraries that can be screened include, for example, small molecule libraries, phage display libraries, fully human antibody yeast display libraries (Adimab, LLC), siRNA libraries, and adenoviral transfection vectors.

XIII. Pharmaceutical Preparations and Therapeutic Uses a. Formulations and Routes of Administration Depending on the form of the modulator along with any optional conjugate, the mode of intended delivery, the disease being treated or monitored and numerous other variables, compositions of the instant invention may be formulated as desired using art recognized techniques. That is, in various embodiments of the instant invention compositions comprising CD46 modulators are formulated with a wide variety of pharmaceutically acceptable carriers (see, e.g., Gennaro, *Remington: The Science and Practice of Pharmacy with Facts and Comparisons: Drugfacts Plus*, 20th ed. (2003); Ansel et al., *Pharmaceutical Dosage Forms and Drug Delivery Systems*, 7$^{th}$ ed., Lippencott Williams and Wilkins (2004); Kibbe et al., *Handbook of Pharmaceutical Excipients*, 3$^{rd}$ ed., Pharmaceutical Press (2000)). Various pharmaceutically acceptable carriers, which include vehicles, adjuvants, and diluents, are readily available from numerous commercial sources. Moreover, an assortment of pharmaceutically acceptable auxiliary substances, such as pH adjusting and buffering agents, tonicity adjusting agents, stabilizers, wetting agents and the like, are also available. Certain non-limiting exemplary carriers include saline, buffered saline, dextrose, water, glycerol, ethanol, and combinations thereof.

More particularly it will be appreciated that, in some embodiments, the therapeutic compositions of the invention may be administered neat or with a minimum of additional components. Conversely the CD46 modulators of the present invention may optionally be formulated to contain suitable pharmaceutically acceptable carriers comprising excipients and auxiliaries that are well known in the art and are relatively inert substances that facilitate administration of the modulator or which aid processing of the active compounds into preparations that are pharmaceutically optimized for delivery to the site of action. For example, an excipient can give form or consistency or act as a diluent to improve the pharmacokinetics of the modulator. Suitable excipients include but are not limited to stabilizing agents, wetting and emulsifying agents, salts for varying osmolarity, encapsulating agents, buffers, and skin penetration enhancers.

Disclosed modulators for systemic administration may be formulated for enteral, parenteral or topical administration. Indeed, all three types of formulation may be used simultaneously to achieve systemic administration of the active ingredient. Excipients as well as formulations for parenteral and nonparenteral drug delivery are set forth in Remington, The Science and Practice of Pharmacy 20th Ed. Mack Publishing (2000). Suitable formulations for parenteral administration include aqueous solutions of the active compounds in water-soluble form, for example, water-soluble salts. In addition, suspensions of the active compounds as appropriate for oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances that increase the viscosity of the suspension and include, for example, sodium carboxymethyl cellulose, sorbitol, and/or dextran. Optionally, the suspension may also contain stabilizers. Liposomes can also be used to encapsulate the agent for delivery into the cell.

Suitable formulations for enteral administration include hard or soft gelatin capsules, pills, tablets, including coated tablets, elixirs, suspensions, syrups or inhalations and controlled release forms thereof.

In general the compounds and compositions of the invention, comprising CD46 modulators may be administered in vivo, to a subject in need thereof, by various routes, including, but not limited to, oral, intravenous, intra-arterial, subcutaneous, parenteral, intranasal, intramuscular, intracardiac, intraventricular, intratracheal, buccal, rectal, intraperitoneal, intradermal, topical, transdermal, and intrathecal, or otherwise by implantation or inhalation. The subject compositions may be formulated into preparations in solid, semi-solid, liquid, or gaseous forms; including, but not limited to, tablets, capsules, powders, granules, ointments, solutions, suppositories, enemas, injections, inhalants, and aerosols. The appropriate formulation and route of administration may be selected according to the intended application and therapeutic regimen.

b. Dosages

Similarly, the particular dosage regimen, i.e., dose, timing and repetition, will depend on the particular individual and that individual's medical history. Empirical considerations, such as the half-life, generally will contribute to the determination of the dosage. Frequency of administration may be determined and adjusted over the course of therapy, and is based on reducing the number of hyperproliferative or neoplastic cells, including tumor initiating cells, maintaining the reduction of such neoplastic cells, reducing the proliferation of neoplastic cells, or delaying the development of metastasis. Alternatively, sustained continuous release formulations of a subject therapeutic composition may be appropriate. As alluded to above various formulations and devices for achieving sustained release are known in the art.

From a therapeutic standpoint the pharmaceutical compositions are administered in an amount effective for treatment or prophylaxis of the specific indication. The therapeutically effective amount is typically dependent on the weight of the subject being treated, his or her physical or health condition, the extensiveness of the condition to be treated, or the age of the subject being treated. In general, the CD46 modulators of the invention may be administered in an amount in the range of about 10 µg/kg body weight to about 100 mg/kg body weight per dose. In certain embodiments, the CD46 modulators of the invention may be administered in an amount in the range of about 50 μg/kg body weight to about 5 mg/kg body weight per dose. In certain other embodiments, the CD46 modulators of the invention may be administered in an amount in the range of about 100 μg/kg body weight to about 10 mg/kg body weight per dose. Optionally, the CD46 modulators of the invention may be administered in an amount in the range of about 100 μg/kg body weight to about 20 mg/kg body weight per dose. Further optionally, the CD46 modulators of the invention may be administered in an amount in the range of about 0.5 mg/kg body weight to about 20 mg/kg body weight per dose. In certain embodiments the compounds of present invention are provided a dose of at least about 100 μg/kg body weight, at least about 250 μg/kg body weight, at least about 750 μg/kg body weight, at least about 3 mg/kg body weight, at least about 5 mg/kg body weight, at least about 10 mg/kg body weight is administered.

Other dosing regimens may be predicated on Body Surface Area (BSA) calculations as disclosed in U.S. Pat. No. 7,744,877 which is incorporated herein by reference in its entirety. As is well known in the art the BSA is calculated using the patient's height and weight and provides a measure of a subject's size as represented by the surface area of his or her body. In selected embodiments of the invention using the BSA the modulators may be administered in dosages from 10 mg/m$^2$ to 800 mg/m$^2$. In other preferred embodiments the modulators will be administered in dosages from 50 mg/m$^2$ to 500 mg/m$^2$ and even more preferably at dosages of 100 mg/m$^2$, 150 mg/m$^2$, 200 mg/m$^2$, 250 mg/m$^2$, 300 mg/m$^2$, 350 mg/m$^2$, 400 mg/m$^2$ or 450 mg/m$^2$. Of course it will be appreciated that, regardless of how the dosages are calculated, multiple dosages may be administered over a selected time period to provide an absolute dosage that is substantially higher than the individual administrations.

In any event, the CD46 modulators are preferably administered as needed to subjects in need thereof. Determination of the frequency of administration may be made by persons skilled in the art, such as an attending physician based on considerations of the condition being treated, age of the subject being treated, severity of the condition being treated, general state of health of the subject being treated and the like. Generally, an effective dose of the CD46 modulator is administered to a subject one or more times. More particularly, an effective dose of the modulator is administered to the subject once a month, more than once a month, or less than once a month. In certain embodiments, the effective dose of the CD46 modulator may be administered multiple times, including for periods of at least a month, at least six months, or at least a year.

Dosages and regimens may also be determined empirically for the disclosed therapeutic compositions in individuals who have been given one or more administration(s). For example, individuals may be given incremental dosages of a therapeutic composition produced as described herein. To assess efficacy of the selected composition, a marker of the specific disease, disorder or condition can be followed. In embodiments where the individual has cancer, these include direct measurements of tumor size via palpation or visual observation, indirect measurement of tumor size by x-ray or other imaging techniques; an improvement as assessed by direct tumor biopsy and microscopic examination of the tumor sample; the measurement of an indirect tumor marker (e.g., PSA for prostate cancer) or an antigen identified according to the methods described herein, a decrease in pain or paralysis; improved speech, vision, breathing or other disability associated with the tumor; increased appetite; or an increase in quality of life as measured by accepted tests or prolongation of survival. It will be apparent to one of skill in the art that the dosage will vary depending on the individual, the type of neoplastic condition, the stage of neoplastic condition, whether the neoplastic condition has begun to metastasize to other location in the individual, and the past and concurrent treatments being used.

c. Combination Therapies

Combination therapies contemplated by the invention may be particularly useful in decreasing or inhibiting unwanted neoplastic cell proliferation (e.g. endothelial cells), decreasing the occurrence of cancer, decreasing or preventing the recurrence of cancer, or decreasing or preventing the spread or metastasis of cancer. In such cases the compounds of the instant invention may function as sensitizing or chemosensitizing agent by removing the TPC propping up and perpetuating the tumor mass (e.g. NTG cells) and allow for more effective use of current standard of care debulking or anti-cancer agents. That is, a combination therapy comprising an CD46 modulator and one or more anti-cancer agents may be used to diminish established cancer e.g., decrease the number of cancer cells present and/or decrease tumor burden, or ameliorate at least one manifestation or side effect of cancer. As such, combination therapy refers to the administration of a CD46 modulator and one or more anti-cancer agent that include, but are not limited to, cytotoxic agents, cytostatic agents, chemotherapeutic agents, targeted anti-cancer agents, biological response modifiers, immunotherapeutic agents, cancer vaccines, anti-angiogenic agents, cytokines, hormone therapies, radiation therapy and anti-metastatic agents.

According to the methods of the present invention, there is no requirement for the combined results to be additive of the effects observed when each treatment (e.g., anti-CD46 antibody and anti-cancer agent) is conducted separately. Although at least additive effects are generally desirable, any increased anti-tumor effect above one of the single therapies is beneficial. Furthermore, the invention does not require the combined treatment to exhibit synergistic effects. However, those skilled in the art will appreciate that with certain selected combinations that comprise preferred embodiments, synergism may be observed.

To practice combination therapy according to the invention, a CD46 modulator (e.g., anti-CD46 antibody) in combination with one or more anti-cancer agent may be administered to a subject in need thereof in a manner effective to result in anti-cancer activity within the subject. The CD46 modulator and anti-cancer agent are provided in amounts effective and for periods of time effective to result in their combined presence and their combined actions in the tumor environment as desired. To achieve this goal, the CD46 modulator and anti-cancer agent may be administered to the subject simultaneously, either in a single composition, or as two or more distinct compositions using the same or different administration routes.

Alternatively, the modulator may precede, or follow, the anti-cancer agent treatment by, e.g., intervals ranging from minutes to weeks. In certain embodiments wherein the anti-cancer agent and the antibody are applied separately to the subject, the time period between the time of each delivery is such that the anti-cancer agent and modulator are able to exert a combined effect on the tumor. In a particular embodiment, it is contemplated that both the anti-cancer agent and the CD46 modulator are administered within about 5 minutes to about two weeks of each other.

In yet other embodiments, several days (2, 3, 4, 5, 6 or 7), several weeks (1, 2, 3, 4, 5, 6, 7 or 8) or several months (1, 2, 3, 4, 5, 6, 7 or 8) may lapse between administration of the modulator and the anti-cancer agent. The CD46 modulator and one or more anti-cancer agent (combination therapy) may be administered once, twice or at least the period of time until the condition is treated, palliated or cured. Preferably, the combination therapy is administered multiple times. The combination therapy may be administered from three times daily to once every six months. The administering may be on a schedule such as three times daily, twice daily, once daily, once every two days, once every three days, once weekly, once every two weeks, once every month, once every two months, once every three months, once every six months or may be administered continuously via a minipump. As previously indicated the combination therapy may be administered via an oral, mucosal, buccal, intranasal, inhalable, intravenous, subcutaneous, intramuscular, parenteral, intratumor or topical route. The combination therapy may be administered at a site distant from the site of the tumor. The combination therapy generally will be administered for as long as the tumor is present provided that the combination therapy causes the tumor or cancer to stop growing or to decrease in weight or volume.

In one embodiment a CD46 modulator is administered in combination with one or more anti-cancer agents for a short treatment cycle to a cancer patient to treat cancer. The duration of treatment with the antibody may vary according to the particular anti-cancer agent used. The invention also contemplates discontinuous administration or daily doses divided into several partial administrations. An appropriate treatment time for a particular anti-cancer agent will be appreciated by the skilled artisan, and the invention contemplates the continued assessment of optimal treatment schedules for each anti-cancer agent.

The present invention contemplates at least one cycle, preferably more than one cycle during which the combination therapy is administered. An appropriate period of time for one cycle will be appreciated by the skilled artisan, as will the total number of cycles, and the interval between cycles. The invention contemplates the continued assessment of optimal treatment schedules for each modulator and anti-cancer agent. Moreover, the invention also provides for more than one administration of either the anti-CD46 antibody or the anti-cancer agent. The modulator and anti-cancer agent may be administered interchangeably, on alternate days or weeks; or a sequence of antibody treatment may be given, followed by one or more treatments of anti-cancer agent therapy. In any event, as will be understood by those of ordinary skill in the art, the appropriate doses of chemotherapeutic agents will be generally around those already employed in clinical therapies wherein the chemotherapeutics are administered alone or in combination with other chemotherapeutics.

In another preferred embodiment the CD46 modulators of the instant invention may be used in maintenance therapy to reduce or eliminate the chance of tumor recurrence following the initial presentation of the disease. Preferably the disorder will have been treated and the initial tumor mass eliminated, reduced or otherwise ameliorated so the patient is asymptomatic or in remission. As such time the subject may be administered pharmaceutically effective amounts of the disclosed effectors one or more times even though there is little or no indication of disease using standard diagnostic procedures. In some embodiments the effectors will be administered on a regular schedule over a period of time. For example the CD46 modulators could be administered weekly, every two weeks, monthly, every six weeks, every two months, every three months every six months or annually. Given the teachings herein one skilled in the art could readily determine favorable dosages and dosing regimens to reduce the potential of disease recurrence. Moreover such treatments could be continued for a period of weeks, months, years or even indefinitely depending on the patient response and clinical and diagnostic parameters.

In yet another preferred embodiment the effectors of the present invention may be used to prophylactically to prevent or reduce the possibility of tumor metastasis following a debulking procedure. As used in the instant disclosure a debulking procedure is defined broadly and shall mean any procedure, technique or method that eliminates, reduces, treats or ameliorates a tumor or tumor proliferation. Exemplary debulking procedures include, but are not limited to, surgery, radiation treatments (i.e., beam radiation), chemotherapy or ablation. At appropriate times readily determined by one skilled in the art in view of the instant disclosure the CD46 modulators may be administered as suggested by clinical and diagnostic procedures to reduce tumor metastasis. The effectors may be administered one or more times at pharmaceutically effective dosages as determined using standard techniques. Preferably the dosing regimen will be accompanied by appropriate diagnostic or monitoring techniques that allow it to be modified as necessary.

d. Anti-Cancer Agents

As used herein the term anti-cancer agent means any agent that can be used to treat a cell proliferative disorder such as cancer, including cytotoxic agents, cytostatic agents, anti-angiogenic agents, debulking agents, chemotherapeutic agents, radiotherapy and radiotherapeutic agents, targeted anti-cancer agents, biological response modifiers, antibodies, and immunotherapeutic agents. It will be appreciated that, in selected embodiments as discussed above, anti-cancer agents may comprise conjugates and may be associated with modulators prior to administration.

The term cytotoxic agent means a substance that decreases or inhibits the function of cells and/or causes destruction of cells, i.e., the substance is toxic to the cells. Typically, the substance is a naturally occurring molecule derived from a living organism. Examples of cytotoxic agents include, but are not limited to, small molecule toxins or enzymatically active toxins of bacteria (e.g., *Diptheria* toxin, *Pseudomonas* endotoxin and exotoxin, Staphylococcal enterotoxin A), fungal (e.g., α-sarcin, restrictocin), plants (e.g., abrin, ricin, modeccin, viscumin, pokeweed anti-viral protein, saporin, gelonin, momoridin, trichosanthin, barley toxin, Aleurites fordii proteins, dianthin proteins, *Phytolacca mericana* proteins (PAPI, PAPII, and PAP-S), *Momordica charantia* inhibitor, curcin, crotin, *saponaria officinalis* inhibitor, gelonin, mitegellin, restrictocin, phenomycin, neomycin, and the tricothecenes) or animals, e.g., cytotoxic RNases, such as extracellular pancreatic RNases; DNase I, including fragments and/or variants thereof.

A chemotherapeutic agent means a chemical compound that non-specifically decreases or inhibits the growth, proliferation, and/or survival of cancer cells (e.g., cytotoxic or cytostatic agents). Such chemical agents are often directed to intracellular processes necessary for cell growth or division, and are thus particularly effective against cancerous cells, which generally grow and divide rapidly. For example, vincristine depolymerizes microtubules, and thus inhibits cells from entering mitosis. In general, chemotherapeutic agents can include any chemical agent that inhibits, or is designed to inhibit, a cancerous cell or a cell likely to become cancerous or generate tumorigenic progeny (e.g., TIC). Such agents are often administered, and are often most effective, in combination, e.g., in the formulation CHOP.

Examples of anti-cancer agents that may be used in combination with (or conjugated to) the modulators of the present invention include, but are not limited to, alkylating agents, alkyl sulfonates, aziridines, ethylenimines and methylamelamines, acetogenins, a camptothecin, bryostatin, callystatin, CC-1065, cryptophycins, dolastatin, duocarmycin, eleutherobin, pancratistatin, a sarcodictyin, spongistatin, nitrogen mustards, antibiotics, enediyne antibiotics, dynemicin, bisphosphonates, an esperamicin, chromoprotein enediyne antiobiotic chromophores, aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites, folic acid analogues, purine analogs, androgens, anti-adrenals, folic acid replenisher such as frolinic acid, aceglatone, aldophosphamide glycoside, aminolevulinic acid, eniluracil, amsacrine, bestrabucil, bisantrene, edatraxate, defofamine, demecolcine, diaziquone, elformithine, elliptinium acetate, an epothilone, etoglucid, gallium nitrate, hydroxyurea, lentinan, lonidainine, maytansinoids, mitoguazone, mitoxantrone, mopidanmol, nitraerine, pentostatin, phenamet, pirarubicin, losoxantrone, podophyllinic acid, 2-ethylhydrazide, procarbazine, PSK® polysaccharide complex (JHS Natural Products, Eugene, Oreg.), razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, chloranbucil; GEMZAR® gemcitabine; 6-thioguanine; mercaptopurine; methotrexate; platinum analogs, vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (Camptosar, CPT-11), topoisomerase inhibitor RFS 2000; difluoromethylornithine (DMFO); retinoids; capecitabine; combretastatin; leucovorin (LV); oxaliplatin; inhibitors of PKC-alpha, Raf, H-Ras, EGFR and VEGF-A that reduce cell proliferation and pharmaceutically acceptable salts, acids or derivatives of any of the above. Also included in this definition are anti-hormonal agents that act to regulate or inhibit hormone action on tumors such as anti-estrogens and selective estrogen receptor modulators (SERMs), aromatase inhibitors that inhibit the enzyme aromatase, which regulates estrogen production in the adrenal glands, and anti-androgens; as well as troxacitabine (a 1,3-dioxolane nucleoside cytosine analog); antisense oligonucleotides; ribozymes such as a VEGF expression inhibitor and a HER2 expression inhibitor; vaccines, PROLEUKIN® rIL-2; LURTOTECAN® topoisomerase 1 inhibitor; ABARELIX® rmRH; Vinorelbine and Esperamicins and pharmaceutically acceptable salts, acids or derivatives of any of the above. Other embodiments comprise the use of antibodies approved for cancer therapy including, but not limited to, rituximab, trastuzumab, gemtuzumab ozogamcin, alemtuzumab, ibritumomab tiuxetan, tositumomab, bevacizumab, cetuximab, patitumumab, ofatumumab, ipilimumab and brentuximab vedotin. Those skilled in the art will be able to readily identify additional anti-cancer agents that are compatible with the teachings herein.

e. Radiotherapy

The present invention also provides for the combination of CD46 modulators with radiotherapy (i.e., any mechanism for inducing DNA damage locally within tumor cells such as gamma.-irradiation, X-rays, UV-irradiation, microwaves, electronic emissions and the like). Combination therapy using the directed delivery of radioisotopes to tumor cells is also contemplated, and may be used in connection with a targeted anti-cancer agent or other targeting means. Typically, radiation therapy is administered in pulses over a period of time from about 1 to about 2 weeks. The radiation therapy may be administered to subjects having head and neck cancer for about 6 to 7 weeks. Optionally, the radiation therapy may be administered as a single dose or as multiple, sequential doses.

f. Neoplastic Conditions

Whether administered alone or in combination with an anti-cancer agent or radiotherapy, the CD46 modulators of the instant invention are particularly useful for generally treating neoplastic conditions in patients or subjects which may include benign or malignant tumors (e.g., renal, liver, kidney, bladder, breast, gastric, ovarian, colorectal, prostate, pancreatic, lung, thyroid, hepatic carcinomas; sarcomas; glioblastomas; and various head and neck tumors); leukemias and lymphoid malignancies; other disorders such as neuronal, glial, astrocytal, hypothalamic and other glandular, macrophagal, epithelial, stromal and blastocoelic disorders; and inflammatory, angiogenic, immunologic disorders and disorders caused by pathogens. Particularly preferred targets for treatment with therapeutic compositions and methods of the present invention are neoplastic conditions comprising solid tumors. In other preferred embodiments the modulators of the present invention may be used for the diagnosis, prevention or treatment of hematologic malignancies. Preferably the subject or patient to be treated will be human although, as used herein, the terms are expressly held to comprise any mammalian species.

More specifically, neoplastic conditions subject to treatment in accordance with the instant invention may be selected from the group including, but not limited to, adrenal gland tumors, AIDS-associated cancers, alveolar soft part sarcoma, astrocytic tumors, bladder cancer (squamous cell carcinoma and transitional cell carcinoma), bone cancer (adamantinoma, aneurismal bone cysts, osteochondroma, osteosarcoma), brain and spinal cord cancers, metastatic brain tumors, breast cancer, carotid body tumors, cervical cancer, chondrosarcoma, chordoma, chromophobe renal cell carcinoma, clear cell carcinoma, colon cancer, colorectal cancer, cutaneous benign fibrous histiocytomas, desmoplastic small round cell tumors, ependymomas, Ewing's tumors, extraskeletal myxoid chondrosarcoma, fibrogenesis imperfecta ossium, fibrous dysplasia of the bone, gallbladder and bile duct cancers, gestational trophoblastic disease, germ cell tumors, head and neck cancers, islet cell tumors, Kaposi's Sarcoma, kidney cancer (nephroblastoma, papillary renal cell carcinoma), leukemias, lipoma/benign lipomatous tumors, liposarcoma/malignant lipomatous tumors, liver cancer (hepatoblastoma, hepatocellular carcinoma), lymphomas, lung cancers (small cell carcinoma, adenocarcinoma, squamous cell carcinoma, large cell carcinoma etc.), medulloblastoma, melanoma, meningiomas, multiple endocrine neoplasia, multiple myeloma, myelodysplastic syndrome, neuroblastoma, neuroendocrine tumors, ovarian cancer, pancreatic cancers, papillary thyroid carcinomas, parathyroid tumors, pediatric cancers, peripheral nerve sheath tumors, phaeochromocytoma, pituitary tumors, prostate cancer, posterious unveal melanoma, rare hematologic disorders, renal metastatic cancer, rhabdoid tumor, rhabdomysarcoma, sarcomas, skin cancer, soft-tissue sarcomas, squamous cell cancer, stomach cancer, synovial sarcoma, testicular cancer, thymic carcinoma, thymoma, thyroid metastatic cancer, and uterine cancers (carcinoma of the cervix, endometrial carcinoma, and leiomyoma). In certain preferred embodiments, the cancerous cells are selected from the group of solid tumors including but not limited to breast cancer, non-small cell lung cancer (NSCLC), small cell lung cancer, pancreatic cancer, colon cancer, prostate cancer, sarcomas, renal metastatic cancer, thyroid metastatic cancer, and clear cell carcinoma.

With regard to hematologic malignancies it will be further be appreciated that the compounds and methods of the present invention may be particularly effective in treating a variety of B-cell lymphomas, including low grade/NHL follicular cell lymphoma (FCC), mantle cell lymphoma (MCL), diffuse large cell lymphoma (DLCL), small lymphocytic (SL) NHL, intermediate grade/follicular NHL, intermediate grade diffuse NHL, high grade immunoblastic NHL, high grade lymphoblastic NHL, high grade small non-cleaved cell NHL, bulky disease NHL, Waldenstrom's Macroglobulinemia, lymphoplasmacytoid lymphoma (LPL), mantle cell lymphoma (MCL), follicular lymphoma (FL), diffuse large cell lymphoma (DLCL), Burkitt's lymphoma (BL), AIDS-related lymphomas, monocytic B cell lymphoma, angioimmunoblastic lymphoadenopathy, small lymphocytic, follicular, diffuse large cell, diffuse small cleaved cell, large cell immunoblastic lymphoblastoma, small, non-cleaved, Burkitt's and non-Burkitt's, follicular, predominantly large cell; follicular, predominantly small cleaved cell; and follicular, mixed small cleaved and large cell lymphomas. See, Gaidono et al., "Lymphomas", IN CANCER: PRINCIPLES & PRACTICE OF ONCOLOGY, Vol. 2: 2131-2145 (DeVita et al., eds., 5.sup.th ed. 1997). It should be clear to those of skill in the art that these lymphomas will often have different names due to changing systems of classification, and that patients having lymphomas classified under different names may also benefit from the combined therapeutic regimens of the present invention.

In yet other preferred embodiments the CD46 modulators may be used to effectively treat certain myeloid and hematologic malignancies including leukemias such as chronic lymphocytic leukemia (CLL or B-CLL). CLL is predominantly a disease of the elderly that starts to increase in incidence after fifty years of age and reaches a peak by late sixties. It generally involves the proliferation of neoplastic peripheral blood lymphocytes. Clinical finding of CLL involves lymphocytosis, lymphadenopatliy, splenomegaly, anemia and thrombocytopenia. A characteristic feature of CLL is monoclonal B cell proliferation and accumulation of B-lymphocytes arrested at an intermediate state of differentiation where such B cells express surface IgM (sIgM) or both sIgM and sIgD, and a single light chain at densities lower than that on the normal B cells. However, as discussed above and shown in the Examples appended hereto, selected CD46 expression (e.g., CD46) is upregulated on B-CLL cells thereby providing an attractive target for the disclosed modulators.

The present invention also provides for a preventative or prophylactic treatment of subjects who present with benign or precancerous tumors. It is not believed that any particular type of tumor or neoplastic disorder should be excluded from treatment using the present invention. However, the type of tumor cells may be relevant to the use of the invention in combination with secondary therapeutic agents, particularly chemotherapeutic agents and targeted anti-cancer agents.

Still other preferred embodiments of the instant invention comprise the use of CD46 modulators to treat subjects suffering from solid tumors. In such subjects many of these solid tumors comprise tissue exhibiting various genetic mutations that may render them particularly susceptible to treatment with the disclosed effectors. For example, KRAS, APC and CTNNB1 mutations are relatively common in patients with colorectal cancer. Moreover, patients suffering from tumors with these mutations are usually the most refractory to current therapies; especially those patients with KRAS mutations. KRAS activating mutations, which typically result in single amino acid substitutions, are also implicated in other difficult to treat malignancies, including lung adenocarcinoma, mucinous adenoma, and ductal carcinoma of the pancreas.

Currently, the most reliable prediction of whether colorectal cancer patients will respond to EGFR- or VEGF-inhibiting drugs, for example, is to test for certain KRAS "activating" mutations. KRAS is mutated in 35-45% of colorectal cancers, and patients whose tumors express mutated KRAS do not respond well to these drugs. For example, KRAS mutations are predictive of a lack of response to panitumumab and cetuximab therapy in colorectal cancer (Lievre et al. *Cancer Res* 66:3992-5; Karapetis et al. *NEJM* 359:1757-1765). Approximately 85% of patients with colorectal cancer have mutations in the APC gene (Markowitz & Bertagnolli. *NEJM* 361:2449-60), and more than 800 APC mutations have been characterized in patients with familial adenomatous polyposis and colorectal cancer. A majority of these mutations result in a truncated APC protein with reduced functional ability to mediate the destruction of beta-catenin. Mutations in the beta-catenin gene, CTNNB1, can also result in increased stabilization of the protein, resulting in nuclear import and subsequent activation of several oncogenic transcriptional programs, which is also the mechanism of oncogenesis resulting from failure of mutated APC to appropriately mediate beta-catenin destruction, which is required to keep normal cell proliferation and differentiation programs in check.

XIV. Articles of Manufacture

Pharmaceutical packs and kits comprising one or more containers, comprising one or more doses of a CD46 modulator are also provided. In certain embodiments, a unit dosage is provided wherein the unit dosage contains a predetermined amount of a composition comprising, for example, an anti-CD46 antibody, with or without one or more additional agents. For other embodiments, such a unit dosage is supplied in single-use prefilled syringe for injection. In still other embodiments, the composition contained in the unit dosage may comprise saline, sucrose, or the like; a buffer, such as phosphate, or the like; and/or be formulated within a stable and effective pH range. Alternatively, in certain embodiments, the composition may be provided as a lyophilized powder that may be reconstituted upon addition of an appropriate liquid, for example, sterile water. In certain preferred embodiments, the composition comprises one or more substances that inhibit protein aggregation, including, but not limited to, sucrose and arginine. Any label on, or associated with, the container(s) indicates that the enclosed composition is used for diagnosing or treating the disease condition of choice.

The present invention also provides kits for producing single-dose or multi-dose administration units of a CD46 modulator and, optionally, one or more anti-cancer agents. The kit comprises a container and a label or package insert on or associated with the container. Suitable containers include, for example, bottles, vials, syringes, etc. The containers may be formed from a variety of materials such as glass or plastic. The container holds a composition that is effective for treating the condition and may have a sterile access port (for example the container may be an intravenous solution bag or a vial having a stopper pierceable by a hypodermic injection needle). Such kits will generally contain in a suitable container a pharmaceutically acceptable formulation of the CD46 modulator and, optionally, one or more anti-cancer agents in the same or different containers. The kits may also contain other pharmaceutically acceptable formulations, either for diagnosis or combined therapy. For example, in addition to the CD46 modulator of the invention such kits may contain any one or more of a range of anti-cancer agents such as chemotherapeutic or radiotherapeutic drugs; anti-angiogenic agents; anti-metastatic agents; targeted anti-cancer agents; cytotoxic agents; and/or other anti-cancer agents. Such kits may also provide appropriate reagents to conjugate the CD46 modulator with an anti-cancer agent or diagnostic agent (e.g., see U.S. Pat. No. 7,422,739 which is incorporated herein by reference in its entirety).

More specifically the kits may have a single container that contains the CD46 modulator, with or without additional components, or they may have distinct containers for each desired agent. Where combined therapeutics are provided for conjugation, a single solution may be pre-mixed, either in a molar equivalent combination, or with one component in excess of the other. Alternatively, the CD46 modulator and any optional anti-cancer agent of the kit may be maintained separately within distinct containers prior to administration to a patient. The kits may also comprise a second/third container means for containing a sterile, pharmaceutically acceptable buffer or other diluent such as bacteriostatic water for injection (BWFI), phosphate-buffered saline (PBS), Ringer's solution and dextrose solution.

When the components of the kit are provided in one or more liquid solutions, the liquid solution is preferably an aqueous solution, with a sterile aqueous solution being particularly preferred. However, the components of the kit may be provided as dried powder(s). When reagents or components are provided as a dry powder, the powder can be reconstituted by the addition of a suitable solvent. It is envisioned that the solvent may also be provided in another container.

As indicated briefly above the kits may also contain a means by which to administer the antibody and any optional components to an animal or patient, e.g., one or more needles or syringes, or even an eye dropper, pipette, or other such like apparatus, from which the formulation may be injected or introduced into the animal or applied to a diseased area of the body. The kits of the present invention will also typically include a means for containing the vials, or such like, and other component in close confinement for commercial sale, such as, e.g., injection or blow-molded plastic containers into which the desired vials and other apparatus are placed and retained. Any label or package insert indicates that the CD46 modulator composition is used for treating cancer, for example colorectal cancer.

XV. Research Reagents

Other preferred embodiments of the invention also exploit the properties of the disclosed modulators as an instrument useful for identifying, isolating, sectioning or enriching populations or subpopulations of tumor initiating cells through methods such as fluorescent activated cell sorting (FACS), magnetic activated cell sorting (MACS) or laser mediated sectioning. Those skilled in the art will appreciate that the modulators may be used in several compatible techniques for the characterization and manipulation of TIC including cancer stem cells (e.g., see U.S. Pat. No. 8,788,213 and U.S.P.Ns. 2010-0273160 and 2011-0020221, each of which is incorporated herein by reference in its entirety).

XVI. Miscellaneous

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. More specifically, as used in this specification and the appended claims, the singular forms "a," "an" and "the" include plural referents unless the context clearly dictates otherwise. Thus, for example, reference to "a protein" includes a plurality of proteins; reference to "a cell" includes mixtures of cells, and the like. In addition, ranges provided in the specification and appended claims include both end points and all points between the end points. Therefore, a range of 2.0 to 3.0 includes 2.0, 3.0, and all points between 2.0 and 3.0.

Generally, nomenclature used in connection with, and techniques of, cell and tissue culture, molecular biology, immunology, microbiology, genetics and protein and nucleic acid chemistry and hybridization described herein are those well known and commonly used in the art. The methods and techniques of the present invention are generally performed according to conventional methods well known in the art and as described in various general and more specific references that are cited and discussed throughout the present specification unless otherwise indicated. See, e.g., Sambrook J. & Russell D. Molecular Cloning: A Laboratory Manual, 3rd ed., Cold Spring Harbor Laboratory Press, Cold Spring Harbor, N.Y. (2000); Ausubel et al., Short Protocols in Molecular Biology: A Compendium of Methods from Current Protocols in Molecular Biology, Wiley, John & Sons, Inc. (2002); Harlow and Lane Using Antibodies: A Laboratory Manual, Cold Spring Harbor Laboratory Press, Cold Spring Harbor, N.Y. (1998); and Coligan et al., Short Protocols in Protein Science, Wiley, John & Sons, Inc. (2003). Enzymatic reactions and purification techniques are performed according to manufacturer's specifications, as commonly accomplished in the art or as described herein. The nomenclature used in connection with, and the laboratory procedures and techniques of, analytical chemistry, synthetic organic chemistry, and medicinal and pharmaceutical chemistry described herein are those well known and commonly used in the art.

All references or documents disclosed or cited within this specification are, without limitation, incorporated herein by reference in their entirety. Moreover, any section headings used herein are for organizational purposes only and are not to be construed as limiting the subject matter described.

EXAMPLES

The present invention, thus generally described, will be understood more readily by reference to the following Examples, which are provided by way of illustration and are not intended to be limiting of the instant invention. The Examples are not intended to represent that the experiments below are all or the only experiments performed. Unless indicated otherwise, parts are parts by weight, molecular weight is weight average molecular weight, temperature is in degrees Centigrade, and pressure is at or near atmospheric.

Example 1

CD46 Expression in Tumor Initiating Cell Populations

To characterize the cellular heterogeneity of solid tumors as they exist in cancer patients, elucidate the identity of tumor perpetuating cells (TPC; i.e. cancer stem cells: CSC) using particular phenotypic markers and identify clinically relevant therapeutic targets, a large non-traditional xenograft (NTX) tumor bank was developed and maintained using art recognized techniques. The NTX tumor bank, comprising a large number of discrete tumor cell lines, was propagated in immunocompromised mice through multiple passages of heterogeneous tumor cells originally obtained from numerous cancer patients afflicted by a variety of solid tumor malignancies. The continued availability of a large number of discrete early passage NTX tumor cell lines having well defined lineages greatly facilitate the identification and isolation of TPC as they allow for the reproducible and repeated characterization of cells purified from the cell lines. More particularly, isolated or purified TPC are most accurately defined retrospectively according to their ability to generate phenotypically and morphologically heterogeneous tumors in mice that recapitulate the patient tumor sample from which the cells originated. Thus, the ability to use small populations of isolated cells to generate fully heterogeneous tumors in mice is strongly indicative of the fact that the isolated cells comprise TPC. In such work the use of minimally passaged NTX cell lines greatly simplifies in vivo experimentation and provides readily verifiable results. Moreover, early passage NTX tumors also respond to therapeutic agents such as irinotecan (i.e. Camptosar®), which provides clinically relevant insights into underlying mechanisms driving tumor growth, resistance to current therapies and tumor recurrence.

As the NTX tumor cell lines were established the constituent tumor cell phenotypes were analyzed using flow cytometry to identify discrete markers that might be used to characterize, isolate, purify or enrich tumor initiating cells (TIC) and separate or analyze TPC and TProg cells within such populations. In this regard the inventors employed a proprietary proteomic based platform (i.e. PhenoPrint™ Array) that provided for the rapid characterization of cells based on protein expression and the concomitant identification of potentially useful markers. The PhenoPrint Array is a proprietary proteomic platform comprising hundreds of discrete binding molecules, many obtained from commercial sources, arrayed in 96 well plates wherein each well contains a distinct antibody in the phycoerythrin fluorescent channel and multiple additional antibodies in different fluorochromes arrayed in every well across the plate. This allows for the determination of expression levels of the antigen of interest in a subpopulation of selected tumor cells through rapid inclusion of relevant cells or elimination of non-relevant cells via non-phycoerythrin channels. When the PhenoPrint Array was used in combination with tissue dissociation, transplantation and stem cell techniques well known in the art (Al-Hajj et al., 2004, Dalerba et al., 2007 and Dylla et al., 2008, all supra, each of which is incorporated herein by reference in its entirety), it was possible to effectively identify relevant markers and subsequently isolate and transplant specific human tumor cell subpopulations with great efficiency.

Accordingly, upon establishing various NTX tumor cell lines as is commonly done for human tumors in severely immune compromised mice, the tumors were resected from mice upon reaching 800-2,000 $mm^3$ and the cells were dissociated into single cell suspensions using art-recognized enzymatic digestion techniques (See for example U.S.P.N. 2007/0292414 which is incorporated herein). Data obtained from these suspensions using the PhenoPrint Array provided both absolute (per cell) and relative (vs. other cells in the population) surface protein expression on a cell-by-cell basis, leading to more complex characterization and stratification of cell populations. More specifically, use of the PhenoPrint Array allowed for the rapid identification of proteins or markers that prospectively distinguished TIC or TPC from NTG bulk tumor cells and tumor stroma and, when isolated from NTX tumor models, provided for the relatively rapid characterization of tumor cell subpopulations expressing differing levels of specific cell surface proteins. In particular, proteins with heterogeneous expression across the tumor cell population allow for the isolation and transplantation of distinct, and highly purified, tumor cell subpopulations expressing either high and low levels of a particular protein or marker into immune-compromised mice, thereby facilitating the assessment of whether TPC were enriched in one subpopulation or another.

The term enriching is used synonymously with isolating cells and means that the yield (fraction) of cells of one type is increased over the fraction of other types of cells as compared to the starting or initial cell population. Preferably, enriching refers to increasing the percentage by about 10%, by about 20%, by about 30%, by about 40%, by about 50% or greater than 50% of one type of cell in a population of cells as compared to the starting population of cells.

As used herein a marker, in the context of a cell or tissue, means any characteristic in the form of a chemical or biological entity that is identifiably associated with, or specifically found in or on a particular cell, cell population or tissue including those identified in or on a tissue or cell population affected by a disease or disorder. As manifested, markers may be morphological, functional or biochemical in nature. In preferred embodiments the marker is a cell surface antigen that is differentially or preferentially expressed by specific cell types (e.g., TPC) or by cells under certain conditions (e.g., during specific points of the cell life cycle or cells in a particular niche). Preferably, such markers are proteins, and more preferably, possess an epitope for antibodies, aptamers or other binding molecules as known in the art. However, a marker may consist of any molecule found on the surface or within a cell including, but not limited to, proteins (peptides and polypeptides), lipids, polysaccharides, nucleic acids and steroids. Examples of morphological marker characteristics or traits include, but are not limited to, shape, size, and nuclear to cytoplasmic ratio. Examples of functional marker characteristics or traits include, but are not limited to, the ability to adhere to particular substrates, ability to incorporate or exclude particular dyes, for example but not limited to exclusions of lipophilic dyes, ability to migrate under particular conditions and the ability to differentiate along particular lineages. Markers can also be a protein expressed from a reporter gene, for example a reporter gene expressed by the cell as a result of introduction of the nucleic acid sequence encoding the reporter gene into the cell and its transcription resulting in the production of the reporter protein that can be used as a marker. Such reporter genes that can be used as markers are, for example but not limited to fluorescent proteins enzymes, chromomeric proteins, resistance genes and the like.

In a related sense the term marker phenotype in the context of a tissue, cell or cell population (e.g., a stable TPC phenotype) means any marker or combination of markers that may be used to characterize, identify, separate, isolate or enrich a particular cell or cell population. In specific embodiments, the marker phenotype is a cell surface phenotype that may be determined by detecting or identifying the expression of a combination of cell surface markers.

Those skilled in the art will recognize that numerous markers (or their absence) have been associated with various populations of cancer stem cells and used to isolate or characterize tumor cell subpopulations. In this respect exemplary cancer stem cell markers comprise OCT4, Nanog, STAT3, EPCAM, CD24, CD34, NB84, TrkA, GD2, CD133, CD20, CD56, CD29, B7H3, CD46, transferrin receptor, JAM3, carboxypeptidase M, ADAM9, oncostatin M, Lgr5, Lgr6, CD324, CD325, nestin, Sox1, Bmi-1, eed, easyh1, easyh2, mf2, yy1, smarcA3, smarckA5, smarcD3, smarcE1, mllt3, FZD1, FZD2, FZD3, FZD4, FZD6, FZD7, FZD8, FZD9, FZD10, WNT2, WNT2B, WNT3, WNT5A, WNT10B, WNT16, AXIN1, BCL9, MYC, (TCF4) SLC7A8, IL1RAP, TEM8, TMPRSS4, MUC16, GPRC5B, SLC6A14, SLC4A11, PPAP2C, CAV1, CAV2, PTPN3, EPHA1, EPHA2, SLC1A1, CX3CL1, ADORA2A, MPZL1, FLJ10052, C4.4A, EDG3, RARRES1, TMEPAI, PTS, CEACAM6, NID2, STEAP, ABCA3, CRIM1, IL1R1, OPN3, DAF, MUC1, MCP, CPD, NMA, ADAM9, GJA1, SLC19A2, ABCA1, PCDH7, ADCY9, SLC39A1, NPC1, ENPP1, N33, GPNMB, LY6E, CELSR1, LRP3, C20orf52, TMEPAI, FLVCR, PCDHA10, GPR54, TGFBR3, SEMA4B, PCDHB2, ABCG2, CD166, AFP, BMP-4, β-catenin, CD2, CD3, CD9, CD14, CD31, CD38, CD44, CD45, CD74, CD90, CXCR4, decorin, EGFR, CD105, CD64, CD16, CD16a, CD16b, GLI1, GLI2, CD49b, and CD49f. See, for example, Schulenburg et al., 2010, PMID: 20185329, U.S. Pat. No. 7,632,678 and U.S.P.N. 2007/0292414, 2008/0175870, 2010/0275280, 2010/0162416 and 2011/0020221 each of which is incorporated herein by reference. It will be appreciated that a number of these markers were included in the PhenoPrint Array described above.

Similarly, non-limiting examples of cell surface phenotypes associated with cancer stem cells of certain tumor types include $CD44^{hi}CD24^{low}$, $ALDH^+$, $CD133^+$, $CD123^+$, $CD34^+CD38^-$, $CD44^+CD24^-$, $CD46^{hi}CD324^+CD66c^-$, $CD133^+CD34^+CD10^-CD19^-$, $CD138^-CD34^-CD19^+$, $CD133^+RC2^+$, $CD44^+\alpha_2\beta_1^{hi}CD133^+$, $CD44^+CD24^+ESA^+$, $CD271^+$, $ABCB5^+$ as well as other cancer stem cell surface phenotypes that are known in the art. See, for example, Schulenburg et al., 2010, supra, Visvader et al., 2008, PMID: 18784658 and U.S.P.N. 2008/0138313, each of which is incorporated herein in its entirety by reference. Those skilled in the art will appreciate that marker phenotypes such as those exemplified immediately above may be used in conjunction with standard flow cytometric analysis and cell sorting techniques to characterize, isolate, purify or enrich TIC and/or TPC cells or cell populations for further analysis. Of interest with regard to the instant invention CD46, CD324 and, optionally, CD66c are either highly or heterogeneously expressed on the surface of many human colorectal ("CR"), breast ("BR"), non-small cell lung (NSCLC), small cell lung (SCLC), pancreatic ("PA"), melanoma ("Mel"), ovarian ("OV"), and head and neck cancer ("HN") tumor cells, regardless of whether the tumor specimens being analyzed were primary patient tumor specimens (FIG. 1A) or patient-derived NTX tumors (FIG. 1B).

Data shown in FIGS. 1A and B are flow cytometry-based protein expression data generated using a FACSCanto II (BD Biosciences) as per the manufacturer's instructions. Data shows individual tumor cells displayed as histogram plots, wherein the background staining of isotype control antibodies is shown in the gray, filled histograms and CD46 expression as determined using the MEM-258 antibody (BioLegend Inc.) is displayed by the bold, black line.

Cells with negative expression (i.e. "−") are herein defined as those cells expressing less than, or equal to, the $95^{th}$ percentile of expression observed with an isotype control antibody in the channel of fluorescence in the presence of the complete antibody staining cocktail labeling for other proteins of interest in additional channels of fluorescence emission. Those skilled in the art will appreciate that this procedure for defining negative events is referred to as "fluorescence minus one", or "FMO", staining. Cells with expression greater than the $95^{th}$ percentile of expression observed with an isotype control antibody using the FMO staining procedure described above are herein defined as "positive" (i.e."+"). As defined herein there are various populations of cells broadly defined as "positive." First, cells with low expression (i.e. "lo") are generally defined as those cells with observed expression above the $95^{th}$ percentile determined using FMO staining with an isotype control antibody and within one standard deviation of the $95^{th}$ percentile of expression observed with an isotype control antibody using the FMO staining procedure described above. Cells with "high" expression (i.e. "hi") may be defined as those cells with observed expression above the $95^{th}$ percentile determined using FMO staining with an isotype control antibody and greater than one standard deviation above the $95^{th}$ percentile of expression observed with an isotype control antibody using the FMO staining procedure described above. In other embodiments the $99^{th}$ percentile may preferably be used as a demarcation point between negative and positive FMO staining and in particularly preferred embodiments the percentile may be greater than 99%.

Figure 1B:
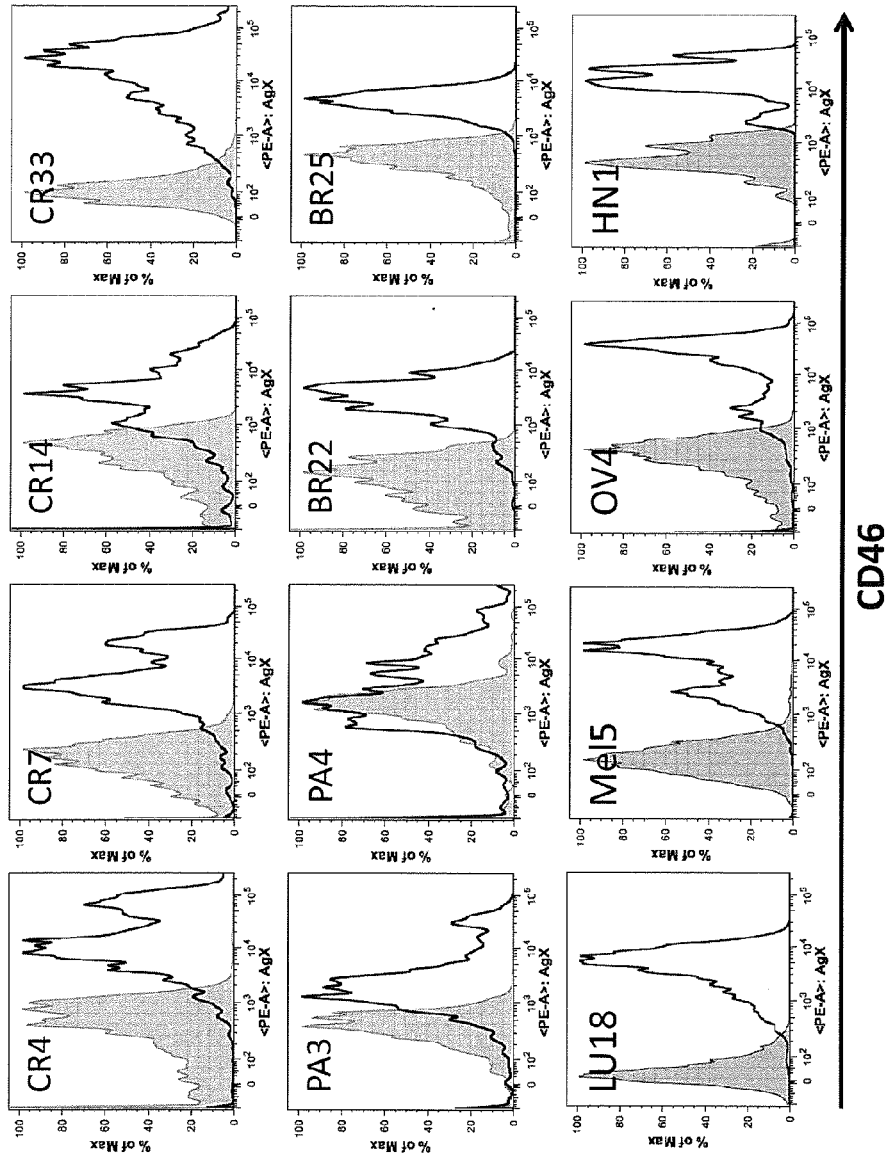

CD46 expression was variable among various patients with solid tumors; however, expression was generally above background staining, as determined using isotype control antibodies (FIGS. 1A & 1B). CD46 expression was especially heterogeneous in tumors derived from most colorectal and pancreatic cancer patients, with distinct cell subpopulations generally demonstrating negative, low and high CD46 expression, respectively (FIG. 1B).

Example 2

Demonstration of Enrichment for Tumor Initiating Cell Populations by FACS and Transplantations In tumors where there was heterogeneous expression of a particular protein of interest, cells were isolated based on their high or no/low expression of these proteins and then transplanted into immune-compromised mice. Surprisingly, it was observed that most distinct markers identified as heterogeneously expressed using the proprietary PhenoPrint Array did not demonstrate utility in enriching for tumor initiating cells. To determine whether colorectal and pancreatic tumor cells that have high or low cell surface expression of CD46 were enriched for tumorigenic activity in immune-compromised mice, respectively, distinct cell populations were isolated from NTX tumors using cell dissociation and FACS techniques well known to those skilled in the art, and then transplanted at 1,000 to 3 cells per mouse. When tumors reached 800-2,000 mm³, mice were euthanized and the tumors were removed and dissociated to a single cell suspension using enzymatic digestion for the purpose of phenotypic characterization to determine whether the tumors generated represented the parental tumor from which the transplanted cells were originally isolated.

Figure 2:
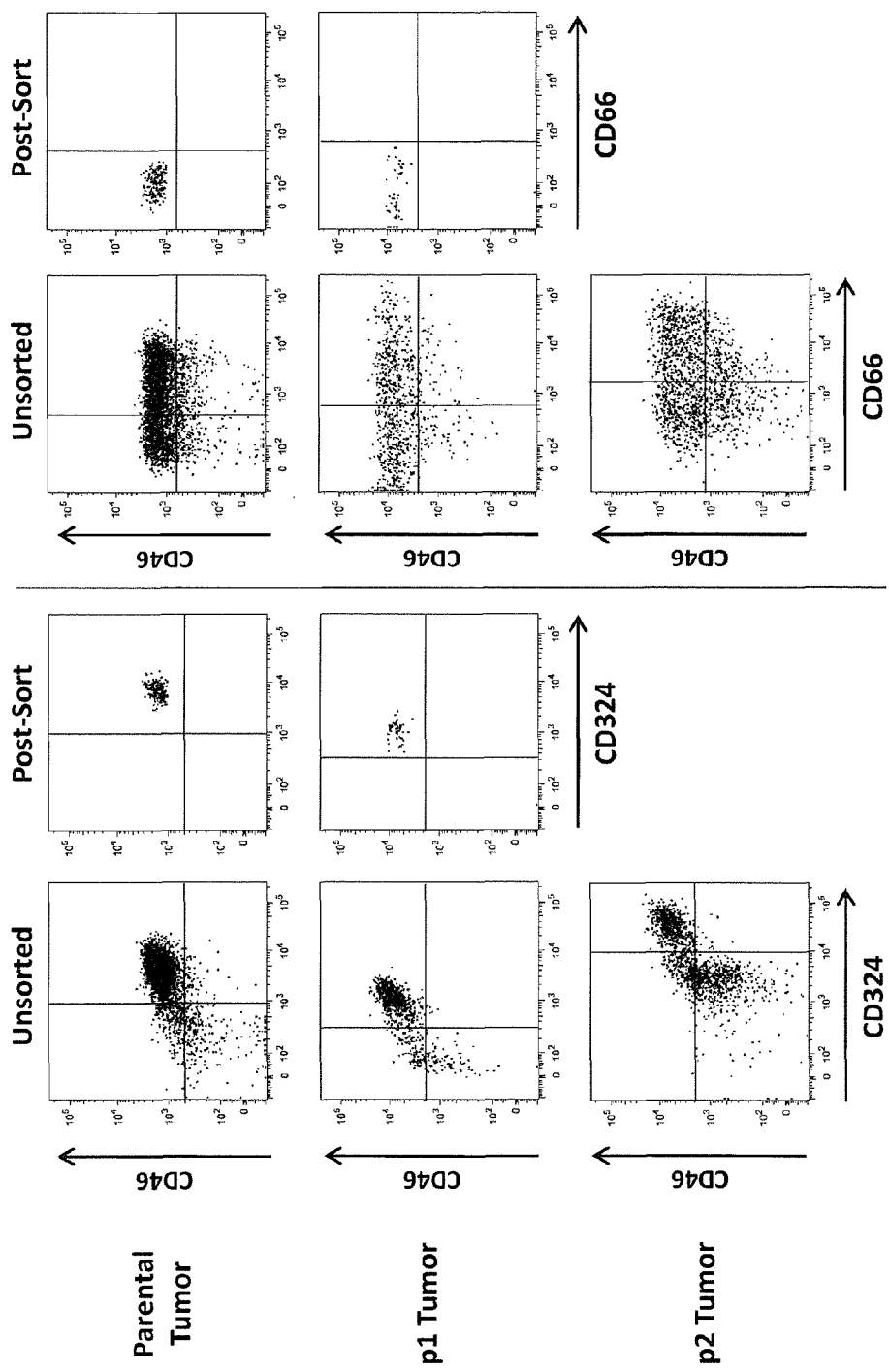
FIG. 2 provides scatter plots showing flow cytometric enrichment of tumor initiating cells using cell surface markers CD46, epithelial surface antigen (ESA), CD66c, and CD324.

TABLE 1 shows the results of those experiments. Blanks indicate that the indicated experiment was not performed. Tumors arising from epithelial specific antigen (ESA)-positive, CD46$^{hi}$ cells consistently generated heterogeneous tumors, albeit required additional markers (i.e. colorectal cancer: CD324$^+$ CD66c$^-$; pancreatic cancer: CD324$^+$) to do so efficiently upon transplantation of cell numbers below 200 cells/mouse.

pose of cell isolation and transplantation. This work led to the identification of two additional cell surface markers for colorectal cancer (CD324 and CD66c) and one additional marker for pancreatic cancer (CD324), which were able to help enrich for tumor initiating cells based on high or negative/low expression of the respective antigens. As a demonstration of the utility of these markers in colorectal cancer, for example, tumors arising from the transplantation of ESA$^+$ CD46$^{hi}$ CD324$^+$ CD66c$^-$ cells (i.e. p1, passage 1) were fully heterogeneous and reflected the parental tumors from which they were derived (FIG. 2; p1 tumor vs. parental tumor). In contrast, transplants with small numbers of ESA$^+$ CD46$^{hi}$ CD324$^+$ CD66c$^+$ cells did not generate fully heterogeneous tumors in that there were significantly less CD66c$^-$ cells, suggesting that ESA$^+$ CD46$^{hi}$ CD324$^+$ CD66c$^+$ cells are tumor progenitor cells (TProg) with significant proliferative capacity, but devoid of self-renewal

TABLE 1

Demonstration of Enrichment for Colorectal and Pancreatic Tumor Initiating Cell Populations by FACS and Transplantation into Immune-Compromised Mice

| Colorectal | | 500 cells | | 51-200 cells | | 3-50 cells | |
|---|---|---|---|---|---|---|---|
| SCRx-CR2 | CD46$^{hi}$ | 3/10 | 30% | | | | |
| | CD46$^{-/lo}$ | 0/5 | 0% | | | | |
| SCRx-CR4 | CD46$^{hi}$ | | | 3/5 | 60% | | |
| | CD46$^{-/lo}$ | | | 0/5 | 0% | | |
| SCRx-CR5 | CD46$^{hi}$ | | | 19/19 | 100% | 12/14 | 86% |
| | CD46$^{-/lo}$ | | | 2/10 | 20% | 1/5 | 20% |
| SCRx-CR7 | CD46$^{hi}$ | 12/13 | 92% | | | | |
| | CD46$^{-/lo}$ | 1/10 | 10% | | | | |
| SCRx-CR10 | CD46$^{hi}$ | | | 4/10 | 40% | | |
| | CD46$^{-/lo}$ | | | 0/5 | 0% | | |
| SCRx-CR14 | CD46$^{hi}$ | | | 37/45 | 82% | | |
| | CD46$^{-/lo}$ | | | 3/20 | 15% | | |
| SCRx-CR16 | CD46$^{hi}$ | | | 5/14 | 36% | | |
| | CD46$^{-/lo}$ | | | 0/5 | 0% | | |
| SCRx-CR21 | CD46$^{hi}$ | | | | | 2/15 | 13% |
| | CD46$^{-/lo}$ | | | | | 0/5 | 0% |
| SCRx-CR33 | CD46$^{hi}$ | | | 4/10 | 40% | | |
| | CD46$^{-/lo}$ | | | 0/5 | 0% | | |
| SUMMARY | CD46$^{hi}$ | 15/23 | 65% | 72/103 | 70% | 14/29 | 48% |
| | CD46$^{-/lo}$ | 1/15 | 7% | 5/50 | 10% | 1/10 | 10% |
| Pancreatic | | 1,000 cells | | 500 cells | | 200 cells | | 100 cells | |
| SCRx-PA3 | CD46$^{hi}$ | | | 13/14 | 93% | 13/20 | 65% | | |
| | CD46$^{-/lo}$ | | | 2/15 | 13% | 1/15 | 7% | | |
| SCRx-PA4 | CD46$^{hi}$ | 8/14 | 80% | | | | | 3/5 | 60% |
| | CD46$^{-/lo}$ | 0/10 | 0% | | | | | 0/5 | 0% |
| SCRx-PA14 | CD46$^{hi}$ | | | | | | | 4/10 | 40% |
| | CD46$^{-/lo}$ | | | | | | | 0/5 | 0% |

Example 3

A Subpopulation of CD46$^{hi}$ Tumor Initiating Cells Demonstrate Tumor Perpetuating Capability by Serial Passage in NTX Models While the majority of tumor cells are devoid of tumor forming ability and can thus be characterized as non-tumorigenic (NTG), there is precedent in both normal embryonic development and hematopoietic tumors for highly proliferative cells being able to reconstitute a tumor and/or tissue upon transplantation, but which do not have self-renewal capacity (i.e. a finite lifespan) and are thus referred to as short-term reconstituting cells or progenitor cells.

To determine whether a subpopulation of CD46$^{hi}$ cells was more or less tumorigenic than others, CD46 was systematically combined with additional markers for the pur-properties. Serial transplantation of prospective TPC (ESA$^+$ CD46$^{hi}$ CD324$^+$ CD66c$^-$ cells) and TProg (ESA$^+$ CD46$^{hi}$ CD324$^+$ CD66c$^+$ cells) confirmed the identity of these tumor cell subpopulations, as the ESA$^+$ CD46$^{hi}$ CD324$^+$ CD66c$^-$ cell subset arising from ESA$^+$ CD46$^{hi}$ CD324$^+$ CD66c$^-$ cells efficiently generated tumors upon serial transplantation of 50 cells (FIG. 2; p2 versus p1 tumor), whereas no cells in tumors arising from ESA$^+$ CD46$^{hi}$ CD324$^+$ CD66c$^+$ cells could efficiently reinitiate tumors upon serial transplantation. To be clear, 50 ESA$^+$ CD46$^{hi}$ CD324$^+$ CD66c$^+$ cells isolated from tumors generated from only 200 CD66c$^-$ or CD66c$^+$ cells, respectively, were rarely tumorigenic: especially those obtained from CD66c$^+$-derived tumors. Surprisingly, these data demonstrate a seminal observation for solid tumors in that ESA$^+$ CD46$^{hi}$ CD324$^+$ CD66c$^-$ cells are TPC and ESA$^+$ CD46$^{hi}$ CD324$^+$ CD66c$^+$ cells are TProg cells.

To determine the accuracy of the above described TPC phenotype in colorectal cancer, ESA$^+$ CD46$^{hi}$ CD324$^+$ CD66c⁻ cells were isolated by FACS as described above (FIG. 3A; post-FACS vs. pre-FACS) and transplanted in limiting dilution: 50, 20, 8 and 3 cells per mouse, respectively. Use of Poisson distribution statistics based on positive events being defined as successful tumorigenesis (see FIGS. 3B & 3C) resulted in the calculation that the true tumor initiating cell frequency among ESA⁺ CD46$^{hi}$ CD324⁺ CD66c⁻ TPC was roughly 1 in 7±3 cells.

Each protein used in combination to enrich for the TPC and TProg cell populations defined above in colorectal tumors has not been known to be associated with cells containing such activity in any tissue or neoplasm, though others have defined cell surface markers or enzymatic activity that can similarly be used to enrich for tumorigenic cells (Dylla et al 2008, supra). This work represents a substantial improvement in the resolution of the method and further improves techniques to identify, isolate and characterize distinct, highly enriched solid tumor cell subpopulations that exclusively contain tumor generating ability upon transplantation and distinguishes between tumorigenic cell subpopulations without or with self-renewal capacity: i.e. TProg and TPC, respectively. Nevertheless, both the TPC and highly proliferative TProg subpopulations express CD46 on the cell surface, thus suggesting that CD46-targeted modulators will benefit cancer patients by eliminating both highly proliferative cells (i.e. TProg) and those cells responsible for tumor growth and recurrence (i.e. TPC).

While most cell surface markers identified using the PhenoPrint Array did not demonstrate an ability to enrich tumor initiating cell populations in colorectal tumors using standard FACS protocols, distinct marker combinations could be used to identify two subpopulations of tumor initiating cells: TPC and TProg.

Example 4

Treatment with Irinotecan Increases the Frequency of CD46$^{hi}$ Tumor Perpetuating Cells A central tenet of the cancer stem cell paradigm is that CSC (i.e. TPC) are relatively resistant to chemotherapeutic agents, such as irinotecan. To determine whether CD46$^{hi}$TPC are resistant to chemotherapy, mice were initiated with SCRx-CR4 and CR14 colorectal tumors. Once the mean tumor burden reached ~300 mm³ the mice were randomized and treated with either 15 mg/kg irinotecan or vehicle control (PBS) twice weekly for a period of twenty days, at which point in time the mice were euthanized (FIG. 4A). At the time of tumor harvest, vehicle-treated control mice bore tumors ~700 mm³ whereas mice being treated with irinotecan had close to half that size (~388 mm³). The frequency of TPC within tumors from the respective treatment groups, as defined using the ESA⁺ CD46$^{hi}$ CD324⁺ CD66c⁻ phenotype defined above, was enriched 2.5-fold in tumors from mice treated with irinotecan versus the vehicle control (n=7; P<0.0001; FIG. 4B). The enrichment for TPC frequency was not biased by the size of the tumors, as the small tumors in the irinotecan treatment group were clearly enriched for TPC when individually compared to vehicle-treated mice (FIG. 4C).

The above observations that both TPC and highly proliferative TProg cell populations express CD46 and that TPC are significantly enriched in residual tumors post-treatment clearly demonstrate that CD46$^{hi}$ cells contribute largely to both tumor growth, recurrence, and resistance to therapy. As such, CD46$^{hi}$ cells were isolated from several solid tumors of both colorectal and pancreatic origin such that their protein and gene expression could be studied more closely by sequencing the whole transcriptome of respective tumor cell subpopulations using the SOLiD3 next-generation sequencing platform.

Example 5

SOLiD Whole Transcriptome Sequencing Reveals CD46 Splice Variants in Tumor Perpetuating Cell Populations Several colorectal (SCRx-CR2, CR4, CR11 and CR14) and pancreatic (SCRx-PA3 and PA6) cancer NTX cell lines generated and passaged as described in Example 1 were used to initiate tumors in immune-compromised mice. Tumors arising from these NTX lines were removed, and TPC, TProg and NTG cells, respectively, were isolated from freshly resected NTX tumors using the FACS as set out in Example 1. More particularly, cell populations were isolated by fluorescence activated cell sorting (FACS) using CD46, CD324 and CD66c markers and immediately pelleted and lysed in Qiagen RLTPlus RNA lysis buffer (Qiagen, Inc.). The lysates were then stored at −80° C. until used. Upon thawing, total RNA was extracted using the Qiagen RNEasy isolation kit (Qiagen, Inc.) following vendor's instructions and quantified on the Nanodrop (Thermo Scientific) and a Bioanalyzer 2100 (Agilent) again using the vendor's protocols and recommended instrument settings. The resulting total RNA preparation was suitable for genetic sequencing and analysis.

The RNA samples obtained from the TPC, TProg and NTG cell populations isolated as described above from vehicle or irinotecan-treated mice were prepared for whole transcriptome sequencing using an Applied Biosystems SOLiD 3.0 (Sequencing by Oligo Ligation/Detection) next generation sequencing platform (Life Technologies), starting with at least 5 ng of total RNA per sample. The data generated by the SOLiD platform mapped to 34,609 genes from the human genome, was able to detect CD46 and provided verifiable measurements of CD46 levels in all samples.

Generally the SOLiD3 next generation sequencing platform enables parallel sequencing of clonally-amplified RNA/DNA fragments linked to beads. Sequencing by ligation with dye-labeled oligonucleotides is then used to generate 50 base reads of each fragment that exists in the sample with a total of greater than 50 million reads generating an accurate representation of the mRNA transcript level expression of proteins in the genome. The SOLiD3 platform is able to capture not only expression, but SNPs, known and unknown alternative splicing events, and potentially new exon discoveries based solely on the read coverage (reads mapped uniquely to genomic locations). Thus, use of this next generation platform allowed the determination of differences in transcript level expression as well as differences or preferences for specific splice variants of those expressed mRNA transcripts. Moreover, analysis with the SOLiD3 platform using a modified whole transcriptome protocol from Applied Biosystems only required approximately 5 ng of starting material pre-amplification. This is significant as extraction of total RNA from sorted cell populations where the TPC subset of cells is, for example, vastly smaller in number than the NTG or bulk tumors and thus results in very small quantities of usable starting material. Duplicate runs of sequencing data from the SOLiD3 platform were normalized and transformed and fold ratios calculated as is standard industry practice. Surprisingly, CD46 gene expression was not noticeably different in CD46$^{hi}$ or CD46$^{-/lo}$ cell populations as measured in colorectal or pancreatic NTX tumor lines, despite being isolated based largely on differential surface expression of the CD46 protein.

A significant source of protein diversity in higher mammals results from the differential inclusion or excision of exons (i.e. alternative splicing) encoded by messenger RNA (mRNA) during translation. By sequencing the transcriptome (i.e. mRNA transcripts), one can gain significant insight into the proteins being encoded in a particular cell population, whereas other techniques that measure mRNA usage and/or gene expression entail significantly more work (targeted resequencing) or are unable to determine exon-exon junction usage (microarray), respectively. As seen in TABLE 2, an analysis of the CD46 transcript data obtained by sequencing the whole transcriptome using a mRNA amplification protocol and Next-Gen sequencing on an ABI SOLiD3 platform showed that the primary variant of CD46 expressed on TPC from several patient samples included the use of exons 1-6, 8-12 and 14, splicing around and thus excluding exons 7 and 13 (variant D; NM_153826) (TABLE 2). The secondary variant expressed in the majority of TPC also skips exon 8, resulting in a CD46 protein varied in its inclusion of exons 1-6, 9-12 and 14 (variant F; NM_172353). In summary, all of the variants expressed in colorectal and pancreatic TPC utilize exons 1-6 and 10-14, but the vast majority of transcripts also skip exon 13, which encodes an intracellular portion of the protein. The primary diversity of expressed CD46 transcripts in colorectal and pancreatic TPC thus originates from the inclusion or excision of exon 8. In contrast to other colorectal tumors, CD46 exon 7 was utilized in transcripts from SCRx-CR14NTX tumors, albeit these CD46 variant J (NM_172356) transcripts were still secondary to CD46 variant D expression (TABLE 2). Use of exon 13 was rarely observed in transcripts from colorectal or pancreatic tumor cell subpopulations.

TABLE 2

Identification of Alternatively Spliced CD46 Isoforms in Colorectal and Pancreatic Tumor Perpetuating Cells by SOLiD Whole Transcriptome Sequencing

| Tumor | Primary Variant | Secondary Variant | Tertiary Variant |
|---|---|---|---|
| SCRx-CR4 TPC | e6-8-9-10 | e6-9-10 | |
| SCRx-CR4 Prog | e6-8-9-10 | e6-9-10 | |
| SCRx-CR4 NTG | e6-8-9-10 | e6-9-10 | |
| SCRx-CR5 TPC | e6-8-9-10 | e6-9-10 | |
| SCRx-CR5 Prog | e6-9-10 | e6-8-9-10 | |
| SCRx-CR5 Bulk Tumor | e6-9-1 0 | e6-8-9-10 | |
| SCRx-CR11 TPC | e6-8-9-10 | e6-9-10 | e6-8-10 |
| SCRx-CR11 Prog | e6-8-9-10 | e6-9-10 | e6-8-10 |
| SCRx-CR14 TPC | e6-8-9-10 | e6-7-8-9-10 | |
| SCRx-CR14 NTG | e6-8-9-10 | e6-7-8-9-10 | |
| SCRx-PA3 TPC | e6-8-9-10 | e6-9-10 | e6-8-10 |
| SCRx-PA3 NTG | e6-8-9-10 | e6-9-10 | |
| SCRx-PA6 TPC | e6-9-10 | e6-8-9-10 | |
| SCRx-PA6 NTG | e6-8-9-10 | | |

Whole transcriptome sequencing of mRNA from distinct NTX tumor cell subpopulations appears able to precisely identify CD46 exon usage post-transcriptionally. Surprisingly, TPC subpopulations do not always appear to encode and or utilize the same CD46 transcripts as their more differentiated progeny; TProg and NTG cells. Nevertheless, knowledge of which transcripts are encoded in the respective tumor cell subpopulations may help the development of therapies targeting the CD46 protein expressed on TIC populations.

Example 6

RT-PCR Validates the Identity of CD46 Splice Variants in Tumor Initiating Cell Enriched Cell Populations To determine whether the identity of CD46 splice forms observed by SOLiD whole transcriptome sequencing were, in fact, expressed in distinct cell populations isolated from NTX tumors by FACS, total RNA was isolated from lysates using the RNeasy Plus Micro Kit (Qiagen, Inc.) after storage in RLT-Plus Buffer (supplied by the manufacturer) containing 1% f3-mercaptoethanol at −70° C. Specifically, the thawed lysates were homogenized using a QIAshredder spin column (Qiagen) and genomic DNA was eliminated using a gDNA Eliminator column before application to a RNeasy MiniElute spin column to capture total RNA. After washing, total RNA was eluted using RNase-free water. The isolated total RNA was quantified using either a NanoDrop 1000 spectrophotometer or the Agilent 2100 Bioanalyzer, using the RNA 6000 Pico Kit according to manufacturer protocols. Next, 20 ng of total RNA was reverse transcribed using Quanta qScript cDNA SuperMix, and PCR amplification was conducted (54° C. annealing and 72° C. extension for 1 min over 40 cycles) using AmpliTaqGold DNA Polymerase with the e6 Forward and e14 Reverse primers listed in FIG. 5A. The primers (SEQ ID NO: 1 and SEQ ID NO: 2) were designed to utilize conserved exons among the observed variants, Exon 6 and 14, using Integrated DNA Technologies' PrimerQuest and OligoAnalyzer 3.0 programs. The amplicon was analyzed on a 2% E-gel with 100 bp DNA ladder (FIG. 5B). Following amplification, PCR products were purified using the QIAGEN QIAquick PCR Purification Kit and cloned into pCR4-TOPO vector. Transformation of the vector was then performed using TOP10 cells (TOPO TA Cloning Kit for Sequencing, Invitrogen), and colonies were screened by PCR for the presence of inserts. The plasmids containing correct inserts were isolated using the EZNA Plasmid MiniPrep Kit I (Omega Bio-Tek) and sequenced using T3 and T4 sequencing primers.

An ethidium bromide stained gel showing CD46 exon 6 through 14 amplification products from CD46$^{hi}$ cells isolated from SCRx-CR5 and SCRx-CR11NTX tumors is shown in FIG. 5B, lanes 1 (CR5) and 2 (CR11). A 100 base pair ladder was depicted in lane L, and no template control (NC) was loaded in the 4$^{th}$ lane. Upon isolating the bands observed visually, cDNA was purified and then cloned into expression vectors and bacteria. Single colonies were picked and inserts were sequenced using T3 and T4 primers, as described above. Specifically, the primary transcript amplified from CR5 tumor cells contained exons 6, 9, 10, 11, 12 and 14 (323 bp amplicon representing variant F; vF), whereas primary transcript confirmed in CR11 tumor cells contained exons 6, 8, 9, 10, 11, 12 and 14 (368 bp amplicon representing variant D; vD) (FIG. 5C). Secondary transcripts were detected and confirmed to be present (denoted in the table in FIG. 5C), although the bands were barely visible by eye (data not shown). mRNA from TPC, TProg and NTG cell populations from SCRx-CR4NTX tumor line were also amplified and sequenced, demonstrating a more ambiguous utilization of variants D and F in the various tumor cell subpopulations (FIG. 5C); nevertheless, variant usage confirmed observations in the whole transcriptome SOLiD3 sequencing work described above.

Figure 6:
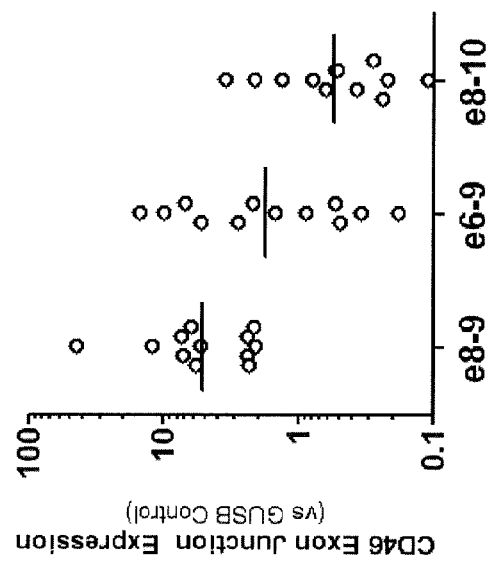
FIG. 6 depicts quantitative real-time PCR data depicting CD46 exon usage in bulk colorectal tumor cell populations.

Example 7 qRT-PCR with Splice Variant Specific Primer/Probe Sets to Determine CD46 Splice Variant Expression in Bulk Tumor and Enriched Cell Populations To more quickly ascertain the expression level of CD46 splice variants, specifically the usage of exons 6 through 12, in given cell populations and/or whole tissue specimens, custom qRT-PCR primers and FAM probes were designed that would be compatible with the ABI 7900HT real-time quantitative PCR machine (FIG. 6). Each of the respective FAM probes were designed to detect specific CD46 exon-exon junctions unique to specific splice variants, and PCR was performed using standard Taqman® qRT-PCR protocols in, at least, duplicate wells in 384-well plates. For example, a FAM-labeled probe was designed to encompass the exon 8-9 junction, which distinguishes the usage of transcripts utilizing exons 6, 8, 9 and 10 (CD46 variants C, D & M) and 6, 7, 8, 9 and 10 (CD46 variants A & B). Similarly, FAM-labeled probes were designed to capture the usage of exon 6-9 and 8-10 pairing, respectively, such that transcripts utilizing exons 6, 9 and 10 (CD46 variants E & F) and 6, 8 and 10 (CD46 variants I & J) could also be quickly distinguished and quantitated by qRT-PCR.

Similar to data described in previous examples, representative data from 12 colorectal NTX tumors suggest that transcripts including CD46 exons 6, 8, 9 and 10 or CD46 exons 6, 7, 8, 9 and 10 are the primary splice variant used in the majority of colorectal tumors (FIG. 6). Both whole transcriptome sequencing and targeted resequencing of capture transcripts, as described in the Examples above, demonstrate that the primary transcript usage is 6, 8, 9 and 10 and these do not generally include exon 7, therefore suggesting that the primary transcript in the majority of colorectal tumors is CD46 variant D. Transcripts utilizing exons 6, 9 and 10 (variant F) and 6, 8 and 10 (variant J) were also present, but to progressively lesser degrees, respectively, in most patients (FIG. 6). One of twelve samples screened with these exon-exon junction specific primers (SEQ ID NOs: 3-8) suggested that variants expressing exons 6, 9 and 10 were the primary CD46 transcript in NTX tumor line SCRx-CR15, while transcripts encoding CD46 exons 6, 8, 9 and 10 were expressed to a lesser extent. Surprisingly, these data and data described in the above Examples suggests that the primary CD46 splice variants in colorectal tumor initiating cells utilize either exons 6, 8, 9 and 10 (variant D) or exon 6, 9, and 10 (variant F). Because CD46 is consistently associated with tumor initiating capacity in both colorectal and pancreatic tumors and these specific exon-exon junctions are generally used in encoding the CD46 protein being expressed on the surface of these cells, exon junctions 6-8, 6-9, and to a lesser degree exon junctions 8-10 and 9-10 (present in variants B, D and F when exon 13 is also spliced out), are targets for empowered antibodies that might, for example, deliver a toxin or recruit cytotoxic T-cells to tumor initiating cells and thereby eliminate them.

Example 8

Protein Expression of CD46 in Exemplary Tumor Samples

After documenting enhanced surface expression of CD46 on TIC and characterizing the exon junctions used to encode for CD46 in these cells and tumors, as described by the previous Examples, evidence was sought for corresponding increases in the CD46 protein in similar tumor samples. In this respect, reverse phase cancer protein lysate arrays (ProteoScan™ Arrays; OriGene Technologies) comprising 4 dilutions of 432 tissue lysates from 11 tumor types, or their respective normal adjacent tissue, were provided along with controls consisting of HEK-293 cells without or with TP53-overexpression driven by an exogenous promoter. CD46 protein expression in the lysates on this array was detected using either a rabbit polyclonal antibody (HPA; Sigma Aldrich) generated against human CD46 or a mouse monoclonal antibody (SC1.N29 from Example 10 below) generated against a protein construct encoding CD46 exons 6, 8, 9 and 10. Colorimetric detection reagents and protocols were provided by the manufacturer of the ProteoScan Arrays. Spots on the fabricated array were converted to a digital image with a flatbed scanner using BZScan2 java Software (http://tagc.univ-mrs.fr/ComputationalBiology/bzscan/) to quantify spot intensity.

The results of these assays are shown in FIGS. 7A-7C and FIGS. 8A-C, and indicate that expression of the CD46 protein is upregulated in several different tumor types. More specifically FIGS. 7A-C employ a pan-CD46 antibody to show the level of expression of human CD46 in normal adjacent tissue or tumor tissue from specimens obtained from patients with different tumor types (i.e., primary tumor samples) across multiple stages of disease. Similarly, FIGS. 8A-C use an antibody that reacts with exon 10 of CD46 to show expression levels in various tumor samples. Data were generated as described above and represented as average pixel intensity per spot (spot density). The line plotted for each data set represents the mean for specimens in each category.

CD46 protein expression, as detected using a pan-CD46 antibody (HPA) recognizing a region within the region encoded by exons 1-6 that is present on all known CD46 splice variants, appears significantly elevated in a subset of colorectal tumor specimens, especially in patients with Stage 1V disease (FIG. 7A). FIG. 7B shows expression levels on tumor samples from pancreatic cancer patients with the neuroendocrine and non-neuroendocrine forms of the disease while FIG. 7C shows the expression levels on samples from ovarian cancer patients with the disease at different stages. Similarly, more selective antibodies recognizing the CD46 exon 10 (SC1.N29; specificity characterized in Example 15 below), which is utilized by all 14 CD46 transcripts, appeared to more specifically react with lysates of late stage colorectal (FIG. 8A), ovarian (FIG. 8B) and the neuroendocrine subtype of pancreatic tumors (FIG. 8C) versus normal adjacent tissue. Moreover, in contrast to the polyclonal, pan anti-CD46 antibody, the spot density and standard deviation among normal adjacent tissue samples were significantly lower when probed with the CD46 exon 10 specific antibody: SC1.N29. These results suggest that CD46 protein expression in the above-mentioned tumors is upregulated in cancer, but minimal in normal tissue.

These data support the observations in above examples that CD46 overexpression may be involved in tumor initiating cell and/or TPC proliferation and survival. In view of the forgoing Examples showing CD46 expression demarcates, at least in part, TPC enriched cell populations in colorectal and pancreatic tumors and that CD46 surface expression is associated with tumorigenesis and tumor propagation, it was decided to construct CD46 immunogens that could be used in the generation of anti-CD46 antibodies.

Example 9

Fabrication and Expression of Soluble CD46 Constructs

Three soluble CD46 constructs were made using the D, F and J isoforms for use in generating CD46 modulators and characterization of the same.

Full length ORFs for CD46 isoform D (comprising exons 1-6, 8-12 and 14 of the CD46 gene; equivalent to the coding sequence of NM_153826) and isoform F (comprising exons 1-6, 9-12, and 14; equivalent to the coding sequence of NM_172353) were PCR cloned into the pENTR vector (Life Technologies) from cDNA obtained from tumor sample Cd4p2. DNA sequencing demonstrated the isoform F clone to be free of mutation relative to the NCBI RefSeq (NM_172353), while the isoform D clone contained a single C→T silent mutation within the open reading frame at nucleotide +822 (where +1=the "A" in the initiating ATG of the wild-type CD46ORF). The full length open reading frame for CD46 isoform J (comprising exons 1-6, 8, 10-12, and 14; equivalent to the cds of NM_172356) was created using splice overlap extension PCR using the CD46 isoform D cDNA as template. DNA sequencing was used to confirm there were no additional mutations in the isoform J clone beyond the silent mutation described above.

Sequences encoding the extracellular domain (ECD) from each of these three CD46 variants were PCR cloned in-frame with the murine Ig κ-chain leader sequence and a 8×His tag in the pSec-2-Hygro vector (Life Technologies). All three CD46 ECD cDNAs encode CD46 proteins starting with the mature N-terminal residue (Cys35) up to the transmembrane domain for each isoform (corresponding to residue 343 in the variant a isoform). All cDNA constructs were generated by PCR using the high fidelity AccuPrime™ Taq DNA Polymerase (Life Technologies) and were cloned into the unique SfiI-PmeI sites of pSec-Tag (Life Technologies). HEK-293T cells were transiently transfected with the plasmids encoding the different CD46 splice variants. Soluble, secreted CD46 ECD proteins fused to a histidine tag were purified from transiently transfected cell culture supernatants using a nickel affinity column. Proteins were further purified by size exclusion chromatography using a Superdex200 column (GE Healthcare) in phosphate buffered saline (PBS), pH 7.2.

The amino acid sequences for the resulting constructs CD46D-His (SEQ ID NO: 9), CD46F-His (SEQ ID NO: 10) and CD46J-His (SEQ ID NO: 11) are set forth immediately below.

```
CD46D-His
                                                      (SEQ ID NO: 9)
  1 AQPACEEPPTFEAMELIGKPKPYYEIGERVDYKCKKGYFYIPPLATHTIC

51 DRNHTWLPVSDDACYRETCPYIRDPLNGQAVPANGTYEFGYQMHFICNEG

101 YYLIGEEILYCELKGSVAIWSGKPPICEKVLCTPPPKIKNGKHTFSEVEV

151 FEYLDAVTYSCDPAPGPDPFSLIGESTIYCGDNSVWSRAAPECKVVKCRF

201 PVVENGKQISGFGKKFYYKATVMFECDKGFYLDGSDTIVCDSNSTWDPPV

251 PKCLKVSTSSTTKSPASSASGPRPTYKPPVSNYPGYPKPEEGILDSLDHH

301 HHHHHH*

CD46F-His
                                                     (SEQ ID NO: 10)
  1 AMVLLLYSFSDACEEPPTFEAMELIGKPKPYYEIGERVDYKCKKGYFYIP

51 PLATHTICDRNHTWLPVSDDACYRETCPYIRDPLNGQAVPANGTYEFGYQ

101 MHFICNEGYYLIGEEILYCELKGSVAIWSGKPPICEKVLCTPPPKIKNGK

151 HTFSEVEVFEYLDAVTYSCDPAPGPDPFSLIGESTIYCGDNSVWSRAAPE

201 CKVVKCRFPVVENGKQISGFGKKFYYKATVMFECDKGFYLDGSDTIVCDS

251 NSTWDPPVPKCLKVSTSSTTKSPASSASGPRPTYKPPVSNYPGYPKPEEG

301 ILDSLDHHHHHHHH*

CD46J-His
                                                     (SEQ ID NO: 11)
  1 AVLLLYSFSDACEEPPTFEAMELIGKPKPYYEIGERVDYKCKKGYFYIPP

51 LATHTICDRNHTWLPVSDDACYRETCPYIRDPLNGQAVPANGTYEFGYQM

101 HFICNEGYYLIGEEILYCELKGSVAIWSGKPPICEKVLCTPPPKIKNGKH

151 TFSEVEVFEYLDAVTYSCDPAPGPDPFSLIGESTIYCGDNSVWSRAAPEC

201 KVVKCRFPVVENGKQISGFGKKFYYKATVMFECDKGFYLDGSDTIVCDSN

251 STWDPPVPKCLKVSTSSTTKSPASSASGPRPTYKPPVSNYPGYPKPEEGI

301 LDSLDHHHHHHHH*
```

Example 10

Generation of CD46 Modulators

CD46 modulators in the form of murine antibodies were produced in accordance with the teachings herein through inoculation with CD46D-His. In this regard three strains of mice were used to generate high affinity, murine, monoclonal antibodies that can be used therapeutically to inhibit the action of CD46 for the treatment of hyperproliferative disorders. Specifically, Balb/c, CD-1 and FVB mouse strains were immunized with human recombinant CD46 and used to produce hybridomas as follows:

Antigen

Mice were immunized with both the recombinant fusion protein comprising the extracellular portion of CD46-D-His from Example 9 and two synthetic peptides derived from the CD46 protein sequence and located within the exon-exon junctions of exons 6-8 and 6-9.

Both peptides (21-22 aa length) were synthesized using solid-phase synthesis (AnaSpec, Inc.). The amino acid sequence of the peptides based on the CD46 protein is as follows:

```
Exons 6-8 junction:
CVPKSLKVSTSSTTKSPASSAS      (SEQ ID NO: 12)

Exons 6-9 junction
PVPKSLKGPRPTYKPPVSNYPG      (SEQ ID NO: 13)
```

Immunization

Mouse monoclonal antibodies to CD46 were prepared using three strains of female mice Balb/c, CD-1 and FVB. Mice were immunized with ten doses of a mixture of synthetic CD46 peptides 1 and 2 (50 μg per mouse for each immunization) in combination with recombinant CD46D-His (10 μg per mouse) via footpad injections. The immunogen mixture was emulsified with an equal volume of TITERMAX or alum adjuvant prior to injection.

Generation of Hybridoma Producing Mouse Monoclonal Antibodies to CD46

Sera positive immunized mice were sacrificed and draining lymph nodes (popliteal and inguinal, if enlarged) were dissected out and used as a source for antibody producing cells. Single cell suspension of B cells (6.35×10$^7$ cells) were fused with non-secreting P3x63Ag8.653 myeloma cells (ATCC #CRL-1580) at a ratio of 1:1 by Electro-fusion. Electro cell fusion was performed using a fusion generator, model ECM2001, (Genetronic, Inc.). Cells were resuspended in hybridoma selection medium supplemented with HAT (Sigma #A9666) (DMEM (Cellgro cat#15-017-CM) medium containing, 15% Fetal Clone I serum (Hyclone), 1 mM sodium pyruvate, 4 mM L-glutamine, 10 μg/mL gentamicin, 50 μM 2-mercaptoethanol, 100 μM hypoxanthine, 0.4 μM aminopterin, and 16 μM thymidine) and then plated at 200 μL/well in twenty 96-well flat bottom tissue culture plates, based on a final plating of 2×10$^6$ B cells per 96-well plate. The plates are then placed in a humidified 37° C. incubator containing 5% $CO_2$ and 95% air for 7-10 days.

Screening of Anti-Human CD46 Antibodies:

Supernatants from fifteen 96 well plates were screened by ELISA. More particularly ELISA microtiter plates were coated with purified recombinant CD46D-His fusion proteins from transfected HEK-293 cells at 100 ng/well in carbonate buffer. Plates incubated at 4° C. overnight and then blocked with 200 μl/well of 3% BSA in PBS/Tween (0.05%). Supernatant from hybridoma plates were added to each well and incubated for 1-2 hours at ambient temperature. The plates were washed with PBS/Tween and than incubated with goat anti-mouse IgG (Fc fragment specific) conjugated with horseradish proxidase (Jackson ImmunoResearch) for one hour at room temperature. After washing, the plates were developed with TMB (3,3',5,5'-tetramethylbenzidine) substrate (Thermo Scientific 34028) and analyzed by spectrophotometer at OD 450.

CD46 specific hybridomas (154 supernatants reacted with the antigen) were expanded in cell culture were re-plated, rescreened and serially subcloned by limiting dilution, or single cell FACS sorting. The resulting clonal populations were expanded and cryopreserved in freezing medium (90% FBS, 10% DMSO) and stored in liquid nitrogen.

Example 11

CD46 Modulator Characterization by Flow Cytometry

For flow cytometric assays, 50×10$^6$ SW480 cells (ATCC Catalog #CCL-228; known to naturally express high levels of human CD46) were mixed with an equal number of chinese hamster ovary cells (CHO-S; which do not express human CD46) to a final concentration of 2.5×10$^6$ cells/mL. 20 μL of this cell mixture was added to 25 μL of CD46 antibody-containing supernatant derived from different clones obtained as set forth in Example 10 in each well of fifteen 96-well plates. The samples were mixed by gentle vortexing and the plates incubated for 30 minutes at 4° C. The cells were then washed once with PBS and then stained for 30 minutes at 4° C. in the dark with DyLight649 anti-mouse IgG (BioLegend Inc.). After incubation the cells were washed with PBS and counterstained with DAPI (4',6-diamidino-2-phenylindole; to eliminate dead cells from the analysis). A positive control sample was prepared with 1:100 dilution of a commercially available mouse monoclonal CD46 antibody (MEM-258; BioLegend), and the negative control was labeled with only anti-mouse IgG. Samples were analyzed by flow cytometry.

Using the flow cytometry protocol described above, 114 of the 154 positive hybridoma supernatants (out of 1,440 prospective CD46 antibody expressing hybridoma clones) were judged to contain antibodies that interact with human CD46 on a cell surface (data not shown). Antibody screening by flow cytometry demonstrates that modulators of the instant invention may be used to effectively characterize cell surface CD46 expression and to isolate CD46 positive cells.

Example 12

CD46 Modulator Internalization

Supernatant from hybridomas producing antibodies raised against CD46 were screened for their ability to internalize in K562 cells, which express CD46 on the cell surface. K562 cells at a starting concentration of 10$^6$/ml (single cells suspension) were blocked with Human TruStain (BioLegend Inc.) for 10 minutes at room temperature, and diluted to 5×10$^4$ cells per condition. Duplicate samples were then stained for 30 minutes on ice with antibody containing supernatant at a final volume of 50 ul. Cells were then washed with FACS staining medium (FSM; 2% fetal bovine serum/Hank's buffered saline solution/25 mM HEPES [pH7.4]) to remove unbound antibody. This step was followed by a second stain with donkey anti-mouse Alexa647 (Life Technologies) for 30 minutes on ice. Samples were washed again to remove unbound antibody and then resuspended in internalization medium (2% fetal bovine serum/Iscove's Modified Dulbecco's Medium).

To allow internalization, samples were incubated in 5% $CO_2$@37° C. (or 4° C. for the control) for 1 hour. Internalization was then stopped by transferring samples to ice and adding excess ice cold FSM. To remove any antibody that did not internalize and remained on the cell surface, samples were treated with low pH PBS (pH 2.0) for 10 minutes on ice. Following this "acid strip" procedure, samples were washed extensively with FSM, resuspended in 150 ul of FSM containing 2 ug/ml of DAPI, and analyzed by flow cytometry. Any signal detected beyond background results from antibody internalization: a process which protects the fluorescent conjugate from removal from the cell surface during the acid strip process. All incubations were performed in FSM unless stated otherwise.

Figure 9A:
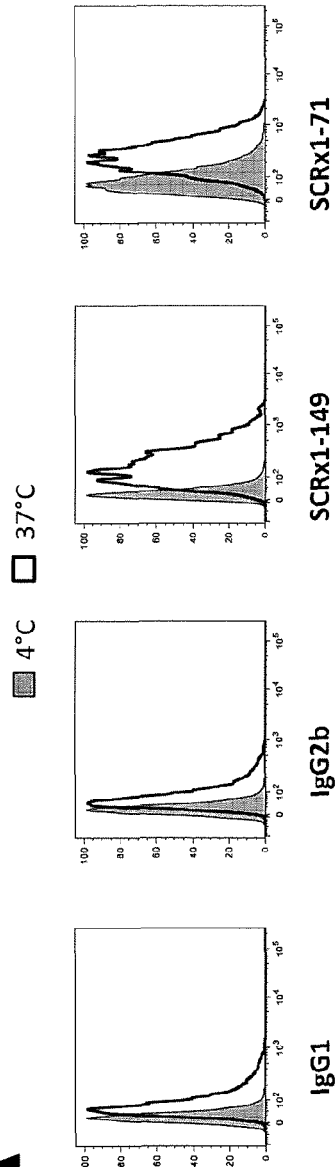
FIGS. 9A and 9B are graphical representations illustrating internalization of CD46 antibodies in K562 cells (FIG. 9A) and killing of K562 cells by mouse monoclonal anti-CD46 antibodies able to internalize a secondary anti-mouse antibody conjugated to Saporin toxin (FIG. 9B.

Upon screening at least 75 of the CD46 antibody-containing hybridoma clone supernatants using the acid strip protocol described above, many supernatants showed a positive shift in fluorescence vs. the IgG1 and IgG2b negative control antibodies (FIG. 9A). The exemplary SC1.N149 and SC1.N71 clones, for instance, demonstrated excellent internalization in as far as antibodies in the supernatant from these clones were able to internalize and protect the Alexa647 secondary antibody from acid stripping. These data demonstrate that a subset of antibodies generated against human CD46 splice variant-specific peptides and CD46D-His bind the antigen as it is presented on cells and is able to internalize (FIG. 9A).

Example 13

CD46 Modulators as Targeting Moieties

Targeting of a cytotoxic drug stably linked to an antibody represents an empowered antibody approach that might have great therapeutic benefit for patients with solid tumors. To determine whether the CD46-specific antibodies described above were able to mediate the delivery of a cytotoxic agent to live cells, an in vitro cell killing assay was performed wherein an anti-mouse secondary antibody conjugated to the ribosome-inactivating protein saporin (Advanced Targeting Systems) was bound to CD46 antibodies via their mouse Fc region, and the ability of these saporin conjugates to internalize and kill cells was measured 72 hours later by measuring cell viability.

Specifically, 5,000 K562 cells per well were plated in wells of a 96-well plate. The anti-CD46 antibodies described above were either screened as antibody-containing supernatants or were purified from supernatants and then diluted to 20 μg/mL. An aliquot of each antibody, respectively, was mixed 1:1 with anti-mouse ZAP or IgG-ZAP (Advanced Targeting Systems), vortexed for 5 seconds, and then incubated at room temperature for 1 hour. Two additional serial 10-fold dilutions of the antibody-saporin conjugate were then made and 50 μL of each mixture, respectively, was added to K562 cell containing wells already containing 50 μL of medium. The cell/antibody-conjugate mixture was then incubated at 37° C. for 24 hours. Following this incubation, cells were spun down in round-bottom 96-well plates, supernatant was removed, and 100 μL of fresh culture medium was added to each well. The cells were then incubated for an additional 72 hours and then viable cell numbers were enumerated using CellTiter-Glo (Promega Inc.) per the manufacturer's protocol.

Figure 9B:
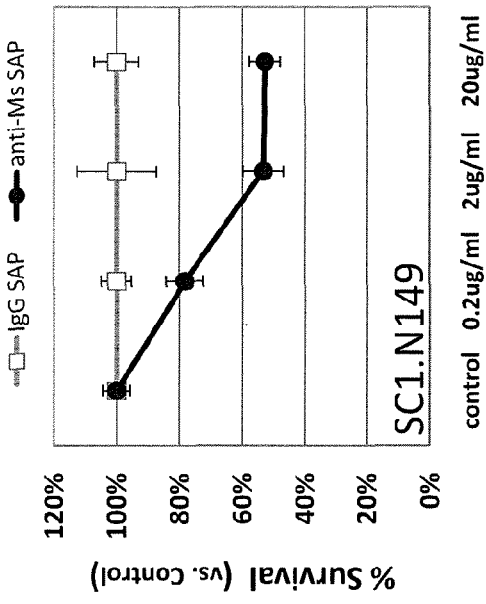

Upon screening of the CD46-specific, internalizing antibody clones for their ability to mediate saporin toxin internalization and cell killing as described above, all antibody clones that were able to internalize in the internalization assay in Example 12 were able to mediate cell killing in vitro, whereas the non-specific mouse IgG SAP antibody control was not able to kill cells (FIG. 9B). These observations confirm that internalizing anti-CD46 antibodies described herein are able to mediate the delivery of a cytotoxic toxin to cells, for example, resulting in the eradication of $CD46^{hi}$ cells. Because colorectal and pancreatic tumor cells responsible for tumor regeneration and resistance to therapy are $CD46^{hi}$ as described above, monoclonal antibodies described herein have great potential as therapeutic agents that might significantly impact overall patient survival beyond current standard of care therapies.

Example 14

Sequencing of CD46 Modulators

Based on the foregoing, a number of exemplary distinct monoclonal antibodies that bind immobilized human CD46 with apparently high affinity were selected. As shown in a tabular fashion in FIGS. 11A and 11B, sequence analysis of the DNA encoding mAbs from Example 10 confirmed that many had a unique VDJ rearrangements and displayed novel complementarity determining regions. Note that the complementarity determining regions set forth in FIG. 11B are derived from VBASE2 analysis.

For initiation of sequencing TRIZOL reagent was purchased from Invitrogen (Life Technologies). One step RT PCR kit and QIAquick PCR Purification Kit were purchased from Qiagen, Inc. with RNasin were from Promega. Custom oligonucleotides were purchased from Integrated DNA Technologies.

Hybridoma cells were lysed in TRIZOL reagent for RNA preparation. Between $10^4$ μL and $10^5$ cells were resuspended in 1 ml TRIZOL. Tubes were shaken vigorously after addition of 200 ml of chloroform. Samples were centrifuged at 4° C. for 10 minutes. The aqueous phase was transferred to a fresh microfuge tube and an equal volume of isopropanol was added. Tubes were shaken vigorously and allowed to incubate at room temperature for 10 minutes. Samples were then centrifuged at 4° C. for 10 minutes. The pellets were washed once with 1 ml of 70% ethanol and dried briefly at room temperature. The RNA pellets were resuspended with 40 μL of DEPC-treated water. The quality of the RNA preparations was determined by fractionating 3 μL in a 1% agarose gel. The RNA was stored in a −80° C. freezer until used.

The variable DNA sequences of the hybridoma amplified with consensus primer sets specific for murine immunoglobulin heavy chains and kappa light chains were obtained using a mix of variable domain primers. One step RT-PCR kit was used to amplify the VH and VK gene segments from each RNA sample. The Qiagen One-Step RT-PCR Kit provides a blend of Sensiscript and Omniscript Reverse Transcriptases, HotStarTaq DNA Polymerase, Qiagen OneStep RT-PCR Buffer, a dNTP mix, and Q-Solution, a novel additive that enables efficient amplification of "difficult" (e.g., GC-rich) templates.

Reaction mixtures were prepared that included 3 μL of RNA, 0.5 of 100 μM of either heavy chain or kappa light chain primers 5 μL of 5×RT-PCR buffer, 1 μL dNTPs, 1 μL of enzyme mix containing reverse transcriptase and DNA polymerase, and 0.4 μL of ribonuclease inhibitor RNasin (1 unit). The reaction mixture contains all of the reagents required for both reverse transcription and PCR. The thermal cycler program was RT step 50° C. for 30 minutes 95° C. for 15 minutes followed by 30 cycles of (95° C. for 30 seconds, 48° C. for 30 seconds, 72° C. for 1.0 minutes). There was then a final incubation at 72° C. for 10 minutes.

To prepare the PCR products for direct DNA sequencing, they were purified using the QIAquick™ PCR Purification Kit according to the manufacturer's protocol. The DNA was eluted from the spin column using 50 µL of sterile water and then sequenced directly from both strands. PCR fragments were sequenced directly and DNA sequences were analyzed using VBASE2 (Retter et al., Nucleic Acid Res. 33; 671-674, 2005).

As discussed above the amino acid and nucleic acid sequences for eighteen (18) exemplary antibody heavy and light chain variable regions are set forth in FIGS. 10A-10R respectively (SEQ ID NOs: 14-85) while the genetic arrangements and derived CDRs (as derived from VBASE2 analysis) of these anti-hCD46 antibodies are set forth, respectively, in a tabular form in FIGS. 11A and 11B (SEQ ID NOs: 86-193).

Of note a significant fraction (50%) of the 18 monoclonal antibodies that were sequenced contained VK10 and VK14 light chain germline segments. More specifically there was a strong bias toward the use of the IGKV10-94 and IGKV14-111 genes in the immunized mouse repertoire. Further analysis showed that 6 of 18 mAbs used the IGKV10-94 gene, and 3 of 19 mAbs used the IGKV14-111 gene. Three antibodies that use IGKV14-111 gene segments (SC1.N56, SC1.N66 and SC1N77) recognize epitopes within the CD46 sushi domain 1. Five out of six antibodies that use IGKV10-94 gene segment recognize epitope within Sushi domains 3-4. While the nature of the clonal selection process is unclear it may be that the CDR regions of these germline gene segments form a favorable conformation for binding the antigenic determinants of CD46. At the same time variable region bias was not observed in the corresponding heavy chains.

Example 15

Epitope Determination of CD46 Modulators

As discussed above CD46 is a type I membrane glycoprotein in which the amino-terminal domains of the extracellular domain (i.e., those encoded by exons 1-6, common to all CD46 transcripts) are composed of four short consensus repeats (SCRs). Each of these SCRs is a cysteine-rich domain of approximately 60 amino acids. The four SCRs of CD46 are then followed by the STP domain that defines the three splice variants CD46D, CD46F and CD46J as described in Karosi et al., supra which is incorporated herein by reference in its entirety. To differentiate between a pan-CD46 antibody (i.e., one that binds one or more of the SCRs) versus isoform specific CD46 antibodies, a pan-CD46 ECD-Fc construct was generated in the pSec-Tag vector generally as set forth in Example 9. This construct encodes the four SCRs (i.e., exons 1-6), and was used to express the CD46 ECD-Fc in HEK-293T cells using the same methods as described above for the CD46 ECD variants (data not shown). Each of the hybridoma supernatants was tested for binding to each of the pan- or isoform specific CD46 ECD proteins. His-tagged purified CD46 antigen derived from the sequence of CD46 exons 1-6 and CD46D-H is, CD46F-His and CD46J-His from Example 9 were used to coat ELISA plates. The binding of each monoclonal antibody was detected by HRP labeled goat anti-mouse IgG. Pan-CD46 antibodies were identified by their ability to react with the CD46 antigen including the first six exons and lacking exons 7-10 of the CD46 extracellular domain. 155 out of 160 mAbs were found to be pan antibodies that bound to all CD46 recombinant expressed ectodomains. Five mAbs failed to recognize an epitope in the first 6 exons of CD46, but recognized the STP domains that define the three splice variants CD46D, CD46F and CD46J.

Figure 12A:
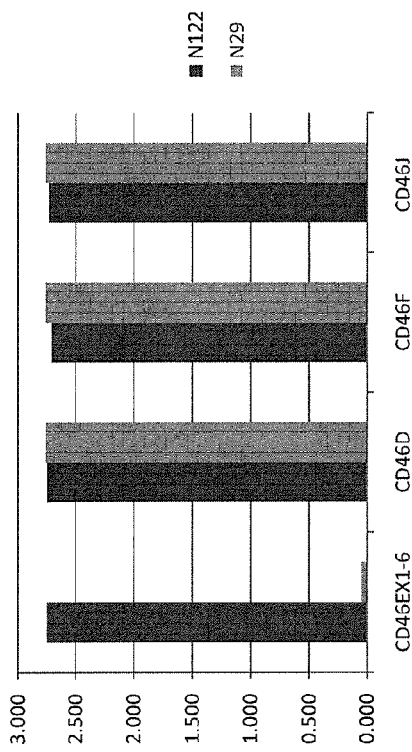
FIGS. 12A and 12B graphically illustrate ELISA data showing binding of anti-CD46 antibodies SC1.N122 and SC1.N29 to various regions of CD46 (FIG. 12A) and a graphical representation of ELISA data showing binding of anti-CD46 antibody SC1.N29 to various CD46 exons (FIG. 12B)

FIG. 12A shows a graphical representation of the ELISA data for the SC1.N122 and SC1.N29 antibodies. The data show that SC1.N122 is a pan-CD46 antibody, as it bound to CD46 exons 1-6 (i.e., CD46ECD-Fc), CD46D-His, CD46F-His and CD46J-His. SC1.N29, on the other hand, showed little to no binding to CD46 Exons 1-6, but did show binding to CD46D-His, CD46F-His, and CD46J-His. Thus, these data indicated that SC1.N29 binds to the ST domain encoded by exon 8, and exon 9, or the membrane proximal domain within exon10.

Figure 12B:
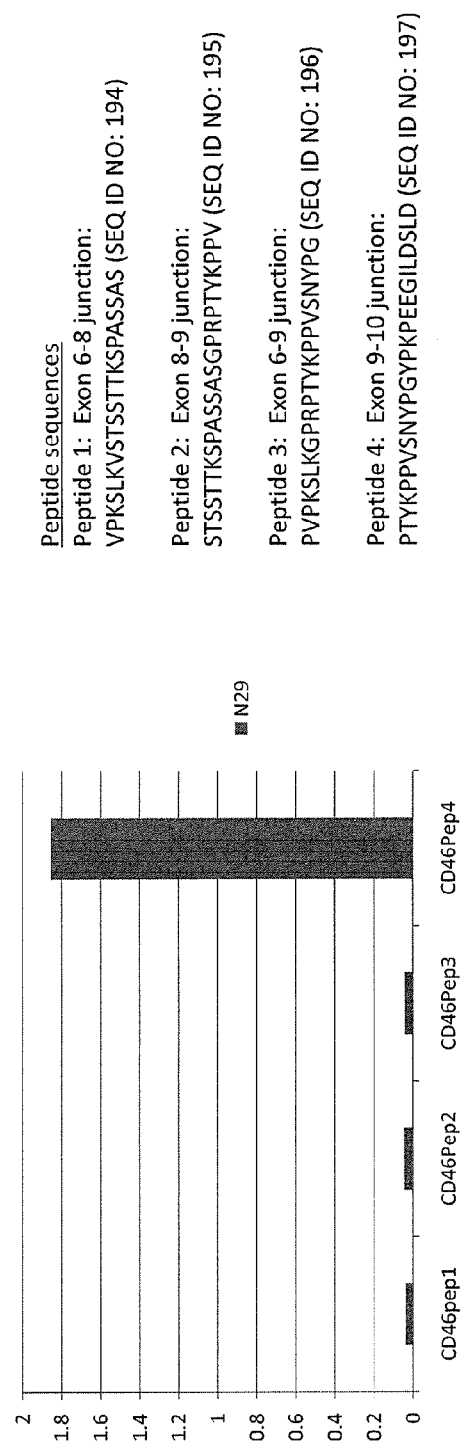

To more specifically identify the region of CD46 recognized by SC1.N29, synthetic peptides derived from various exon-exon junctions of CD46 were directly coated on ELISA plates. Binding of SC1.N29 to those peptides was detected by HRP labeled goat anti-mouse IgG. As shown in FIG. 12B, SC1.N29 bound to peptide 4, which is derived from the exon 9-exon 10 junction. Because SC1.N29 bound to peptide 4 (FIG. 12B) and CD46J (FIG. 12A), these data suggest that SC1.N29 binds to a region in exon 10 since only these residues are common to both the peptide and the CD46J protein.

Example 16

Humanization of a Monoclonal Antibody CD46 Modulators

Murine antibodies SC1.N71 and SC1.N149 were humanized using a computer-aided CDR-grafting method (Abysis Database, UCL Business Plc.) and standard molecular engineering techniques to provide hSC1.N71 and hSC1.N149 modulators. The human framework regions of the variable regions were selected based on their highest sequence homology to the mouse framework sequence and its canonical structure. For the purposes of the analysis the assignment of amino acids to each of the CDR domains is in accordance with the Kabat et al. numbering. Several humanized antibody variants were made in order to generate the optimal humanized antibody. Both humanized antibodies retain the antigen-binding complementarity-determining regions (CDRs) from the mouse hybridoma in association with human framework regions. The humanized SC1.N71 mAb binds to CD46 antigen with improved binding affinity while the humanized SC1.N149 mAb retains the same antigen binding affinity as its mouse counterpart.

Molecular engineering procedures were conducted using art-recognized techniques. To that end total mRNA was extracted from the hybridomas according to the manufacturer's protocol (Trizol® Plus RNA Purification System, Life Technologies). A primer mix comprising thirty-two mouse specific 5' leader sequence primers, designed to target the complete mouse repertoire, was used in combination with 3' mouse Cγ1 primer to amplify and sequence the variable region of the antibody heavy chains. Similarly thirty-two 5' Vk leader sequence primer mix designed to amplify each of the Vk mouse families combined with a single reverse primer specific to the mouse kappa constant region were used to amplify and sequence the kappa light chain. The $V_H$ and $V_L$ transcripts were amplified from 100 ng total RNA using reverse transcriptase polymerase chain reaction (RT-PCR).

A total of eight RT-PCR reactions were run for each hybridoma: four for the V kappa light chain and four for the V gamma heavy chain (γ1). The QIAGEN One Step RT-PCR kit was used for amplification, (Qiagen, Inc.). The extracted PCR products were directly sequenced using specific V region primers. Nucleotide sequences were analyzed using IMGT to identify germline V, D and J gene members with the highest sequence homology. The derived sequences were compared to known germline DNA sequences of the Ig V- and J-regions using V-BASE2 (Retter et al., supra) and by alignment of $V_H$ and $V_L$ genes to the mouse germ line database.

From the nucleotide sequence information, data regarding V, D and J gene segments of the heavy and light chains of SC1.N71 and SC1.N149 were obtained. Based on the sequence data new primer sets specific to the leader sequence of the Ig $V_H$ and $V_K$ chain of the antibodies were designed for cloning of the recombinant monoclonal antibody. Subsequently the V-(D)-J sequences were aligned with mouse Ig germ line sequences. Heavy chain genes of N71 were identified as VHQ52.a1 3.37 (V), DSP2.9 (D) and JH3 whereas the heavy chain of genes of N149 were identified as IGHV1-18 (V), DSP2.8(D) and JH3. Light chains genes were, from IGKV10-94 and JK1 germline gene families for both mAbs.

The obtained heavy and light chain sequences from SC1.N71 were aligned to the functional human variable region sequences and reviewed for homology and canonical structure. Based on the analysis the $V_H$4-59 germ line and the JH4 J segment were selected with no framework amino acid substitutions for use in the humanized SC1.N71 construct. The variable region of the humanized SC1.N71 heavy chain shows 88% homology to the human VH4-59 germline sequence and 78% sequence homology to the mouse variable region. For the light chain of SC1.N71a similar process was followed and resulted in the selection of human germ line $V_K$ O2 and J segment JK1, with no frame work amino acid substitutions. The resulting variable region of the hSC1.N71 kappa light chain shows 90% homology to the human $V_K$O2 germ line sequence (positive Z score value of 0.945) and 85% sequence homology to the mouse variable region. The nucleic acid sequences and corresponding amino acid sequences of the humanized SC1.N71 heavy chain (SEQ ID NOs: 198 and 199), and the humanized light chain (SEQ ID NOs: 200 and 201) are shown in FIG. 13A wherein the CDRs (as defined by Kabat et al.) are underlined.

A similar procedure was followed to derive hSC1.N149. This analysis provided a humanized heavy chain comprising the $V_H$1-18 gene segment and J segment JH4 with no framework amino acid substitutions. The variable region of the humanized SC1.N149 heavy chain shows 87% homology to the human VH1-18 germ line sequence and 77% sequence homology to the mouse variable region. For the light chain variable region the analysis indicated that $V_K$O$_2$ and J segment JK1 with no framework substitutions would be effective. The variable region of the humanized SC1.N149 kappa light chain shows 87% homology to the human $V_K$O$_2$ germ line sequence (positive Z score value of 0.942) and 80% sequence homology to the mouse variable region. The nucleic acid sequences and corresponding amino acid sequences of the humanized SC1.N149 heavy chain (SEQ ID NOs: 202 and 203), and the humanized light chain (SEQ ID NOs: 204 and 205) are shown in FIG. 13A wherein the CDRs (as defined by Kabat et al.) are underlined.

Synthetic humanized variable DNA fragments (Integrated DNA Technologies) of both heavy chains were cloned into human IgG1 expression vector. The variable light chain fragments were cloned into human C-kappa expression vector. Antibodies were expressed by co-transfection of the heavy and the light chain into CHO cells.

More particularly, for antibody production directional cloning of the murine and humanized variable gene PCR products into human immunoglobulin expression vectors was undertaken. All primers used in Ig gene-specific PCRs included restriction sites (AgeI and XhoI for IgH, XmaI and DraIII for IgK, which allowed direct cloning into expression vectors containing the human IgG1, and IGK constant regions, respectively. In brief, PCR products were purified with Qiaquick PCR purification kit (Qiagen, Inc.) followed by digestion with AgeI and XhoI (IgH), XmaI and DraIII (IgK), respectively. Digested PCR products were purified prior to ligation into expression vectors. Ligation reactions were performed in a total volume of 10 μL with 200U T4-DNA Ligase (New England Biolabs), 7.5 μL of digested and purified gene-specific PCR product and 25 ng linearized vector DNA. Competent E. coli DH10B bacteria (Life Technologies) were transformed via heat shock at 42° C. with 3 μL ligation product and plated onto ampicillin plates (100 μg/mL). The AgeI-EcoRI fragment of the $V_H$ region was than inserted into the same sites of pEE6.4HuIgG1 expression vector while the synthetic XmaI-DraIII $V_K$ insert was cloned into the XmaI-DraIII sites of the respective pEE12.4Hu-Kappa expression vector.

Cells producing humanized antibodies were generated by transfection of HEK 293 cells with the appropriate plasmids using 293fectin. In this respect plasmid DNA was purified with QIAprep Spin columns (Qiagen). Human embryonic kidney (HEK) 293T (ATCC No CRL-11268) cells were cultured in 150 mm plates (Falcon, Becton Dickinson) under standard conditions in Dulbecco's Modified Eagle's Medium (DMEM) supplemented with 10% heat inactivated FCS, 100 μg/mL streptomycin, 100 U/mL penicillin G (all from Life Technologies).

For transient transfections cells were grown to 80% confluency. Equal amounts of IgH and corresponding IgL chain vector DNA (12.5 μg of each vector DNA) was added to 1.5 mL Opti-MEM mixed with 50 μL HEK 293 transfection reagent in 1.5 mL opti-MEM. The mix was incubated for 30 min at room temperature and distributed evenly to the culture plate. Supernatants were harvested three days after transfection, replaced by 20 mL of fresh DMEM supplemented with 10% FBS and harvested again at day 6 after transfection. Culture supernatants were cleared from cell debris by centrifugation at 800×g for 10 min and stored at 4° C. Recombinant chimeric and humanized antibodies were purified with Protein G beads (GE Healthcare).

Example 17

Determination of Binding Characteristics of CD46 Modulators

Various methods were used to analyze the biding characteristics of selected CD46 modulators generated as set forth above. Specifically, a number of CD46 antibodies were characterized as to affinity, kinetics, binning, and cross reactivity with regard to three CD46 homologs generated and expressed generally using standard techniques as set forth in Example 9 above. More specifically, macaque (protein sequenced and expressed in-house, data not shown), marmoset (Callithrix jacchus; GenBank Accession No.: □8HYX8.2) and squirrel monkey (Saimiri sciureus; construct made using a combination of GenBank Accession Nos.: AAB66819.1 and AAC39671.1, data not shown) CD46 homologs were expressed and purified prior to analysis by ForteBIO. Reactivity of the antibodies to reduced and unreduced antigen by Western blot was also measured and very few of the antibodies that were tested bound to reduced antigen. The results of these experiments are set forth in tabular form in FIG. 14.

With regard to the data, affinity was measured in three ways to ensure accuracy. First, binding signal was measured for a fixed amount of antibody probed against serial dilutions of antigen in an ELISA to determine relative modulator activity (data not shown). Second, the affinities and kinetic constants $k_{on}$ and $k_{off}$ of the selected modulators were then measured using bio-layer interferometry analysis on a ForteBIO RED (ForteBIO, Inc.) with a standard antigen concentration series. Finally, the affinity of selected modulators was measured by surface plasmon resonance (Biacore System, GE Healthcare). Based on a standard antigen concentration series and using a 1:1 Langmuir binding model, the $K_d$ of the antibody binding to antigen and the kinetic constants $k_{on}$ and $k_{off}$ were determined. FIG. 14 identifies the method (F for ForteBIO, B for Biacore) used to generate the affinity measurement included in the table. In general, the selected modulators exhibited relatively high affinities in the nanomolar range.

To further characterize the CD46 modulators truncated protein constructs were fabricated each of which deleted one of the four sushi domains. Binding to these constructs was tested using ELISA to identify the CD46 target region of a particular modulator. The experimental details of this work are laid out in Example 14 with the binding domain of each tested antibody set out in FIG. 14.

In order to determine whether the epitope recognized by the CD46 modulator comprises contiguous amino acids or is formed by noncontiguous amino acids juxtaposed by secondary structure of the antigen, Western blots were run under reducing and non-reducing conditions. More particularly, using standard electrophoresis techniques well known in the art, CD46 antigen in both states was exposed to the selected modulator. As detailed in FIG. 14 most CD46 modulators substantially reacted only with antigen where disulphide bonds were intact (NR), while two modulators reacted with both non-reduced and reduced antigen (NR/R).

Finally, cross-reactivity with regard to cynomolgus, marmoset, and squirrel monkey CD46 homologs were evaluated in ForteBIO using a concentration series with recombinantly expressed, monomeric CD46 antigens. As listed in FIG. 14 the selected modulators were reactive with any number of the homologs. In particular, SC1.N71 and SC1.N149 were reactive with cynomolgus and marmoset, but not reactive with squirrel monkey. ND in the table indicates that the data was not determined.

Example 18

Epitope Determination of Selected CD46 Modulators

In order to determine the epitopes defined by selected CD46 modulators generated as set forth above several different variants of the CD46 ECD were constructed and expressed. More specifically CD46 deletion mutants were designed using primers which amplified various CD46 SCR domains (as described in Adams et al., Journ. Immunol., Vol. 147:3005, 1991 which is incorporated herein by reference in its entirety) and fused these to a His tag for affinity purification (Qiagen, Ni-NTA). Four separate H is fusion constructs, each omitting one of the four SCR domains, were then cloned and expressed generally as set forth in Example 9 using standard biochemical. Isolated endotoxin free Plasmids DNA (Qiagen) were used for transfection of adherent HEK-293 cell using 293Fectin (Life Technologies). Supernatants from HEK-293 transfected cells comprising the expressed deletion mutants were harvested 72 hours post transfection. Several monoclonal antibodies against CD46 were tested by their ability to recognize the various CD46 proteins with deletions of defined SCR domains. More particularly, through an ELISA assay generally performed using the methods set forth elsewhere herein, selected antibody modulators were identified as being directed against any combination of the SCR domains one through four, respectively. This data for twelve of these modulators can be found in tabular form in FIG. 14 under the heading "Domain" where the derived binding domains are specified. It should be noted that one antibody, SC1.N29, did not bind to any of the sushi domains but rather bound to exon 9 as demonstrated in Example 15.

This Example again demonstrates the ability to generate and select CD46 modulators that immunospecifically associate with selected isoforms or splice variants of the therapeutic target.

Example 19

Characterization of Monoclonal Antibody CD46 Modulators

Using techniques set forth in Example 17 the humanized constructs hSC1.N71 and hSC1.N149 were analyzed to determine their binding characteristics. More particularly, humanized antibody binding was directly compared with the parent murine antibody for both antibodies to identify any subtle changes in rate constants brought about by the humanization process.

In this regard the affinity of murine SC1.N71 was measured by a Biacore using surface plasmon resonance (SPR) to provide the results set forth in FIG. 15A. Based on a concentration series of 12.5, 6.25, 3.125 and 1.5625 nM (generating the curves from top to bottom in the FIGS. 15A and 15B) and using a 1:1 Langmuir binding model, the $K_d$ of the antibody binding to antigen was estimated to be 1.1 nM. Similar experiments then run with the humanized construct showed equivalent results (FIG. 15B) indicating that the humanization process had not adversely impacted the affinity. In this regard the measurements indicated that the humanized construct had a $K_d$ of $0.7 \times 10^{-9}$ vs. a $K_d$ of $1.1 \times 10^{-9}$ for the parent murine antibody when tested using human CD46 (FIG. 15C).

Similar experiments were then performed to compare the binding of hSC1.N149 with that of its murine parent SC1.N149 (data not shown). As may be seen in FIG. 15C the humanized antibody had a $K_d$ of $1.2 \times 10^{-9}$ vs. a IQ of $1.1 \times 10^{-9}$ for the parent murine antibody.

Besides the affinity measurements the antibodies were further tested to determine cross reactivity with regard to marmoset and cynomolgus antigens. As set out in FIG. 15C both SC1.N71 and SC1.N149 strongly cross-reacts with both cynomolgus and marmoset CD46 homologs thereby facilitating toxicology studies. The reactivity with marmoset and cynomolgus, though slightly lower than for the human target, is still well within an acceptable therapeutic window.

Example 20

CD46 Modulators May be Used as Diagnostic Agents

In accordance with the teachings herein, the disclosed CD46 modulators may be used as diagnostic agents to detect CD46 associated biomarkers in biological samples from patients.

As previously alluded to CD46 is a type I glycoprotein known to reside in the plasma membrane of cells but can be cleaved off membranes by the action of metalloproteinases. CD46 exists in multiple molecular weight isoforms due to alternative splicing of its mRNA based on exon switching and/or skipping of membrane proximal regions on both side of the transmembrane domain. Exhibiting such properties CD46 should be detectable in body fluids such as serum or plasma in certain disease conditions and could therefore be useful for diagnostic purposes or serve as disease biomarker. To confirm this aspect of the invention a standard curve was generated with anti-CD46 antibodies using a sandwich ELISA format as shown in FIG. 16A (insert) and a portion of this standard curve FIG. 16A, (main figure) was used to quantitate CD46 levels in serum samples obtained from healthy subjects and patients suffering from diverse solid tumors (FIG. 16B).

More specifically, monoclonal antibody SC1.N35.6 was absorbed to standard ELISA plates at 1 µg/ml in a 50 mM Sodium Carbonate buffer, pH9.6. After washing the plates with PBS containing 0.05% (v/v) Tween-20 (PBST), the plates were blocked in PBS containing 2% (w/v) bovine serum albumin (called 'diluent' from here on out) for two hours at ambient temperature. The content of the plates was flicked off, and purified recombinant CD46D-His at varying concentrations or serum samples diluted in diluents were added to the plates for a minimum of two hours at ambient temperature. The plates were washed in PBST before a CD46-specific goat polyclonal antibody conjugated to biotin was added at 0.5 µg/ml in diluent. After incubation for one hour, the plate was washed again with PBST and incubated for 30 minutes with a 1:2000 dilution of Streptavidin conjugated to horseradish peroxidase (Jackson Immuno Research). After washing all plates twice with PBST, 100 µL TMB substrate (Thermo Scientific) was added to the wells and incubated for 30 minutes in the dark. Color reaction was stopped by adding 100 µL/well 2M sulfuric acid. Absorbance at $\lambda$=450 nm was read in all wells using a standard plate reader.

In this data set, CD46 levels in serum from 12 healthy adults is compared to serum samples from 17 colorectal cancer patients, 6 melanoma patients, 15 breast cancer patients, 7 ovarian cancer patients, 10 non small cell lung cancer patients, 14 prostate cancer patients and 9 pancreatic cancer patients. As illustrated in FIG. 16B these data show that average CD46 concentrations in serum samples of healthy adults is approx. 12.1±2.2 ng/ml while CD46 concentration in colorectal, breast and non small cell lung cancer patients are significantly higher (26.6±3.4, 30.6±2.3 and 42.0±7.1 ng/ml, respectively). These results clearly demonstrate that the disclosed modulators of the instant invention can effectively act as a diagnostic agent for the detection and/or monitoring of neoplastic disorders.

Example 21

CD46 Modulators Function as Targeting Moieties

Targeting of a cytotoxic drug stably linked to an antibody represent an empowered antibody approach that might have great therapeutic benefit for patients with solid tumors. To determine whether the CD46-specific antibodies described above were able to mediate the delivery of a cytotoxic agent to live cells, an in vitro cell killing assay was performed wherein streptavidin conjugated to the ribosome-inactivating protein saporin (Advanced Targeting Systems) was bound to biotinylated CD46 antibody modulators, and the ability of these saporin complexes to internalize and kill cells was measured 72 hours later by measuring cell viability. More specifically, 10,000 HEK-293T cells per well were plated in wells of a 96-well plate. The following day, purified and biotinylated anti-CD46 antibodies described above diluted to 100 nM. An aliquot of each antibody, respectively, was mixed at a molar ratio of 1:1 with streptavidin-ZAP (Advanced Targeting Systems), and then incubated at room temperature for 30 minutes. The antibody—streptavidin-ZAP conjugates were serially diluted and all dilutions were added to the cells. The cell/antibody-saporin mixture was then incubated at 37° C./5% $CO_2$ for 72 hours. Following this incubation, viable cell numbers were enumerated using CellTiter-Glo (Promega Corp.) per the manufacturer's protocol. Cultures without antibody—streptavidin-ZAP served as reference, and their luminescence values were set to "100% live cells".

Figure 17:
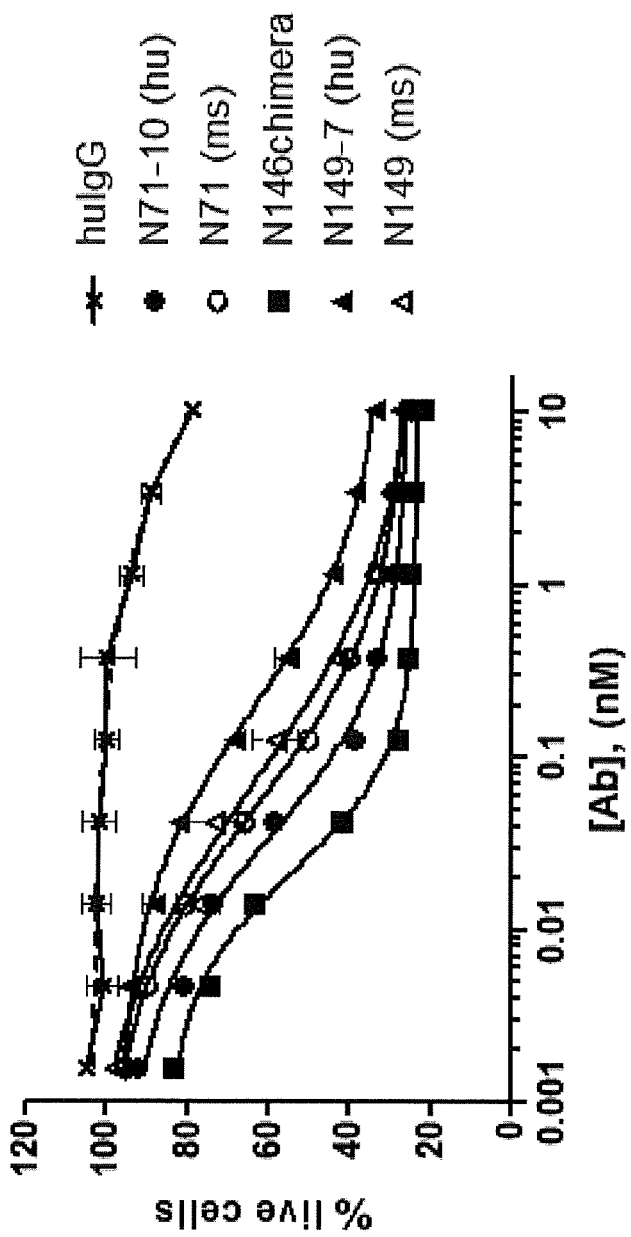
FIG. 17 is a graphical representation depicting the ability of the disclosed CD46 modulators to function as targeting agents through mediation of cell death using streptavidin conjugated to saporin.

Using this protocol several antibodies that were able to internalize as described in the previous Examples were also able to mediate cell killing in vitro whereas a biotinylated isotype control antibody was not able to kill cells. That is, several of these internalizing modulators were able to mediate saporin toxin internalization that resulted in cell death. FIG. 17 illustrates this cell killing capacity for the exemplary internalizing modulator SC1.N71, SC1.N146 (as mouse/human chimeric antibody) and SC1.N149 where the downward slope of the curves represents cell death in a concentration dependent manner as compared to the control. In addition, the data set forth in FIG. 17 demonstrates that two anti-CD46 antibodies, hSC1.N71 and hSC1.N149 from Example 16 retain the ability of the original mouse antibodies to mediate CD46 depended toxin uptake by cells. Specifically, the following effective concentrations causing 50% cell death ($EC_{50}$) were recorded: biotin-human IgG1, 53.1 nM; biotin-mouse SC1.N71, 51.4 µM; biotin human SC1.N71, 26.6 µM; biotin chimeric SC1.N146, 12.1 µM; biotin-mouse SC1.N149, 70.4 µM; biotin human SC1.N149, 174 µM.

Example 22

CD46 Modulators Interact with Receptors on the Cell Surface

To demonstrate that cell killing is mediated by the interaction between CD46 modulators and CD46 receptor expressed on the cell surface, a lentivirus was used to stably deliver a small hairpin RNA (shRNA) which, upon transduction into host cells, integrates into the genome of host cells and, following expression, binds specifically to a region of the CD46 mRNA causing rapid mRNA degradation inside the cells and reduction or loss of CD46 expression by the host cells.

Third-generation lentivirus stocks containing CD46 hairpins (Life Technologies) were prepared and concentrated using established techniques. HEK293T cells were transduced with a lentivirus stocks encoding shRNAs specific for CD46 and blue fluorescent protein as marker for successful transduction. Six days post transduction, cells were analyzed by flow cytometry for CD46 expression and high blue fluorescent protein expression (not shown) and cells exhibiting the greatest CD46 downregulation and highest blue fluorescent protein expression (i.e., those expressing shRNA C1), were sorted by FACS. Sorted cells were cultured for an additional 7 days and then tested side-by-side with their parental counterpart in an in vitro killing assay similar to the one described above in Example 21. Additionally, both cell lines were stained with anti-CD46 antibodies conjugated to the fluorophore phycoerythrin (R&D Systems) and analyzed by flow cytometry to demonstrate downregulation of CD46 expression in lentivirally transduced (and sorted) cell line. Results are shown in FIGS. 18A and 18B.

More particularly FIG. 18A demonstrates that HEK-293T-C1 cells have a ten-fold reduced mean fluorescence intensity (gray peak) compared to their parental counterparts (white peak) when stained with anti-CD46 antibody. HEK-293T cells but not their derivative HEK293T-C1 expressing a shRNA down regulating CD46 expression are efficiently killed by CD46 modulators (FIG. 18B). In this particular Example, purified antibodies at the indicated concentrations and 120 nM of a Fab fragment of an anti-mouse IgG molecule conjugated to the ribosome-inactivating protein saporin (Advanced Targeting Systems; FAB-ZAP) were added to either HEK293T cells or sorted HEK293T-C1 cells. Following incubation for 72 hours viable cell numbers were determined using CellTiter-Glo (Promega Corp.) per the manufacturer's protocol. Cultures containing cells and FAB-ZAP only served as reference, and their luminescence values were set to "100% live cells."

Example 23

CD46 Modulators Mediate Receptor Dependent Toxin Uptake

Traditional cell lines grown in vitro over many passages differ significantly in their biology from primary patient derived tumor cells. To assess whether CD46 modulators can mediate receptor depended toxin uptake by cancer cells that resemble patient tumors, patient derived, non-traditional xenotransplants, passaged in immunocompromised mice were tested in an in vitro killing assay.

Specifically, BR31p6 cells, a cell line derived from a breast cancer patient, were seeded at 10,000/well in a Primaria TC plate and cultured in a low oxygen incubator for 24 hour. Culture media was exchanged and biotinylated antibodies and streptavidin-ZAP conjugates prepared as described in Example 21 were added to the cultures for 72 hours. Viable cell numbers were enumerated using CellTiter-Glo (Promega Corp.) per the manufacturer's protocol. Cultures without antibody—streptavidin-ZAP served as reference, and their luminescence values were set to "100% live cells." BR31 cells are killed only when biotinylated SC1.N149 and streptavidin-ZAP are present together. Neither SC1.N149 alone nor biotinylated isotype control antibody plus streptavidin-ZAP mediate significant cell killing (FIG. 19A)

To demonstrate that CD46 modulators can be used as vehicle for cytotoxic payloads across many solid tumor indications, tumors derived from the non-traditional xenotransplants CR42p3, a cell line derived from a colorectal cancer patient, and PA20p6, a cell line derived from a pancreatic cancer patient, were seeded at 2000 cells per well in a Primaria TC plate. After 72 hours of culture in a low oxygen incubator, 1.0 nM purified antibodies (CD46 modulators or their isotype controls) and 40 nM FAB-ZAP (see FIG. 19B) were added to the cultures for an additional 168 hours of culture. Viable cell numbers were enumerated using CellTiter-Glo (Promega Corp.) per the manufacturer's protocol. Cultures containing cells and FAB-ZAP only served as reference, and their luminescence values were set to "100% live cells." Antibodies SC1.N71 and SC1.N149 specifically kill CR42 and PA20 cells with SC1.N71 appearing to be more somewhat more potent than SC1.N149 (FIG. 19B).

These data clearly demonstrate the specificity and broad effectiveness of the disclosed modulators when acting as vectors for the selective internalization of cytotoxic payloads in tumorigenic cells expressing CD46 ligands.

Example 24

CD46 Modulators Sensitize Pancreatic Tumors to Chemotherapy

To assess whether the disclosed modulators can increase the chemosensitivity of pancreatic tumors anti-CD46 antibodies were combined with an anti-cancer agent in an in vivo assay.

Figures 20A, 20B:
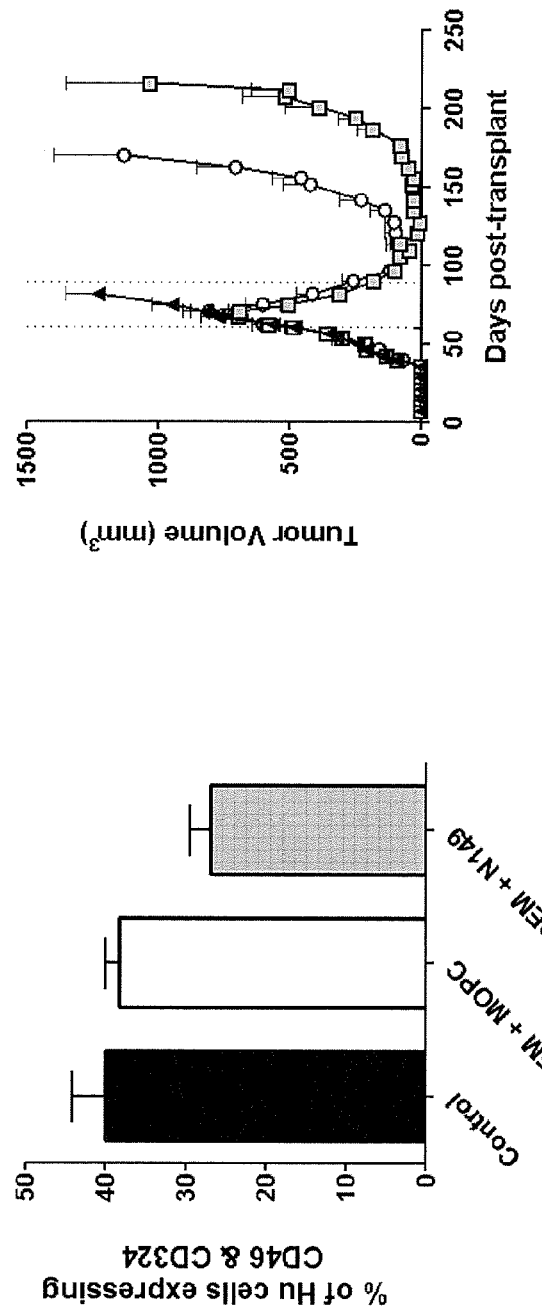

More particularly tumors were initiated in immunocompromised mice using the NTX-PA14 patient-derived tumor line and then randomized into one of three groups (10 mice per group) when the mean tumor volume of all mice reached approximately 500 mm$^3$. Two groups were treated twice weekly with 20 mg/kg doses of gemcitabine and 10 mg/kg of either an antibody targeting CD46 (SC1.N149) or a control non-specific isotype matched antibody (MOPC). The remaining group, which serves as a control, received once weekly 2 mg/kg doses of an anti-CD46 antibody drug conjugate that was unable to internalize or mediate cell killing. One day after the 3$^{rd}$ treatment (day 8 post-randomization), and as tumors were actively responding to the corresponding regimens, 2 mice from each group were euthanized and the frequency of residual TPC were enumerated by flow cytometry. Specifically, single cell suspensions of tumor cells isolated from mice treated as described above were contacted by antibodies to markers that allow for the identification and quantitation of TPC subpopulations. In tumors from mice being treated with the combination of the anti-CD46 antibody SC1.N149 and gemcitabine, the percentage of human cells expressing cell surface markers associated with the TPC population (i.e. CD46 and CD324) was significantly less (27% of human cells vs. ~39%) than the control group and gemcitabine plus MOPC antibody treated groups (FIG. 20A).

With the exception of mice serving as controls in this study, which had to be euthanized due to their large tumor burden, the remaining 8 mice per group went on to receive an additional 11 treatments (total of 14 treatments) of gemcitabine and antibody over the course of 7 weeks, after which mice were treated twice weekly with only antibody (MOPC or SC1.N149, respectively) and monitored for tumor burden (i.e. tumor volume measurements). Overall, tumors in both gemcitabine-treated groups responded to their respective treatment regimens and regressed to below 100 mm$^3$; however, those mice that were treated with the SC1.N149 antibody and gemcitabine showed a longer progression-free survival than tumors in mice treated with gemcitabine alone (75 days vs. 30 days, respectively) (FIG. 20B).

These data demonstrate that antibodies targeting CD46 are able to sensitize tumor cells to the standard of care chemotherapeutic, gemcitabine, in pancreatic cancer. Given previous demonstrations that TIC fuel tumor recurrence, which was significantly delayed in mice treated with both the naked anti-CD46 antibody and gemcitabine versus gemcitabine alone, data presented here suggests that the naked SC1.N149 antibody is able to specifically facilitate TIC sensitivity to chemotherapeutic drugs such as gemcitabine.

Example 25

CD46 Modulators can Reduce Tumor Initiating Cells in NTX Mice

Mice are xenografted with subcutaneous, kidney capsule or ectopic implantation of a human tumor fragment or single cell suspension of human tumor cells, of which at least a subpopulation express CD46, are allowed to harbor human tumors. Mice bearing human tumors are then randomized once tumors reached a burden of 100-500 mm$^3$ and treated with an antibody drug conjugate (ADC) targeting human CD46, for instance, by dosing the drug once or twice weekly at up to 10 mg/kg either alone or in combination with standard of care chemotherapeutics such as irinotecan or gemcitabine. Preferably the ADC will comprise an anti-CD46 antibody conjugated to a cytotoxic drug moiety or toxin.

After several weeks of treatment the tumor is observed to either shrink until no tumor mass remains, undergo partial regression wherein some mass remains, or maintains its mass without continuing to grow. In the latter case(s), examination of the residual tumor mass reveals either no human cells remaining in the tumor mass (i.e., it is composed of residual murine stromal cells), or it shows a reduction or elimination of tumor initiating cells as determined by various in vitro (e.g., counting colony forming cells) and in vivo (e.g., limiting dilution analysis to demonstrate an absolute reduction or elimination of tumor initiating cells in the treated tumor) assays. Further observation of the mice confirms the reduction or elimination of TIC as manifested by a significant delay before tumor growth recurred (i.e. >60 days) or prevention of tumor recurrence altogether.

Those skilled in the art will further appreciate that the present invention may be embodied in other specific forms without departing from the spirit or central attributes thereof. In that the foregoing description of the present invention discloses only exemplary embodiments thereof, it is to be understood that other variations are contemplated as being within the scope of the present invention. Accordingly, the present invention is not limited to the particular embodiments that have been described in detail herein. Rather, reference should be made to the appended claims as indicative of the scope and content of the invention.

The invention claimed is:

1. An isolated anti-CD46 antibody or immunoreactive fragment thereof, wherein the antibody or immunoreactive fragment thereof is selected from the group consisting of:

a) an antibody comprising three heavy chain complementarity determining regions set forth as residues 31-35 of SEQ ID NO: 15 for CDR-H1, residues 50-65 of SEQ ID NO: 15 for CDR-H2, and residues 95-102 of SEQ ID NO: 15 for CDR-H3, and comprising three light chain complementarity determining regions set forth as residues 24-34 of SEQ ID NO: 17 for CDR-L1, residues 50-56 of SEQ ID NO: 17 for CDR-L2 and residues 89-97 of SEQ ID NO: 17 for CDR-L3, wherein the residues are numbered according to Kabat;

b) an antibody comprising three heavy chain complementarity determining regions set forth as residues 31-35 of SEQ ID NO: 19 for CDR-H1, residues 50-65 of SEQ ID NO: 19 for CDR-H2, and residues 95-102 of SEQ ID NO: 19 for CDR-H3, and comprising three light chain complementarity determining regions set forth as residues 24-34 of SEQ ID NO: 21 for CDR-L1, residues 50-56 of SEQ ID NO: 21 for CDR-L2 and residues 89-97 of SEQ ID NO: 21 for CDR-L3, wherein the residues are numbered according to Kabat;

c) an antibody comprising three heavy chain complementarity determining regions set forth as residues 31-35 of SEQ ID NO: 23 for CDR-H1, residues 50-65 of SEQ ID NO: 23 for CDR-H2, and residues 95-102 of SEQ ID NO: 23 for CDR-H3, and comprising three light chain complementarity determining regions set forth as residues 24-34 of SEQ ID NO: 25 for CDR-L1, residues 50-56 of SEQ ID NO: 25 for CDR-L2 and residues 89-97 of SEQ ID NO: 25 for CDR-L3, wherein the residues are numbered according to Kabat;

d) an antibody comprising three heavy chain complementarity determining regions set forth as residues 31-35 of SEQ ID NO: 27 for CDR-H1, residues 50-65 of SEQ ID NO: 27 for CDR-H2, and residues 95-102 of SEQ ID NO: 27 for CDR-H3, and comprising three light chain complementarity determining regions set forth as residues 24-34 of SEQ ID NO: 29 for CDR-L1, residues 50-56 of SEQ ID NO: 29 for CDR-L2 and residues 89-97 of SEQ ID NO: 29 for CDR-L3, wherein the residues are numbered according to Kabat;

e) an antibody comprising three heavy chain complementarity determining regions set forth as residues 31-35 of the polypeptide encoded by the polynucleotide set forth as SEQ ID NO: 30 for CDR-H1, residues 50-65 of the polypeptide encoded by the polynucleotide set forth as SEQ ID NO: 30 for CDR-H2, and residues 95-102 of the polypeptide encoded by the polynucleotide set forth as SEQ ID NO: 30 for CDR-H3, and comprising three light chain complementarity determining regions set forth as residues 24-34 of SEQ ID NO: 33 for CDR-L1, residues 50-56 of SEQ ID NO: 33 for CDR-L2 and residues 89-97 of SEQ ID NO: 33 for CDR-L3, wherein the residues are numbered according to Kabat;

f) an antibody comprising three heavy chain complementarity determining regions set forth as residues 31-35 of SEQ ID NO: 35 for CDR-H1, residues 50-65 of SEQ ID NO: 35 for CDR-H2, and residues 95-102 of SEQ ID NO: 35 for CDR-H3, and comprising three light chain complementarity determining regions set forth as residues 24-34 of SEQ ID NO: 37 for CDR-L1, residues 50-56 of SEQ ID NO: 37 for CDR-L2 and residues 89-97 of SEQ ID NO: 37 for CDR-L3, wherein the residues are numbered according to Kabat;

g) an antibody comprising three heavy chain complementarity determining regions set forth as residues 31-35 of SEQ ID NO: 39 for CDR-H1, residues 50-65 of SEQ ID NO: 39 for CDR-H2, and residues 95-102 of SEQ ID NO: 39 for CDR-H3, and comprising three light chain complementarity determining regions set forth as residues 24-34 of SEQ ID NO: 41 for CDR-L1, residues 50-56 of SEQ ID NO: 41 for CDR-L2 and residues 89-97 of SEQ ID NO: 41 for CDR-L3, wherein the residues are numbered according to Kabat;

h) an antibody comprising three heavy chain complementarity determining regions set forth as residues 31-35 of SEQ ID NO: 43 for CDR-H1, residues 50-65 of SEQ ID NO: 43 for CDR-H2, and residues 95-102 of SEQ ID NO: 43 for CDR-H3, and comprising three light chain complementarity determining regions set forth as residues 24-34 of SEQ ID NO: 45 for CDR-L1, residues 50-56 of SEQ ID NO: 45 for CDR-L2 and residues 89-97 of SEQ ID NO: 45 for CDR-L3, wherein the residues are numbered according to Kabat;

i) an antibody comprising three heavy chain complementarity determining regions set forth as residues 31-35 of SEQ ID NO: 47 for CDR-H1, residues 50-65 of SEQ ID NO: 47 for CDR-H2, and residues 95-102 of SEQ ID NO: 47 for CDR-H3, and comprising three light chain complementarity determining regions set forth as residues 24-34 of SEQ ID NO: 49 for CDR-L1, residues 50-56 of SEQ ID NO: 49 for CDR-L2 and residues 89-97 of SEQ ID NO: 49 for CDR-L3, wherein the residues are numbered according to Kabat;

j) an antibody comprising three heavy chain complementarity determining regions set forth as residues 31-35 of SEQ ID NO: 51 for CDR-H1, residues 50-65 of SEQ ID NO: 51 for CDR-H2, and residues 95-102 of SEQ ID NO: 51 for CDR-H3, and comprising three light chain complementarity determining regions set forth as residues 24-34 of SEQ ID NO: 53 for CDR-L1, residues 50-56 of SEQ ID NO: 53 for CDR-L2 and residues 89-97 of SEQ ID NO: 53 for CDR-L3, wherein the residues are numbered according to Kabat;

k) an antibody comprising three heavy chain complementarity determining regions set forth as residues 31-35 of SEQ ID NO: 55 for CDR-H1, residues 50-65 of SEQ ID NO: 55 for CDR-H2, and residues 95-102 of SEQ ID NO: 55 for CDR-H3, and comprising three light chain complementarity determining regions set forth as residues 24-34 of SEQ ID NO: 57 for CDR-L1, residues 50-56 of SEQ ID NO: 57 for CDR-L2 and residues 89-97 of SEQ ID NO: 57 for CDR-L3, wherein the residues are numbered according to Kabat;

l) an antibody comprising three heavy chain complementarity determining regions set forth as residues 31-35 of SEQ ID NO: 59 for CDR-H1, residues 50-65 of SEQ ID NO: 59 for CDR-H2, and residues 95-102 of SEQ ID NO: 59 for CDR-H3, and comprising three light chain complementarity determining regions set forth as residues 24-34 of SEQ ID NO: 61 for CDR-L1, residues 50-56 of SEQ ID NO: 61 for CDR-L2 and residues 89-97 of SEQ ID NO: 61 for CDR-L3, wherein the residues are numbered according to Kabat;

m) an antibody comprising three heavy chain complementarity determining regions set forth as residues 31-35 of SEQ ID NO: 63 for CDR-H1, residues 50-65 of SEQ ID NO: 63 for CDR-H2, and residues 95-102 of SEQ ID NO: 63 for CDR-H3, and comprising three light chain complementarity determining regions set forth as residues 24-34 of SEQ ID NO: 65 for CDR-L1, residues 50-56 of SEQ ID NO: 65 for CDR-L2 and residues 89-97 of SEQ ID NO: 65 for CDR-L3, wherein the residues are numbered according to Kabat;

n) an antibody comprising three heavy chain complementarity determining regions set forth as residues 31-35 of SEQ ID NO: 67 for CDR-H1, residues 50-65 of SEQ ID NO: 67 for CDR-H2, and residues 95-102 of SEQ ID NO: 67 for CDR-H3, and comprising three light chain complementarity determining regions set forth as residues 24-34 of SEQ ID NO: 69 for CDR-L1, residues 50-56 of SEQ ID NO: 69 for CDR-L2 and residues 89-97 of SEQ ID NO: 69 for CDR-L3, wherein the residues are numbered according to Kabat;

o) an antibody comprising three heavy chain complementarity determining regions set forth as residues 31-35 of SEQ ID NO: 71 for CDR-H1, residues 50-65 of SEQ ID NO: 71 for CDR-H2, and residues 95-102 of SEQ ID NO: 71 for CDR-H3, and comprising three light chain complementarity determining regions set forth as residues 24-34 of SEQ ID NO: 73 for CDR-L1, residues 50-56 of SEQ ID NO: 73 for CDR-L2 and residues 89-97 of SEQ ID NO: 73 for CDR-L3, wherein the residues are numbered according to Kabat;

p) an antibody comprising three heavy chain complementarity determining regions set forth as residues 31-35 of SEQ ID NO: 75 for CDR-H1, residues 50-65 of SEQ ID NO: 75 for CDR-H2, and residues 95-102 of SEQ ID NO: 75 for CDR-H3, and comprising three light chain complementarity determining regions set forth as residues 24-34 of SEQ ID NO: 77 for CDR-L1, residues 50-56 of SEQ ID NO: 77 for CDR-L2 and residues 89-97 of SEQ ID NO: 77 for CDR-L3, wherein the residues are numbered according to Kabat;

q) an antibody comprising three heavy chain complementarity determining regions set forth as residues 31-35 of SEQ ID NO: 79 for CDR-H1, residues 50-65 of SEQ ID NO: 79 for CDR-H2, and residues 95-102 of SEQ ID NO: 79 for CDR-H3, and comprising three light chain complementarity determining regions set forth as residues 24-34 of SEQ ID NO: 81 for CDR-L1, residues 50-56 of SEQ ID NO: 81 for CDR-L2 and residues 89-97 of SEQ ID NO: 81 for CDR-L3, wherein the residues are numbered according to Kabat;

r) an antibody comprising three heavy chain complementarity determining regions set forth as residues 31-35 of SEQ ID NO: 83 for CDR-H1, residues 50-65 of SEQ ID NO: 83 for CDR-H2, and residues 95-102 of SEQ ID NO: 83 for CDR-H3, and comprising three light chain complementarity determining regions set forth as residues 24-34 of SEQ ID NO: 85 for CDR-L1, residues 50-56 of SEQ ID NO: 85 for CDR-L2 and residues 89-97 of SEQ ID NO: 85 for CDR-L3, wherein the residues are numbered according to Kabat;

s) an antibody comprising three heavy chain complementarity determining regions set forth as residues 31-35 of SEQ ID NO: 199 for CDR-H1, residues 50-65 of SEQ ID NO: 199 for CDR-H2, and residues 95-102 of SEQ ID NO: 199 for CDR-H3, and comprising three light chain complementarity determining regions set forth as residues 24-34 of SEQ ID NO: 201 for CDR-L1, residues 50-56 of SEQ ID NO: 201 for CDR-L2 and residues 89-97 of SEQ ID NO: 201 for CDR-L3, wherein the residues are numbered according to Kabat; and t) an antibody comprising three heavy chain complementarity determining regions set forth as residues 31-35 of SEQ ID NO: 203 for CDR-H1, residues 50-65 of SEQ ID NO: 203 for CDR-H2, and residues 95-102 of SEQ ID NO: 203 for CDR-H3, and comprising three light chain complementarity determining regions set forth as residues 24-34 of SEQ ID NO: 205 for CDR-L1, residues 50-56 of SEQ ID NO: 205 for CDR-L2 and residues 89-97 of SEQ ID NO: 205 for CDR-L3, wherein the residues are numbered according to Kabat.

2. The isolated anti-CD46 antibody or immunoreactive fragment thereof according to claim 1, wherein the antibody or immunoreactive fragment thereof is selected from the group consisting of:

a) an antibody comprising a heavy chain variable region set forth as SEQ ID NO: 15, and comprising a light chain variable region set forth as SEQ ID NO: 17;

b) an antibody comprising a heavy chain variable region encoded by the polynucleotide set forth as set forth as SEQ ID NO: 18, and comprising a light chain variable region encoded by the polynucleotide set forth as set forth as SEQ ID NO: 20;

c) an antibody comprising a heavy chain variable region set forth as SEQ ID NO: 23, and comprising a light chain variable region set forth as SEQ ID NO: 25;

d) an antibody comprising a heavy chain variable region set forth as SEQ ID NO: 27, and comprising a light chain variable region set forth as SEQ ID NO: 29;

e) an antibody comprising a heavy chain variable region encoded by the polynucleotide set forth as set forth as SEQ ID NO: 30, and comprising a light chain variable region encoded by the polynucleotide set forth as set forth as SEQ ID NO: 32;

f) an antibody comprising a heavy chain variable region set forth as SEQ ID NO: 35, and comprising a light chain variable region set forth as SEQ ID NO: 37;

g) an antibody comprising a heavy chain variable region set forth as SEQ ID NO: 39, and comprising a light chain variable region set forth as SEQ ID NO: 41;

h) an antibody comprising a heavy chain variable region encoded by the polynucleotide set forth as set forth as SEQ ID NO: 42, and comprising a light chain variable region encoded by the polynucleotide set forth as set forth as SEQ ID NO: 44;

i) an antibody comprising a heavy chain variable region encoded by the polynucleotide set forth as set forth as SEQ ID NO: 46, and comprising a light chain variable region encoded by the polynucleotide set forth as set forth as SEQ ID NO: 48;

j) an antibody comprising a heavy chain variable region set forth as SEQ ID NO: 51, and comprising a light chain variable region set forth as SEQ ID NO: 53;

k) an antibody comprising a heavy chain variable region set forth as SEQ ID NO: 55, and comprising a light chain variable region set forth as SEQ ID NO: 57;

l) an antibody comprising a heavy chain variable region set forth as SEQ ID NO: 59, and comprising a light chain variable region set forth as SEQ ID NO: 61;

m) an antibody comprising a heavy chain variable region set forth as SEQ ID NO: 63, and comprising a light chain variable region set forth as SEQ ID NO: 65;

n) an antibody comprising a heavy chain variable region set forth as SEQ ID NO: 67, and comprising a light chain variable region set forth as SEQ ID NO: 69;

o) an antibody comprising a heavy chain variable region encoded by the polynucleotide set forth as set forth as SEQ ID NO: 70, and comprising a light chain variable region encoded by the polynucleotide set forth as set forth as SEQ ID NO: 72;

p) an antibody comprising a heavy chain variable region set forth as SEQ ID NO: 75, and comprising a light chain variable region set forth as SEQ ID NO: 77;

q) an antibody comprising a heavy chain variable region set forth as SEQ ID NO: 79, and comprising a light chain variable region set forth as SEQ ID NO: 81 r) an antibody comprising a heavy chain variable region set forth as SEQ ID NO: 83, and comprising a light chain variable region set forth as SEQ ID NO: 85;

s) an antibody comprising a heavy chain variable region set forth as SEQ ID NO: 199, and comprising a light chain variable region set forth as SEQ ID NO: 201; and t) an antibody comprising a heavy chain variable region set forth as SEQ ID NO: 203, and comprising a light chain variable region set forth as SEQ ID NO: 205.

3. The isolated anti-CD46 antibody or immunoreactive fragment thereof according to claim 1, wherein the isolated anti-CD46 antibody or immunoreactive fragment thereof is selected from the group consisting of monoclonal antibodies, chimeric antibodies, CDR-grafted antibodies, and humanized antibodies.

4. An isolated anti-CD46 antibody or immunoreactive fragment thereof comprising a heavy chain variable region set forth as SEQ ID NO: 199, and comprising a light chain variable region set forth as SEQ ID NO: 201.

5. An isolated anti-CD46 antibody or immunoreactive fragment thereof comprising a heavy chain variable region set forth as SEQ ID NO: 203, and comprising a light chain variable region set forth as SEQ ID NO: 205.

6. The isolated anti-CD46 antibody or immunoreactive fragment thereof according to claim 1, wherein the isolated anti-CD46 antibody or immunoreactive fragment thereof is conjugated to a cytotoxic agent and optionally comprises a pharmaceutically acceptable carrier.

7. The isolated anti-CD46 antibody or immunoreactive fragment thereof according to claim 2, wherein the isolated anti-CD46 antibody or immunoreactive fragment thereof is conjugated to a cytotoxic agent and optionally comprises a pharmaceutically acceptable carrier.

8. The isolated anti-CD46 antibody or immunoreactive fragment thereof according to claim 6, wherein the isolated anti-CD46 antibody or immunoreactive fragment thereof comprises a heavy chain variable region and light chain variable region selected from the group consisting of:

(a) a heavy chain variable region set forth as SEQ ID NO: 199, and comprising a light chain variable region set forth as SEQ ID NO: 201; and (b) a heavy chain variable region set forth as SEQ ID NO: 203, and comprising a light chain variable region set forth as SEQ ID NO: 205.

9. A vector comprising a polynucleotide, wherein the polynucleotide encodes a polypeptide comprising a heavy chain variable region set forth as SEQ ID NO: 199 or SEQ ID NO: 203 or a light chain variable region set forth as SEQ ID NO: 201 or SEQ ID NO: 205.

* * * * *

SEQUENCE LISTING

```
<160> NUMBER OF SEQ ID NOS: 207

<210> SEQ ID NO 1
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1
ttacctcgat ggcagcgaca caat                                            24

<210> SEQ ID NO 2
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 2
tctgctctgc tggagtggtt gatt                                            24

<210> SEQ ID NO 3
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 3
```

```
cacaattgtc tgtgacagta acagtactt                                    29

<210> SEQ ID NO 4
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 4
acacaaatta ctgcaactcc aacaa                                        25

<210> SEQ ID NO 5
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 5
taggacctga ggcactggac gctgg                                        25

<210> SEQ ID NO 6
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 6
ccagttccaa agtgtcttaa aggtcctagg cc                                32

<210> SEQ ID NO 7
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 7
tttaggatat cctgaggcac tggacgctg                                    29

<210> SEQ ID NO 8
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 8
ttgggtcatt gctgtgattg ttattgcca                                    29

<210> SEQ ID NO 9
<211> LENGTH: 306
<212> TYPE: PRT
<213> ORGANISM: Artificial Sequence
<220> FEATURE:
<221> NAME/KEY: source
```

<223> OTHER INFORMATION: /note="Description of Artificial Sequence:
      Synthetic polypeptide"

<400> SEQUENCE: 9

```
Ala Gln Pro Ala Cys Glu Glu Pro Thr Phe Glu Ala Met Glu Leu
1               5                   10                  15
Ile Gly Lys Pro Lys Pro Tyr Tyr Glu Ile Gly Arg Val Asp Tyr
            20                  25                  30
Lys Cys Lys Lys Gly Tyr Phe Tyr Ile Pro Pro Leu Ala Thr His Thr
35                  40                  45
Ile Cys Asp Arg Asn His Thr Trp Leu Pro Val Ser Asp Ala Cys
    50                  55                  60
Tyr Arg Glu Thr Cys Pro Tyr Ile Arg Asp Pro Leu Asn Gly Gln Ala
65              70                  75                  80
Val Pro Ala Asn Gly Thr Tyr Glu Phe Gly Tyr Gln Met His Phe Ile
                85                  90                  95
Cys Asn Glu Gly Tyr Tyr Leu Ile Gly Glu Glu Ile Leu Tyr Cys Glu
            100                 105                 110
Leu Lys Gly Ser Val Ala Ile Trp Ser Gly Lys Pro Pro Ile Cys Glu
        115                 120                 125
Lys Val Leu Cys Thr Pro Pro Pro Lys Ile Lys Asn Gly Lys His Thr
130                 135                 140
Phe Ser Glu Val Glu Val Phe Glu Tyr Leu Asp Ala Val Thr Tyr Ser
145                 150                 155                 160
Cys Asp Pro Ala Pro Gly Pro Asp Pro Phe Ser Leu Ile Gly Glu Ser
                165                 170                 175
Thr Ile Tyr Cys Gly Asp Asn Ser Val Trp Ser Arg Ala Ala Pro Glu
            180                 185                 190
Cys Lys Val Val Lys Cys Arg Phe Pro Val Val Glu Asn Gly Lys Gln
        195                 200                 205
Ile Ser Gly Phe Gly Lys Lys Phe Tyr Tyr Lys Ala Thr Val Met Phe
    210                 215                 220
Glu Cys Asp Lys Gly Phe Tyr Leu Asp Gly Ser Asp Thr Ile Val Cys
225                 230                 235                 240
Asp Ser Asn Ser Thr Trp Asp Pro Pro Val Pro Lys Cys Leu Lys Val
                245                 250                 255
Ser Thr Ser Ser Thr Thr Lys Ser Pro Ala Ser Ser Ala Ser Gly Pro
            260                 265                 270
Arg Pro Thr Tyr Lys Pro Pro Val Ser Asn Tyr Pro Gly Tyr Pro Lys
        275                 280                 285
Pro Glu Glu Gly Ile Leu Asp Ser Leu Asp His His His His His His
    290                 295                 300
His His
305
```

<210> SEQ ID NO 10
<211> LENGTH: 314
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 10

```
Ala Met Val Leu Leu Leu Tyr Ser Phe Ser Asp Ala Cys Glu Glu Pro
1               5                   10                  15
```

Pro Thr Phe Glu Ala Met Glu Leu Ile Gly Lys Pro Lys Pro Tyr Tyr
                20                  25                  30

Glu Ile Gly Glu Arg Val Asp Tyr Lys Cys Lys Lys Gly Tyr Phe Tyr
            35                  40                  45

Ile Pro Pro Leu Ala Thr His Thr Ile Cys Asp Arg Asn His Thr Trp
50                  55                  60

Leu Pro Val Ser Asp Asp Ala Cys Tyr Arg Glu Thr Cys Pro Tyr Ile
65                  70                  75                  80

Arg Asp Pro Leu Asn Gly Gln Ala Val Pro Ala Asn Gly Thr Tyr Glu
                85                  90                  95

Phe Gly Tyr Gln Met His Phe Ile Cys Asn Glu Gly Tyr Tyr Leu Ile
            100                 105                 110

Gly Glu Glu Ile Leu Tyr Cys Glu Leu Lys Gly Ser Val Ala Ile Trp
        115                 120                 125

Ser Gly Lys Pro Pro Ile Cys Glu Lys Val Leu Cys Thr Pro Pro Pro
130                 135                 140

Lys Ile Lys Asn Gly Lys His Thr Phe Ser Glu Val Glu Val Phe Glu
145                 150                 155                 160

Tyr Leu Asp Ala Val Thr Tyr Ser Cys Asp Pro Ala Pro Gly Pro Asp
                165                 170                 175

Pro Phe Ser Leu Ile Gly Glu Ser Thr Ile Tyr Cys Gly Asp Asn Ser
            180                 185                 190

Val Trp Ser Arg Ala Ala Pro Glu Cys Lys Val Val Lys Cys Arg Phe
        195                 200                 205

Pro Val Val Glu Asn Gly Lys Gln Ile Ser Gly Phe Gly Lys Lys Phe
        210                 215                 220

Tyr Tyr Lys Ala Thr Val Met Phe Glu Cys Asp Lys Gly Phe Tyr Leu
225                 230                 235                 240

Asp Gly Ser Asp Thr Ile Val Cys Asp Ser Asn Ser Thr Trp Asp Pro
                245                 250                 255

Pro Val Pro Lys Cys Leu Lys Val Ser Thr Ser Ser Thr Thr Lys Ser
            260                 265                 270

Pro Ala Ser Ser Ala Ser Gly Pro Arg Pro Thr Tyr Lys Pro Pro Val
        275                 280                 285

Ser Asn Tyr Pro Gly Tyr Pro Lys Pro Glu Glu Gly Ile Leu Asp Ser
        290                 295                 300

Leu Asp His His His His His His His His
305                 310

<210> SEQ ID NO 11
<211> LENGTH: 313
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 11

Ala Val Leu Leu Leu Tyr Ser Phe Ser Asp Ala Cys Glu Glu Pro Pro
1               5                   10                  15

Thr Phe Glu Ala Met Glu Leu Ile Gly Lys Pro Lys Pro Tyr Tyr Glu
                20                  25                  30

Ile Gly Glu Arg Val Asp Tyr Lys Cys Lys Lys Gly Tyr Phe Tyr Ile
            35                  40                  45

```
Pro Pro Leu Ala Thr His Thr Ile Cys Asp Arg Asn His Thr Trp Leu
    50                  55                  60

Pro Val Ser Asp Asp Ala Cys Tyr Arg Glu Thr Cys Pro Tyr Ile Arg
 65                  70                  75                  80

Asp Pro Leu Asn Gly Gln Ala Val Pro Ala Asn Gly Thr Tyr Glu Phe
                 85                  90                  95

Gly Tyr Gln Met His Phe Ile Cys Asn Glu Gly Tyr Tyr Leu Ile Gly
            100                 105                 110

Glu Glu Ile Leu Tyr Cys Glu Leu Lys Gly Ser Val Ala Ile Trp Ser
            115                 120                 125

Gly Lys Pro Pro Ile Cys Glu Lys Val Leu Cys Thr Pro Pro Pro Lys
        130                 135                 140

Ile Lys Asn Gly Lys His Thr Phe Ser Glu Val Glu Val Phe Glu Tyr
145                 150                 155                 160

Leu Asp Ala Val Thr Tyr Ser Cys Asp Pro Ala Pro Gly Pro Asp Pro
                165                 170                 175

Phe Ser Leu Ile Gly Glu Ser Thr Ile Tyr Cys Gly Asp Asn Ser Val
            180                 185                 190

Trp Ser Arg Ala Ala Pro Glu Cys Lys Val Val Lys Cys Arg Phe Pro
            195                 200                 205

Val Val Glu Asn Gly Lys Gln Ile Ser Gly Phe Gly Lys Lys Phe Tyr
        210                 215                 220

Tyr Lys Ala Thr Val Met Phe Glu Cys Asp Lys Gly Phe Tyr Leu Asp
225                 230                 235                 240

Gly Ser Asp Thr Ile Val Cys Asp Ser Asn Ser Thr Trp Asp Pro Pro
                245                 250                 255

Val Pro Lys Cys Leu Lys Val Ser Thr Ser Ser Thr Thr Lys Ser Pro
            260                 265                 270

Ala Ser Ser Ala Ser Gly Pro Arg Pro Thr Tyr Lys Pro Pro Val Ser
            275                 280                 285

Asn Tyr Pro Gly Tyr Pro Lys Pro Glu Glu Gly Ile Leu Asp Ser Leu
        290                 295                 300

Asp His His His His His His His
305                 310

<210> SEQ ID NO 12
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Cys Val Pro Lys Ser Leu Lys Val Ser Thr Ser Ser Thr Thr Lys Ser
1               5                   10                  15

Pro Ala Ser Ser Ala Ser
            20

<210> SEQ ID NO 13
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 13

Pro Val Pro Lys Ser Leu Lys Gly Pro Arg Pro Thr Tyr Lys Pro Pro
1               5                   10                  15

Val Ser Asn Tyr Pro Gly
            20

<210> SEQ ID NO 14
<211> LENGTH: 366
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 14
gaggttcagc tgcagcagtc tggggcagag cttgtgaagc caggggcctc agtcaagttg      60
tcctgcacag cttctggctt caacattaaa gacacctata tgcactgggt gaagcagagg     120
cctgaacagg gcctggagtg gattggaagg attgatcctg cgaatggtaa tattaaatat     180
gacccgaagt tccagggcaa ggccactata acatcagaca catcctccaa cacagcctac     240
ctgcagctca gcagcctgac atctgaggac actgccgtct attactgtgc tcaccccctcc    300 tatgattacg acaggaacta tgctatggac tactggggtc aaggaaccct cagtcaccgtc    360 tcctca                                                                366

<210> SEQ ID NO 15
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 15

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Met His Trp Val Lys Gln Arg Pro Glu Gln Gly Leu Glu Trp Ile
        35                  40                  45

Gly Arg Ile Asp Pro Ala Asn Gly Asn Ile Lys Tyr Asp Pro Lys Phe
    50                  55                  60

Gln Gly Lys Ala Thr Ile Thr Ser Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala His Pro Ser Tyr Asp Tyr Asp Arg Asn Tyr Ala Met Asp Tyr Trp
            100                 105                 110

Gly Gln Gly Thr Ser Val Thr Val Ser Ser
        115                 120

<210> SEQ ID NO 16
<211> LENGTH: 327
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
```

<400> SEQUENCE: 16

```
gacatcgtgc tgactcagtt ccagccatc ctgtctgtga gtccaggaga aagagtcagt      60
ttctcctgca gggccagtca gagcattggc acaagcttac actggtatca gcaaagaaca    120
aatggttctc caaggcttct catgaagtat gcttctgagt ctatctctgg gatcccttcc    180
aggtttagtg gcagtggatc agggacagat tttactctta gcatcaacag tgtggagtct    240
gaagatattg cagattatta ctgtcaacaa agttatagct ggccgctcac gttcggtgct    300
gggaccaagc tggagctgaa acgggct                                        327
```

<210> SEQ ID NO 17
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 17

```
Asp Ile Val Leu Thr Gln Phe Pro Ala Ile Leu Ser Val Ser Pro Gly
1               5                   10                  15
Glu Arg Val Ser Phe Ser Cys Arg Ala Ser Gln Ser Ile Gly Thr Ser
            20                  25                  30
Leu His Trp Tyr Gln Gln Arg Thr Asn Gly Ser Pro Arg Leu Leu Met
        35                  40                  45
Lys Tyr Ala Ser Glu Ser Ile Ser Gly Ile Pro Ser Arg Phe Ser Gly
    50                  55                  60
Ser Gly Ser Gly Thr Asp Phe Thr Leu Ser Ile Asn Ser Val Glu Ser
65                  70                  75                  80
Glu Asp Ile Ala Asp Tyr Tyr Cys Gln Gln Ser Tyr Ser Trp Pro Leu
                85                  90                  95
Thr Phe Gly Ala Gly Thr Lys Leu Glu Leu Lys Arg
            100                 105
```

<210> SEQ ID NO 18
<211> LENGTH: 387
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 18

```
gaagtgcagc tggtggagtc tggggaggc ttagtgaagc ctggagggtc cctgaaactc      60
tcctgtgcag cctctggatt cactttcagt gactattaca tgtattgggt tcgccagact    120
ccggaaaaga ggctggagtg gtcgcaacc attagtgatg gtggtactta catttactat    180
ccagacagtg tgaaggggcg attcaccatc tccagagaca tgccaagaa caacctgtac    240
ctgcaaatga gcagtctgaa gtctgaggac acagccatgt attactgtgt tagagatata    300
gactacgata ctagctatcc ctggtttgct tactggggcc aagggactct ggtcactgtc    360
tctgcagcca aaacaacagc cccatcg                                        387
```

<210> SEQ ID NO 19
<211> LENGTH: 130
<212> TYPE: PRT
<213> ORGANISM: Artificial Sequence

```
<220> FEATURE:
<221> NAME/KEY: source
<223> OTHER INFORMATION: /note="Description of Artificial Sequence:
      Synthetic polypeptide"

<400> SEQUENCE: 19

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Asp Tyr
            20                  25                  30

Tyr Met Tyr Trp Val Arg Gln Thr Pro Glu Lys Arg Leu Glu Trp Val
        35                  40                  45

Ala Thr Ile Ser Asp Gly Gly Thr Tyr Ile Tyr Tyr Pro Asp Ser Val
    50                  55                  60

Lys Gly Arg Phe Thr Ile Ser Arg Asp Asn Ala Lys Asn Asn Leu Tyr
65                  70                  75                  80

Leu Gln Met Ser Ser Leu Lys Ser Glu Asp Thr Ala Met Tyr Tyr Cys
                85                  90                  95

Val Arg Asp Ile Asp Tyr Asp Thr Ser Tyr Pro Trp Phe Ala Tyr Trp
            100                 105                 110

Gly Gln Gly Thr Leu Val Thr Val Ser Ala Ala Lys Thr Thr Ala Pro
        115                 120                 125

Ser Val
    130

<210> SEQ ID NO 20
<211> LENGTH: 344
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 20
gatatccaga tgacacagac tacatcctcc ctgtctgcct ctctgggaga cagagtcacc    60
atcagttgca gtgcaagtca gggcattagc aattatttaa actggtatca gcagaaacca   120
gatggaactg ttaaactcct gatctattac acatcaagtt tacactcagg agtcccatca   180
aggttcagtg gcagtgggtc tgggacagat tattctctca ccatcaacaa cctggaacct   240
gaagatattg ccacttacta ttgtcagcag tatagtaagc ttccgtggac gttcggtgga   300
ggcaccaagc tggaaatcaa acgggctgat gctgcaccaa ctgt                    344

<210> SEQ ID NO 21
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 21

Arg Cys Asp Ile Gln Met Thr Gln Thr Thr Ser Ser Leu Ser Ala Ser
1               5                   10                  15

Leu Gly Asp Arg Val Thr Ile Ser Cys Ser Ala Ser Gln Gly Ile Ser
            20                  25                  30

Asn Tyr Leu Asn Trp Tyr Gln Gln Lys Pro Asp Gly Thr Val Lys Leu
        35                  40                  45
```

```
Leu Ile Tyr Tyr Thr Ser Ser Leu His Ser Gly Val Pro Ser Arg Phe
 50                  55                  60
Ser Gly Ser Gly Ser Gly Thr Asp Tyr Ser Leu Thr Ile Asn Asn Leu
 65                  70                  75                  80
Glu Pro Glu Asp Ile Ala Thr Tyr Tyr Cys Gln Gln Tyr Ser Lys Leu
                 85                  90                  95
Pro Trp Thr Phe Gly Gly Gly Thr Lys Leu Glu Ile Lys Arg Ala Asp
                100                 105                 110
Ala Ala Pro Thr
        115
```

<210> SEQ ID NO 22
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 22

```
gaggtcctgc tgcatcagtc tggacctgag ctggtgaagc ctggggcttc agtgaagatt      60
ccctgcaagg cttctggata cacattcact gactacaaca tggactgggt gaagcagagc     120
catggaaaga gccttgagtg gattggagat attaatccta acaatggtgg tactttctac     180
aaccagaagt tcaagggcaa ggccacattg actgtacaca gtcctccag cacagccttc     240 atggagctcc gcagcctgac atctgaggac actgcagtct attattgtac aagatcaaag    300
tatgataact atccctggtt tgcttactgg ggccaaggga ctctggtcac tgtctctgca    360
```

<210> SEQ ID NO 23
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 23

```
Glu Val Leu Leu His Gln Ser Gly Pro Glu Leu Val Lys Pro Gly Ala
1                5                  10                  15
Ser Val Lys Ile Pro Cys Lys Ala Ser Gly Tyr Thr Phe Thr Asp Tyr
                 20                  25                  30
Asn Met Asp Trp Val Lys Gln Ser His Gly Lys Ser Leu Glu Trp Ile
             35                  40                  45
Gly Asp Ile Asn Pro Asn Asn Gly Gly Thr Phe Tyr Asn Gln Lys Phe
 50                  55                  60
Lys Gly Lys Ala Thr Leu Thr Val His Lys Ser Ser Ser Thr Ala Phe
 65                  70                  75                  80
Met Glu Leu Arg Ser Leu Thr Ser Glu Asp Thr Ala Val Tyr Tyr Cys
                 85                  90                  95
Thr Arg Ser Lys Tyr Asp Asn Tyr Pro Trp Phe Ala Tyr Trp Gly Gln
                100                 105                 110
Gly Thr Leu Val Thr Val Ser Ala
        115                 120
```

<210> SEQ ID NO 24
<211> LENGTH: 324
<212> TYPE: DNA

<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 24

```
gatatccaga tgacacagat tacatcctcc ctgtctgcct ctctgggaga cagagtcacc    60
atcagttgca gtgcaagtca gggcattagc aactatttaa actggtatca gcagaaacca   120
gatggaactg ttaaactcct gatctattac acatcaagtt tacactcagg agtcccatca   180
aggttccgtg gcagtgggtc tgggacaaat tattctctca ccatcagcaa cctggaacct   240
gaagatattg ccacttacta ttgtcagcag tatattaagc ttccgtggac gttcggtgga   300
ggcaccaagc tggaaatcaa acgg                                          324
```

<210> SEQ ID NO 25
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 25

```
Asp Ile Gln Met Thr Gln Ile Thr Ser Ser Leu Ser Ala Ser Leu Gly
1               5                  10                  15
Asp Arg Val Thr Ile Ser Cys Ser Ala Ser Gln Gly Ile Ser Asn Tyr
            20                  25                  30
Leu Asn Trp Tyr Gln Gln Lys Pro Asp Gly Thr Val Lys Leu Leu Ile
        35                  40                  45
Tyr Tyr Thr Ser Ser Leu His Ser Gly Val Pro Ser Arg Phe Arg Gly
    50                  55                  60
Ser Gly Ser Gly Thr Asn Tyr Ser Leu Thr Ile Ser Asn Leu Glu Pro
65                  70                  75                  80
Glu Asp Ile Ala Thr Tyr Tyr Cys Gln Gln Tyr Ile Lys Leu Pro Trp
                85                  90                  95
Thr Phe Gly Gly Gly Thr Lys Leu Glu Ile Lys Arg
            100                 105
```

<210> SEQ ID NO 26
<211> LENGTH: 357
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 26

```
caggttcagc tgcagcagtc tggacctgag ctggtgaagc ctggggcttc agtgaagttg    60
tcctgcaagg cttctggcta caccttcaca aactacgata taaactgggt gaagcagagg   120
cctggacagg gacttgagtg gattggatgg atttatccta gagatggtag ttttaagtac   180
aatgagaagt tcaagggcaa ggccacattg actgtagaca catcctccag cacagcgtac   240
atggacctcc acagcctgac atctgaggac tctgcggtct ttttctgtgc agtttcggag   300
gatggttacc cctggtttcc ttactggggc caagggactc tggtcactgt ctctgca      357
```

<210> SEQ ID NO 27

```
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 27
```

Gln Val Gln Leu Gln Gln Ser Gly Pro Glu Leu Val Lys Pro Gly Ala
1               5                   10                  15

Ser Val Lys Leu Ser Cys Lys Ala Ser Gly Tyr Thr Phe Thr Asn Tyr
            20                  25                  30

Asp Ile Asn Trp Val Lys Gln Arg Pro Gly Gln Gly Leu Glu Trp Ile
        35                  40                  45

Gly Trp Ile Tyr Pro Arg Asp Gly Ser Phe Lys Tyr Asn Glu Lys Phe
    50                  55                  60

Lys Gly Lys Ala Thr Leu Thr Val Asp Thr Ser Ser Ser Thr Ala Tyr
65                  70                  75                  80

Met Asp Leu His Ser Leu Thr Ser Glu Asp Ser Ala Val Phe Phe Cys
                85                  90                  95

Ala Val Ser Glu Asp Gly Tyr Pro Trp Phe Pro Tyr Trp Gly Gln Gly
            100                 105                 110

Thr Leu Val Thr Val Ser Ala
        115

```
<210> SEQ ID NO 28
<211> LENGTH: 324
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 28
ggtatccaga tgacacagac aacatcctcc ctgtctgcct ctctgggaga cagagtcacc      60
atcagttgca gtgcaagtca gggcattagc aactatttaa actggtatca gcagaaacca    120
gatggaactg ttaaactcct gatctattac acatcaagtt acactcagg  agtcccatca    180
aggttcagtg gcagtgggtc tgggacagat tattctctca ccatcagcaa cctggaacct    240
gaagatattg ccacttacta ttgtcagcag tatattaagc ttccattcac gttcggctcg    300
gggacaaaat tggaaataaa acgg                                           324

<210> SEQ ID NO 29
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 29
```

Gly Ile Gln Met Thr Gln Thr Thr Ser Ser Leu Ser Ala Ser Leu Gly
1               5                   10                  15

Asp Arg Val Thr Ile Ser Cys Ser Ala Ser Gln Gly Ile Ser Asn Tyr
            20                  25                  30

Leu Asn Trp Tyr Gln Gln Lys Pro Asp Gly Thr Val Lys Leu Leu Ile
        35                  40                  45

```
Tyr Tyr Thr Ser Ser Leu His Ser Gly Val Pro Ser Arg Phe Ser Gly
     50                  55                  60

Ser Gly Ser Gly Thr Asp Tyr Ser Leu Thr Ile Ser Asn Leu Glu Pro
65                  70                  75                  80

Glu Asp Ile Ala Thr Tyr Tyr Cys Gln Gln Tyr Ile Lys Leu Pro Phe
                85                  90                  95

Thr Phe Gly Ser Gly Thr Lys Leu Glu Ile Lys Arg
            100                 105
```

<210> SEQ ID NO 30
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence:
       Synthetic polynucleotide"

<400> SEQUENCE: 30

```
caggtgcaac tgaaggagtc aggacctggc ctggtggcgc cctcacagaa cctgtccatt      60
acctgcactg tctctgggtt ctcattaacc agctatgata taagctggat tcgccagcca     120
ccaggaaagg gtctggagtg gcttggagta atatggactg atggaggcac aaattataat     180
tcagctttca gtccagact gagcatcagc aaggacaact ccaagagcca gttttctta      240 aaaatgaaca gtctgcaaac tgatgacaca gccatatatt actgtgtaag ggtctatgat     300
ggttatccct ggtttgctta ctggggccaa gggactctgg tcactgtctc tgca           354
```

<210> SEQ ID NO 31
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
       Synthetic polypeptide"

<400> SEQUENCE: 31

```
Ser Gln Val Gln Leu Lys Glu Ser Gly Pro Gly Leu Val Ala Pro Ser
1               5                   10                  15

Gln Asn Leu Ser Ile Thr Cys Thr Val Ser Gly Phe Ser Leu Thr Ser
                20                  25                  30

Tyr Asp Ile Ser Trp Ile Arg Gln Pro Pro Gly Lys Gly Leu Glu Trp
            35                  40                  45

Leu Gly Val Ile Trp Thr Asp Gly Gly Thr Asn Tyr Asn Ser Ala Phe
50                  55                  60

Met Ser Arg Leu Ser Ile Ser Lys Asp Asn Ser Lys Ser Gln Val Phe
65                  70                  75                  80

Leu Lys Met Asn Ser Leu Gln Thr Asp Asp Thr Ala Ile Tyr Tyr Cys
                85                  90                  95

Val Arg Val Tyr Asp Gly Tyr Pro Trp Phe Ala Tyr Trp Gly Gln Gly
            100                 105                 110

Thr Leu Val Thr Val Ser Ala
        115
```

<210> SEQ ID NO 32
<211> LENGTH: 324
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 32

```
gatatccaga tgacacagac tccatcctcc ctgtctgcct ctctgggaga cagagtcacc    60
atcagttgca gtgcaagtca gggcattagc aattatttaa actggtatca gcagaaacca   120
gatggaactg ttaaactcct gatctattac acatcaagtt tacactcagg agtcccatca   180
aggttcagtg gcagtgggtc tgggacagat tattctctca ccatcagcaa cctggaacct   240
gaagatattg ccacttacta ttgtcagcag tatattaagc ttccgtggac gttcggtgga   300
ggcaccaagc tggcaatcaa acgg                                          324
```

<210> SEQ ID NO 33
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 33

```
Asp Ile Gln Met Thr Gln Thr Pro Ser Ser Leu Ser Ala Ser Leu Gly
1               5                   10                  15
Asp Arg Val Thr Ile Ser Cys Ser Ala Ser Gln Gly Ile Ser Asn Tyr
            20                  25                  30
Leu Asn Trp Tyr Gln Gln Lys Pro Asp Gly Thr Val Lys Leu Leu Ile
        35                  40                  45
Tyr Tyr Thr Ser Ser Leu His Ser Gly Val Pro Ser Arg Phe Ser Gly
    50                  55                  60
Ser Gly Ser Gly Thr Asp Tyr Ser Leu Thr Ile Ser Asn Leu Glu Pro
65                  70                  75                  80
Glu Asp Ile Ala Thr Tyr Tyr Cys Gln Gln Tyr Ile Lys Leu Pro Trp
                85                  90                  95
Thr Phe Gly Gly Gly Thr Lys Leu Ala Ile Lys Arg Ala Asp Ala Ala
            100                 105                 110
Pro Thr Val Ser Ile Phe Pro Pro
        115                 120
```

<210> SEQ ID NO 34
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 34

```
cagatccagt tggtgcagtc tggacctgaa ctgaagaagc ctggagagac agtcaagatc    60
tcctgcaagg cttctggtta taccttcaca gactattcaa tgcactgggt gaagcaggct   120
ccaggaaagg gtttaaagtg gatgggcttg ataaacactg agactggtga gccagcatat   180
gcagatgact tcaggggacg gttagacttc tctttggaaa cctctgccag cactgcctac   240
ttgcagatca acaacctcaa gaatgaggac acggctacat atttctgtgt taggtttgcc   300
tactggggcc acgggactct ggtcactgtc tctgca                             336
```

<210> SEQ ID NO 35

```
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 35

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
            20                  25                  30

Ser Met His Trp Val Lys Gln Ala Pro Gly Lys Gly Leu Lys Trp Met
        35                  40                  45

Gly Leu Ile Asn Thr Glu Thr Gly Glu Pro Ala Tyr Ala Asp Asp Phe
    50                  55                  60

Arg Gly Arg Leu Asp Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Val Arg Phe Ala Tyr Trp Gly His Gly Thr Leu Val Thr Val Ser Ala
            100                 105                 110

<210> SEQ ID NO 36
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 36
gacattgtga tgtcacagtc tccatcctcc ctggctgtgt cagcaggaga gaaggtcact     60
atgagctgca aatccagtca gagtctgctc aacagtagaa cccgaaagaa ctacttggct    120
tggtaccaac agaaaccagg gcagtctcct aaactgctga tctactgggc atctactagg    180
gaatctgggg tccctgatcg cttcacaggc agtggatctg gacagatttc actctcacc    240 atcagcagtg tgcaggctga agacctggca gtttattact gcaagcaatc ttataatctg    300
tggacgttcg gtggaggcac caagctggaa atcaaacgg                          339

<210> SEQ ID NO 37
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 37

Asp Ile Val Met Ser Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60
```

-continued

```
Pro Asp Arg Phe Thr Gly Ser Gly Ser Gly Thr Asp Phe Thr Leu Thr
 65                  70                  75                  80

Ile Ser Ser Val Gln Ala Glu Asp Leu Ala Val Tyr Tyr Cys Lys Gln
                 85                  90                  95

Ser Tyr Asn Leu Trp Thr Phe Gly Gly Gly Thr Lys Leu Glu Ile Lys
            100                 105                 110

Arg
```

<210> SEQ ID NO 38
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 38

```
cagatccagt tggtgcagtc tggacctgag ctgaagaagc ctggagagac agtcaagatc      60
tcctgcaagg cttctggtta tgccttcaca gacttttcaa tgcactgggt gaaacaggct     120
ccaggaaagg gtttaaggtg gatgggctgg ataaacactg agactggtga gccaacatat     180
gcagatgact tcaagggacg gtttgccttc tctttggaaa cctctgccag cactgcctat     240
ttgcagatca agaacctcaa aaatgaggac acggcaacat atttctgtgt taggtttgct     300
tactggggcc aagggactct ggtcacggtc tctgca                               336
```

<210> SEQ ID NO 39
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 39

```
Gln Ile Gln Leu Val Gln Ser Gly Pro Glu Leu Lys Lys Pro Gly Glu
 1               5                  10                  15

Thr Val Lys Ile Ser Cys Lys Ala Ser Gly Tyr Ala Phe Thr Asp Phe
             20                  25                  30

Ser Met His Trp Val Lys Gln Ala Pro Gly Lys Gly Leu Arg Trp Met
         35                  40                  45

Gly Trp Ile Asn Thr Glu Thr Gly Glu Pro Thr Tyr Ala Asp Asp Phe
     50                  55                  60

Lys Gly Arg Phe Ala Phe Ser Leu Glu Thr Ser Ala Ser Thr Ala Tyr
 65                  70                  75                  80

Leu Gln Ile Lys Asn Leu Lys Asn Glu Asp Thr Ala Thr Tyr Phe Cys
                 85                  90                  95

Val Arg Phe Ala Tyr Trp Gly Gln Gly Thr Leu Val Thr Val Ser Ala
            100                 105                 110
```

<210> SEQ ID NO 40
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 40

```
gacattgtga tgtcacagtc tccatcctcc ctggctgtgt cagcaggaga gaaggtcact    60
atgagctgca aatccagtca gagtctgctc aacagtagaa cccgaaagaa ctacttggct   120
tggtaccagc agaaaccagg gcagtctcct aaactgctga tctactgggc atccactagg   180
gaatctgggg tccctgatcg cttcacaggc agtggatctg ggacagattt cactctcacc   240
atcagcagtg tgcaggctga agacctggca gtttattact gcaagcaatc ttataatctt   300
tggacgttcg gtggaggcac caagctggaa atcaga                             336
```

<210> SEQ ID NO 41
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 41

```
Asp Ile Val Met Ser Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Asn Leu Trp Thr Phe Gly Gly Gly Thr Lys Leu Glu Ile Arg
            100                 105                 110
```

<210> SEQ ID NO 42
<211> LENGTH: 369
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 42

```
caggtccaac tgcagcagcc tggggctgag ctggtgaggc ctggggcttc agtgaagctg    60
tcctgcaagg cttctggcta caccttcacc gccttctgga taaactgggt gaaacagagg   120
cctggacaag gccttgagtg gatcggaaat atttatcctt ctgatagtta tactaactac   180
aatcaaaact caaggacaa ggccacattg actgtagaca atcctccag cacagcctac    240 atgcagctca gcagcccgac atctgaggac tctgcggtct attactgtgc aagatccgat   300
tactacggta gtagctacta tgctctggac tactggggtc aaggaacctc agtcaccgtc   360
tcctcagcc                                                          369
```

<210> SEQ ID NO 43
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 43

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Thr Phe Thr Ala Phe
            20                  25                  30

Trp Ile Asn Trp Val Lys Gln Arg Pro Gly Gln Gly Leu Glu Trp Ile
        35                  40                  45

Gly Asn Ile Tyr Pro Ser Asp Ser Tyr Thr Asn Tyr Asn Gln Asn Phe
    50                  55                  60

Lys Asp Lys Ala Thr Leu Thr Val Asp Lys Ser Ser Thr Ala Tyr
65                  70                  75                  80

Met Gln Leu Ser Ser Pro Thr Ser Glu Asp Ser Ala Val Tyr Tyr Cys
                85                  90                  95

Ala Arg Ser Asp Tyr Tyr Gly Ser Ser Tyr Tyr Ala Leu Asp Tyr Trp
            100                 105                 110

Gly Gln Gly Thr Ser Val Thr Val Ser Ser
        115                 120

<210> SEQ ID NO 44
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 44
gacattgtgg tgacccaatc tccagcctct ttggctgtgt ctctagggca gagggccacc      60
atctcctgca gagccagcga aagtgttgat aattatggca ttagttttat gaactggttc     120
caacagaaac caggacagcc acccaaactc ctcatctatg ctgcatccaa ccaaggatcc     180
ggggtccctg ccaggtttag tggcagtggg tctgggtcag acttcagcct caacatccat     240
cctatggagg aggatgatcc tgcaatgtat ttctgtcagc aaagtaagga ggttccattc     300
acgttcggct cggggacaaa gttggaaata aaacgg                              336

<210> SEQ ID NO 45
<211> LENGTH: 124
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 45

Asp Ile Val Val Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Tyr
            20                  25                  30

Gly Ile Ser Phe Met Asn Trp Phe Gln Gln Lys Pro Gly Gln Pro Pro
        35                  40                  45

Lys Leu Leu Ile Tyr Ala Ala Ser Asn Gln Gly Ser Gly Val Pro Ala
    50                  55                  60

Arg Phe Ser Gly Ser Gly Ser Gly Ser Asp Phe Ser Leu Asn Ile His
65                  70                  75                  80

```
Pro Met Glu Glu Asp Asp Pro Ala Met Tyr Phe Cys Gln Gln Ser Lys
            85                  90                  95

Glu Val Pro Phe Thr Phe Gly Ser Gly Thr Lys Leu Glu Ile Lys Arg
            100                 105                 110

Ala Asp Ala Ala Pro Thr Val Ser Ile Phe Pro Thr
            115                 120

<210> SEQ ID NO 46
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 46
gaggtcctgc tgcaacagtc tggacctgaa ctggtgaagc ctggggcttc agtgaagatt     60
ccctgcaagg cttctggata cacattcact gactacaaca tggactgggt gaagcagagc    120
catggaaaga gccttgagtg gattggagat attaatccta acaatggtga ctttctac      180 aaccagaagt tcaagggcaa ggccacattg actgtacaca gtcctccag cacagccttc    240 atggagctcc gcagcctgac atctgaggac actgcagtct attactgtac aagatcaaag    300
tatgataact atccctggtt tgcttactgg ggccaaggga ctctggtcac tgtctctgca    360

<210> SEQ ID NO 47
<211> LENGTH: 144
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 47

Glu Val Leu Leu Gln Gln Ser Gly Pro Glu Leu Val Lys Pro Gly Ala
1               5                   10                  15

Ser Val Lys Ile Pro Cys Lys Ala Ser Gly Tyr Thr Phe Thr Asp Tyr
            20                  25                  30

Asn Met Asp Trp Val Lys Gln Ser His Gly Lys Ser Leu Glu Trp Ile
        35                  40                  45

Gly Asp Ile Asn Pro Asn Asn Gly Asp Thr Phe Tyr Asn Gln Lys Phe
    50                  55                  60

Lys Gly Lys Ala Thr Leu Thr Val His Lys Ser Ser Ser Thr Ala Phe
65                  70                  75                  80

Met Glu Leu Arg Ser Leu Thr Ser Glu Asp Thr Ala Val Tyr Tyr Cys
                85                  90                  95

Thr Arg Ser Lys Tyr Asp Asn Tyr Pro Trp Phe Ala Tyr Trp Gly Gln
            100                 105                 110

Gly Thr Leu Val Thr Val Ser Ala Ala Lys Thr Thr Pro Pro Ser Val
        115                 120                 125

Tyr Pro Leu Ala Pro Gly Cys Gly Asp Thr Thr Gly Ser Ser Val Thr
    130                 135                 140

<210> SEQ ID NO 48
<211> LENGTH: 324
<212> TYPE: DNA
<213> ORGANISM: Artificial Sequence
<220> FEATURE:
```

<221> NAME/KEY: source
<223> OTHER INFORMATION: /note="Description of Artificial Sequence:
      Synthetic polynucleotide"

<400> SEQUENCE: 48
gatatccaga tgacacagac tacatcctcc ctgtctgcct ctctgggaga cagagtcacc    60
atcagttgca gtgcaagtca ggacattaac aattatttaa actggtatca gcagaaacca   120
gatggaactg ttaaactcct gatctattac acatcaagtt tacactcagg agtcccatca   180
aggttcagtg gcagtgggtc tgggacagat tattctctca ccatcagcaa cctggaacct   240
gaagatattg ccacttacta ttgtcagcag tatattaagc ttccgtggac gttcggtgga   300
ggcaccaagc tggaaatcaa acgg                                          324

<210> SEQ ID NO 49
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 49

Asp Ile Gln Met Thr Gln Thr Thr Ser Ser Leu Ser Ala Ser Leu Gly
1               5                   10                  15

Asp Arg Val Thr Ile Ser Cys Ser Ala Ser Gln Asp Ile Asn Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Ser Leu His Ser Gly Val Pro Ser Arg Phe Ser Gly
    50                  55                  60

Ser Gly Ser Gly Thr Asp Tyr Ser Leu Thr Ile Ser Asn Leu Glu Pro
65                  70                  75                  80

Glu Asp Ile Ala Thr Tyr Tyr Cys Gln Gln Tyr Ile Lys Leu Pro Trp
                85                  90                  95

Thr Phe Gly Gly Gly Thr Lys Leu Glu Ile Lys Arg
            100                 105

<210> SEQ ID NO 50
<211> LENGTH: 357
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 50
gaggtccagc tgcaacagtt tggagctgag ctggtgaagc ctggggcttc agtgaagata    60
tcttgcaagg cttctggcta cacattcact gactacaaca tggactgggt gaaacagagc   120
cctggaaaga gccttgagtg gattggagat attcatccta attatgatac ttctacctac   180
aaccagaagt tcaagggaaa ggccacattg actgtagaca gtcctccag cacagcctac    240 atggaactcc gcagcctgac atctgaggac actgcagtct attactgtgc aagagaggtg   300
cgacggggtt acttctttga cttctggggc caaggcacca ctctcacagt ctcctca      357

<210> SEQ ID NO 51
<211> LENGTH: 119
<212> TYPE: PRT

<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 51

Glu Val Gln Leu Gln Gln Phe Gly Ala Glu Leu Val Lys Pro Gly Ala
1               5                   10                  15

Ser Val Lys Ile Ser Cys Lys Ala Ser Gly Tyr Thr Phe Thr Asp Tyr
            20                  25                  30

Asn Met Asp Trp Val Lys Gln Ser Pro Gly Lys Ser Leu Glu Trp Ile
        35                  40                  45

Gly Asp Ile His Pro Asn Tyr Asp Thr Ser Thr Tyr Asn Gln Lys Phe
    50                  55                  60

Lys Gly Lys Ala Thr Leu Thr Val Asp Lys Ser Ser Thr Ala Tyr
65                  70                  75                  80

Met Glu Leu Arg Ser Leu Thr Ser Glu Asp Thr Ala Val Tyr Tyr Cys
                85                  90                  95

Ala Arg Glu Val Arg Arg Gly Tyr Phe Phe Asp Phe Trp Gly Gln Gly
            100                 105                 110

Thr Thr Leu Thr Val Ser Ser
        115

<210> SEQ ID NO 52
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 52
gatgtgttga tgacccagtc tccactctcc ctgcctgtca gtcttggaga tcaagcctcc      60
atctcttgca gatctagtca gagcattgta catagtaatg gaaacaccta tttagaatgg     120
tacctgcaga aaccaggcca gtctccaaag ctcctgatct acaaagtttc caaccgattt     180
tctggggtcc cagacaggtt cagtggcagt ggatcaggga cagatttcac actcaagatc     240
agcagagtgg aggctgagga tctgggagtt tatttctgct ttcaaggttc acatgttccg     300
ctcacgttcg gtgctgggac caagcttgag ctgaaacgg                            339

<210> SEQ ID NO 53
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 53

Asp Val Leu Met Thr Gln Ser Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

```
Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Phe Cys Phe Gln Gly
                 85                  90                  95

Ser His Val Pro Leu Thr Phe Gly Ala Gly Thr Lys Leu Glu Leu Lys
            100                 105                 110

Arg
```

<210> SEQ ID NO 54
<211> LENGTH: 345
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 54

```
caggtccaac tgcagcagcc tggggctgaa ctggtgaagc ctggggcttc agtgaaactg      60
tcctgccaga cttctggcta caccttcacc agctactgga tgcactgggt aaagcagagg     120
cctggacaag gccttgagtg gattggagag attaatccca gcaacggtcg tactaactac     180
aatgagaagt tcaagaccaa ggccacactg actgtagaca atcctccac cacagcctac      240 attcaactca cagcctgac atctgaagac tctgcggtct attactgtgc aagattgcgg      300
gattacggag gtggggcca agggactctg gtcactgtct ctgca                      345
```

<210> SEQ ID NO 55
<211> LENGTH: 115
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 55

```
Gln Val Gln Leu Gln Gln Pro Gly Ala Glu Leu Val Lys Pro Gly Ala
  1               5                  10                  15

Ser Val Lys Leu Ser Cys Gln Thr Ser Gly Tyr Thr Phe Thr Ser Tyr
                 20                  25                  30

Trp Met His Trp Val Lys Gln Arg Pro Gly Gln Gly Leu Glu Trp Ile
             35                  40                  45

Gly Glu Ile Asn Pro Ser Asn Gly Arg Thr Asn Tyr Asn Glu Lys Phe
 50                  55                  60

Lys Thr Lys Ala Thr Leu Thr Val Asp Lys Ser Ser Thr Thr Ala Tyr
 65                  70                  75                  80

Ile Gln Leu Asn Ser Leu Thr Ser Glu Asp Ser Ala Val Tyr Tyr Cys
                 85                  90                  95

Ala Arg Leu Arg Asp Tyr Gly Gly Trp Gly Gln Gly Thr Leu Val Thr
            100                 105                 110

Val Ser Ala
        115
```

<210> SEQ ID NO 56
<211> LENGTH: 324
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 56
aacattgtta tgacccaatc tcccaaatcc gtgtccatgt cagtaggaga gagggtcacc      60
ttgagctgca aggccagtga aatgtgaat acttttgtat cctggtttca acagaaacca      120
gatcagtctc ctaaactgct gatttacggg gcatccaacc ggtaccctgg ggtccccgat     180
cgcttcacag gcagtggatc tgcaacagaa ttcactctga ccatcagcag tgttcaggct     240
gaagaccttg cagattatca ctgtggacag agttacagtt atccgtacac gttcggaggg     300
gggaccaagc tggaaataaa acgg                                            324

<210> SEQ ID NO 57
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 57

Asn Ile Val Met Thr Gln Ser Pro Lys Ser Val Ser Met Ser Val Gly
1               5                   10                  15

Glu Arg Val Thr Leu Ser Cys Lys Ala Ser Glu Asn Val Asn Thr Phe
            20                  25                  30

Val Ser Trp Phe Gln Gln Lys Pro Asp Gln Ser Pro Lys Leu Leu Ile
        35                  40                  45

Tyr Gly Ala Ser Asn Arg Tyr Pro Gly Val Pro Asp Arg Phe Thr Gly
    50                  55                  60

Ser Gly Ser Ala Thr Glu Phe Thr Leu Thr Ile Ser Ser Val Gln Ala
65                  70                  75                  80

Glu Asp Leu Ala Asp Tyr His Cys Gly Gln Ser Tyr Ser Tyr Pro Tyr
                85                  90                  95

Thr Phe Gly Gly Gly Thr Lys Leu Glu Ile Lys Arg
            100                 105

<210> SEQ ID NO 58
<211> LENGTH: 366
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 58
cagatccagc tgcagcagtc tggacctgag ctggtgaagc ctggggcttc agtgaagata     60
tcctgcaagg cttctggcta caccttcact gactactata taaactgggt gaagcagagg    120
cctggacagg gacttgagtg gattggatgg atttatcctg aagcggtaa tactaggtac     180 aatgagaagt tcaagggcaa ggccacattg actgtagaca catcctccag cacagcctac    240
atgcagctca gcagcctgac ctctgaggac tctgcggtct atttctgtac aagatattac    300
tacgctggtc ggtacgactg gtacttcgat gtctggggcg ctaggaccac ggtcaccgtc    360
tcctca                                                               366

<210> SEQ ID NO 59
<211> LENGTH: 122

<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 59

Gln Ile Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
            20                  25                  30

Tyr Ile Asn Trp Val Lys Gln Arg Pro Gly Gln Gly Leu Glu Trp Ile
        35                  40                  45

Gly Trp Ile Tyr Pro Gly Ser Gly Asn Thr Arg Tyr Asn Glu Lys Phe
    50                  55                  60

Lys Gly Lys Ala Thr Leu Thr Val Asp Thr Ser Ser Thr Ala Tyr
65                  70                  75                  80

Met Gln Leu Ser Ser Leu Thr Ser Glu Asp Ser Ala Val Tyr Phe Cys
                85                  90                  95

Thr Arg Tyr Tyr Tyr Ala Gly Arg Tyr Asp Trp Tyr Phe Asp Val Trp
            100                 105                 110

Gly Ala Arg Thr Thr Val Thr Val Ser Ser
        115                 120

<210> SEQ ID NO 60
<211> LENGTH: 324
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 60
ggcatcaaga tgacccagtc tccatcttcc atgtatgcat ctctcggaga gagagtcact      60
atcacttgca aggcgagtca ggacgttaat agctatttaa gctggttcca gcagaaacca    120
gggaaatctc ctaagaccct gatctatcgt gcaaacagat tggtagatgg ggtcccatca    180
aggttcagtg gcagtggatc tgggcaagat tattctctca ccatcagcag cctggagtat    240
gaagatatgg gaatttatta ttgtctacag tatgatgagt ttccgtacac gttcggaggg    300
gggaccaagc tggaaataaa acgg                                            324

<210> SEQ ID NO 61
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 61

Gly Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Val Asn Ser Tyr
            20                  25                  30

Leu Ser Trp Phe Gln Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly

Ser Gly Ser Gly Gln Asp Tyr Ser Leu Thr Ile Ser Ser Leu Glu Tyr
65                  70                  75                  80

Glu Asp Met Gly Ile Tyr Tyr Cys Leu Gln Tyr Asp Glu Phe Pro Tyr
                85                  90                  95

Thr Phe Gly Gly Gly Thr Lys Leu Glu Ile Lys Arg Ala
            100                 105

<210> SEQ ID NO 62
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 62
gagatccagc tgcagcagac tggacctgag ctggtgaagc ctggggcttc agtgaagata      60
tcctgcaagg cttctggtta ttcattcact gactccatca tgctctgggt gaagcagagc     120
catggaaaga gccttgaatg gattggaaat attaatcctt actatggtag tactacctac     180
aatctgaagt tcaagggcaa ggccacattg actgtagaca atcttccag cacagcctac      240 atgcagctca acagtctgac atctgaggac tctgcagtct attactgtgc aagaggacta     300
cggggttacg gaggatactt tgactactgg ggccaaggca ccactctcac agtctcctca     360

<210> SEQ ID NO 63
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 63

Glu Ile Gln Leu Gln Gln Thr Gly Pro Glu Leu Val Lys Pro Gly Ala
1               5                   10                  15

Ser Val Lys Ile Ser Cys Lys Ala Ser Gly Tyr Ser Phe Thr Asp Ser
            20                  25                  30

Ile Met Leu Trp Val Lys Gln Ser His Gly Lys Ser Leu Glu Trp Ile
        35                  40                  45

Gly Asn Ile Asn Pro Tyr Tyr Gly Ser Thr Thr Tyr Asn Leu Lys Phe
    50                  55                  60

Lys Gly Lys Ala Thr Leu Thr Val Asp Lys Ser Ser Ser Thr Ala Tyr
65                  70                  75                  80

Met Gln Leu Asn Ser Leu Thr Ser Glu Asp Ser Ala Val Tyr Tyr Cys
                85                  90                  95

Ala Arg Gly Leu Arg Gly Tyr Gly Gly Tyr Phe Asp Tyr Trp Gly Gln
            100                 105                 110

Gly Thr Thr Leu Thr Val Ser Ser
        115                 120

<210> SEQ ID NO 64
<211> LENGTH: 333
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic polynucleotide"

<400> SEQUENCE: 64

```
gtgatgaccc agtctccact ctctctgcct gtcaatattg gagatcaagc ctctatctct    60
tgcaagtcta ctaagagtct tctgaatagt gatggattca cttatttgga ctggtacctg   120
cagaagccag gccagtctcc acagctccta atatatttgg tttctaatcg atttctgga    180
gttccagaca ggttcagtgg cagtgggtca ggaacagatt tcacactcaa gatcagcaga   240
gtggaggctg aggatttggg agtttattat tgcttccaga gtaactctct tccattcacg   300
ttcggctcgg ggacaaagtt ggaaataaaa cgg                                333
```

<210> SEQ ID NO 65
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 65

```
Val Met Thr Gln Ser Pro Leu Ser Leu Pro Val Asn Ile Gly Asp Gln
 1               5                  10                  15

Ala Ser Ile Ser Cys Lys Ser Thr Lys Ser Leu Leu Asn Ser Asp Gly
             20                  25                  30

Phe Thr Tyr Leu Asp Trp Tyr Leu Gln Lys Pro Gly Gln Ser Pro Gln
         35                  40                  45

Leu Leu Ile Tyr Leu Val Ser Asn Arg Phe Ser Gly Val Pro Asp Arg
     50                  55                  60

Phe Ser Gly Ser Gly Ser Gly Thr Asp Phe Thr Leu Lys Ile Ser Arg
 65                  70                  75                  80

Val Glu Ala Glu Asp Leu Gly Val Tyr Tyr Cys Phe Gln Ser Asn Ser
                 85                  90                  95

Leu Pro Phe Thr Phe Gly Ser Gly Thr Lys Leu Glu Ile Lys Arg
            100                 105                 110
```

<210> SEQ ID NO 66
<211> LENGTH: 357
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 66

```
gaggtccagc tgcaacagtc tggacctgta ctggtgaagc ctggggcttc agtgaggatg    60
tcctgtaagg cttctggata cacattcact gactactata tgaactgggt gaagcagagc   120
catggaaaga gccttgagtg gattggagtt tttaatcctt acaacggtgg cactaactac   180
aaccagaagt tcaagggcaa ggccacattg actgttgaca gtcctccag tacagcctac    240
atggagctca acggcctgac atctgaggac tctgcagtct attactgtgc cgatggttac   300
tacagttact atgctatgga ctactgggt caaggaacct cactcaccgt ctcctca      357
```

<210> SEQ ID NO 67
<211> LENGTH: 119
<212> TYPE: PRT
<213> ORGANISM: Artificial Sequence
<220> FEATURE:

<220> FEATURE:
<221> NAME/KEY: source
<223> OTHER INFORMATION: /note="Description of Artificial Sequence:
      Synthetic polypeptide"

<400> SEQUENCE: 67

Glu Val Gln Leu Gln Gln Ser Gly Pro Val Leu Val Lys Pro Gly Ala
1               5                   10                  15

Ser Val Arg Met Ser Cys Lys Ala Ser Gly Tyr Thr Phe Thr Asp Tyr
            20                  25                  30

Tyr Met Asn Trp Val Lys Gln Ser His Gly Lys Ser Leu Glu Trp Ile
        35                  40                  45

Gly Val Phe Asn Pro Tyr Asn Gly Gly Thr Asn Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Asn Gly Leu Thr Ser Glu Asp Ser Ala Val Tyr Tyr Cys
                85                  90                  95

Ala Asp Gly Tyr Tyr Ser Tyr Tyr Ala Met Asp Tyr Trp Gly Gln Gly
            100                 105                 110

Thr Ser Leu Thr Val Ser Ser
        115

<210> SEQ ID NO 68
<211> LENGTH: 324
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 68
gacatcaaga tgacccagtc tccatcttcc atgtatgcat ctctaggaga gagagtcact    60
atcacttgca aggcgagtca ggacattaat agctatttaa gctggttcca ccagaaacca   120
gggaaatctc ctaagaccct gatctatcgt gcaaacagat tggtagatgg ggtcccatca   180
aggttcagtg gcagtggatc tgggcaagat tattctctca ccatcagcag cctggagttt   240
gaagatatgg gaatttatta ttgtctacag tatgatgact ttccgtacac gttcggaggg   300
gggaccaagc tggaaataaa acgg                                          324

<210> SEQ ID NO 69
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 69

Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Ser Tyr
            20                  25                  30

Leu Ser Trp Phe His Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Tyr Ser Leu Thr Ile Ser Ser Leu Glu Phe

```
                65                  70                  75                  80
Glu Asp Met Gly Ile Tyr Tyr Cys Leu Gln Tyr Asp Asp Phe Pro Tyr
                        85                  90                  95

Thr Phe Gly Gly Gly Thr Lys Leu Glu Ile Lys Arg
                100                 105
```

<210> SEQ ID NO 70
<211> LENGTH: 369
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 70

```
cagatccagc tgcagcagtc tggacctgaa ctggtgaagc ctggggcttc agtgaagata      60
tcctgcaagg cttctggcta caccttcact gactactata taaactgggt gaagcagaag     120
cctggacagg gacttgagtg gattggatgg atttatcctg gaagcggtaa tactaagtac     180
aatgagaagt tcaagggcaa ggccacattg actgtagaca catcctccag cacagcctac     240
atgcagctca gcagcctgac atctgaagac actgctgtct atttctgtgc aagactggga     300
tatttctacg gtagtagttc ctggtacttc gatgtctggg gcgcaggga  cacggtcacc    360
gtctcctca                                                              369
```

<210> SEQ ID NO 71
<211> LENGTH: 123
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 71

```
Gln Ile Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
            20                  25                  30

Tyr Ile Asn Trp Val Lys Gln Lys Pro Gly Gln Gly Leu Glu Trp Ile
        35                  40                  45

Gly Trp Ile Tyr Pro Gly Ser Gly Asn Thr Lys Tyr Asn Glu Lys Phe
    50                  55                  60

Lys Gly Lys Ala Thr Leu Thr Val Asp Thr Ser Ser Ser Thr Ala Tyr
65                  70                  75                  80

Met Gln Leu Ser Ser Leu Thr Ser Glu Asp Thr Ala Val Tyr Phe Cys
                85                  90                  95

Ala Arg Leu Gly Tyr Phe Tyr Gly Ser Ser Trp Tyr Phe Asp Val
            100                 105                 110

Trp Gly Ala Gly Thr Thr Val Thr Val Ser Ser
        115                 120
```

<210> SEQ ID NO 72
<211> LENGTH: 325
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

-continued

<400> SEQUENCE: 72
gacatcaaga tgacccagtc tccatcttcc atgtatgcat ctctaggaga gagagtcact    60
atcacctgca aggcgagtca ggacattaat agctattcag ctggttcca gcagaaacca    120 ggaaaatctc ctaagaccct gatctatcgt acaaacagat tggtagatgg ggtcccatca    180
aggttcagtg gcagtggatc tgggcaagat tattctctca gcatcagcag cctggagtat    240
gaagatatgg gaatttatta ttgtctacag tatgatgagt ttccgtacac gttcggaggg    300
gggaccaagc tggaaataaa acggg    325

<210> SEQ ID NO 73
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 73

Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Ser Tyr
            20                  25                  30

Ser Gly Trp Phe Gln Gln Lys Pro Gly Lys Ser Pro Lys Thr Leu Ile
        35                  40                  45

Tyr Arg Thr Asn Arg Leu Val Asp Gly Val Pro Ser Arg Phe Ser Gly
    50                  55                  60

Ser Gly Ser Gly Gln Asp Tyr Ser Leu Ser Ile Ser Ser Leu Glu Tyr
65                  70                  75                  80

Glu Asp Met Gly Ile Tyr Tyr Cys Leu Gln Tyr Asp Glu Phe Pro Tyr
                85                  90                  95

Thr Phe Gly Gly Gly Thr Lys Leu Glu Ile Lys Arg Ala Asp Ala Ala
            100                 105                 110

Pro Thr Val Ser Ile Phe Pro Thr
        115                 120

<210> SEQ ID NO 74
<211> LENGTH: 351
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 74
caggttcagc tgcagcagtc tggagctgag ctggcgaggc ctggggcttc agtgaagctg    60
tcctgcaagg cttctgacta caccttcaca agctatggta taagctgggt gaagcagaga    120
actggacagg gccttgagtg gattggagag atttttccta gaagtggcaa tacttactac    180
aatgagaagt tcaagggcaa ggccacactg actgcagaca atcctccag cacagcgtac    240 atggagctcc gcagcctgac atctgaggac tctgcggtct atttctgtgc aaggggactg    300
ggaggtgcta tggactactg gggtcaagga acctcagtca tcgtctcctc a              351

<210> SEQ ID NO 75
<211> LENGTH: 117
<212> TYPE: PRT

<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 75

```
Gln Val Gln Leu Gln Gln Ser Gly Ala Glu Leu Ala Arg Pro Gly Ala
1               5                   10                  15
Ser Val Lys Leu Ser Cys Lys Ala Ser Asp Tyr Thr Phe Thr Ser Tyr
            20                  25                  30
Gly Ile Ser Trp Val Lys Gln Arg Thr Gly Gln Gly Leu Glu Trp Ile
        35                  40                  45
Gly Glu Ile Phe Pro Arg Ser Gly Asn Thr Tyr Tyr Asn Glu Lys Phe
    50                  55                  60
Lys Gly Lys Ala Thr Leu Thr Ala Asp Lys Ser Ser Thr Ala Tyr
65                  70                  75                  80
Met Glu Leu Arg Ser Leu Thr Ser Glu Asp Ser Ala Val Tyr Phe Cys
                85                  90                  95
Ala Arg Gly Leu Gly Gly Ala Met Asp Tyr Trp Gly Gln Gly Thr Ser
            100                 105                 110
Val Ile Val Ser Ser
        115
```

<210> SEQ ID NO 76
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 76

```
gatattgtga tgactcaggc tgcaccctct gtacctgtca ctcctggaga gtcagtatcc    60
atctcctgca ggtctagtaa gagtctcctg catagtaatg gcaacactta cttgtattgg   120
ttcctgcaga ggccaggcca gtctcctcag ctcctgatat atcggatgtc aaccttgcc    180
tcaggagtcc cagacaggtt cagtggcagt gggtcaggaa caactttcac actgagaatc   240
agtgagagtg gaggctgagga tgtgggtgtt tattattgta tgcaacatct agaatatccg   300
tgcacgttcg gaggggggac caagctggaa ataaaacgg                          339
```

<210> SEQ ID NO 77
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 77

```
Asp Ile Val Met Thr Gln Ala Ala Pro Ser Val Pro Val Thr Pro Gly
1               5                   10                  15
Glu Ser Val Ser Ile Ser Cys Arg Ser Ser Lys Ser Leu Leu His Ser
            20                  25                  30
Asn Gly Asn Thr Tyr Leu Tyr Trp Phe Leu Gln Arg Pro Gly Gln Ser
        35                  40                  45
Pro Gln Leu Leu Ile Tyr Arg Met Ser Asn Leu Ala Ser Gly Val Pro
    50                  55                  60
```

```
Asp Arg Phe Ser Gly Ser Gly Ser Gly Thr Thr Phe Thr Leu Arg Ile
 65                  70                  75                  80

Ser Gly Val Glu Ala Glu Asp Val Gly Val Tyr Tyr Cys Met Gln His
                 85                  90                  95

Leu Glu Tyr Pro Cys Thr Phe Gly Gly Gly Thr Lys Leu Glu Ile Lys
            100                 105                 110

Arg

<210> SEQ ID NO 78
<211> LENGTH: 352
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 78
gatgtgcagc tggtggagtc tgggggaggc ttagtgcagc ctggagggtc ccggaaactc     60
tcctgtgcag cctctggatt cactttcagt agctttggaa tgcactgggt tcgtcaggct    120
ccagagaagg ggctggagtg ggtcgcatac attagtagtg ccactagtgc catctactat    180
gcagacacag tgaagggccg attcaccatc tccagagaca atcccacgaa caccctgttc    240
ctgcaaatga ccagtctaag gtctgaggac acggccatgt attactgtgc aagaaagggg    300
aacaactact ttgactactg gggccaaggc accactctca cagtctcctc ac            352

<210> SEQ ID NO 79
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 79

Asp Val Gln Leu Val Glu Ser Gly Gly Gly Leu Val Gln Pro Gly Gly
 1               5                  10                  15

Ser Arg Lys Leu Ser Cys Ala Ala Ser Gly Phe Thr Phe Ser Ser Phe
                20                  25                  30

Gly Met His Trp Val Arg Gln Ala Pro Glu Lys Gly Leu Glu Trp Val
            35                  40                  45

Ala Tyr Ile Ser Ser Ala Thr Ser Ala Ile Tyr Tyr Ala Asp Thr Val
 50                  55                  60

Lys Gly Arg Phe Thr Ile Ser Arg Asp Asn Pro Thr Asn Thr Leu Phe
 65                  70                  75                  80

Leu Gln Met Thr Ser Leu Arg Ser Glu Asp Thr Ala Met Tyr Tyr Cys
                85                  90                  95

Ala Arg Lys Gly Asn Asn Tyr Phe Asp Tyr Trp Gly Gln Gly Thr Thr
            100                 105                 110

Leu Thr Val Ser Ser
        115

<210> SEQ ID NO 80
<211> LENGTH: 318
<212> TYPE: DNA
<213> ORGANISM: Artificial Sequence
<220> FEATURE:
<221> NAME/KEY: source
```

<223> OTHER INFORMATION: /note="Description of Artificial Sequence:
Synthetic polynucleotide"

<400> SEQUENCE: 80

```
caaattgttc tcacccagtc tccagcaatc atgtctgcat ctccagggga gaaggtcacc      60
ttatcctgca gtgccacctc aagtgtaact tacatgcact ggctccagca gaagccagga    120
tcctccccca aaccctggat ttatcgcaca tccaacctgg cttctggagt ccctgctcgc    180
ttccgtggca gtgggtctgg gacctcttac tctctcacaa tcagcagcat ggaggctgaa    240
gatgctgcca cttattactg ccagcagtat catagttacc caccgacgtt cggtggaggc    300
accaagctgg aaatcaaa                                                  318
```

<210> SEQ ID NO 81
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 81

Gln Ile Val Leu Thr Gln Ser Pro Ala Ile Met Ser Ala Ser Pro Gly
1               5                   10                  15

Glu Lys Val Thr Leu Ser Cys Ser Ala Thr Ser Ser Val Thr Tyr Met
            20                  25                  30

His Trp Leu Gln Gln Lys Pro Gly Ser Ser Pro Lys Pro Trp Ile Tyr
        35                  40                  45

Arg Thr Ser Asn Leu Ala Ser Gly Val Pro Ala Arg Phe Arg Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Tyr His Ser Tyr Pro Pro Thr
                85                  90                  95

Phe Gly Gly Gly Thr Lys Leu Glu Ile Lys Arg
            100                 105

<210> SEQ ID NO 82
<211> LENGTH: 345
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 82

```
gaggtgcagc tggtggagtc tgggggaggc ttagtgaagc ctggagggtc cctgaaactc     60
tcctgtgcag cctctggatt cactttcagt agctttggca tgtcttgggt tcgccagact   120
ccggagaaga ggctggagtg ggtcgcagcc attaatagta tggtggtaa cacatactat    180
tcagacactg tgaagggccg attcaccatc tccagagaca atgccaagaa caccctgtac    240
ctgcaaatga gcagtctgag gtctgcggac actgccttgt attactgtgc aagagtggtg    300
cacttcgatg tctggggcgc agggaccacg gtcaccgtct cctca                    345
```

<210> SEQ ID NO 83
<211> LENGTH: 115
<212> TYPE: PRT
<213> ORGANISM: Artificial Sequence -continued

```
<220> FEATURE:
<221> NAME/KEY: source
<223> OTHER INFORMATION: /note="Description of Artificial Sequence:
      Synthetic polypeptide"

<400> SEQUENCE: 83

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Phe
            20                  25                  30

Gly Met Ser Trp Val Arg Gln Thr Pro Glu Lys Arg Leu Glu Trp Val
        35                  40                  45

Ala Ala Ile Asn Ser Asn Gly Gly Asn Thr Tyr Tyr Ser Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ser Ala Asp Thr Ala Leu Tyr Tyr Cys
                85                  90                  95

Ala Arg Val Val His Phe Asp Val Trp Gly Ala Gly Thr Thr Val Thr
            100                 105                 110

Val Ser Ser
        115

<210> SEQ ID NO 84
<211> LENGTH: 324
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 84
gctatccaga tgacacagac tacatcctcc ctgtctgcct ctctgggaga cagagtcacc      60
atcagttgca gtgcaagtca ggacattagc aattatttaa actggtatca gcagaaacca     120
gatggaactg ttaaactcct gatctattac acatcaagtt acactcagg  agtcccatca     180 cggttcagtg gcagtgggtc tgggacagat tattctctca ccatcagcaa cgtggaacct     240
gaagatgttg ccacttacta ttgtcagcaa tatagtgagc ttccgtacac gttcggaggg     300
gggaccaagc tggaaataaa ccgg                                            324

<210> SEQ ID NO 85
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 85

Ala Ile Gln Met Thr Gln Thr Thr Ser Ser Leu Ser Ala Ser Leu Gly
1               5                   10                  15

Asp Arg Val Thr Ile Ser Cys Ser Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Ser Leu His Ser Gly Val Pro Ser Arg Phe Ser Gly
    50                  55                  60
```

```
Ser Gly Ser Gly Thr Asp Tyr Ser Leu Thr Ile Ser Asn Val Glu Pro
 65                  70                  75                  80

Glu Asp Val Ala Thr Tyr Tyr Cys Gln Gln Tyr Ser Glu Leu Pro Tyr
                 85                  90                  95

Thr Phe Gly Gly Gly Thr Lys Leu Glu Ile Asn Arg
            100                 105

<210> SEQ ID NO 86
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 86

Gly Tyr Thr Phe Thr Asp Tyr Asn
1               5

<210> SEQ ID NO 87
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 87

Gly Phe Asn Ile Lys Asp Thr Tyr
1               5

<210> SEQ ID NO 88
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 88

Gly Phe Thr Phe Ser Asp Tyr Tyr
1               5

<210> SEQ ID NO 89
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 89

Gly Tyr Thr Phe Thr Asp Tyr Asn
1               5

<210> SEQ ID NO 90
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 90

Gly Tyr Thr Phe Thr Asn Tyr Asp
1               5

<210> SEQ ID NO 91
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 91

Gly Tyr Thr Phe Thr Ser Tyr Trp
1               5

<210> SEQ ID NO 92
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 92

Gly Tyr Thr Phe Thr Asp Tyr Tyr
1               5

<210> SEQ ID NO 93
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 93

Gly Tyr Ser Phe Thr Asp Ser Ile
1               5

<210> SEQ ID NO 94
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 94

Gly Tyr Thr Phe Thr Asp Tyr Tyr
1               5

<210> SEQ ID NO 95
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 95

Gly Phe Ser Leu Thr Ser Tyr Asp
1               5
```

```
<210> SEQ ID NO 96
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 96

Gly Tyr Thr Phe Thr Asp Tyr Tyr
1               5

<210> SEQ ID NO 97
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 97

Gly Tyr Thr Phe Thr Asp Tyr Ser
1               5

<210> SEQ ID NO 98
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 98

Asp Tyr Thr Phe Thr Ser Tyr Gly
1               5

<210> SEQ ID NO 99
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 99

Gly Tyr Ala Phe Thr Asp Phe Ser
1               5

<210> SEQ ID NO 100
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 100

Gly Tyr Thr Phe Thr Ala Phe Trp
1               5

<210> SEQ ID NO 101
<211> LENGTH: 8
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 101

Gly Phe Thr Phe Ser Ser Phe Gly
1               5

<210> SEQ ID NO 102
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 102

Thr Phe Thr Phe Ser Ser Phe Gly
1               5

<210> SEQ ID NO 103
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 103

Gly Tyr Thr Phe Thr Asp Tyr Asn
1               5

<210> SEQ ID NO 104
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 104

Ile His Pro Asn Tyr Asp Thr Ser
1               5

<210> SEQ ID NO 105
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 105

Ile Asp Pro Ala Asn Gly Asn Ile
1               5

<210> SEQ ID NO 106
<211> LENGTH: 8
<212> TYPE: PRT
<213> ORGANISM: Artificial Sequence
<220> FEATURE:
<221> NAME/KEY: source
```

```
<223> OTHER INFORMATION: /note="Description of Artificial Sequence:
      Synthetic peptide"

<400> SEQUENCE: 106

Ile Ser Asp Gly Gly Thr Tyr Ile
1               5

<210> SEQ ID NO 107
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 107

Ile Asn Pro Asn Asn Gly Gly Thr
1               5

<210> SEQ ID NO 108
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 108

Ile Tyr Pro Arg Asp Gly Ser Phe
1               5

<210> SEQ ID NO 109
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 109

Ile Asn Pro Ser Asn Gly Arg Thr
1               5

<210> SEQ ID NO 110
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 110

Ile Tyr Pro Gly Ser Gly Asn Thr
1               5

<210> SEQ ID NO 111
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 111
```

```
Ile Asn Pro Tyr Tyr Gly Ser Thr
1               5

<210> SEQ ID NO 112
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 112

Phe Asn Pro Tyr Asn Gly Gly Thr
1               5

<210> SEQ ID NO 113
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 113

Ile Trp Thr Asp Gly Gly Thr
1               5

<210> SEQ ID NO 114
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 114

Ile Tyr Pro Gly Ser Gly Asn Thr
1               5

<210> SEQ ID NO 115
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 115

Ile Asn Thr Glu Thr Gly Glu Pro
1               5

<210> SEQ ID NO 116
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 116

Ile Phe Pro Arg Ser Gly Asn Thr
1               5
```

-continued

```
<210> SEQ ID NO 117
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 117

Ile Asn Thr Glu Thr Gly Glu Pro
1               5

<210> SEQ ID NO 118
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 118

Ile Tyr Pro Ser Asp Ser Tyr Thr
1               5

<210> SEQ ID NO 119
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 119

Ile Ser Ser Ala Thr Ser Ala Ile
1               5

<210> SEQ ID NO 120
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 120

Ile Asn Ser Asn Gly Gly Asn Thr
1               5

<210> SEQ ID NO 121
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 121

Ile Asn Pro Asn Asn Gly Asp Thr
1               5

<210> SEQ ID NO 122
<211> LENGTH: 12
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 122

Ala Arg Glu Val Arg Arg Gly Tyr Phe Phe Asp Phe
1               5                   10

<210> SEQ ID NO 123
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 123

Ala His Pro Ser Tyr Asp Tyr Asp Arg Asn Tyr Ala Met Asp Tyr
1               5                   10                  15

<210> SEQ ID NO 124
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 124

Val Arg Asp Ile Asp Tyr Asp Thr Ser Tyr Pro Trp Phe Ala Tyr
1               5                   10                  15

<210> SEQ ID NO 125
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 125

Thr Arg Ser Lys Tyr Asp Asn Tyr Pro Trp Phe Ala Tyr
1               5                   10

<210> SEQ ID NO 126
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 126

Ala Val Ser Glu Val Gly His Pro Trp Phe Pro Tyr
1               5                   10

<210> SEQ ID NO 127
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic peptide"

<400> SEQUENCE: 127

Ala Arg Leu Arg Asp Tyr Gly Gly
1               5

<210> SEQ ID NO 128
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 128

Thr Arg Tyr Tyr Tyr Ala Gly Arg Tyr Asp Trp Tyr Phe Asp Val
1               5                   10                  15

<210> SEQ ID NO 129
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 129

Ala Arg Gly Leu Arg Gly Tyr Gly Gly Tyr Phe Asp Tyr
1               5                   10

<210> SEQ ID NO 130
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 130

Ala Asp Gly Tyr Tyr Ser Tyr Tyr Ala Met Asp Tyr
1               5                   10

<210> SEQ ID NO 131
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 131

Val Arg Val Tyr Asp Gly Tyr Pro Trp Phe Ala Tyr
1               5                   10

<210> SEQ ID NO 132
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 132

```
Ala Arg Leu Gly Tyr Phe Tyr Gly Ser Ser Ser Trp Tyr Phe Asp Val
1               5                   10                  15
```

```
<210> SEQ ID NO 133
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 133

Val Arg Phe Ala Tyr
1               5
```

```
<210> SEQ ID NO 134
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 134

Ala Arg Gly Leu Gly Gly Ala Met Asp Tyr
1               5                   10
```

```
<210> SEQ ID NO 135
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 135

Val Arg Phe Ala Tyr
1               5
```

```
<210> SEQ ID NO 136
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 136

Ala Arg Ser Asp Tyr Tyr Gly Ser Ser Tyr Tyr Ala Leu Asp Tyr
1               5                   10                  15
```

```
<210> SEQ ID NO 137
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 137

Ala Arg Lys Gly Asn Asn Tyr Phe Asp Tyr
1               5                   10
```

```
<210> SEQ ID NO 138
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 138

Ala Arg Val Val His Phe Asp Val
1               5

<210> SEQ ID NO 139
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 139

Thr Arg Ser Lys Tyr Asp Asn Tyr Pro Trp Phe Ala Tyr
1               5                   10

<210> SEQ ID NO 140
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 140

Gln Ser Ile Val His Ser Asn Gly Asn Thr Tyr
1               5                   10

<210> SEQ ID NO 141
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 141

Gln Ser Ile Gly Thr Ser
1               5

<210> SEQ ID NO 142
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 142

Gln Gly Ile Asn Asn Tyr
1               5

<210> SEQ ID NO 143
<211> LENGTH: 6
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 143

Gln Gly Ile Ser Asn Tyr
1               5

<210> SEQ ID NO 144
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 144

Gln Gly Ile Ser Asn Tyr
1               5

<210> SEQ ID NO 145
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 145

Glu Asn Val Asn Thr Phe
1               5

<210> SEQ ID NO 146
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 146

Gln Asp Val Asn Ser Tyr
1               5

<210> SEQ ID NO 147
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 147

Lys Ser Leu Leu Asn Ser Asp Gly Phe Thr Tyr
1               5                   10

<210> SEQ ID NO 148
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 148

Gln Asp Ile Asn Ser Tyr
1               5

<210> SEQ ID NO 149
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 149

Gln Gly Ile Ser Asn Tyr
1               5

<210> SEQ ID NO 150
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 150

Gln Asp Ile Asn Ser Tyr
1               5

<210> SEQ ID NO 151
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 151

Gln Ser Leu Leu Asn Ser Arg Thr Arg Lys Asn Tyr
1               5                   10

<210> SEQ ID NO 152
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 152

Lys Ser Leu Leu His Ser Asn Gly Asn Thr Tyr
1               5                   10

<210> SEQ ID NO 153
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 153

Gln Ser Leu Leu Asn Ser Arg Thr Arg Lys Asn Tyr
```

<210> SEQ ID NO 154
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 154

Glu Ser Val Asp Asn Tyr Gly Ile Ser Phe
1               5                   10

<210> SEQ ID NO 155
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 155

Ser Ser Val Thr Tyr
1               5

<210> SEQ ID NO 156
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 156

Gln Asp Ile Ser Asn Tyr
1               5

<210> SEQ ID NO 157
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 157

Gln Asp Ile Asn Asn Tyr
1               5

<210> SEQ ID NO 158
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 158

Lys Val Ser Asn Arg Phe Ser
1               5

<210> SEQ ID NO 159

```
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 159

Tyr Ala Ser Glu Ser Ile Ser
1               5

<210> SEQ ID NO 160
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 160

Tyr Thr Ser Ser Leu His Ser
1               5

<210> SEQ ID NO 161
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 161

Tyr Thr Ser Ser Leu His Ser
1               5

<210> SEQ ID NO 162
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 162

Tyr Thr Ser Ser Leu His Ser
1               5

<210> SEQ ID NO 163
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 163

Gly Ala Ser Asn Arg Tyr Pro
1               5

<210> SEQ ID NO 164
<211> LENGTH: 7
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"

<400> SEQUENCE: 164

Arg Ala Asn Arg Leu Val Asp
1               5

<210> SEQ ID NO 165
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 165

Leu Val Ser Asn Arg Phe Ser
1               5

<210> SEQ ID NO 166
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 166

Arg Ala Asn Arg Leu Val Asp
1               5

<210> SEQ ID NO 167
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 167

Tyr Thr Ser Ser Leu His Ser
1               5

<210> SEQ ID NO 168
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 168

Arg Thr Asn Arg Leu Val Asp
1               5

<210> SEQ ID NO 169
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 169

Trp Ala Ser Thr Arg Glu Ser
1               5

<210> SEQ ID NO 170
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 170

Arg Met Ser Asn Leu Ala Ser
1               5

<210> SEQ ID NO 171
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 171

Trp Ala Ser Thr Arg Glu Ser
1               5

<210> SEQ ID NO 172
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 172

Ala Ala Ser Asn Gln Gly Ser
1               5

<210> SEQ ID NO 173
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 173

Arg Thr Ser Asn Leu Ala Ser
1               5

<210> SEQ ID NO 174
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 174

Tyr Thr Ser Ser Leu His Ser
1               5
```

```
<210> SEQ ID NO 175
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 175

Tyr Thr Ser Ser Leu His Ser
1               5

<210> SEQ ID NO 176
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 176

Phe Gln Gly Ser His Val Pro Leu Thr
1               5

<210> SEQ ID NO 177
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 177

Gln Gln Ser Tyr Ser Trp Pro Leu Thr
1               5

<210> SEQ ID NO 178
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 178

Gln Gln Tyr Ser Lys Leu Pro Trp Thr
1               5

<210> SEQ ID NO 179
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 179

Gln Gln Tyr Ile Lys Leu Pro Trp Thr
1               5

<210> SEQ ID NO 180
<211> LENGTH: 9
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 180

Gln Gln Tyr Ile Lys Leu Pro Phe Thr
1               5

<210> SEQ ID NO 181
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 181

Gly Gln Ser Tyr Ser Tyr Pro Tyr Thr
1               5

<210> SEQ ID NO 182
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 182

Leu Gln Tyr Asp Glu Phe Pro Tyr Thr
1               5

<210> SEQ ID NO 183
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 183

Phe Gln Ser Asn Ser Leu Pro Phe Thr
1               5

<210> SEQ ID NO 184
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 184

Leu Gln Tyr Asp Asp Phe Pro Tyr Thr
1               5

<210> SEQ ID NO 185
<211> LENGTH: 9
<212> TYPE: PRT
<213> ORGANISM: Artificial Sequence
<220> FEATURE:
<221> NAME/KEY: source
```

```
<223> OTHER INFORMATION: /note="Description of Artificial Sequence:
      Synthetic peptide"

<400> SEQUENCE: 185

Gln Gln Tyr Ile Lys Leu Pro Trp Thr
1               5

<210> SEQ ID NO 186
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 186

Leu Gln Tyr Asp Glu Phe Pro Tyr Thr
1               5

<210> SEQ ID NO 187
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 187

Lys Gln Ser Tyr Asn Leu Trp Thr
1               5

<210> SEQ ID NO 188
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 188

Met Gln His Leu Glu Tyr Pro Cys Thr
1               5

<210> SEQ ID NO 189
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 189

Lys Gln Ser Tyr Asn Leu Trp Thr
1               5

<210> SEQ ID NO 190
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 190
```

```
Gln Gln Ser Lys Glu Val Pro Phe Thr
1               5

<210> SEQ ID NO 191
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 191

Gln Gln Tyr His Ser Tyr Pro Pro Thr
1               5

<210> SEQ ID NO 192
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 192

Gln Gln Tyr Ser Glu Leu Pro Tyr Thr
1               5

<210> SEQ ID NO 193
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 193

Gln Gln Tyr Ile Lys Leu Pro Trp Thr
1               5

<210> SEQ ID NO 194
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 194

Val Pro Lys Ser Leu Lys Val Ser Thr Ser Thr Thr Lys Ser Pro
1               5                   10                  15

Ala Ser Ser Ala Ser
            20

<210> SEQ ID NO 195
<211> LENGTH: 24
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 195
```

Ser Thr Ser Ser Thr Thr Lys Ser Pro Ala Ser Ser Ala Ser Gly Pro
1               5                   10                  15

Arg Pro Thr Tyr Lys Pro Pro Val
            20

<210> SEQ ID NO 196
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 196

Pro Val Pro Lys Ser Leu Lys Gly Pro Arg Pro Thr Tyr Lys Pro Pro
1               5                   10                  15

Val Ser Asn Tyr Pro Gly
            20

<210> SEQ ID NO 197
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 197

Pro Thr Tyr Lys Pro Pro Val Ser Asn Tyr Pro Gly Tyr Pro Lys Pro
1               5                   10                  15

Glu Glu Gly Ile Leu Asp Ser Leu Asp
            20                  25

<210> SEQ ID NO 198
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: CDS
<222> LOCATION: (1)..(354)

<400> SEQUENCE: 198 cag gtg cag ctg cag gag tcg ggc cca gga ctg gtg aag cct tcg gag     48
Gln Val Gln Leu Gln Glu Ser Gly Pro Gly Leu Val Lys Pro Ser Glu
1               5                   10                  15 acc ctg tcc ctc acc tgc act gtc tct ggt ggc tcc gtc agt agt tac     96
Thr Leu Ser Leu Thr Cys Thr Val Ser Gly Gly Ser Val Ser Ser Tyr
            20                  25                  30 gac att agc tgg atc cgg cag ccc cca ggg aag gga ctg gag tgg att    144
Asp Ile Ser Trp Ile Arg Gln Pro Pro Gly Lys Gly Leu Glu Trp Ile
        35                  40                  45 ggg gtt atc tgg acc gat ggg ggc acc aac tac aac tcc gcc ttc atg    192
Gly Val Ile Trp Thr Asp Gly Gly Thr Asn Tyr Asn Ser Ala Phe Met
    50                  55                  60 agt cga gtc acc ata tca gta gac acg tcc aag aac cag ttc tcc ctg    240
Ser Arg Val Thr Ile Ser Val Asp Thr Ser Lys Asn Gln Phe Ser Leu
65                  70                  75                  80 aag ctg agc tct gtg acc gct gcg gac acg gcc gtg tat tac tgt gcg    288
Lys Leu Ser Ser Val Thr Ala Ala Asp Thr Ala Val Tyr Tyr Cys Ala

```
aga gtc tat gat ggt tat ccc tgg ttt gct tac tgg ggc cag ggc acc    336
Arg Val Tyr Asp Gly Tyr Pro Trp Phe Ala Tyr Trp Gly Gln Gly Thr
            100                 105                 110 ctg gtc acc gtc tcc tca                                            354
Leu Val Thr Val Ser Ser
        115
```

<210> SEQ ID NO 199
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 199

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Tyr
            20                  25                  30

Asp Ile Ser Trp Ile Arg Gln Pro Pro Gly Lys Gly Leu Glu Trp Ile
        35                  40                  45

Gly Val Ile Trp Thr Asp Gly Gly Thr Asn Tyr Asn Ser Ala Phe Met
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Val Tyr Asp Gly Tyr Pro Trp Phe Ala Tyr Trp Gly Gln Gly Thr
            100                 105                 110

Leu Val Thr Val Ser Ser
        115
```

<210> SEQ ID NO 200
<211> LENGTH: 324
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"
<220> FEATURE:
<221> NAME/KEY: CDS
<222> LOCATION: (1)..(324)

<400> SEQUENCE: 200

```
gac atc cag atg acc cag tct cca tcc tcc ctg tct gca tct gta gga    48
Asp Ile Gln Met Thr Gln Ser Pro Ser Ser Leu Ser Ala Ser Val Gly
1               5                   10                  15 gac aga gtc acc atc act tgc cgg gca agt cag ggc att agc aat tat    96
Asp Arg Val Thr Ile Thr Cys Arg Ala Ser Gln Gly Ile Ser Asn Tyr
            20                  25                  30 tta aat tgg tat cag cag aaa cca ggg aaa gcc cct aag ctc ctg atc    144
Leu Asn Trp Tyr Gln Gln Lys Pro Gly Lys Ala Pro Lys Leu Leu Ile
        35                  40                  45 tat tac aca tcc agt ttg cac agt ggg gtc cca tca agg ttc agt ggc    192
Tyr Tyr Thr Ser Ser Leu His Ser Gly Val Pro Ser Arg Phe Ser Gly
    50                  55                  60 agt gga tct ggg aca gat ttc act ctc acc atc agc agt ctg caa cct    240
Ser Gly Ser Gly Thr Asp Phe Thr Leu Thr Ile Ser Ser Leu Gln Pro
```

```
                65                  70                  75                  80
gaa gat ttt gca act tac tac tgt caa cag tat att aag ctt ccg tgg          288
Glu Asp Phe Ala Thr Tyr Tyr Cys Gln Gln Tyr Ile Lys Leu Pro Trp
                85                  90                  95 acg ttc ggt gga ggc acc aag ctg gaa atc aaa cgg                          324
Thr Phe Gly Gly Gly Thr Lys Leu Glu Ile Lys Arg
            100                 105
```

<210> SEQ ID NO 201
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 201

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
                20                  25                  30

Leu Asn Trp Tyr Gln Gln Lys Pro Gly Lys Ala Pro Lys Leu Leu Ile
            35                  40                  45

Tyr Tyr Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ile Lys Leu Pro Trp
                85                  90                  95

Thr Phe Gly Gly Gly Thr Lys Leu Glu Ile Lys Arg
            100                 105
```

<210> SEQ ID NO 202
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: CDS
<222> LOCATION: (1)..(360)

<400> SEQUENCE: 202

```
cag gtt cag ctg gtg cag tct gga gct gag gtg aag aag cct ggg gcc          48
Gln Val Gln Leu Val Gln Ser Gly Ala Glu Val Lys Lys Pro Gly Ala
1               5                   10                  15 tca gtg aag gtc tcc tgc aag gct tct ggt tac acc ttt acc gac tac          96
Ser Val Lys Val Ser Cys Lys Ala Ser Gly Tyr Thr Phe Thr Asp Tyr
                20                  25                  30 aac atg gac tgg gtg cga cag gcc cct gga caa ggg ctt gag tgg atg         144
Asn Met Asp Trp Val Arg Gln Ala Pro Gly Gln Gly Leu Glu Trp Met
            35                  40                  45 gga gat att aat cct aac aat ggt gat act ttc tac aac cag aag ttc         192
Gly Asp Ile Asn Pro Asn Asn Gly Asp Thr Phe Tyr Asn Gln Lys Phe
    50                  55                  60 aag ggc aga gtc acc atg acc aca gac aca tcc acg agc aca gcc tac         240
Lys Gly Arg Val Thr Met Thr Thr Asp Thr Ser Thr Ser Thr Ala Tyr
65                  70                  75                  80 atg gag ctg agg agc ctg aga tct gac gac acg gcc gtg tat tac tgt         288
```

```
Met Glu Leu Arg Ser Leu Arg Ser Asp Asp Thr Ala Val Tyr Tyr Cys
                85                  90                  95 gcg aga tca aag tat gat aac tat ccc tgg ttt gct tac tgg ggc caa        336
Ala Arg Ser Lys Tyr Asp Asn Tyr Pro Trp Phe Ala Tyr Trp Gly Gln
            100                 105                 110 ggg act ctg gtc act gtc tct tcc                                        360
Gly Thr Leu Val Thr Val Ser Ser
        115                 120

<210> SEQ ID NO 203
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 203

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Asn Met Asp Trp Val Arg Gln Ala Pro Gly Gln Gly Leu Glu Trp Met
            35                  40                  45

Gly Asp Ile Asn Pro Asn Asn Gly Asp Thr Phe Tyr Asn Gln Lys Phe
        50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ser Lys Tyr Asp Asn Tyr Pro Trp Phe Ala Tyr Trp Gly Gln
            100                 105                 110

Gly Thr Leu Val Thr Val Ser Ser
        115                 120

<210> SEQ ID NO 204
<211> LENGTH: 325
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: CDS
<222> LOCATION: (2)..(325)

<400> SEQUENCE: 204 g gac atc cag atg acc cag tct cca tcc tcc ctg tct gca tct gta gga      49
  Asp Ile Gln Met Thr Gln Ser Pro Ser Ser Leu Ser Ala Ser Val Gly
  1               5                   10                  15 gac aga gtc acc atc act tgc cgg gca agt cag gac att aac aat tat       97
Asp Arg Val Thr Ile Thr Cys Arg Ala Ser Gln Asp Ile Asn Asn Tyr
                20                  25                  30 tta aat tgg tat cag cag aaa cca ggg aaa gcc cct aag ctc ctg atc      145
Leu Asn Trp Tyr Gln Gln Lys Pro Gly Lys Ala Pro Lys Leu Leu Ile
            35                  40                  45 tat tac aca tcc agt ttg cac agt ggg gtc cca tca agg ttc agt ggc      193
Tyr Tyr Thr Ser Ser Leu His Ser Gly Val Pro Ser Arg Phe Ser Gly
        50                  55                  60 agt gga tct ggg aca gat ttc act ctc acc atc agc agt ctg caa cct      241
```

-continued

```
Ser Gly Ser Gly Thr Asp Phe Thr Leu Thr Ile Ser Ser Leu Gln Pro
 65                  70                  75                  80 gaa gat ttt gca act tac tac tgt caa cag tat att aag ctt ccg tgg      289
Glu Asp Phe Ala Thr Tyr Tyr Cys Gln Gln Tyr Ile Lys Leu Pro Trp
                 85                  90                  95 acg ttc ggt gga ggc acc aag ctg gaa atc aaa cgg                      325
Thr Phe Gly Gly Gly Thr Lys Leu Glu Ile Lys Arg
            100                 105
```

<210> SEQ ID NO 205
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 205

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Asn Asn Tyr
             20                  25                  30

Leu Asn Trp Tyr Gln Gln Lys Pro Gly Lys Ala Pro Lys Leu Leu Ile
         35                  40                  45

Tyr Tyr Thr Ser Ser Leu His Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Ile Lys Leu Pro Trp
                 85                  90                  95

Thr Phe Gly Gly Gly Thr Lys Leu Glu Ile Lys Arg
            100                 105
```

<210> SEQ ID NO 206
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic 6xHis tag"

<400> SEQUENCE: 206

```
His His His His His His
 1               5
```

<210> SEQ ID NO 207
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic 8xHis tag"

<400> SEQUENCE: 207

```
His His His His His His His His
 1               5
```